US012753166B2

(12) United States Patent
Chen et al.

(10) Patent No.: US 12,753,166 B2
(45) Date of Patent: Oct. 6, 2026

(54) SALT CONTAINING PIPERAZINE POLYCYCLIC DERIVATIVE, CRYSTAL FORM THEREOF, PREPARATION METHOD THEREFOR, AND USE THEREOF

(71) Applicants: Shanghai Hansoh Biomedical Co., Ltd., Shanghai (CN); Jiangsu Hansoh Pharmaceutical Group Co., Ltd., Lianyungang (CN)

(72) Inventors: Jinyao Chen, Shanghai (CN); Yuanyuan Li, Shanghai (CN)

(73) Assignees: Shanghai Hansoh Biomedical Co., Ltd., Shanghai (CN); Jiangsu Hansoh Pharmaceutical Group Co., Ltd., Lianyungang (CN)

( * ) Notice: Subject to any disclaimer, the term of this patent is extended or adjusted under 35 U.S.C. 154(b) by 400 days.

(21) Appl. No.: 18/558,165

(22) PCT Filed: Apr. 27, 2022

(86) PCT No.: PCT/CN2022/089419

§ 371 (c)(1),
(2) Date: Oct. 30, 2023

(87) PCT Pub. No.: WO2022/228447

PCT Pub. Date: Nov. 3, 2022

(65) Prior Publication Data

US 2024/0254109 A1 Aug. 1, 2024

(30) Foreign Application Priority Data

Apr. 28, 2021 (CN) ........................ 202110468491.2

(51) Int. Cl.
*C07D 403/12* (2006.01)
*A61K 31/496* (2006.01)
(Continued)

(52) U.S. Cl.
CPC .......... *C07D 403/12* (2013.01); *A61K 31/496* (2013.01); *A61K 31/551* (2013.01);
(Continued)

(58) Field of Classification Search
CPC ..... A61K 31/496; A61K 31/551; A61P 25/00; A61P 25/18; C07B 2200/13;
(Continued)

(56) References Cited

U.S. PATENT DOCUMENTS 9,376,396 B2 6/2016 Haupt et al.
9,388,148 B2 7/2016 Haupt et al.
(Continued)

FOREIGN PATENT DOCUMENTS

CN 104854103 A 8/2015
CN 105339357 A 2/2016
(Continued)

OTHER PUBLICATIONS

Ando et al (Remington, 2000, 20th Edition, chapter 38, pp. 704-712). (Year: 2000).*
(Continued)

*Primary Examiner* — Savitha M Rao
(74) *Attorney, Agent, or Firm* — Foley Hoag LLP; Dana M. Gordon; Alexander J. Chatterley

(57) ABSTRACT

Provided are a salt containing a piperazine polycyclic derivative, a crystal form thereof, a preparation method therefor, and the use thereof. In particular, the present invention relates to a salt containing a compound of general formula (I) and a stereoisomer thereof, a crystal form of the salt, a preparation method, a pharmaceutical composition containing a therapeutically effective amount of the crystal form, and the use as a G protein-coupled receptor regulator in treatment or prevention of central nervous system diseases and/or mental diseases.
(Continued)

(I)

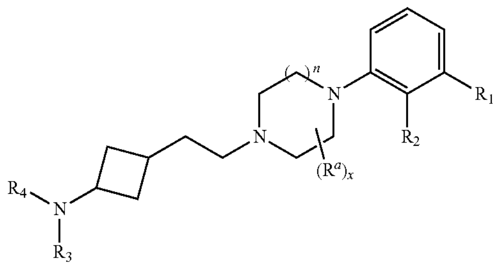

20 Claims, 12 Drawing Sheets

(51) Int. Cl.

| | |
|---|---|
| ***A61K 31/551*** | (2006.01) |
| ***A61P 25/18*** | (2006.01) |
| ***C07D 241/04*** | (2006.01) |
| ***C07D 401/12*** | (2006.01) |
| ***C07D 405/12*** | (2006.01) |
| ***C07D 409/12*** | (2006.01) |
| ***C07D 413/12*** | (2006.01) |
| ***C07D 417/12*** | (2006.01) |

(52) U.S. Cl.
CPC ............ *A61P 25/18* (2018.01); *C07D 241/04* (2013.01); *C07D 401/12* (2013.01); *C07D 405/12* (2013.01); *C07D 409/12* (2013.01); *C07D 413/12* (2013.01); *C07D 417/12* (2013.01)

(58) Field of Classification Search
CPC .. C07D 205/04; C07D 213/82; C07D 215/48; C07D 233/54; C07D 241/04; C07D 261/08; C07D 261/18; C07D 263/32; C07D 263/34; C07D 277/56; C07D 295/135; C07D 307/68; C07D 401/12; C07D 403/12; C07D 405/12; C07D 409/12; C07D 413/12; C07D 417/12
See application file for complete search history.

(56) References Cited

U.S. PATENT DOCUMENTS

| | | | |
|---|---|---|---|
| 12,617,759 B2 | 5/2026 | Su et al. | |
| 2014/0194437 A1 | 7/2014 | Haupt | |
| 2014/0303176 A1 | 10/2014 | Haupt et al. | |
| 2023/0076435 A1* | 3/2023 | Su | A61P 25/00 |

FOREIGN PATENT DOCUMENTS

| | | | |
|---|---|---|---|
| CN | 113056454 | A | 6/2021 |
| WO | 2005012266 | A1 | 2/2005 |
| WO | 2007093540 | A1 | 8/2007 |
| WO | 2009013212 | A2 | 1/2009 |
| WO | 2010031735 | A1 | 3/2010 |
| WO | WO-2012/110470 | A1 | 8/2012 |
| WO | 2012117001 | A1 | 9/2012 |
| WO | WO-2014/064038 | A1 | 5/2014 |
| WO | 2014086098 | A1 | 6/2014 |
| WO | WO-2014/140246 | A1 | 9/2014 |
| WO | 2020156312 | A1 | 8/2020 |
| WO | WO-2021/022890 | A1 | 2/2021 |
| WO | 2021083246 | A1 | 5/2021 |
| WO | WO-2022/228447 | A1 | 11/2022 |

OTHER PUBLICATIONS

Callear (Thesis , "Preparation, Characterisation and Structural Assessment of Salts and Co-Crystals of Organic Compounds" University of Southampton, 2008, pp. 1-222 (Year: 2008).*
International Preliminary Report on Patentability; The International Bureau of WIPO; International Application No. PCT/CN2022/089419; Nov. 9, 2023; 17 pages.
Written Opinion of the International Searching Authority; China National Intellectual Property Administration; International Application No. PCT/CN2022/089419; Oct. 28, 2023; 15 pages.
International Search Report, China National Intellectual Property Administration, International Application No. PCT/CN2022/089419, Jul. 27, 2022, 6 pages.
Written Opinion of the International Searching Authority, China National Intellectual Property Administration, International Application No. PCT/CN2022/089419, Jul. 27, 2022, 15 pages.
Bellioti et al., "Novel Cyclohexyl Amides as Potent and Selective D3 Dopamine Receptor Ligands", Bioorganic & Medicinal Chemistry Letters, vol. 7, No. 18, Sep. 23, 1997, 2403-2407.
International Search Report and Written Opinion for International Application No. PCT/CN20/124609 dated Jan. 4, 2021.
Kiss et al., Cariprazine (RGH—188), a Dopamine D3 receptor—preferring, D3/D2 Dopamine Receptor antagonist—partial agonist antipsychotic candidate: in vitro and neurochemical profile, Journal of Pharmacology and Experimental Therapeutics, 2010, vol. 333, No. 1, pp. 328-340, DOI:10.1124/jpet.109.160432.
Supplementary European Search Report for EP Application No. 20880440.1 dated Nov. 8, 2023.
Supplementary European Search Report for EP Application No. 22794917.9 dated Mar. 28, 2025.

* cited by examiner

SALT CONTAINING PIPERAZINE POLYCYCLIC DERIVATIVE, CRYSTAL FORM THEREOF, PREPARATION METHOD THEREFOR, AND USE THEREOF

CROSS-REFERENCE TO RELATED APPLICATIONS

This application is a U.S. National Phase of International PCT Application No. PCT/CN2022/089419 filed on Apr. 27, 2022, which claims priority to Chinese Application No. 202110468491.2 filed on Apr. 28, 2021, the contents of each application are incorporated herein by reference in their entireties.

FIELD OF THE INVENTION

The present invention belongs to the field of biomedicine, and specifically relates to a salt of piperazine-containing polycyclic derivative, crystal form thereof, preparation method therefor, and use thereof.

BACKGROUND OF THE INVENTION

Dopamine D3 receptor is a member of the G protein-coupled receptor family, which is a subtype of the dopamine receptor and belongs to D2-like inhibitory receptor as dopamine D2 and D4 receptors. Upon binding to DA, it reduces cAMP level by inhibiting G-protein. D3 receptors are mainly distributed in the mesolimbic system, especially the nucleus accumbens, olfactory tubercle and calleja's islets which are not related to motor function. Highly active D3 receptor modulators may have good anti-schizophrenia activity. D3 receptor is closely related to mood, cognition, spirit, addiction, etc., and can improve the negative symptoms of schizophrenia patients. D3 receptor may play a regulating role in cognition by regulating the release of acetylcholine and regulating glutamate receptor. Partial agonism of D3 receptor can improve cognition.

5-Hydroxytryptamine 2A (5-HT2A) receptor is a member of the G protein-coupled receptor family, and is a major excitatory receptor subtype of the 5-HT receptor. They are distributed in the center and periphery, and are closely related to spirit, emotion, learning, memory, etc. Highly active 5-HT2A receptor inhibitors have significant anti-schizophrenia effects, and can reduce the side effects of extrapyramidal tract.

Schizophrenia is a mental illness with the highest prevalence, which has a slow course of disease and is prone to repeated attacks, aggravation or exacerbation, resulting in serious burden and adverse consequences for patients and their families. Psychopaths may experience positive symptoms such as delusion, hallucination and disturbance in thought, language and behavior, negative symptoms such as lack of emotion and expression, poor speech and lack of pleasure, and other symptoms such as cognitive disorder. Although the research, development and clinical application of anti-schizophrenia drugs have developed greatly in the past few decades, both traditional antipsychotics (first-generation) (haloperidol, droperidol, thioridazine, etc.) and atypical antipsychotics (second-generation) (clozapine, risperidone, olanzapine, aripiprazole, etc.) are effective in treating positive symptoms, while poor in improving negative symptoms and cognitive disorder. Therefore, there is an urgent need to develop anti-schizophrenia drugs that can improve not only positive symptoms but also negative symptoms and cognitive disorder. Highly active dopamine D3 receptor modulators can improve negative symptoms, positive symptoms and cognitive disorder in patients with schizophrenia, without the side effects of the first- and second-generation antipsychotics such as extrapyramidal tract and weight gain.

Antagonists or partial agonists of D3 receptor have a good efficacy on improving the positive symptoms, negative symptoms and cognitive disorder of schizophrenia. International patent applications WO2007093540, WO2009013212A2, WO2010031735A1 and WO2012117001A1 reported D3 receptor and $5HT_{2A}$ dual modulator compounds, but most of the binding activities Ki of the compounds to D3 receptor and $5HT_{2A}$ are above 10 nM. Patent application WO2014086098A1 filed by Jiangsu Hengyi Pharmaceutical Co., LTD reported D3 selective inhibitors, but no study on the binding activity to $5HT_{2A}$ is reported. Cariprazine, a D3 antagonist developed by Gedeon Richter Plc., was available in 2015 and applied for the international patent application WO2005012266A1. Cariprazine has a potent D3 receptor agonist activity, and its use in the treatment of schizophrenia for negative symptoms has significant advantages over existing drugs. However, Cariprazine has weak inhibitory activity on 5-HT2A receptor, resulting in severe side effects of extrapyramidal symptoms (ESP). Therefore, there is an urgent need to develop highly active D3 receptor modulators with optimized $5HT_{2A}$ binding activity to reduce the side effects of extrapyramidal symptoms and improve the effects on negative symptoms and cognitive improvement in schizophrenia.

The compounds of the present invention not only have potent D3 receptor agonist activity, but also are significantly better than Cariprazine for 5-HT2A inhibitory activity. They are expected to have good clinical therapeutic effects on negative symptoms of schizophrenia and significantly reduce the risk of EPS side effects.

PCT patent application (application number: PCT/CN2020/124609) and Chinese patent application (application number: 202080006212.4) disclosed a series of four-membered ring derivatives modulator structure. In the subsequent research and development, in order to improve the solubility and stability of the product, suitable crystal which is easy stored and has long-term stability and high bioavailability is to be seeked. The present invention conducts a comprehensive study of the salt form and the crystal form of the salt of the above compounds.

SUMMARY OF THE INVENTION

The whole content involved in the patent application PCT/CN2020/073153 and CN202080006212.4 is incorporated into the present invention by reference.

The objective of the present invention is to provide a salt of a compound of formula (I) or a stereoisomer thereof and a crystal form thereof, wherein the structure of formula (I) is as follows:

(I)

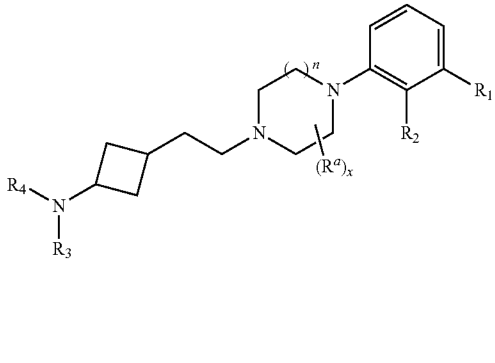

wherein:

each $R^a$ is independently selected from the group consisting of hydrogen, deuterium and $C_{1-6}$ alkyl;

$R_1$ is selected from the group consisting of hydrogen, deuterium, cyano, halogen, $C_{1-6}$ alkyl, $C_{1-6}$ hydroxyalkyl and $C_{1-6}$ alkoxy;

$R_2$ is selected from the group consisting of hydrogen, deuterium, cyano, halogen, $C_{1-6}$ alkyl, $C_{1-6}$ hydroxyalkyl and $C_{1-6}$ alkoxy;

or, $R_1$ and $R_2$ together with the carbon atom to which they are attached form a 5 to 6 membered heteroaryl, wherein the 5 to 6 membered heteroaryl is optionally further substituted by one or more substituents selected from the group consisting of deuterium, halogen, amino, nitro, hydroxy, cyano, $C_{1-6}$ alkyl, $C_{1-6}$ deuterated alkyl, $C_{1-6}$ haloalkyl, $C_{1-6}$ hydroxyalkyl, $C_{1-6}$ alkoxy, $C_{1-6}$ haloalkoxy, $C_{2-6}$ alkenyl, $C_{2-6}$ alkynyl, $C_{3-12}$ cycloalkyl, 3 to 12 membered heterocyclyl, $C_{6-14}$ aryl and 5 to 14 membered heteroaryl;

$R_3$ is selected from the group consisting of hydrogen, deuterium and $C_{1-6}$ alkyl;

$R_4$ is selected from the group consisting of hydrogen, deuterium, halogen, amino, nitro, hydroxy, cyano, $C_{1-6}$ alkyl, $C_{1-6}$ deuterated alkyl, $C_{1-6}$ haloalkyl, $C_{1-6}$ hydroxyalkyl, $C_{1-6}$ alkoxy, $C_{1-6}$ haloalkoxy, $C_{2-6}$ alkenyl, $C_{2-6}$ alkynyl, $C_{3-12}$ cycloalkyl, 3 to 12 membered heterocyclyl, $C_{6-14}$ aryl, 5 to 14 membered heteroaryl, $-(CH_2)_{n1}R_a$, $-(CH_2)_{n1}C(O)R_a$, $-(CH_2)_{n1}C(O)NR_aR_b$, $-C(O)(CHR_a)_{n1}R_b$, $-C(O)NR_a(CH_2)_{n1}R_b$, $-(CH_2)_{n1}S(O)_2R_a$, $-(CH_2)_{n1}S(O)_2NR_aR_b$ and $-(CH_2)_{n1}C(O)OR_a$, the amino, $C_{1-6}$ alkyl, $C_{1-6}$ deuterated alkyl, $C_{1-6}$ haloalkyl, $C_{1-6}$ alkoxy, $C_{1-6}$ hydroxyalkyl, $C_{1-6}$ haloalkoxy, $C_{2-6}$ alkenyl, $C_{2-6}$ alkynyl, $C_{3-12}$ cycloalkyl, 3 to 12 membered heterocyclyl, $C_{6-14}$ aryl and 5 to 14 membered heteroaryl are each optionally further substituted by one or more substituents selected from the group consisting of deuterium, halogen, amino, nitro, hydroxy, cyano, $C_{1-6}$ alkyl, $C_{1-6}$ deuterated alkyl, $C_{1-6}$ haloalkyl, $C_{1-6}$ hydroxyalkyl, $C_{1-6}$ alkoxy, $C_{1-6}$ haloalkoxy, $C_{2-6}$ alkenyl, $C_{2-6}$ alkynyl, $C_{3-12}$ cycloalkyl, 3 to 12 membered heterocyclyl, $C_{6-14}$ aryl and 5 to 14 membered heteroaryl;

or, $R_3$ and $R_4$ together with the nitrogen atom to which they are attached form a 3 to 6 membered heterocyclyl or 5 to 6 membered heteroaryl, the 3 to 6 membered heterocyclyl or 5 to 6 membered heteroaryl is optionally further substituted by one or more substituents selected from the group consisting of deuterium, halogen, amino, nitro, hydroxy, cyano, $C_{1-6}$ alkyl, $C_{1-6}$ deuterated alkyl, $C_{1-6}$ haloalkyl, $C_{1-6}$ alkoxy, $C_{1-6}$ haloalkoxy, $C_{2-6}$ alkenyl, $C_{2-6}$ alkynyl, $C_{3-12}$ cycloalkyl, 3 to 12 membered heterocyclyl, $C_{6-14}$ aryl and 5 to 14 membered heteroaryl;

$R_a$ and $R_b$ are each independently selected from the group consisting of hydrogen, deuterium, amino, $C_{1-6}$ alkyl, $C_{1-6}$ haloalkyl, $C_{1-6}$ alkoxy, $C_{3-12}$ cycloalkyl, 3 to 12 membered heterocyclyl, $C_{6-14}$ aryl and 5 to 14 membered heteroaryl, the amino, $C_{1-6}$ alkyl, $C_{1-6}$ haloalkyl, $C_{1-6}$ alkoxy, $C_{3-12}$ cycloalkyl, 3 to 12 membered heterocyclyl, $C_{6-14}$ aryl and 5 to 14 membered heteroaryl are each optionally further substituted by one or more substituents selected from the group consisting of deuterium, halogen, hydroxy, cyano, oxo, $C_{1-6}$ alkyl, $C_{1-6}$ haloalkyl, $C_{1-6}$ alkoxy, $C_{1-6}$ haloalkoxy, $C_{2-6}$ alkenyl, $C_{2-6}$ alkynyl, $C_{3-12}$ cycloalkyl, 3 to 12 membered heterocyclyl, $C_{6-14}$ aryl and 5 to 14 membered heteroaryl;

wherein the acid in the acid salt is an inorganic acid or an organic acid; preferably, the inorganic acid is selected from the group consisting of hydrochloric acid, sulfuric acid, nitric acid, hydrobromic acid, hydrofluoric acid, hydroiodic acid and phosphoric acid; the organic acid is selected from the group consisting of 2,5-dihydroxybenzoic acid, 1-hydroxy-2-naphthoic acid, acetic acid, dichloroacetic acid, trichloroacetic acid, acetohydroxamic acid, adipic acid, benzenesulfonic acid, 4-chlorobenzenesulfonic acid, benzoic acid, 4-acetamidobenzoic acid, 4-aminobenzoic acid, capric acid, caproic acid, caprylic acid, cinnamic acid, citric acid, cyclamic acid, camphorsulfonic acid, aspartic acid, camphoric acid, gluconic acid, glucuronic acid, glutamic acid, isoascorbic acid, lactic acid, malic acid, mandelic acid, pyroglutamic acid, tartaric acid, dodecyl sulfuric acid, dibenzoyl tartaric acid, ethane-1,2-disulfonic acid, ethanesulfonic acid, formic acid, fumaric acid, galactonic acid, gentisic acid, glutaric acid, 2-ketoglutaric acid, glycolic acid, hippuric acid, isethionic acid, lactobionic acid, ascorbic acid, aspartic acid, lauric acid, camphoric acid, maleic acid, malonic acid, methanesulfonic acid, 1,5-naphthalenedisulfonic acid, naphthalene-2-sulfonic acid, nicotinic acid, oleic acid, orotic acid, oxalic acid, palmitic acid, embonic acid, propionic acid, salicylic acid, 4-aminosalicylic acid, decanedioic acid, stearic acid, succinic acid, thiocyanic acid, pamoic acid, methanoic acid, undecylenic acid, trifluoroacetic acid, benzenesulfonic acid, p-toluenesulfonic acid and L-malic acid;

x is 0, 1, 2 or 3;

n is 0, 1 or 2; and n1 is 0, 1, 2 or 3.

The present invention further relates to a crystal form of an acid salt of the compound of formula (I) or the stereoisomer thereof.

In a further preferred embodiment of the present invention, the compound of formula (I) or the stereoisomer thereof is further as shown in formula (Ia) or formula (Ib):

(Ia)

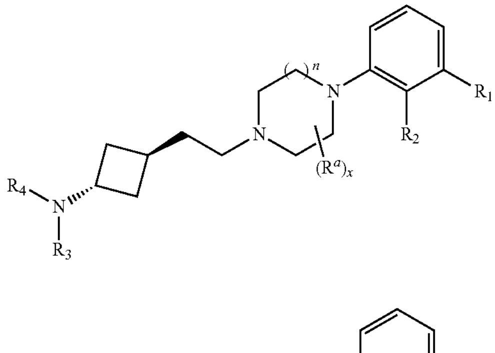

(Ib)

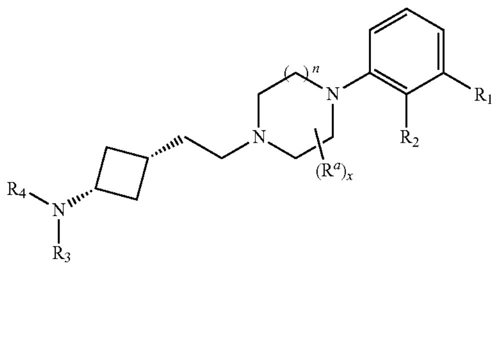

.

In a further preferred embodiment of the present invention, the compound of formula (I) or the stereoisomer thereof is further as shown in formula (II):

(II)

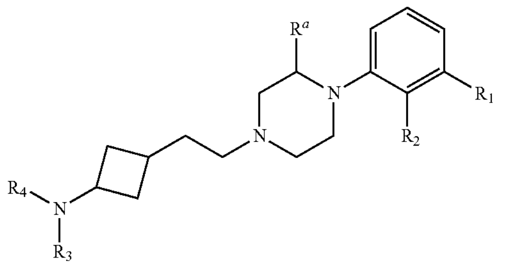

wherein:

$R^a$ is selected from the group consisting of hydrogen, deuterium and $C_{1-6}$ alkyl; preferably hydrogen, deuterium and methyl.

In a further preferred embodiment of the present invention, the compound of formula (II) or the stereoisomer thereof is further as shown in formula (IIa) or formula (IIb):

(IIa)

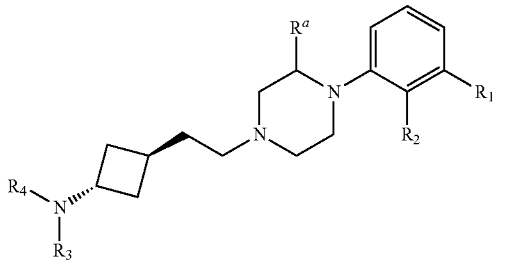

(IIb)

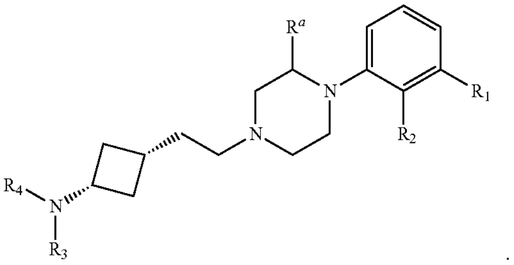

.

In a further preferred embodiment of the present invention, $R_1$ is selected from the group consisting of hydrogen, deuterium, halogen and $C_{1-3}$ alkyl; preferably fluorine, chlorine and bromine;

$R_2$ is selected from the group consisting of hydrogen, deuterium, halogen and $C_{1-3}$ alkyl; preferably fluorine, chlorine and bromine;

or, $R_1$ and $R_2$ together with the carbon atom to which they are attached form a 5 to 6 membered sulfur-containing heteroaryl;

preferably, $R_1$ and $R_2$ together with the carbon atom to which they are attached form a thienyl.

In a further preferred embodiment of the present invention, $R_3$ is selected from the group consisting of hydrogen, deuterium and $C_{1-3}$ alkyl.

In a further preferred embodiment of the present invention, $R_3$ is selected from the group consisting of hydrogen, deuterium and methyl.

In a further preferred embodiment of the present invention, $R_4$ is selected from the group consisting of hydrogen, deuterium, $C_{1-6}$ alkyl, $C_{3-8}$ cycloalkyl, 3 to 8 membered heterocyclyl, $C_{6-10}$ aryl, 5 to 10 membered heteroaryl, $-(CH_2)_{n1}R_a$, $-C(O)R_a$, $-C(O)NR_aR_b$, $-C(O)(CHR_a)_{n1}R_b$, $-C(O)NR_a(CH_2)_{n1}R_b$, $-S(O)_2R_a$, $-S(O)_2NR_aR_b$ and $-C(O)OR_a$, the $C_{1-6}$ alkyl, $C_{3-8}$ cycloalkyl, 3 to 8 membered heterocyclyl, $C_{6-10}$ aryl and 5 to 10 membered heteroaryl are each optionally further substituted by one or more substituents selected from the group consisting of deuterium, cyano, halogen, hydroxy, $C_{1-6}$ alkyl and $C_{1-6}$ alkoxy;

or, $R_3$ and $R_4$ are attached to form a 3 to 8 membered heterocyclyl or 5 to 14 membered heteroaryl, the 3 to 8 membered heterocyclyl or 5 to 10 membered heteroaryl is optionally further substituted by one or more substituents selected from the group consisting of halogen, amino, cyano, hydroxy, oxo, thioxo, $C_{1-6}$ alkyl, $C_{3-8}$ alkoxy, $C_{3-8}$ haloalkoxy and $C_{3-8}$ hydroxyalkyl;

$R_a$ and $R_b$ are each independently selected from the group consisting of hydrogen, deuterium, amino, $C_{1-6}$ alkyl, $C_{1-6}$ haloalkyl, $C_{1-6}$ alkoxy, $C_{1-6}$ hydroxyalkyl, $C_{3-8}$ cycloalkyl, 3 to 8 membered heterocyclyl, $C_{6-14}$ aryl and 5 to 14 membered heteroaryl, the amino, $C_{1-6}$ alkyl, $C_{1-6}$ haloalkyl, $C_{1-6}$ alkoxy, $C_{1-6}$ hydroxyalkyl, $C_{3-8}$ cycloalkyl, 3 to 8 membered heterocyclyl, $C_{6-14}$ aryl and 5 to 14 membered heteroaryl are each optionally further substituted by one or more substituents selected from the group consisting of halogen, hydroxy, cyano, oxo, $C_{1-6}$ alkyl, $C_{1-6}$ haloalkyl, $C_{1-6}$ alkoxy, $C_{3-8}$ cycloalkyl, 3 to 8 membered heterocyclyl, $C_{6-14}$ aryl and 5 to 14 membered heteroaryl; and n1 is 0, 1, 2 or 3.

In a further preferred embodiment of the present invention, the acid salt of the compound of formula (II) or the stereoisomer thereof or the crystal form thereof is further as shown in formula (III):

(III)

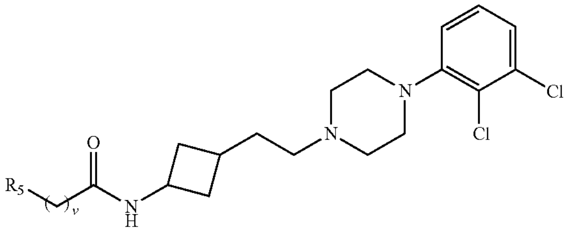

wherein:

$R_5$ is selected from the group consisting of amino, $C_{1-6}$ alkyl, $C_{1-6}$ alkoxy, $C_{1-6}$ hydroxyalkyl, $C_{3-8}$ cycloalkyl, $C_{6-10}$ phenyl, 3 to 8 membered heterocyclyl and 5 to 10 membered heteroaryl, the amino, $C_{1-6}$ alkyl, $C_{1-6}$ alkoxy, $C_{1-6}$ hydroxyalkyl, $C_{3-8}$ cycloalkyl, $C_{6-10}$ phenyl, 3 to 8 membered heterocyclyl and 5 to 10 membered heteroaryl are each optionally further substituted by one or more substituents selected from the group consisting of hydrogen, deuterium, halogen, hydroxy, cyano, oxo, $C_{1-6}$ alkyl, $C_{1-6}$ alkoxy and $C_{1-6}$ hydroxyalkyl;

preferably, $R_5$ is selected from the group consisting of hydrogen, amino, $C_{1-3}$ alkyl, $C_{1-3}$ alkoxy, $C_{1-3}$ hydroxyalkyl, $C_{3-8}$ cycloalkyl, $C_{6-10}$ aryl, 3 to 8 membered heterocyclyl containing one nitrogen or oxygen atom and 5 to 10 membered heteroaryl containing 1 to 3 heteroatoms selected from the group consisting of nitrogen, oxygen and sulfur atoms, the amino, $C_{1-3}$ alkyl, $C_{1-3}$ alkoxy, $C_{1-3}$ hydroxyalkyl, $C_{3-8}$ cycloalkyl, $C_{6-10}$ aryl, 3 to 8 membered heterocyclyl containing one nitrogen or oxygen atom and 5 to 10 membered heteroaryl containing 1 to 3 heteroatoms are each optionally further substituted by one or more substituents selected from the group consisting of deuterium, halogen, hydroxy, cyano, oxo, $C_{1-3}$ alkyl, $C_{1-3}$ alkoxy and $C_{1-3}$ hydroxyalkyl;

more preferably, $R_5$ is selected from the group consisting of hydrogen, amino, $C_{1-3}$ alkyl, $C_{1-3}$ alkoxy, $C_{1-3}$ hydroxyalkyl, $C_{3-8}$ cycloalkyl, phenyl, oxiranyl, thiiranyl, aziridinyl, oxetanyl, azetidinyl, thietanyl, tetrahydrofuryl, tetrahydrothienyl, furyl, thienyl, pyrrolyl, pyrazolyl, imidazolyl, oxazolyl, isoxazolyl, thiazolyl, isothiazolyl, pyridyl, pyridazinyl, pyrimidinyl, pyrazinyl, 1,3,5-triazinyl, benzofuryl, benzothienyl, indolyl, benzimidazolyl, indazolyl, benzoxazolyl, benzotriazolyl, quinolinyl and isoquinolyl, the amino, $C_{1-3}$ alkyl, $C_{1-3}$ alkoxy, $C_{1-3}$ hydroxyalkyl, $C_{3-8}$ cycloalkyl, phenyl, oxiranyl, thiiranyl, aziridinyl, oxetanyl, azetidinyl, thietanyl, tetrahydrofuryl, tetrahydrothienyl, furyl, thienyl, pyrrolyl, pyrazolyl, imidazolyl, oxazolyl, isoxazolyl, thiazolyl, isothiazolyl, pyridyl, pyridazinyl, pyrimidinyl, pyrazinyl, 1,3,5-triazinyl, benzofuryl, benzothienyl, indolyl, benzimidazolyl, indazolyl, benzoxazolyl, benzotriazolyl, quinolinyl and isoquinolyl are each optionally further substituted by one or more substituents selected from the group consisting of deuterium, halogen, hydroxy, cyano, oxo, $C_{1-3}$ alkyl, $C_{1-3}$ alkoxy and $C_{1-3}$ hydroxyalkyl;

further preferably, $R_5$ is selected from the group consisting of: H—, $(CH_3)_2N$—, $CH_3NH$—, $CH_3$—, $CH_3O$—, $CH_3CH_2$—, $CH_3CH_2NH$—, $CH_3CH_2N(CH_3)$—, $(CH_3)_2C(OH)$—, $(CH_3)_2C(OH)CH_2$—, $CH_3OCH_2$—,

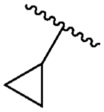, 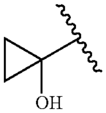, 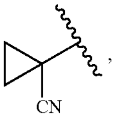, 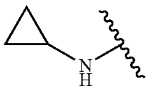,

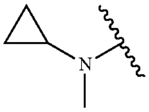, 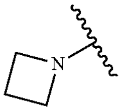, 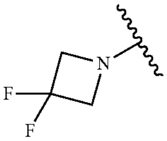,

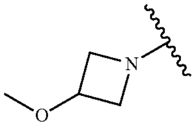, 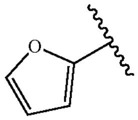, 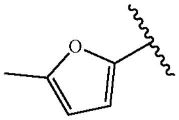,

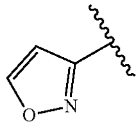, 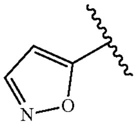, 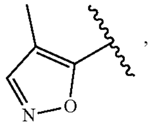,

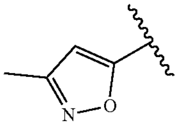, 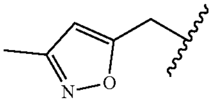, 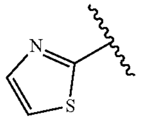,

-continued

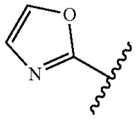, 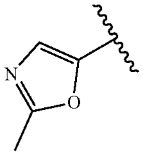, 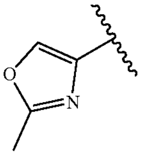,

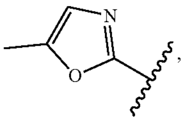, 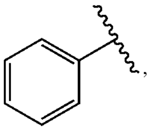, 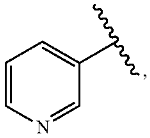,

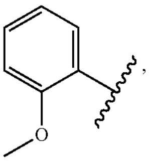, 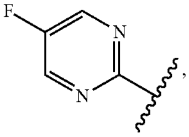, 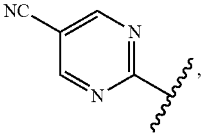,

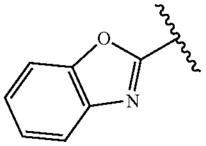,

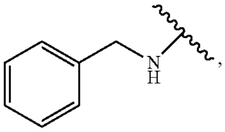, 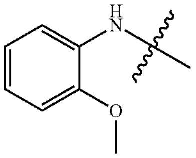,

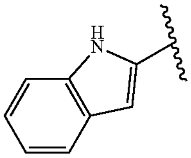 and 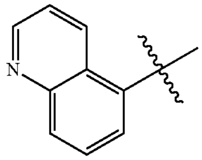;

and

V is 0 or 1.

In a further preferred embodiment of the present invention, the acid salt of the compound of formula (III) or the stereoisomer thereof or the crystal form thereof is further as shown in formula (IIIa) or formula (IIIb):

(IIIa)

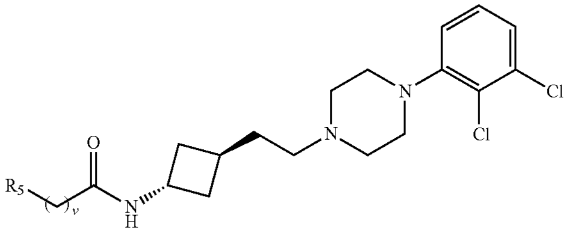

-continued
(IIIb)
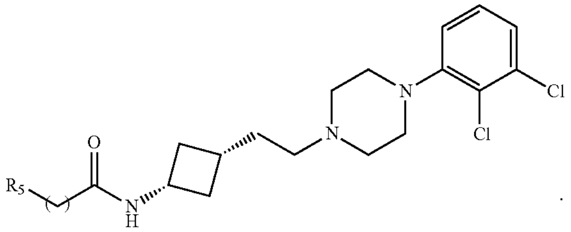
In a further preferred embodiment of the present invention, the acid salt of the compound of formula (I) or the stereoisomer thereof or the crystal form thereof is selected from the following compounds:
1
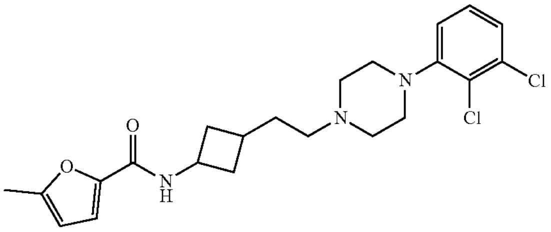
1A
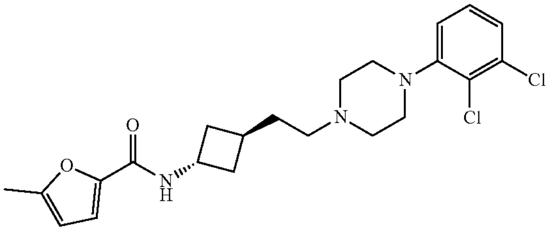
1B
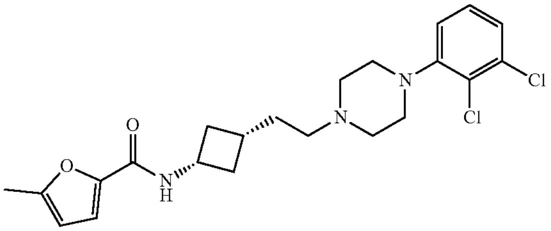
2
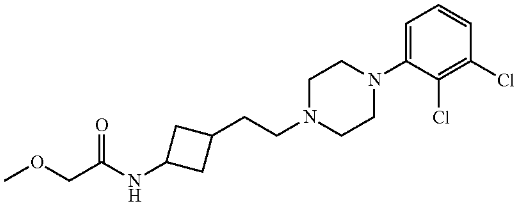
2A
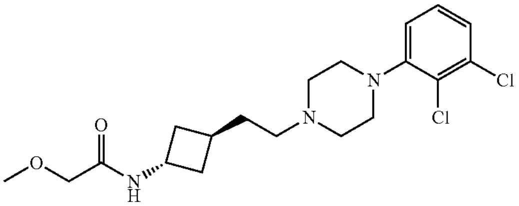
-continued
2B
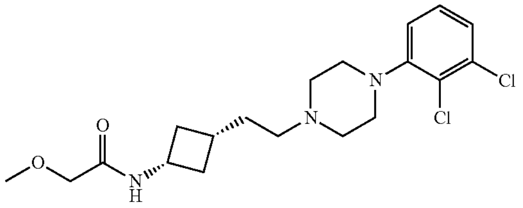
3
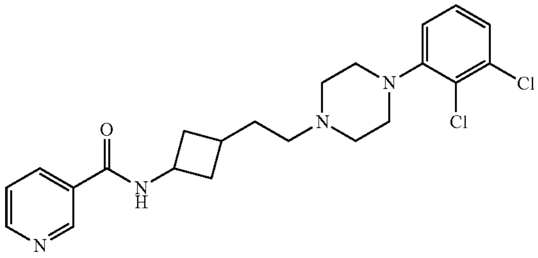
3A
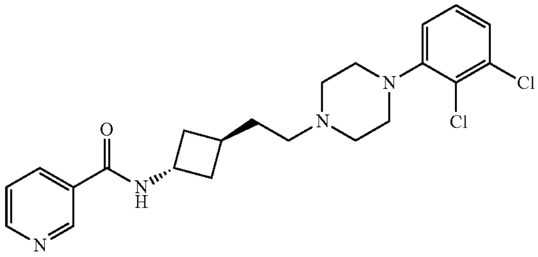
3B
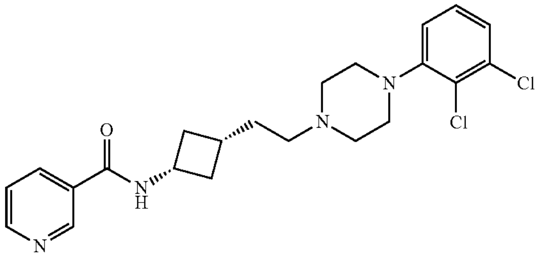
4
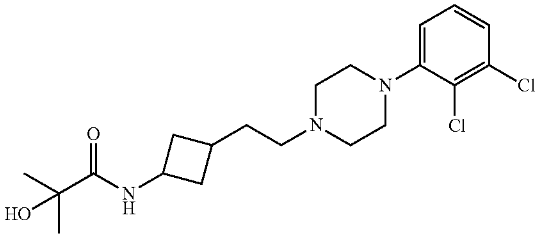
4A
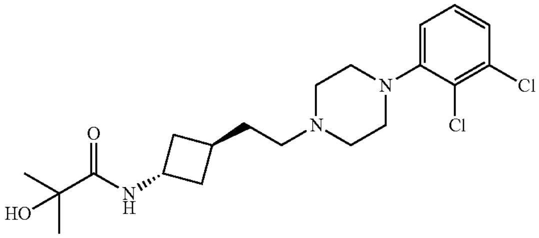

4B
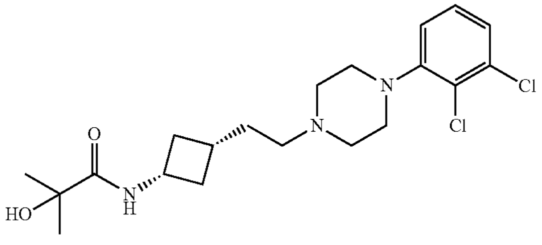
5
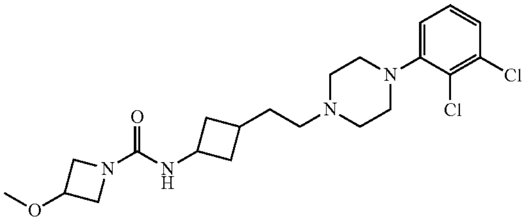
5A
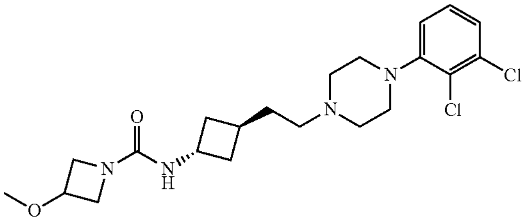
5B
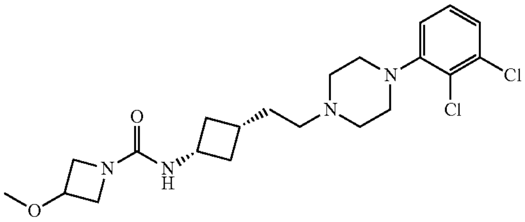
6
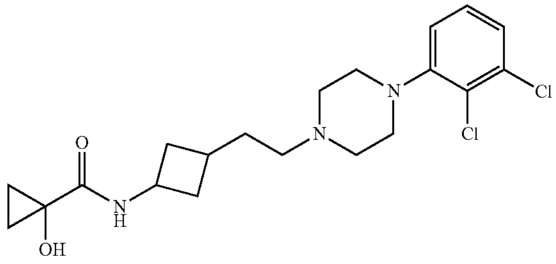
6A
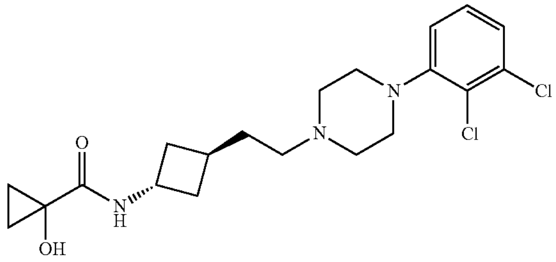
6B
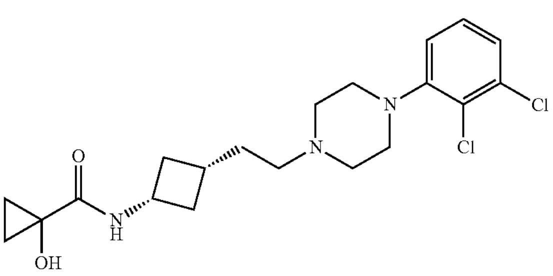
7
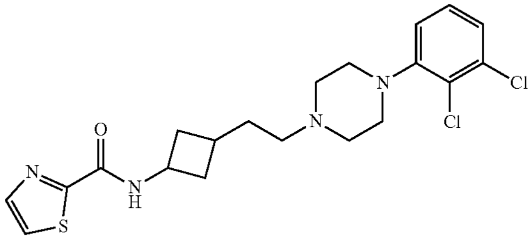
7A
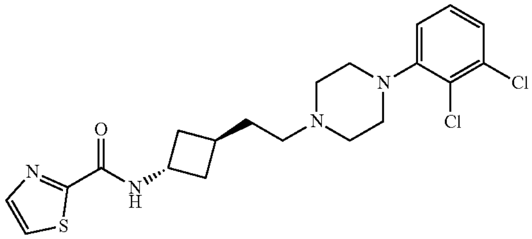
7B
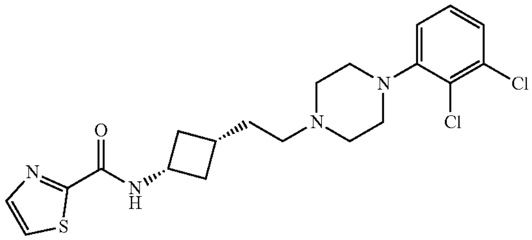
8
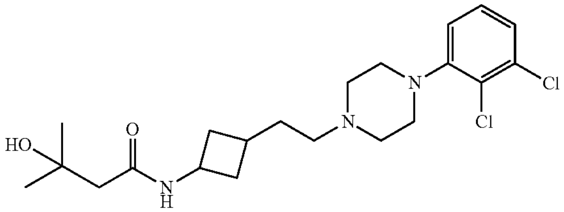
8A
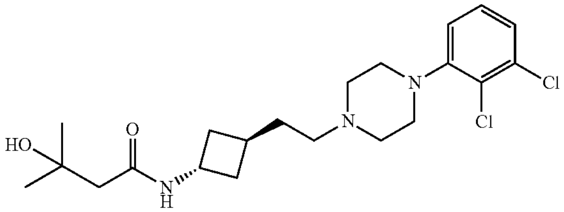

-continued
8B
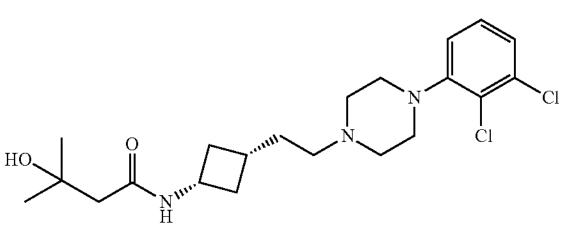
9
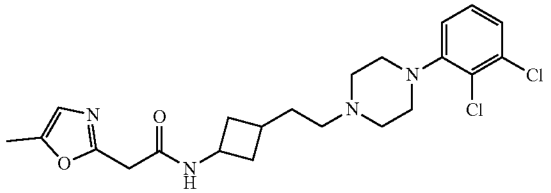
9A
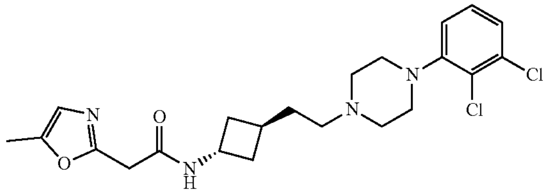
9B
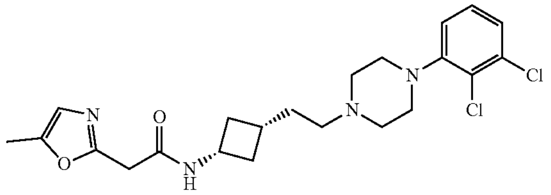
10
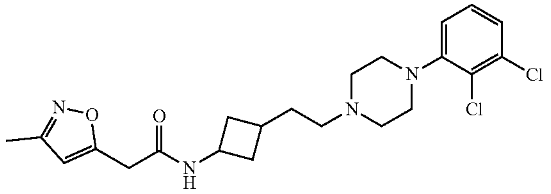
10A
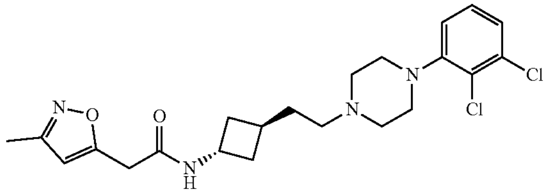
10B
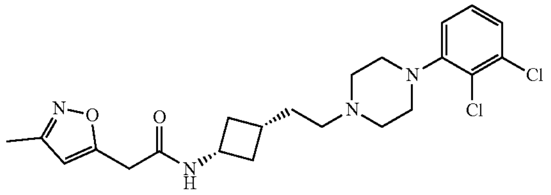
-continued
11
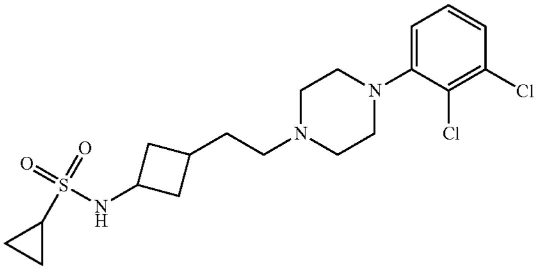
11A
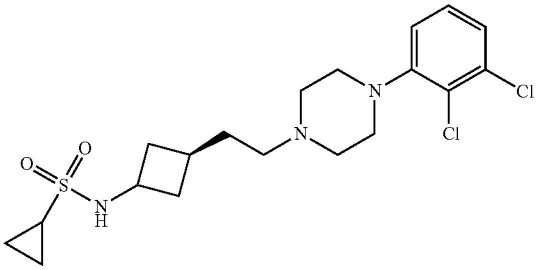
11B
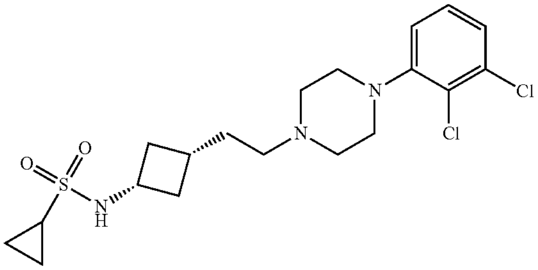
12
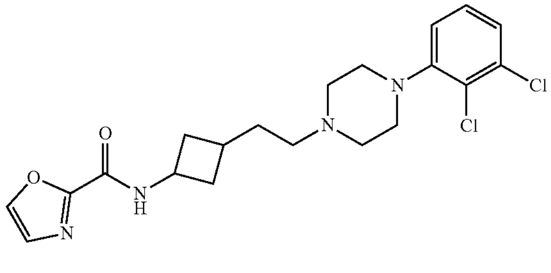
12A
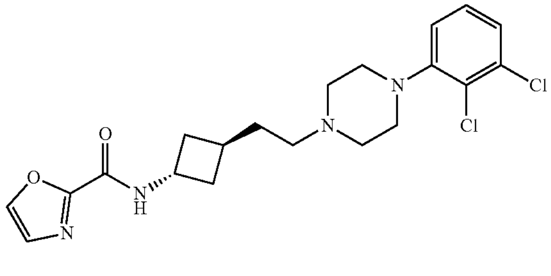

-continued
12B
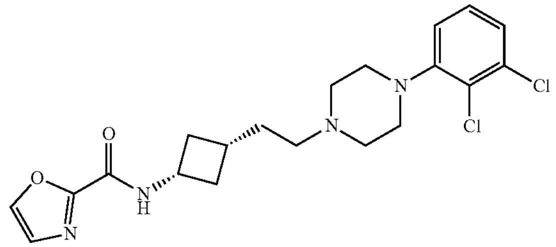
13
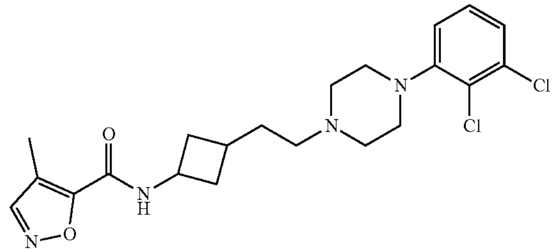
13A
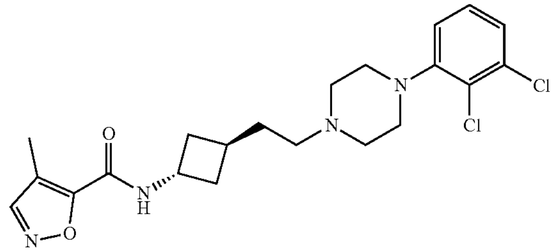
13B
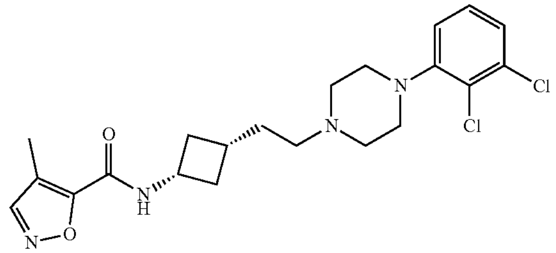
14
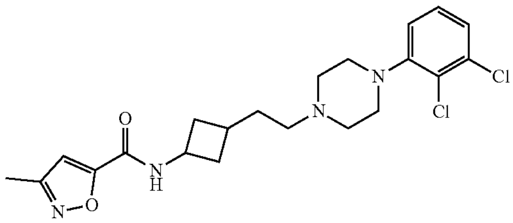
14A
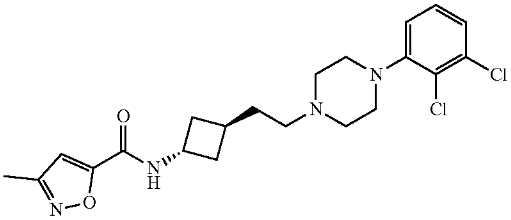
-continued
14B
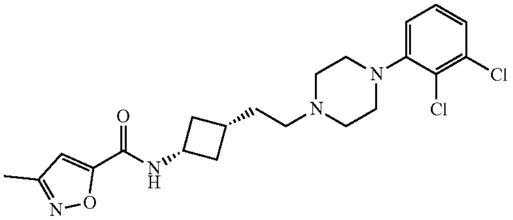
15
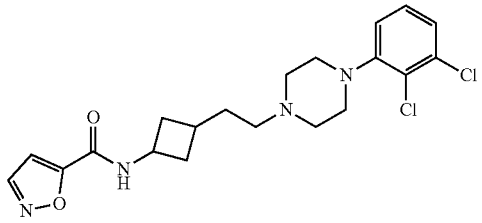
15A
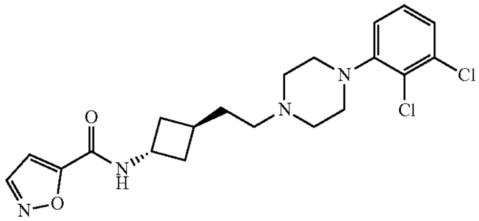
15B
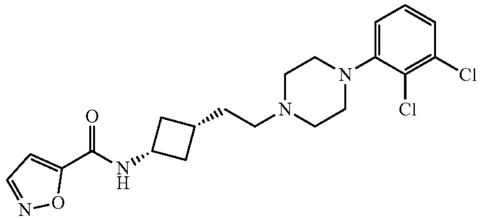
16
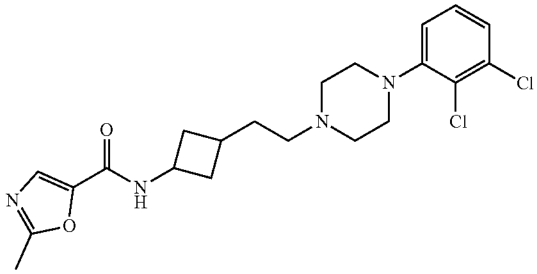
16A
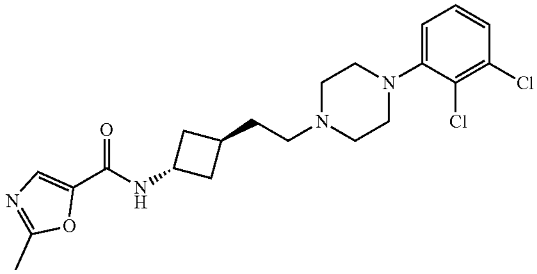

-continued
16B
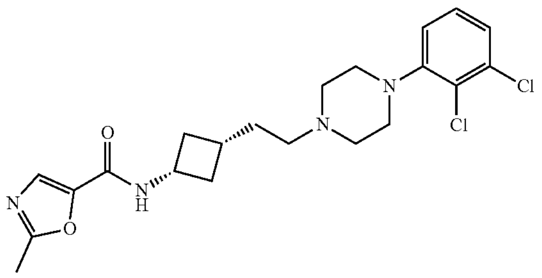
17
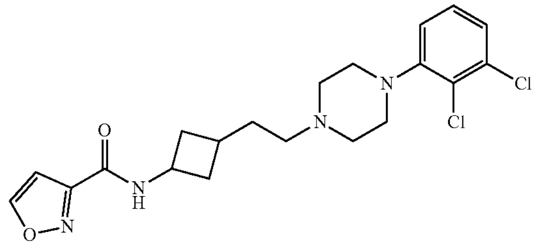
17A
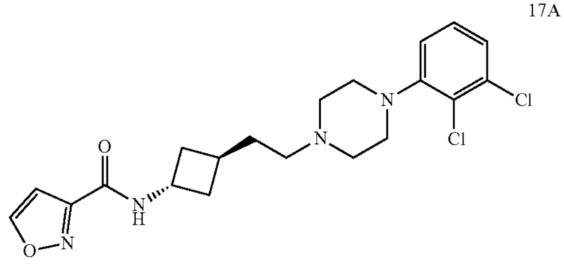
17B
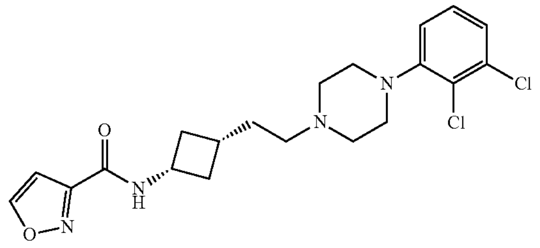
18
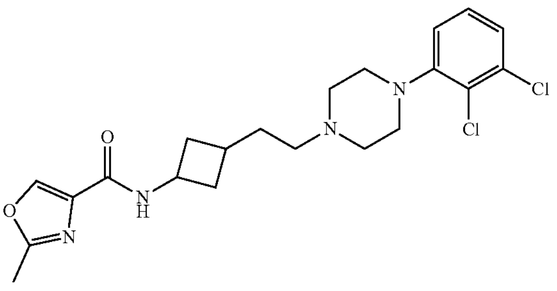
-continued
18A
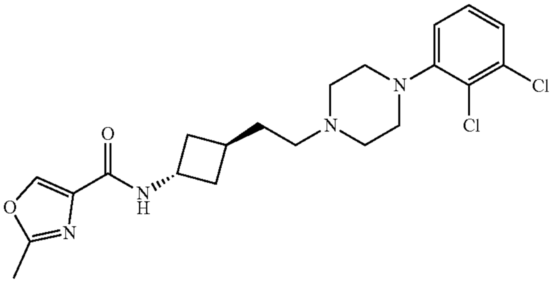
18B
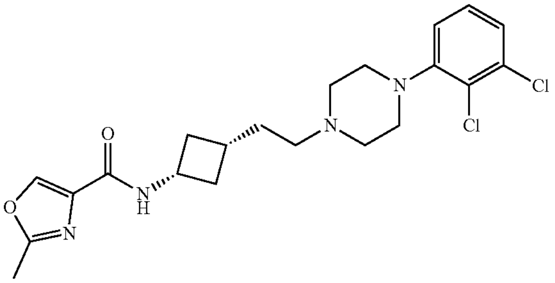
19
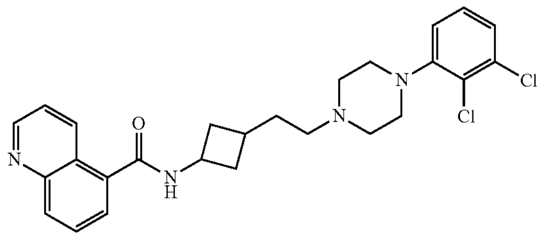
19A
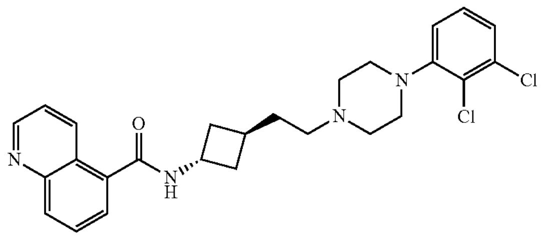
19B
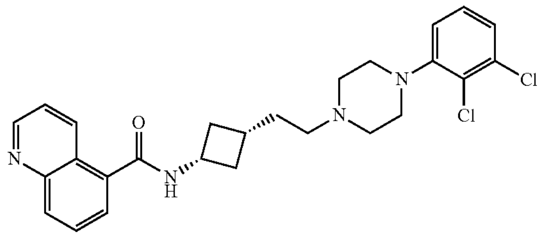
20
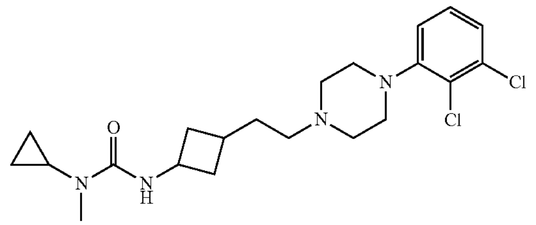

-continued
20A
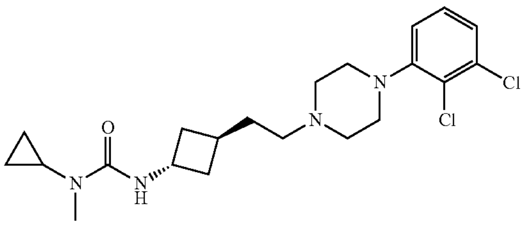
20B
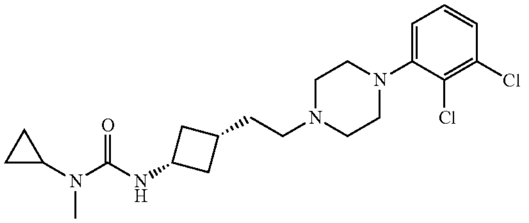
21
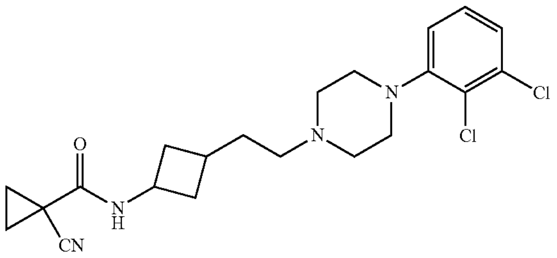
21A
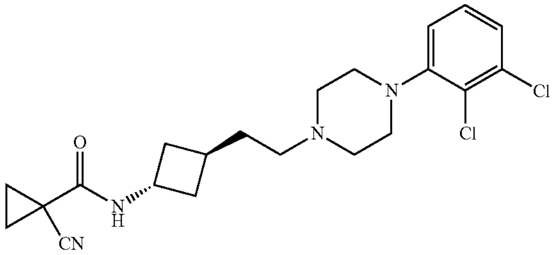
21B
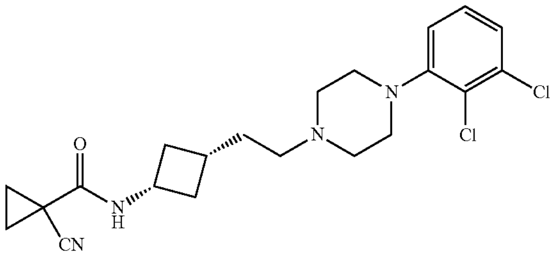
22
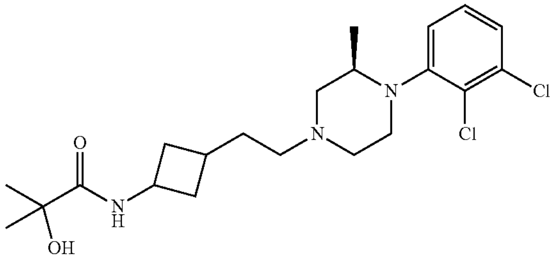
-continued
22A
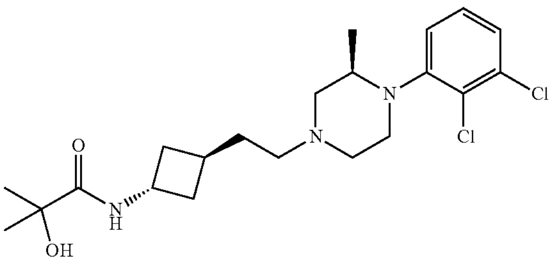
22B
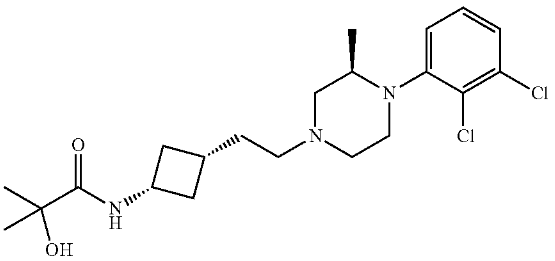
23
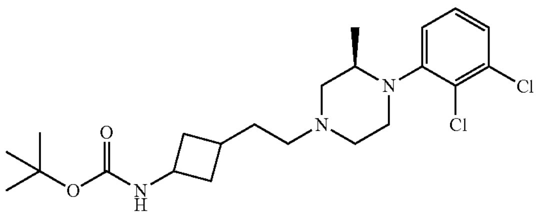
23A
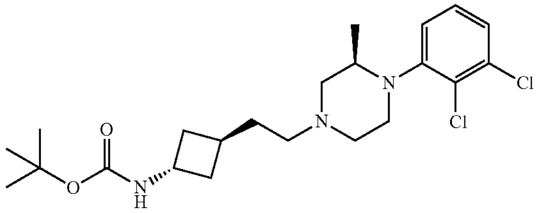
23B
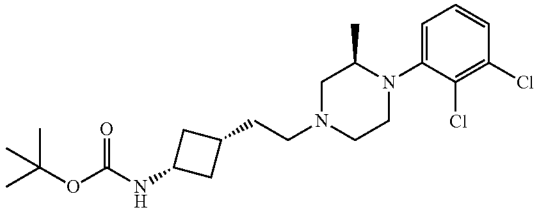
24
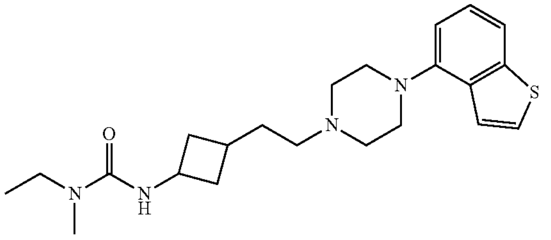

-continued

24A

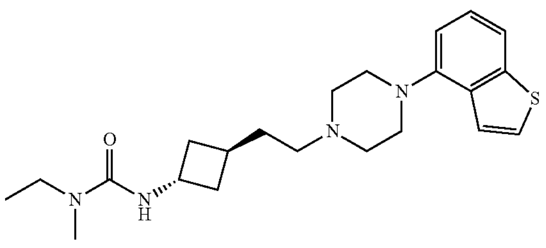

24B

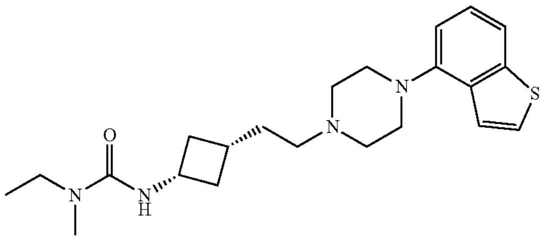

25

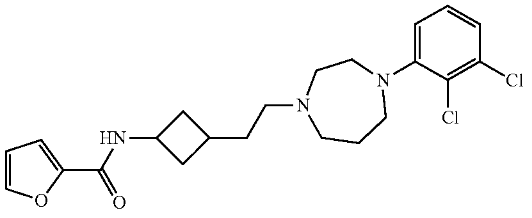

25A

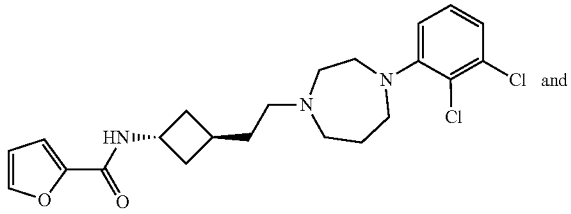

and

25B

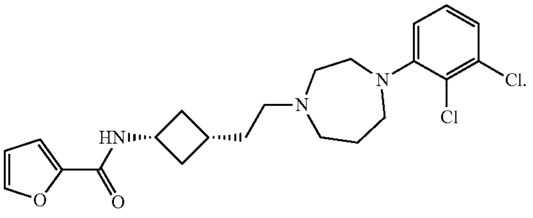

In a further preferred embodiment of the present invention, provided is an acid salt of any general formula and any compound or the stereoisomer thereof, the acid salt is selected from the group consisting of nitrate, phosphate, succinate, acetate, ethanesulfonate, benzoate, pamoate, malonate, methanesulfonate, malate, hydrochloride, maleate, benzenesulfonate, isethionate, 1,5-naphthalenedisulfonate, tartrate, adipate, sulfate, p-toluenesulfonate, hydrobromide, oxalate, fumarate, formate, hippurate, laurate and stearate;

preferably, the acid salt is selected from the group consisting of nitrate, hydrochloride, sulfate, p-toluenesulfonate, methanesulfonate, oxalate, sulfate, hydrobromide, phosphate, succinate, acetate, ethanesulfonate, benzoate, pamoate, malonate, malate, maleate, benzenesulfonate, fumarate, hippurate, isethionate, 1,5-naphthalenedisulfonate, tartrate and adipate;

further preferably, the acid salt is selected from the group consisting of hydrochloride, p-toluenesulfonate, oxalate, sulfate, hydrobromide, methanesulfonate, 1,5-naphthalenedisulfonate, acetate and nitrate.

In a further preferred embodiment of the present invention, provided is an an acid salt of N-(trans-3-(2-(4-(2,3-dichlorophenyl)piperazin-1-yl)ethyl)cyclobutyl)oxazole-2-carboxamide, wherein the acid salt is selected from the group consisting of nitrate, hydrochloride, sulfate, p-toluenesulfonate, methanesulfonate, oxalate, sulfate, hydrobromide, phosphate, succinate, acetate, ethanesulfonate, benzoate, pamolate, malonate, malate, maleate, benzenesulfonate, fumarate, hippurate, isethionate, 1,5-naphthalenedisulfonate, tartrate and adipicate; preferably hydrochloride, p-toluenesulfonate, oxalate, sulfate, hydrobromide, methanesulfonate, 1,5-naphthalenedisulfonate, fumarate, acetate and nitrate.

In a further preferred embodiment of the present invention, provided is an acid salt of the compound of any general formula or the stereoisomer thereof, the number of acid is 0.5 to 2, preferably 0.5, 1, 1.5 or 2, more preferably 0.5, 1 or 2.

In a further preferred embodiment of the present invention, provided is an acid salt of the compound of any general formula or the stereoisomer thereof, the acid salt is a hydrate or anhydrate, preferably anhydrate; when the acid salt is a hydrate, the number of water is 0.5 to 3, preferably 0.5, 1, 1.5, 2, 2.5 or 3, more preferably 0.5, 1 or 2.

In a further preferred embodiment of the present invention, provided is an an acid salt of N-(trans-3-(2-(4-(2,3-dichlorophenyl)piperazin-1-yl)ethyl)cyclobutyl)oxazole-2-carboxamide, wherein the acid salt is hydrochloride, and the number of hydrochloric acid is 1.

In a further preferred embodiment of the present invention, the acid salt of N-(trans-3-(2-(4-(2,3-dichlorophenyl)piperazin-1-yl)ethyl)cyclobutyl)oxazole-2-carboxamide is a crystal form, selected from the group consisting of hydrochloride crystal form, acetate crystal form, nitrate crystal form, oxalate crystal form, hydrobromide crystal form, sulfate crystal form, benzenesulfonate crystal form, p-toluenesulfonate crystal form, methanesulfonate crystal form, 1,5-naphthalenedisulfonate crystal form, oxalate crystal form, isethionate crystal form, maleate crystal form, phosphate crystal form, ethanesulfonate crystal form, malonate crystal form, fumarate crystal form, citrate crystal form, malate crystal form, hippurate crystal form and succinate crystal form;

preferably, hydrochloride crystal form, p-toluenesulfonate crystal form, sulfate crystal form, oxalate crystal form, methanesulfonate crystal form, 1,5-naphthalenedisulfonate crystal form, acetate crystal form, nitrate crystal form, fumarate crystal form and hydrobromide crystal form.

In a further preferred embodiment of the present invention, provided is a crystal form of the acid salt of N-(trans-3-(2-(4-(2,3-dichlorophenyl)piperazin-1-yl)ethyl)cyclobutyl)oxazole-2-carboxamide, the number of acid is 0.5 to 2, preferably 0.5, 1, 1.5 or 2, more preferably 0.5, 1 or 2.

In a further preferred embodiment of the present invention, provided is a crystal form of the acid salt of N-(trans-3-(2-(4-(2,3-dichlorophenyl)piperazin-1-yl)ethyl)cyclobutyl)oxazole-2-carboxamide, the acid salt is a hydrate or anhydrate, preferably anhydrate; when the acid salt is a hydrate, the number of water is 0.5 to 3, preferably 0.5, 1, 1.5, 2, 2.5 or 3, more preferably 0.5, 1 or 2.

In a further preferred embodiment of the present invention, provided is a the crystal form of the acid salt of N-(trans-3-(2-(4-(2,3-dichlorophenyl)piperazin-1-yl)ethyl) cyclobutyl)oxazole-2-carboxamide, the acid salt is hydrochloride, and the number of hydrochloric acid is 1.

In a further preferred embodiment of the present invention, provided is a crystal form of the acid salt of N-(trans-3-(2-(4-(2,3-dichlorophenyl)piperazin-1-yl)ethyl)cyclobutyl)oxazole-2-carboxamide, the crystal form of the acid salt is a hydrate or anhydrate, preferably anhydrate; when the crystal form of the acid salt is a hydrate, the number of water is 0.5 to 3, preferably 0.5, 1, 1.5, 2, 2.5 or 3, more preferably 0.5, 1 or 2; further, the water in the hydrate is pipeline water or crystal water or a combination of both.

In a preferred embodiment of the present invention, provided is a salt of N-(trans-3-(2-(4-(2,3-dichlorophenyl) piperazin-1-yl)ethyl)cyclobutyl)oxazole-2-carboxamide (Example 12A) and a crystal form of the salt, and the structure of the compound is as follows:

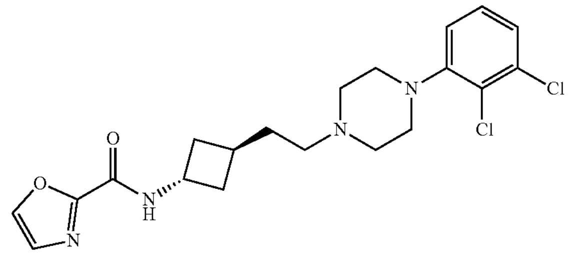 [SMILES: O=C(N[C@H]1C[C@H](CCN2CCN(c3cccc(Cl)c3Cl)CC2)C1)c1ncco1]

In a further preferred embodiment of the present invention, provided is crystal form A of hydrochloride of the compound of Example 12A, the X-ray powder diffraction pattern thereof has a diffraction peak of 23.9±0.2°, or a diffraction peak of 19.3±0.2°, or a diffraction peak of 22.8±0.2°, or a diffraction peak of 18.7±0.2°, or a diffraction peak of 17.1±0.2°, or a diffraction peak of 17.7±0.2°, or a diffraction peak of 15.1±0.2°, or a diffraction peak of 25.8±0.2°, or a diffraction peak of 22.3±0.2°, or a diffraction peak of 21.0±0.2°; preferably comprises any 2 to 5, or 3 to 5, or 3 to 6, or 3 to 8, or 5 to 8, or 6 to 8 of the above diffraction peaks, more preferably comprises any 6, 7 or 8 of the above diffraction peaks;

preferably, the X-ray powder diffraction pattern of crystal form A of hydrochloride comprises at least one or more diffraction peaks at 2θ of 23.9±0.2°, 22.8±0.2°, 19.3±0.2° and 18.7±0.2°; preferably comprises 2 of the above diffraction peaks, more preferably comprises 3 of the above diffraction peaks; optionally further comprises at least one diffraction peaks at 2θ of 17.1±0.2°, 17.7±0.2°, 15.1±0.2°, 25.8±0.2° and 21.0±0.2°, preferably comprises 2, 3, 4 or 5 of the above diffraction peaks;

for example, the X-ray powder diffraction pattern of crystal form A of hydrochloride has diffraction peaks at 2θ of the following positions:

23.9±0.2° and 19.3±0.2°,
or, 17.7±0.2° and 22.8±0.2°,
or, 18.7±0.2° and 17.1±0.2°,
or, 23.9±0.2°, 19.3±0.2° and 22.8±0.2°,
or, 17.7±0.2°, 19.3±0.2° and 18.7±0.2°,
or, 18.7±0.2°, 23.9±0.2° and 15.1±0.2°,
or, 23.9±0.2°, 19.3±0.2°, 17.1±0.2° and 15.1±0.2°,
or, 23.9±0.2°, 17.7±0.2°, 19.3±0.2° and 22.8±0.2°,
or, 22.8±0.2°, 19.3±0.2°, 25.8±0.2° and 21.0±0.2°,
or, 23.9±0.2°, 19.3±0.2°, 22.8±0.2°, 25.8±0.2° and 21.0±0.2°,
or, 23.9±0.2°, 19.3±0.2°, 22.8±0.2°, 25.8±0.2° and 21.0±0.2°,
or, 23.9±0.2°, 19.3±0.2°, 22.8±0.2°, 17.1±0.2° and 25.8±0.2°,
or, 23.9±0.2°, 22.8±0.2°, 19.3±0.2°, 18.7±0.2°, 17.1±0.2° and 15.1±0.2°,
or, 18.7±0.2°, 19.3±0.2°, 22.8±0.2°, 17.1±0.2°, 17.7±0.2° and 15.1±0.2°,
or, 19.3±0.2°, 22.8±0.2°, 17.1±0.2°, 17.7±0.2°, 25.8±0.2° and 15.1±0.2°,
or, 23.9±0.2°, 19.3±0.2°, 22.8±0.2°, 18.7±0.2°, 17.1±0.2° and 15.1±0.2°,
or, 18.7±0.2°, 19.3±0.2°, 22.8±0.2°, 17.1±0.2°, 15.1±0.2°, 21.0±0.2° and 25.8±0.2°;

more preferably, the X-ray powder diffraction pattern of crystal form A of hydrochloride optionally also comprises at least one or more diffraction peaks at 2θ of 22.3±0.2°, 31.3±0.2°, 25.4±0.2°, 23.4±0.2°, 31.9±0.2°, 32.7±0.2° and 21.7±0.2°; preferably comprises any 2 to 3, or 4 to 5, or 6 to 7 of the above diffraction peaks; further preferably comprises any 2, 3, 4, 5, 6 or 7 of the above diffraction peaks;

for example, the X-ray powder diffraction pattern of crystal form A of hydrochloride has diffraction peaks at 2θ of the following positions:

23.9±0.2°, 22.8±0.2°, 19.3±0.2°, 17.7±0.2°, 22.3±0.2°, 31.3±0.2°, 25.4±0.2° and 23.4±0.2°,
or, 23.9±0.2°, 18.7±0.2°, 19.3±0.2°, 22.8±0.2°, 17.1±0.2°, 17.7±0.2°, 15.1±0.2°, 23.4±0.2° and 21.7±0.2°,
or, 23.9±0.2°, 18.7±0.2°, 19.3±0.2°, 22.8±0.2°, 17.1±0.2°, 17.7±0.2°, 15.1±0.2°, 23.4±0.2°, 22.3±0.2° and 21.7±0.2°;

further preferably, the X-ray powder diffraction pattern of crystal form A of hydrochloride comprises one or more diffraction peaks at 2θ of 23.9±0.2°, 22.8±0.2°, 19.3±0.2°, 18.7±0.2°, 17.1±0.2°, 17.7±0.2°, 15.1±0.2°, 25.8±0.2°, 21.0±0.2°, 22.3±0.2°, 31.3±0.2°, 25.4±0.2°, 23.4±0.2°, 31.9±0.2°, 32.7±0.2°, 21.7±0.2°, 12.4±0.2°, 26.6±0.2° and 24.7±0.2°; preferably comprises any 4, 5, 6, 8 or 10 of the above diffraction peaks;

for example, the X-ray powder diffraction pattern of crystal form A of hydrochloride has diffraction peaks at 2θ of the following positions:

23.9±0.2°, 22.8±0.2°, 19.3±0.2° and 18.7±0.2°,
or, 23.9±0.2°, 22.8±0.2°, 17.1±0.2° and 17.7±0.2°,
or, 22.8±0.2°, 19.3±0.2°, 18.7±0.2° and 17.1±0.2°,
or, 19.3±0.2°, 18.7±0.2°, 17.1±0.2° and 25.8±0.2°,
or, 23.9±0.2°, 22.8±0.2°, 19.3±0.2°, 18.7±0.2°, 17.1±0.2° and 17.7±0.2°,
or, 22.8±0.2°, 19.3±0.2°, 18.7±0.2°, 17.7±0.2°, 15.1±0.2° and 25.8±0.2°,
or, 23.9±0.2°, 22.8±0.2°, 17.1±0.2°, 17.7±0.2°, 21.0±0.2° and 22.3±0.2°,
or, 19.3±0.2°, 18.7±0.2°, 15.1±0.2°, 25.8±0.2°, 21.0±0.2° and 22.3±0.2°,
or, 23.9±0.2°, 22.8±0.2°, 19.3±0.2°, 18.7±0.2°, 17.1±0.2°, 17.7±0.2°, 15.1±0.2° and 25.8±0.2°,
or, 19.3±0.2°, 18.7±0.2°, 17.1±0.2°, 17.7±0.2°, 15.1±0.2°, 25.8±0.2°, 21.0±0.2° and 22.3±0.2°,
or, 22.8±0.2°, 19.3±0.2°, 18.7±0.2°, 17.1±0.2°, 17.7±0.2°, 15.1±0.2°, 25.8±0.2° and 21.0±0.2°, or, 23.9±0.2°, 18.7±0.2°, 17.1±0.2°, 17.7±0.2°, 21.0±0.2°, 22.3±0.2°, 26.6±0.2° and 24.7±0.2°, or, 23.9±0.2°, 22.8±0.2°, 19.3±0.2°, 18.7±0.2°, 17.1±0.2°, 17.7±0.2°, 15.1±0.2°, 25.8±0.2°, 21.0±0.2° and 22.3±0.2°, or, 22.8±0.25, 19.3±0.2, 18.7±0.2°, 17.1±0.2°, 17.7±0.2°, 15.1±0.2°, 25.8±0.2°, 21.0±0.2°, 12.4±0.20 and 24.7±0.2°, or, 19.3±0.25, 18.7±0.2°, 17.1±0.2°, 17.7±0.2, 15.1±0.2°, 25.8±0.2°, 21.0±0.2°, 22.3±0.2, 31.3±0.20 and 25.4±0.2°, or, 23.9±0.2°, 18.7±0.2°, 17.1±0.2°, 17.7±0.2°, 15.1±0.2°, 25.8±0.2°, 21.0±0.2°, 22.3±0.2, 31.3±0.20 and 25.4±0.2°, or, 22.8±0.2°, 19.3±0.2°, 18.7±0.2°, 17.1±0.2°, 17.7±0.2°, 15.1±0.2°, 25.8±0.2°, 21.0±0.2, 22.3±0.2° and 31.3±0.2°, or, 23.9±0.2°, 22.8±0.2, 19.3±0.2°, 18.7±0.2°, 17.1±0.2°, 17.7±0.2°, 15.1±0.2°, 25.8±0.2°, 21.0±0.2, 22.3±0.2°, 31.3±0.2° and 25.4±0.2°, or, 22.8±0.2°, 19.3±0.2°, 18.7±0.2°, 17.1±0.2°, 17.7±0.2°, 15.1±0.2°, 25.8±0.2°, 21.0±0.2°, 22.3±0.2°, 31.3±0.2°, 26.6±0.20 and 24.7±0.2°.

The characteristic X-ray diffraction peaks represented by the 2θ angle and the interplanar spacing d value by using Cu-Kα radiation are as shown in Table 1.

TABLE 1

The XRPD data of crystal form A of hydrochloride

| No. | 2θ (±0.2°) | d value | Peak height | Proportion (I %) |
|---|---|---|---|---|
| 1 | 5.7 | 15.4282 | 80 | 9.5 |
| 2 | 12.4 | 7.1595 | 127 | 15 |
| 3 | 15.1 | 5.8745 | 252 | 29.8 |
| 4 | 17.1 | 5.1944 | 332 | 39.2 |
| 5 | 17.7 | 5.0056 | 331 | 39.1 |
| 6 | 18.7 | 4.7319 | 452 | 53.4 |
| 7 | 19.3 | 4.584 | 491 | 58 |
| 8 | 21.0 | 4.2329 | 235 | 27.8 |
| 9 | 21.7 | 4.0962 | 134 | 15.8 |
| 10 | 22.3 | 3.9782 | 223 | 26.4 |
| 11 | 22.8 | 3.905 | 644 | 76.1 |
| 12 | 23.4 | 3.8048 | 166 | 19.6 |
| 13 | 23.9 | 3.7219 | 846 | 100 |
| 14 | 24.7 | 3.6073 | 115 | 13.6 |
| 15 | 25.4 | 3.5028 | 177 | 20.9 |
| 16 | 25.8 | 3.4457 | 247 | 29.2 |
| 17 | 26.6 | 3.3526 | 116 | 13.7 |
| 18 | 29.9 | 2.9811 | 66 | 7.8 |
| 20 | 31.3 | 2.8581 | 194 | 22.9 |
| 21 | 31.9 | 2.7998 | 157 | 18.6 |
| 22 | 32.7 | 2.7324 | 144 | 17 |
| 23 | 34.4 | 2.6085 | 82 | 9.7 |
| 24 | 34.7 | 2.5849 | 94 | 11.1 |

Provided is crystal form A of hydrochloride of the compound of Example 12A according to the present invention, the X-ray powder diffraction pattern thereof is substantially as shown in FIG. 1, the DSC spectrum thereof is substantially as shown in FIG. 2, the TGA spectrum thereof is substantially as shown in FIG. 3.

In a further preferred embodiment of the present invention, provided is crystal form B of hydrochloride of the compound of Example 12A, the X-ray powder diffraction pattern thereof has a diffraction peak of 18.4±0.2°, or a diffraction peak of 14.9±0.2°, or a diffraction peak of 26.4±0.2°, or a diffraction peak of 17.1±0.2°, or a diffraction peak of 21.1±0.2°, or a diffraction peak of 25.1±0.2°, or a diffraction peak of 28.0±0.2°, or a diffraction peak of 7.5±0.2°, or a diffraction peak of 14.2±0.2°, or a diffraction peak of 13.0±0.2°; preferably comprises any 2 to 5, or 3 to 5, or 3 to 6, or 3 to 8, or 5 to 8, or 6 to 8 of the above diffraction peaks, more preferably comprises any 6, 7 or 8 of the above diffraction peaks;

preferably, the X-ray powder diffraction pattern of crystal form B of hydrochloride comprises at least one or more diffraction peaks at 2θ of 18.4±0.2°, 26.4±0.2°, 25.1±0.2° and 14.9±0.2°; preferably comprises 2 of the above diffraction peaks, more preferably comprises 3 of the above diffraction peaks; optionally further comprises at least one diffraction peaks at 2θ of 17.1±0.2°, 21.1±0.2°, 28.0±0.2°, 14.2±0.2° and 13.0±0.2°, preferably comprises 2, 3, 4 or 5 of the above diffraction peaks;

for example, the X-ray powder diffraction pattern of crystal form B of hydrochloride has diffraction peaks at 2θ of the following positions:

14.9±0.2° and 26.4±0.2°, or, 18.4±0.2° and 17.1±0.2°, or, 21.1±0.2° and 25.1±0.2°, or, 14.9±0.2°, 26.4±0.2° and 17.1±0.2°, or, 18.4±0.2°, 26.4±0.2° and 25.1±0.2°, or, 21.1±0.2°, 28.0±0.2° and 14.2±0.2°, or, 14.9±0.2°, 26.4±0.2°, 28.0±0.2° and 14.2±0.2°, or, 14.9±0.2°, 18.4±0.2°, 26.4±0.2° and 17.1±0.2°, or, 18.4±0.2°, 21.1±0.2°, 26.4±0.2° and 25.1±0.2°, or, 14.9±0.2°, 26.4±0.2°, 17.1±0.2°, 28.0±0.2° and 14.2±0.2°, or, 18.4±0.2°, 26.4±0.2°, 17.1±0.2°, 25.1±0.2° and 28.0±0.2°, or, 21.1±0.2°, 26.4±0.2°, 17.1±0.2°, 25.1±0.2° and 28.0±0.2°, or, 14.9±0.2°, 18.4±0.2°, 26.4±0.2°, 17.1±0.2°, 28.0±0.2° and 14.2±0.2°, or, 21.1±0.2°, 26.4±0.2°, 17.1±0.2°, 25.1±0.2°, 13.0±0.2° and 28.0±0.2°, or, 18.4±0.2°, 26.4±0.2°, 17.1±0.2°, 25.1±0.2°, 28.0±0.2° and 14.2±0.2°, or, 21.1±0.2°, 26.4±0.2°, 17.1±0.2°, 25.1±0.2°, 28.0±0.2° and 14.2±0.2°, or, 21.1±0.2°, 26.4±0.2°, 17.1±0.2°, 25.1±0.2°, 14.2±0.2°, 13.0±0.2° and 28.0±0.2°;

more preferably, the X-ray powder diffraction pattern of crystal form B of hydrochloride optionally also comprises at least one or more diffraction peaks at 2θ of 23.1±0.2°, 7.5±0.2°, 19.2±0.2°, 28.5±0.2°, 20.3±0.2°, 30.2±0.2° and 29.5±0.2°; preferably comprises any 2 to 3, or 4 to 5, or 6 to 7 of the above diffraction peaks; further preferably comprises any 2, 3, 4, 5, 6 or 7 of the above diffraction peaks;

for example, the X-ray powder diffraction pattern of crystal form B of hydrochloride has diffraction peaks at 2θ of the following positions:

14.9±0.2°, 18.4±0.2°, 21.1±0.2°, 26.3±0.2°, 17.1±0.2°, 25.1±0.2°, 7.5±0.2° and 8.5±0.2°, or, 14.9±0.2°, 18.4±0.2°, 21.1±0.2°, 26.3±0.2°, 17.1±0.2°, 25.1±0.2°, 7.5±0.2°, 8.5±0.2° and 13.0±0.2°, or, 14.9±0.2°, 18.4±0.2°, 21.1±0.2°, 26.3±0.2°, 17.1±0.2°, 25.1±0.2°, 7.5±0.2°, 8.5±0.2°, 13.0±0.2° and 14.2±0.2°;

further preferably, the X-ray powder diffraction pattern of crystal form B of hydrochloride comprises one or more diffraction peaks at 2θ of 18.4±0.2°, 14.9±0.2°, 26.4±0.2°, 25.1±0.2°, 17.1±0.2°, 21.1±0.2°, 28.0±0.2°, 14.2±0.2°, 13.0±0.2°, 23.1±0.2°, 7.5±0.2°, 19.2±0.2°, 28.5±0.2°, 20.3±0.2°, 29.5±0.2°, 30.2±0.2°, 8.5±0.2° and 35.5±0.2°; preferably comprises any 4, 5, 6, 8 or 10 of the above diffraction peaks;

for example, the X-ray powder diffraction pattern of crystal form B of hydrochloride has diffraction peaks at 2θ of the following positions:

14.9±0.2°, 18.4±0.2°, 21.1±0.2° and 26.4±0.2°, or, 14.9±0.2°, 18.4±0.2°, 17.1±0.2° and 25.1±0.2°, or, 14.9±0.2°, 18.4±0.2°, 21.1±0.2°, 26.4±0.2°, 17.1±0.2°, 25.1±0.2°, or, 18.4±0.2°, 26.4±0.2°, 17.1±0.2°, 28.0±0.2°, 7.5±0.2° and 8.5±0.2°, or, 14.9±0.2°, 18.4±0.2°, 21.1±0.2°, 26.4±0.2°, 17.1±0.2°, 25.1±0.2°, 28.0±0.2° and 7.5±0.2°, or, 14.9±0.2°, 21.1±0.2°, 17.1±0.2°, 25.1±0.2°, 28.0±0.2°, 7.5±0.2°, 8.5±0.2° and 13.0±0.2°, or, 14.9±0.2°, 18.4±0.2°, 21.1±0.2°, 26.4±0.2°, 17.1±0.2°, 25.1±0.2°, 28.0±0.2°, 7.5±0.2°, 8.5±0.2° and 13.0±0.2°, or, 18.4±0.2°, 26.4±0.2°, 28.0±0.2°, 7.5±0.2°, 8.5±0.2°, 13.0±0.2°, 14.2±0.2°, 18.1±0.2°, 18.7±0.2°, 23.1±0.2° and 25.3±0.2°.

The characteristic X-ray diffraction peaks represented by the 2θ angle and the interplanar spacing d value by using Cu-Kα radiation are as shown in Table 2.

TABLE 2

| The XRPD data of crystal form B of hydrochloride | | | | |
|---|---|---|---|---|
| No. | 2θ (±0.2°) | d value | Peak height | Proportion (I %) |
| 1 | 7.5 | 11.7401 | 402 | 14.8 |
| 2 | 8.5 | 10.3381 | 211 | 7.8 |
| 3 | 13.0 | 6.803 | 529 | 19.5 |
| 4 | 14.2 | 6.226 | 600 | 22.1 |
| 5 | 14.9 | 5.9297 | 1519 | 56 |
| 6 | 17.1 | 5.194 | 770 | 28.4 |
| 7 | 18.1 | 4.8885 | 362 | 13.3 |
| 8 | 18.4 | 4.8136 | 2712 | 100 |
| 9 | 18.7 | 4.7424 | 371 | 13.7 |
| 10 | 19.2 | 4.6228 | 292 | 10.8 |
| 11 | 20.3 | 4.3706 | 232 | 8.6 |
| 12 | 21.1 | 4.2133 | 689 | 25.4 |
| 13 | 23.1 | 3.8407 | 414 | 15.3 |
| 14 | 25.1 | 3.5469 | 941 | 34.7 |
| 15 | 25.3 | 3.522 | 530 | 19.5 |
| 16 | 26.4 | 3.3782 | 1346 | 49.6 |
| 17 | 28.0 | 3.1858 | 719 | 26.5 |
| 18 | 28.5 | 3.1281 | 274 | 10.1 |
| 20 | 29.5 | 3.023 | 225 | 8.3 |
| 21 | 30.2 | 2.9617 | 228 | 8.4 |
| 22 | 33.4 | 2.6825 | 207 | 7.6 |
| 23 | 35.5 | 2.5292 | 210 | 7.7 |

Provided is crystal form B of hydrochloride of the compound according to the present invention, the X-ray powder diffraction pattern thereof is substantially as shown in FIG. 4.

In a further preferred embodiment of the present invention, provided is crystal form A of p-toluenesulfonate of the compound of Example 12A, the number of acid is 1, the X-ray powder diffraction pattern thereof has a diffraction peak of 20.1±0.20, or a diffraction peak of 18.7±0.20, or a diffraction peak of 19.5±0.20, or a diffraction peak of 5.3±0.20, or a diffraction peak of 21.2±0.20, or a diffraction peak of 18.3±0.20, or a diffraction peak of 11.9±0.20, or a diffraction peak of 15.1±0.20, or a diffraction peak of 15.9±0.20, or a diffraction peak of 32.0±0.20; preferably comprises any 2 to 5, or 3 to 5, or 3 to 6, or 3 to 8, or 5 to 8, or 6 to 8 of the above diffraction peaks, more preferably comprises any 6, 7 or 8 of the above diffraction peaks;

preferably, the X-ray powder diffraction pattern of crystal form A of p-toluenesulfonate comprises at least one or more diffraction peaks at 2θ of 20.1±0.2°, 18.7±0.2°, 19.5±0.20 and 5.3±0.2°; preferably comprises 2 of the above diffraction peaks, more preferably comprises 3 of the above diffraction peaks; optionally further comprises at least one diffraction peaks at 2θ of 21.2±0.2°, 18.3±0.2°, 11.9±0.2°, 15.1±0.2° and 15.9±0.2°, preferably comprises 2, 3, 4 or 5 of the above diffraction peaks;

for example, the X-ray powder diffraction pattern of crystal form A of p-toluenesulfonate has diffraction peaks at 2θ of the following positions:

18.7±0.2° and 20.1±0.2°, or, 18.7±0.2° and 21.2±0.2°, or, 20.1±0.2° and 18.3±0.2°, or, 18.7±0.2°, 20.1±0.2° and 21.2±0.2°, or, 18.3±0.2°, 20.1±0.2° and 18.7±0.2°, or, 20.1±0.2°, 19.5±0.2° and 11.9±0.2°, or, 18.7±0.2°, 20.1±0.2°, 21.2±0.2° and 11.9±0.2°, or, 18.7±0.2°, 18.3±0.2°, 20.1±0.2° and 21.2±0.2°, or, 18.3±0.2°, 21.2±0.2°, 20.1±0.2° and 5.3±0.2°, or, 18.7±0.2°, 20.1±0.2°, 21.2±0.2°, 18.3±0.2° and 11.9±0.2°, or, 18.7±0.2°, 20.1±0.2°, 21.2±0.2°, 18.3±0.2° and 15.1±0.2°, or, 20.1±0.2°, 18.7±0.2°, 19.5±0.2°, 5.3±0.2° and 21.2±0.2°, or, 18.7±0.2°, 18.3±0.2°, 20.1±0.2°, 21.2±0.2°, 15.1±0.2° and 11.9±0.2°, or, 20.1±0.2°, 19.5±0.2°, 5.3±0.2°, 21.2±0.2°, 15.1±0.2° and 15.9±0.2°, or, 20.1±0.2°, 18.7±0.2°, 19.5±0.2°, 5.3±0.2°, 21.2±0.2° and 18.3±0.2°, or, 20.1±0.2°, 18.7±0.2°, 21.2±0.2°, 18.3±0.2°, 15.1±0.2° and 15.9±0.2°, or, 19.5±0.2°, 5.3±0.2°, 21.2±0.2°, 18.3±0.2°, 11.9±0.2° and 15.1±0.2° and;

more preferably, the X-ray powder diffraction pattern of crystal form A of p-toluenesulfonate optionally also comprises at least one or more diffraction peaks at 2θ of 32.0±0.2°, 22.2±0.2°, 23.7±0.2°, 20.5±0.2°, 25.8±0.2°, 15.5±0.2° and 21.7±0.2°; preferably comprises any 2 to 3, or 4 to 5, or 6 to 8 of the above diffraction peaks; further preferably comprises any 2, 3, 4, 5, 6 or 7 of the above diffraction peaks;

for example, the X-ray powder diffraction pattern of crystal form A of p-toluenesulfonate has diffraction peaks at 2θ of the following positions:

8.7±0.2°, 18.3±0.2°, 22.2±0.2°, 20.1±0.2°, 21.7±0.2°, 23.7±0.2°, 11.9±0.2° and 19.5±0.2°, or, 18.7±0.2°, 18.3±0.2°, 22.2±0.2°, 20.1±0.2°, 21.7±0.2°, 23.7±0.2°, 11.9±0.2°, 19.5±0.2° and 15.9±0.2°, or, 18.7±0.2°, 18.3±0.2°, 22.2±0.2°, 20.1±0.2°, 21.7±0.2°, 23.7±0.2°, 11.9±0.2°, 19.5±0.2°, 15.9±0.2° and 32.0±0.2°;

further preferably, the X-ray powder diffraction pattern of crystal form A of p-toluenesulfonate comprises one or more diffraction peaks at 2θ of 20.1±0.2°, 18.7±0.2°, 19.5±0.2°, 5.3±0.2°, 21.2±0.2°, 18.3±0.2°, 11.9±0.2°, 15.9±0.2°, 15.1±0.2°, 32.0±0.2°, 22.2±0.2°, 23.7±0.2°, 20.5±0.2°, 25.8±0.20 and 15.5±0.20; preferably comprises any 4, 5, 6, 8 or 10 of the above diffraction peaks;

for example, the X-ray powder diffraction pattern of crystal form A of p-toluenesulfonate has diffraction peaks at 2θ of the following positions:

18.7±0.2°, 18.3±0.2°, 21.2±0.2° and 20.1±0.2°, or, 18.7±0.2°, 18.3±0.2°, 21.2±0.2° and 25.8±0.2°, or, 18.7±0.2°, 18.3±0.2°, 21.2±0.2°, 20.1±0.2°, 22.2±0.2°, 25.8±0.2°, or, 20.1±0.2°, 18.7±0.2°, 19.5±0.2°, 5.3±0.2°, 21.2±0.2° and 18.3±0.2°, or, 20.1±0.2°, 18.7±0.2°, 19.5±0.2°, 5.3±0.2°, 21.2±0.2°, 18.3±0.2°, 11.9±0.2° and 15.9±0.2°, or, 18.7±0.2°, 19.5±0.2°, 5.3±0.2°, 21.2±0.2°, 18.3±0.2°, 11.9±0.2°, 15.9±0.2° and 15.1±0.2°, or, 20.1±0.2°, 18.7±0.2°, 19.5±0.2°, 5.3±0.2°, 21.2±0.2°, 18.3±0.2°, 11.9±0.2°, 15.9±0.2°, 15.1±0.2° and 32.0±0.2°, or, 18.7±0.2°, 19.5±0.2°, 5.3±0.2°, 21.2±0.2°, 18.3±0.2°, 11.9±0.2°, 15.9±0.2°, 15.1±0.2°, 32.0±0.2°, 22.2±0.2°, 25.8±0.2° and 15.5±0.2°.

The characteristic X-ray diffraction peaks represented by the 2θ angle and the interplanar spacing d value by using Cu-Kα radiation are as shown in Table 3.

TABLE 3

| | The XRPD data of crystal form A of p-toluenesulfonate | | | |
|---|---|---|---|---|
| No. | 2θ (±0.2°) | d value | Peak height | Proportion (I %) |
| 1 | 5.0 | 17.6077 | 103 | 23.4 |
| 2 | 5.3 | 16.5533 | 307 | 69.8 |
| 3 | 11.9 | 7.4525 | 172 | 39.1 |
| 4 | 13.2 | 6.6811 | 80 | 18.2 |
| 5 | 15.1 | 5.8583 | 145 | 33 |
| 6 | 15.5 | 5.714 | 102 | 23.2 |
| 7 | 15.9 | 5.5702 | 138 | 31.4 |
| 8 | 17.9 | 4.9487 | 93 | 21.1 |
| 9 | 18.3 | 4.8355 | 189 | 43 |
| 10 | 18.7 | 4.7302 | 350 | 79.5 |
| 11 | 19.5 | 4.5551 | 313 | 71.1 |
| 12 | 20.1 | 4.4101 | 440 | 100 |
| 13 | 20.5 | 4.3236 | 108 | 24.5 |
| 14 | 21.2 | 4.1854 | 222 | 50.5 |
| 15 | 21.7 | 4.0923 | 96 | 21.8 |
| 16 | 22.2 | 3.9971 | 132 | 30 |
| 17 | 23.7 | 3.7534 | 126 | 28.6 |
| 18 | 25.8 | 3.4546 | 104 | 23.6 |
| 20 | 27.1 | 3.2865 | 87 | 19.8 |

Provided is crystal form A of p-toluenesulfonate of the compound according to the present invention, the X-ray powder diffraction pattern thereof is substantially as shown in FIG. 5.

In a further preferred embodiment of the present invention, provided is crystal form B of p-toluenesulfonate of the compound of Example 12A, the number of acid is 1, the X-ray powder diffraction pattern thereof has a diffraction peak of 5.0±0.2°, or a diffraction peak of 11.8±0.2°, or a diffraction peak of 14.9±0.2°, or a diffraction peak of 15.5±0.2°, or a diffraction peak of 18.8±0.2°, or a diffraction peak of 20.0±0.2°, or a diffraction peak of 19.1±0.2°, or a diffraction peak of 23.7±0.2°, or a diffraction peak of 20.9±0.2°, or a diffraction peak of 20.5±0.2°; preferably comprises any 2 to 5, or 3 to 5, or 3 to 6, or 3 to 8, or 5 to 8, or 6 to 8 of the above diffraction peaks, more preferably comprises any 6, 7 or 8 of the above diffraction peaks;

preferably, the X-ray powder diffraction pattern of crystal form B of p-toluenesulfonate comprises at least one or more diffraction peaks at 2θ of 5.0±0.2°, 14.9±0.2°, 15.5±0.2° and 11.8±0.2°; preferably comprises 2 of the above diffraction peaks, more preferably comprises 3 of the above diffraction peaks; optionally further comprises at least one diffraction peaks at 2θ of 18.8±0.2°, 20.0±0.2°, 19.1±0.2°, 23.7±0.2° and 20.9±0.2°, preferably comprises 2, 3, 4 or 5 of the above diffraction peaks;

for example, the X-ray powder diffraction pattern of crystal form B of p-toluenesulfonate has diffraction peaks at 2θ of the following positions:

11.8±0.2° and 14.9±0.2°, or, 5.0±0.2° and 15.5±0.2°, or, 20.0±0.2° and 19.1±0.2°, or, 11.8±0.2°, 14.9±0.2° and 15.5±0.2°, or, 5.0±0.2°, 14.9±0.2° and 19.1±0.2°, or, 20.0±0.2°, 23.7±0.2° and 18.8±0.2°, or, 11.8±0.2°, 14.9±0.2°, 23.7±0.2° and 18.8±0.2°, or, 11.8±0.2°, 5.0±0.2°, 14.9±0.2° and 15.5±0.2°, or, 5.0±0.2°, 20.0±0.2°, 14.9±0.2° and 19.1±0.2°, or, 11.8±0.2°, 14.9±0.2°, 15.5±0.2°, 23.7±0.2° and 18.8±0.2°, or, 5.0±0.2°, 14.9±0.2°, 15.5±0.2°, 19.1±0.2° and 23.7±0.2°, or, 20.0±0.2°, 14.9±0.2°, 15.5±0.2°, 19.1±0.2° and 23.7±0.2°, or, 11.8±0.2°, 5.0±0.2°, 14.9±0.2°, 15.5±0.2°, 23.7±0.2° and 18.8±0.2°, or, 20.0±0.2°, 14.9±0.2°, 15.5±0.2°, 19.1±0.2°, 20.9±0.2° and 23.7±0.2°, or, 5.0±0.2°, 14.9±0.2°, 15.5±0.2°, 19.1±0.2°, 23.7±0.2° and 18.8±0.2°, or, 20.0±0.2°, 14.9±0.2°, 15.5±0.2°, 19.1±0.2°, 23.7±0.2° and 18.8±0.2°, or, 20.0±0.2°, 14.9±0.2°, 15.5±0.2°, 19.1±0.2°, 18.8±0.2°, 20.9±0.2° and 23.7±0.2°;

more preferably, the X-ray powder diffraction pattern of crystal form B of p-toluenesulfonate optionally also comprises at least one or more diffraction peaks at 2θ of 20.5±0.2°, 17.5±0.2°, 28.8±0.2°, 21.8±0.2°, 29.1±0.2°, 18.4±0.2° and 26.5±0.2°; preferably comprises any 2 to 3, or 4 to 5, or 6 to 8 of the above diffraction peaks; further preferably comprises any 2, 3, 4, 5, 6, 7 or 8 of the above diffraction peaks;

for example, the X-ray powder diffraction pattern of crystal form B of p-toluenesulfonate has diffraction peaks at 2θ of the following positions:

11.8±0.2°, 5.0±0.2°, 20.0±0.2°, 14.9±0.2°, 15.5±0.2°, 19.1±0.2°, 18.8±0.2° and 28.8±0.2°, or, 11.8±0.2°, 5.0±0.2°, 20.0±0.2°, 14.9±0.2°, 15.5±0.2°, 19.1±0.2°, 18.8±0.2°, 28.8±0.2° and 29.1±0.2°, or, 11.8±0.2°, 5.0±0.2°, 20.0±0.2°, 14.9±0.2°, 15.5±0.2°, 19.1±0.2°, 18.8±0.2°, 28.8±0.2°, 29.1±0.2° and 26.5±0.2°;

further preferably, the X-ray powder diffraction pattern of crystal form B of p-toluenesulfonate comprises one or more diffraction peaks at 2θ of 5.0±0.2°, 14.9±0.2°, 15.5±0.2°, 11.8±0.2°, 18.8±0.2°, 20.0±0.2°, 19.1±0.2°, 23.7±0.2°, 20.9±0.2°, 20.5±0.2°, 17.5±0.2°, 28.8±0.2°, 21.8±0.2°, 29.1±0.2° and 18.4±0.2°; preferably comprises any 4, 5, 6, 8 or 10 of the above diffraction peaks;

for example, the X-ray powder diffraction pattern of crystal form B of p-toluenesulfonate has diffraction peaks at 2θ of the following positions:

11.8±0.2°, 5.0±0.2°, 20.0±0.2° and 14.9±0.2°, or, 11.8±0.2°, 5.0±0.2°, 15.5±0.2° and 19.1±0.2°, or, 11.8±0.2°, 5.0±0.2°, 20.0±0.2°, 14.9±0.2°, 15.5±0.2°, 19.1±0.2°, or, 5.0±0.2°, 14.9±0.2°, 15.5±0.2°, 23.7±0.2°, 18.8±0.2° and 28.8±0.2°, or, 11.8±0.2°, 5.0±0.2°, 20.0±0.2°, 14.9±0.2°, 15.5±0.2°, 19.1±0.2°, 23.7±0.2° and 18.8±0.2°, or, 11.8±0.2°, 20.0±0.2°, 15.5±0.2°, 19.1±0.2°, 23.7±0.2°, 18.8±0.2°, 28.8±0.2° and 29.1±0.2°, or, 111.8±0.2°, 5.0±0.2°, 20.0±0.2°, 14.9±0.2°, 15.5±0.2°, 19.1±0.2°, 23.7±0.2°, 18.8±0.2°, 28.8±0.2° and 29.1±0.2°, or, 5.0±0.2°, 14.9±0.2°, 15.5±0.2°, 11.8±0.2°, 18.8±0.2°, 20.0±0.2°, 19.1±0.2°, 23.7±0.2°, 20.9±0.2°, 20.5±0.2° and 17.5±0.2°.

The characteristic X-ray diffraction peaks represented by the 2θ angle and the interplanar spacing d value by using Cu-Kα radiation are as shown in Table 4.

TABLE 4

| The XRPD data of crystal form B of p-toluenesulfonate | | | | |
|---|---|---|---|---|
| No. | 2θ (±0.2°) | d value | Peak height | Proportion (I %) |
| 1 | 5.0 | 17.7417 | 1844 | 100 |
| 2 | 9.5 | 9.3242 | 90 | 4.9 |
| 3 | 11.8 | 7.466 | 980 | 53.1 |
| 4 | 14.9 | 5.9297 | 1121 | 60.8 |
| 5 | 15.5 | 5.7211 | 917 | 49.7 |
| 6 | 17.5 | 5.0749 | 235 | 12.7 |
| 7 | 18.4 | 4.8241 | 126 | 6.8 |
| 8 | 18.8 | 4.7211 | 492 | 26.7 |
| 9 | 19.1 | 4.6522 | 361 | 19.6 |
| 10 | 20.0 | 4.4375 | 448 | 24.3 |
| 11 | 20.5 | 4.3238 | 296 | 16.1 |
| 12 | 20.9 | 4.2379 | 299 | 16.2 |
| 13 | 21.8 | 4.0702 | 210 | 11.4 |
| 14 | 23.7 | 3.7506 | 307 | 16.6 |
| 15 | 26.4 | 3.3734 | 99 | 5.4 |
| 16 | 26.5 | 3.3548 | 107 | 5.8 |
| 17 | 27.6 | 3.2268 | 101 | 5.5 |
| 18 | 28.8 | 3.098 | 224 | 12.1 |
| 20 | 29.1 | 3.0643 | 147 | 8 |

Provided is crystal form B of p-toluenesulfonate of the compound of Example 12A according to the present invention, the X-ray powder diffraction pattern thereof is substantially as shown in FIG. 6.

In a further preferred embodiment of the present invention, provided is crystal form A of hydrobromide of the compound of Example 12A, the number of acid is 1, the X-ray powder diffraction pattern thereof has a diffraction peak of 25.8±0.2°, or a diffraction peak of 18.1±0.2°, or a diffraction peak of 18.7±0.2°, or a diffraction peak of 11.3±0.2°, or a diffraction peak of 17.8±0.2°, or a diffraction peak of 14.0±0.2°, or a diffraction peak of 14.6±0.2°, or a diffraction peak of 24.4±0.2°, or a diffraction peak of 28.3±0.2°, or a diffraction peak of 20.8±0.2°; preferably comprises any 2 to 5, or 3 to 5, or 3 to 6, or 3 to 8, or 5 to 8, or 6 to 8 of the above diffraction peaks, more preferably comprises any 6, 7 or 8 of the above diffraction peaks;

preferably, the X-ray powder diffraction pattern of crystal form A of hydrobromide comprises at least one or more diffraction peaks at 2θ of 25.8±0.2°, 18.1±0.2°, 18.7±0.2° and 11.3±0.2°; preferably comprises 2 of the above diffraction peaks, more preferably comprises 3 of the above diffraction peaks; optionally further comprises at least one diffraction peaks at 2θ of 17.8±0.2°, 14.0±0.2°, 14.6±0.2°, 24.4±0.2° and 28.3±0.2°, preferably comprises 2, 3, 4 or 5 of the above diffraction peaks;

for example, the X-ray powder diffraction pattern of crystal form A of hydrobromide has diffraction peaks at 2θ of the following positions:

25.8±0.2° and 18.1±0.2°, or, 18.1±0.2° and 11.3±0.2°, or, 18.1±0.2° and 18.7±0.2°, or, 14.0±0.2°, 14.6±0.2° and 25.8±0.2°, or, 11.3±0.2°, 14.6±0.2° and 18.7±0.2°, or, 18.1±0.2°, 11.3±0.2° and 17.8±0.2°, or, 14.0±0.2°, 14.6±0.2°, 11.3±0.2° and 17.8±0.2°, or, 14.0±0.2°, 11.3±0.2°, 14.6±0.2° and 25.8±0.2°, or, 11.3±0.2°, 18.1±0.2°, 14.6±0.2° and 18.7±0.2°, or, 14.0±0.2°, 14.6±0.2°, 25.8±0.2°, 11.3±0.2° and 17.8±0.2°, or, 11.3±0.2°, 14.6±0.2°, 25.8±0.2°, 18.7±0.2° and 28.3±0.2°, or, 18.1±0.2°, 14.6±0.2°, 25.8±0.2°, 18.7±0.2° and 28.3±0.2°, or, 14.0±0.2°, 11.3±0.2°, 14.6±0.2°, 25.8±0.2°, 28.3±0.2° and 17.8±0.2°, or, 18.1±0.2°, 14.6±0.2°, 25.8±0.2°, 18.7±0.2°, 24.4±0.2° and 28.3±0.2°, or, 11.3±0.2°, 14.6±0.2°, 25.8±0.2°, 18.7±0.2°, 18.1±0.2° and 17.8±0.2°, or, 18.1±0.2°, 14.6±0.2°, 25.8±0.2°, 18.7±0.2°, 11.3±0.2° and 17.8±0.2°, or, 18.1±0.2°, 14.6±0.2°, 25.8±0.2°, 18.7±0.2°, 17.8±0.2°, 24.4±0.2° and 28.3±0.2°;

more preferably, the X-ray powder diffraction pattern of crystal form A of hydrobromide optionally also comprises at least one or more diffraction peaks at 2θ of 27.5±0.2°, 23.4±0.2°, 25.5±0.2°, 22.7±0.2°, 19.3±0.2°, 21.2±0.2° and 29.4±0.2°; preferably comprises any 2 to 3, or 4 to 5, or 6 to 8 of the above diffraction peaks; further preferably comprises any 2, 3, 4, 5, 6, 7 or 8 of the above diffraction peaks;

for example, the X-ray powder diffraction pattern of crystal form A of hydrobromide has diffraction peaks at 2θ of the following positions:

25.8±0.2°, 18.1±0.2°, 18.7±0.2°, 11.3±0.2°, 17.8±0.2°, 14.0±0.2°, 14.6±0.2° and 27.5±0.2°, or, 25.8±0.2°, 18.1±0.2°, 18.7±0.2°, 17.8±0.2°, 14.0±0.2°, 27.5±0.2°, 23.4±0.2°, 25.5±0.2° and 22.7±0.2°, or, 18.1±0.2°, 18.7±0.2° and 11.3±0.2°, 24.4±0.2°, 28.3±0.2°, 25.5±0.2°, 22.7±0.2°, 19.3±0.2°, 21.2±0.2° and 29.4±0.2°;

further preferably, the X-ray powder diffraction pattern of crystal form A of hydrobromide comprises one or more diffraction peaks at 2θ of 25.8±0.2°, 18.1±0.2°, 18.7±0.2°, 11.3±0.2°, 17.8±0.2°, 14.6±0.2°, 14.0±0.2°, 24.4±0.2°, 28.3±0.2°, 20.8±0.2°, 27.5±0.2°, 23.4±0.2°, 25.5±0.2°, 22.7±0.2° and 19.3±0.2°; preferably comprises any 4, 5, 6, 8 or 10 of the above diffraction peaks;

for example, the X-ray powder diffraction pattern of crystal form A of hydrobromide has diffraction peaks at 2θ of the following positions:

14.0±0.2°, 11.3±0.2°, 18.1±0.2° and 14.6±0.2°, or, 14.0±0.2°, 11.3±0.2°, 25.8±0.20 and 18.7±0.2°, or, 14.0±0.2°, 11.3±0.2°, 18.1±0.2°, 14.6±0.2°, 25.8±0.2°, 18.7±0.2°, or, 11.3±0.2°, 14.6±0.2°, 25.8±0.2°, 19.3±0.2°, 17.8±0.20 and 20.8±0.2°, or, 14.0±0.2°, 11.3±0.2°, 18.1±0.2°, 14.6±0.2°, 25.8±0.2°, 18.7±0.2°, 19.3±0.20 and 17.8±0.2°, or, 14.0±0.2°, 18.1±0.2°, 25.8±0.2°, 18.7±0.2°, 19.3±0.2°, 17.8±0.2°, 20.8±0.20 and 22.7±0.2°, or, 14.0±0.2°, 11.3±0.2°, 18.1±0.2°, 14.6±0.2°, 25.8±0.2°, 18.7±0.2°, 19.3±0.2°, 17.8±0.2°, 20.8±0.20 and 22.7±0.2°, or, 25.8±0.2°, 18.1±0.2°, 18.7±0.2°, 11.3±0.2°, 17.8±0.2°, 14.6±0.2°, 14.0±0.2°, 24.4±0.2°, 28.3±0.2°, 20.8±0.20 and 27.5±0.2°.

The characteristic X-ray diffraction peaks represented by the 2θ angle and the interplanar spacing d value by using Cu-Kα radiation are as shown in Table 5.

TABLE 5

| No. | 2θ (±0.2°) | d value | Peak height | Proportion (I %) |
|---|---|---|---|---|
| | The XRPD data of crystal form A of hydrobromide | | | |
| 1 | 7.6 | 11.6153 | 112 | 19.1 |
| 2 | 11.3 | 7.8112 | 531 | 90.5 |
| 3 | 14.0 | 6.3151 | 395 | 67.3 |
| 4 | 14.6 | 6.0534 | 377 | 64.2 |
| 5 | 17.8 | 4.9882 | 446 | 76 |
| 6 | 18.1 | 4.9054 | 551 | 93.9 |
| 7 | 18.7 | 4.7308 | 536 | 91.3 |
| 8 | 19.3 | 4.5891 | 178 | 30.3 |
| 9 | 20.5 | 4.3285 | 189 | 32.2 |
| 10 | 20.8 | 4.2617 | 262 | 44.6 |
| 11 | 21.2 | 4.1938 | 175 | 29.8 |
| 12 | 22.7 | 3.9081 | 189 | 32.2 |
| 13 | 23.4 | 3.8054 | 209 | 35.6 |
| 14 | 24.0 | 3.6995 | 136 | 23.2 |
| 15 | 24.4 | 3.6454 | 373 | 63.5 |
| 16 | 25.5 | 3.4945 | 197 | 33.6 |
| 17 | 25.8 | 3.4541 | 587 | 100 |
| 18 | 27.5 | 3.2365 | 251 | 42.8 |
| 20 | 28.3 | 3.1562 | 326 | 55.5 |
| 21 | 29.4 | 3.0392 | 157 | 26.7 |
| 22 | 30.0 | 2.981 | 125 | 21.3 |
| 23 | 32.0 | 2.791 | 127 | 21.6 |

Provided is crystal form A of hydrobromide of the compound according to the present invention, the X-ray powder diffraction pattern thereof is substantially as shown in FIG. 7.

In a further preferred embodiment of the present invention, provided is crystal form A of oxalate of the compound of Example 12A, the number of acid is 1, the X-ray powder diffraction pattern thereof has a diffraction peak of 21.2±0.2°, or a diffraction peak of 19.7±0.2°, or a diffraction peak of 25.6±0.2°, or a diffraction peak of 20.4±0.2°, or a diffraction peak of 9.1±0.2°, or a diffraction peak of 18.7±0.2°, or a diffraction peak of 18.0±0.2°, or a diffraction peak of 26.0±0.2°, or a diffraction peak of 11.7±0.2°, or a diffraction peak of 23.4±0.2°; preferably comprises any 2 to 5, or 3 to 5, or 3 to 6, or 3 to 8, or 5 to 8, or 6 to 8 of the above diffraction peaks, more preferably comprises any 6, 7 or 8 of the above diffraction peaks;

preferably, the X-ray powder diffraction pattern of crystal form A of oxalate comprises at least one or more diffraction peaks at 2θ of 21.2±0.2°, 25.6±0.2°, 20.4±0.2° and 19.7±0.2°; preferably comprises 2 of the above diffraction peaks, more preferably comprises 3 of the above diffraction peaks; optionally further comprises at least one diffraction peaks at 2θ of 9.1±0.2°, 18.7±0.2°, 18.0±0.2°, 26.0±0.2° and 23.4±0.2°, preferably comprises 2, 3, 4 or 5 of the above diffraction peaks;

for example, the X-ray powder diffraction pattern of crystal form A of oxalate has diffraction peaks at 2θ of the following positions:

19.7±0.2° and 21.2±0.2°, or, 9.1±0.2° and 20.4±0.2°, or, 25.6±0.2° and 18.7±0.2°, or, 19.7±0.2°, 21.2±0.2° and 20.4±0.2°, or, 9.1±0.2°, 21.2±0.2° and 18.7±0.2°, or, 25.6±0.2°, 20.4±0.2° and 9.1±0.2°, or, 19.7±0.2°, 21.2±0.2°, 20.4±0.2° and 18.7±0.2°, or, 19.7±0.2°, 9.1±0.2°, 21.2±0.2° and 20.4±0.2°, or, 9.1±0.2°, 25.6±0.2°, 21.2±0.2° and 18.7±0.2°, or, 19.7±0.2°, 21.2±0.2°, 20.4±0.2°, 18.7±0.2° and 18.0±0.2°, or, 9.1±0.2°, 21.2±0.2°, 20.4±0.2°, 18.7±0.2° and 18.0±0.2°, or, 25.6±0.2°, 21.2±0.2°, 20.4±0.2°, 18.7±0.2° and 26.0±0.2°, or, 19.7±0.2°, 9.1±0.2°, 21.2±0.2°, 20.4±0.2°, 18.7±0.2° and 18.0±0.2°, or, 25.6±0.2°, 21.2±0.2°, 20.4±0.2°, 18.7±0.2°, 23.4±0.2° and 19.7±0.2°, or, 9.1±0.2°, 21.2±0.2°, 20.4±0.2°, 18.7±0.2°, 19.7±0.2° and 14.2±0.2°, or, 25.6±0.2°, 21.2±0.2°, 20.4±0.2°, 18.7±0.2°, 19.7±0.2° and 9.1±0.2°, or, 25.6±0.2°, 21.2±0.2°, 20.4±0.2°, 18.7±0.2°, 18.0±0.2°, 23.4±0.2° and 19.7±0.2°;

more preferably, the X-ray powder diffraction pattern of crystal form A of oxalate optionally also comprises at least one or more diffraction peaks at 2θ of 11.7±0.2°, 23.9±0.2°, 29.1±0.2°, 14.2±0.2°, 29.4±0.2°, 17.3±0.2° and 28.3±0.2°; preferably comprises any 2 to 3, or 4 to 5, or 6 to 7 of the above diffraction peaks; further preferably comprises any 2, 3, 4, 5, 6 or 7 of the above diffraction peaks;

for example, the X-ray powder diffraction pattern of crystal form A of oxalate has diffraction peaks at 2θ of the following positions:

19.7±0.2°, 9.1±0.2°, 25.6±0.2°, 21.2±0.2°, 20.4±0.2°, 18.7±0.2°, 14.2±0.2° and 29.4±0.2°, or, 19.7±0.2°, 9.1±0.2°, 25.6±0.2°, 21.2±0.2°, 20.4±0.2°, 18.7±0.2°, 14.2±0.2°, 11.7±0.2° and 23.9±0.2°, or, 19.7±0.2°, 9.1±0.2°, 25.6±0.2°, 21.2±0.2°, 20.4±0.2°, 18.7±0.2°, 14.2±0.2°, 11.7±0.2°, 29.4±0.2° and 23.9±0.2°;

further preferably, the X-ray powder diffraction pattern of crystal form A of oxalate comprises one or more diffraction peaks at 2θ of 21.2±0.2°, 19.7±0.2°, 25.6±0.2°, 20.4±0.2°, 9.1±0.2°, 18.7±0.2°, 18.0±0.2°, 26.0±0.2°, 23.4±0.2°, 11.7±0.2°, 23.9±0.2°, 14.2±0.2°, 29.1±0.2°, 29.4±0.2° and 17.3±0.2°; preferably comprises any 4, 5, 6, 8 or 10 of the above diffraction peaks;

for example, the X-ray powder diffraction pattern of crystal form A of oxalate has diffraction peaks at 2θ of the following positions:

19.7±0.2°, 9.1±0.2°, 25.6±0.2° and 21.2±0.2°, or, 19.7±0.2°, 9.1±0.2°, 20.4±0.2° and 18.7±0.2°, or, 19.7±0.2°, 9.1±0.2°, 25.6±0.2°, 21.2±0.2°, 20.4±0.2°, 18.7±0.2°, or, 9.1±0.2°, 21.2±0.2°, 20.4±0.2°, 11.7±0.2°, 14.2±0.2° and 18.0±0.2°, or, 19.7±0.2°, 9.1±0.2°, 25.6±0.2°, 21.2±0.2°, 20.4±0.2°, 18.7±0.2°, 11.7±0.2° and 14.2±0.2°, or, 19.7±0.2°, 25.6±0.2°, 20.4±0.2°, 18.7±0.2°, 11.7±0.2°, 14.2±0.2°, 18.0±0.2° and 23.4±0.2°, or, 19.7±0.2°, 9.1±0.2°, 25.6±0.2°, 21.2±0.2°, 20.4±0.2°, 18.7±0.2°, 11.7±0.2°, 14.2±0.2°, 18.0±0.2° and 23.4±0.2°, or, 9.1±0.2°, 21.2±0.2°, 11.7±0.2°, 14.2±0.2°, 18.0±0.2°, 23.4±0.2°, 23.9±0.2°, 26.0±0.2°, 29.1±0.2° and 29.4±0.2°.

The characteristic X-ray diffraction peaks represented by the 2θ angle and the interplanar spacing d value by using Cu-Kα radiation are as shown in Table 6.

TABLE 6

| | The XRPD data of crystal form A of oxalate | | | |
|---|---|---|---|---|
| No. | 2θ (±0.2°) | d value | Peak height | Proportion (I %) |
| 1 | 9.1 | 9.6618 | 356 | 12.5 |
| 2 | 11.7 | 7.5691 | 300 | 10.5 |
| 3 | 14.2 | 6.2259 | 260 | 9.1 |
| 4 | 17.3 | 5.1175 | 205 | 7.2 |
| 5 | 18.0 | 4.9155 | 310 | 10.9 |
| 6 | 18.3 | 4.8465 | 163 | 5.7 |
| 7 | 18.7 | 4.7325 | 317 | 11.1 |
| 8 | 19.7 | 4.4958 | 830 | 29.1 |
| 9 | 20.4 | 4.3547 | 456 | 16 |
| 10 | 21.2 | 4.1886 | 2854 | 100 |
| 11 | 23.1 | 3.8406 | 150 | 5.3 |
| 12 | 23.4 | 3.7919 | 307 | 10.8 |
| 13 | 23.7 | 3.7535 | 279 | 9.8 |
| 14 | 23.9 | 3.7278 | 298 | 10.4 |
| 15 | 24.5 | 3.6339 | 117 | 4.1 |
| 16 | 25.6 | 3.4831 | 534 | 18.7 |
| 17 | 26.0 | 3.4298 | 310 | 10.9 |
| 18 | 28.3 | 3.1458 | 198 | 6.9 |
| 20 | 29.1 | 3.0662 | 277 | 9.7 |
| 21 | 29.4 | 3.0393 | 232 | 8.1 |
| 22 | 29.7 | 3.0068 | 159 | 5.6 |

Provided is crystal form A of oxalate of the compound according to the present invention, the X-ray powder diffraction pattern thereof is substantially as shown in FIG. 8.

In a further preferred embodiment of the present invention, provided is crystal form A of sulfate of the compound of Example 12A, the number of acid is 1, the X-ray powder diffraction pattern thereof has a diffraction peak of 11.0±0.2°, or a diffraction peak of 17.9±0.2°, or a diffraction peak of 21.9±0.2°, or a diffraction peak of 24.9±0.2°, or a diffraction peak of 18.9±0.2°, or a diffraction peak of 19.6±0.2°, or a diffraction peak of 23.0±0.2°, or a diffraction peak of 14.7±0.2°, or a diffraction peak of 27.6±0.2°, or a diffraction peak of 13.4±0.2°; preferably comprises any 2 to 5, or 3 to 5, or 3 to 6, or 3 to 8, or 5 to 8, or 6 to 8 of the above diffraction peaks, more preferably comprises any 6, 7 or 8 of the above diffraction peaks;

preferably, the X-ray powder diffraction pattern of crystal form A of sulfate comprises at least one or more diffraction peaks at 2θ of 11.0±0.2°, 21.9±0.2°, 24.9±0.2° and 17.9±0.2°; preferably comprises 2 of the above diffraction peaks, more preferably comprises 3 of the above diffraction peaks; optionally further comprises at least one diffraction peaks at 2θ of 14.7±0.2°, 18.9±0.2°, 19.6±0.2°, 23.0±0.2° and 27.6±0.2°, preferably comprises 2, 3, 4 or 5 of the above diffraction peaks;

for example, the X-ray powder diffraction pattern of crystal form A of sulfate has diffraction peaks at 2θ of the following positions:

17.9±0.2° and 21.9±0.2°, or, 11.0±0.2° and 24.9±0.2°, or, 14.7±0.2° and 18.9±0.2°, or, 17.9±0.2°, 21.9±0.2° and 24.9±0.2°, or, 11.0±0.2°, 21.9±0.2° and 18.9±0.2°, or, 14.7±0.2°, 19.6±0.2° and 11.0±0.2°, or, 17.9±0.2°, 21.9±0.2°, 19.6±0.2° and 11.0±0.2°, or, 17.9±0.2°, 11.0±0.2°, 21.9±0.2° and 24.9±0.2°, or, 11.0±0.2°, 14.7±0.2°, 21.9±0.2° and 18.9±0.2°, or, 17.9±0.2°, 21.9±0.2°, 24.9±0.2°, 19.6±0.2° and 11.0±0.2°, or, 11.0±0.2°, 21.9±0.2°, 24.9±0.2°, 18.9±0.2° and 19.6±0.2°, or, 14.7±0.2°, 21.9±0.2°, 24.9±0.2°, 18.9±0.2° and 19.6±0.2°, or, 17.9±0.2°, 11.0±0.2°, 21.9±0.2°, 24.9±0.2°, 19.6±0.2° and 11.0±0.2°, or, 14.7±0.2°, 21.9±0.2°, 24.9±0.2°, 18.9±0.2°, 23.0±0.2° and 19.6±0.2°, or, 11.0±0.2°, 21.9±0.2°, 24.9±0.2°, 18.9±0.2°, 19.6±0.2° and 14.7±0.2°, or, 14.7±0.2°, 21.9±0.2°, 24.9±0.2°, 18.9±0.2°, 19.6±0.2° and 23.0±0.2°, or, 14.7±0.2°, 21.9±0.2°, 24.9±0.2°, 18.9±0.2°, 23.0±0.2°, 27.6±0.2° and 19.6±0.2°;

more preferably, the X-ray powder diffraction pattern of crystal form A of sulfate optionally also comprises at least one or more diffraction peaks at 2θ of 13.4±0.2°, 30.1±0.2°, 20.8±0.2°, 22.5±0.2°, 16.0±0.2°, 33.6±0.2° and 31.3±0.2°; preferably comprises any 2 to 3, or 4 to 5, or 6 to 7 of the above diffraction peaks; further preferably comprises any 2, 3, 4, 5, 6 or 7 of the above diffraction peaks;

for example, the X-ray powder diffraction pattern of crystal form A of sulfate has diffraction peaks at 2θ of the following positions:

17.9±0.2°, 11.0±0.2°, 14.7±0.2°, 21.9±0.2°, 24.9±0.2°, 18.9±0.2°, 16.0±0.2° and 13.4±0.2°, or, 117.9±0.2°, 11.0±0.2°, 14.7±0.2°, 21.9±0.2°, 24.9±0.2°, 18.9±0.2°, 16.0±0.2°, 13.4±0.2° and 20.8±0.2°, or, 17.9±0.2°, 11.0±0.2°, 14.7±0.2°, 21.9±0.2°, 24.9±0.2°, 18.9±0.2°, 19.6±0.2°, 13.4±0.2°, 20.8±0.2° and 16.0±0.2°;

further preferably, the X-ray powder diffraction pattern of crystal form A of sulfate comprises one or more diffraction peaks at 2θ of 11.0±0.2°, 21.9±0.2°, 24.9±0.2°, 17.9±0.2°, 18.9±0.2°, 19.6±0.2°, 23.0±0.2°, 14.7±0.2°, 27.6±0.2°, 13.4±0.2°, 30.1±0.2°, 20.8±0.2°, 22.5±0.2°, 16.0±0.2° and 33.6±0.2°; preferably comprises any 4, 5, 6, 8 or 10 of the above diffraction peaks;

for example, the X-ray powder diffraction pattern of crystal form A of sulfate has diffraction peaks at 2θ of the following positions:

17.9±0.2°, 11.0±0.2°, 14.7±0.2° and 21.9±0.2°, or, 17.9±0.2°, 11.0±0.2°, 24.9±0.2° and 18.9±0.2°, or, 17.9±0.2°, 11.0±0.2°, 14.7±0.2°, 21.9±0.2°, 24.9±0.2°, 18.9±0.2°, or, 11.0±0.2°, 21.9±0.2°, 24.9±0.2°, 19.6±0.2°, 16.0±0.20 and 13.4±0.2°, or, 17.9±0.2°, 11.0±0.2°, 14.7±0.2°, 21.9±0.2°, 24.9±0.2°, 18.9±0.2°, 19.6±0.20 and 16.0±0.2°, or, 17.9±0.2°, 14.7±0.2°, 24.9±0.2°, 18.9±0.2°, 19.6±0.2°, 16.0±0.2°, 13.4±0.20 and 20.8±0.2°, or, 17.9±0.2°, 11.0±0.2°, 14.7±0.2°, 21.9±0.2°, 24.9±0.2°, 18.9±0.2°, 19.6±0.2°, 16.0±0.2°, 13.4±0.20 and 20.8±0.2°, or, 11.0±0.2°, 21.9±0.2°, 19.6±0.2°, 14.7±0.2°, 13.4±0.2°, 20.8±0.2°, 16.0±0.2°, 23.0±0.2°, 27.6±0.20 and 30.1±0.2°.

The characteristic X-ray diffraction peaks represented by the 2θ angle and the interplanar spacing d value by using Cu-Kα radiation are as shown in Table 7.

TABLE 7

| No. | 2θ (±0.2°) | d value | Peak height | Proportion (I %) |
|---|---|---|---|---|
| | The XRPD data of crystal form A of sulfate | | | |
| 1 | 10.0 | 8.8609 | 107 | 9.2 |
| 2 | 11.0 | 8.0248 | 1169 | 100 |
| 3 | 13.4 | 6.6171 | 274 | 23.4 |
| 4 | 14.7 | 6.0049 | 297 | 25.4 |
| 5 | 16.0 | 5.5415 | 200 | 17.1 |
| 6 | 17.9 | 4.9497 | 709 | 60.7 |
| 7 | 18.9 | 4.6871 | 462 | 39.5 |
| 8 | 19.6 | 4.5272 | 339 | 29 |
| 9 | 20.8 | 4.2734 | 242 | 20.7 |
| 10 | 21.3 | 4.1619 | 105 | 9 |
| 11 | 21.9 | 4.0514 | 1030 | 88.1 |
| 12 | 22.5 | 3.9507 | 226 | 19.3 |
| 13 | 23.0 | 3.8675 | 301 | 25.7 |
| 14 | 23.4 | 3.799 | 137 | 11.7 |
| 15 | 24.9 | 3.5785 | 1159 | 99.1 |
| 16 | 26.7 | 3.3353 | 100 | 8.6 |
| 17 | 27.6 | 3.2248 | 275 | 23.5 |
| 18 | 30.1 | 2.9673 | 260 | 22.2 |
| 20 | 31.3 | 2.8549 | 143 | 12.2 |
| 21 | 33.6 | 2.6652 | 160 | 13.7 |

Provided is crystal form A of sulfate of the compound of Example 12A according to the present invention, the X-ray powder diffraction pattern thereof is substantially as shown in FIG. 9.

In a further preferred embodiment of the present invention, provided is crystal form A of methanesulfonate of the compound of Example 12A, the X-ray powder diffraction pattern thereof has a diffraction peak of 21.2±0.2°, or a diffraction peak of 14.7±0.2°, or a diffraction peak of 21.4±0.2°, or a diffraction peak of 25.4±0.2°, or a diffraction peak of 20.1±0.2°, or a diffraction peak of 17.1±0.2°, or a diffraction peak of 22.5±0.2°, or a diffraction peak of 13.1±0.2°, or a diffraction peak of 23.8±0.2°, or a diffraction peak of 20.6±0.2°; preferably comprises any 2 to 5, or 3 to 5, or 3 to 6, or 3 to 8, or 5 to 8, or 6 to 8 of the above diffraction peaks, more preferably comprises any 6, 7 or 8 of the above diffraction peaks;

preferably, the X-ray powder diffraction pattern of crystal form A of methanesulfonate comprises at least one or more diffraction peaks at 2θ of 21.2±0.2°, 21.4±0.2°, 25.4±0.2° and 14.7±0.2°; preferably comprises 2 of the above diffraction peaks, more preferably comprises 3 of the above diffraction peaks; optionally further comprises at least one diffraction peaks at 2θ of 20.1±0.2°, 17.1±0.2°, 22.5±0.2°, 13.1±0.2° and 23.8±0.2°, preferably comprises 2, 3, 4 or 5 of the above diffraction peaks;

for example, the X-ray powder diffraction pattern of crystal form A of methanesulfonate has diffraction peaks at 2θ of the following positions:

14.7±0.2° and 21.4±0.2°, or, 21.2±0.2° and 25.4±0.2°, or, 13.1±0.2° and 17.1±0.2°, or, 14.7±0.2°, 21.4±0.2° and 25.4±0.2°, or, 21.2±0.2°, 21.4±0.2° and 17.1±0.2°, or, 13.1±0.2°, 20.1±0.2° and 22.5±0.2°, or, 14.7±0.2°, 21.4±0.2°, 20.1±0.2° and 22.5±0.2°, or, 14.7±0.2°, 21.2±0.2°, 21.4±0.2° and 25.4±0.2°, or, 21.2±0.2°, 13.1±0.2°, 21.4±0.2° and 17.1±0.2°, or, 14.7±0.2°, 21.4±0.2°, 25.4±0.2°, 20.1±0.2° and 22.5±0.2°, or, 21.2±0.2°, 21.4±0.2°, 25.4±0.2°, 17.1±0.2° and 20.1±0.2°, or, 13.1±0.2°, 21.4±0.2°, 25.4±0.2°, 17.1±0.2° and 20.1±0.2°, or, 14.7±0.2°, 21.2±0.2°, 21.4±0.2°, 25.4±0.2°, 20.1±0.2° and 22.5±0.2°, or, 13.1±0.2°, 21.4±0.2°, 25.4±0.2°, 17.1±0.2°, 14.7±0.2° and 20.61±0.2°, or, 21.2±0.2°, 21.4±0.2°, 25.4±0.2°, 17.1±0.2°, 20.1±0.2° and 22.5±0.2°, or, 13.1±0.2°, 21.4±0.2°, 25.4±0.2°, 17.1±0.2°, 20.1±0.2° and 22.5±0.2°, or, 13.1±0.2°, 21.4±0.2°, 25.4±0.2°, 17.1±0.2°, 23.8±0.2°, 14.7±0.2° and 20.6±0.2°;

more preferably, the X-ray powder diffraction pattern of crystal form A of methanesulfonate optionally also comprises at least one or more diffraction peaks at 2θ of 20.6±0.2°, 10.7±0.2°, 11.4±0.2°, 26.4±0.2°, 19.0±0.2°, 21.6±0.2° and 13.7±0.2; preferably comprises any 2 to 3, or 4 to 5, or 6 to 7 of the above diffraction peaks; further preferably comprises any 2, 3, 4, 5, 6 or 7 of the above diffraction peaks;

for example, the X-ray powder diffraction pattern of crystal form A of methanesulfonate has diffraction peaks at 2θ of the following positions:

14.7±0.2°, 21.2±0.2°, 13.1±0.2°, 21.4±0.2°, 25.4±0.2°, 17.1±0.2°, 20.6±0.2° and 10.7±0.2°, or, 14.7±0.2°, 21.2±0.2°, 13.1±0.2°, 21.4±0.2°, 25.4±0.2°, 20.6±0.2°, 10.7±0.2°, 11.4±0.2° and 26.4±0.2°, or, 14.7±0.2°, 21.2±0.2°, 13.1±0.2°, 21.4±0.2°, 25.4±0.2°, 17.1±0.2°, 26.4±0.2°, 19.0±0.2°, 21.6±0.2° and 13.7±0.2°;

further preferably, the X-ray powder diffraction pattern of crystal form A of methanesulfonate comprises one or more diffraction peaks at 2θ of 21.2±0.2°, 21.4±0.2°, 25.4±0.2°, 14.7±0.2°, 20.1±0.2°, 17.1±0.2°, 20.6±0.2°, 13.1±0.2°, 23.8±0.2°, 20.6±0.2°, 10.7±0.2°, 11.4±0.2°, 26.4±0.2°, 19.0±0.2° and 21.6±0.2°; preferably comprises any 4, 5, 6, 8 or 10 of the above diffraction peaks;

for example, the X-ray powder diffraction pattern of crystal form A of methanesulfonate has diffraction peaks at 2θ of the following positions:

14.7±0.2°, 21.2±0.2°, 13.1±0.2° and 21.4±0.2°, or, 14.7±0.2°, 21.2±0.2°, 25.4±0.2° and 17.1±0.2°, or, 14.7±0.2°, 21.2±0.2°, 13.1±0.2°, 21.4±0.2° and 17.1±0.2°, or, 21.2±0.2°, 21.4±0.2°, 25.4±0.2°, 20.6±0.2°, 22.5±0.2° and 23.8±0.2°, or, 14.7±0.2°, 21.2±0.2°, 13.1±0.2°, 21.4±0.2°, 25.4±0.2°, 17.1±0.2°, 20.6±0.2° and 22.5±0.2°, or, 14.7±0.2°, 13.1±0.2°, 25.4±0.2°, 17.1±0.2°, 20.6±0.2°, 22.5±0.2°, 23.8±0.2° and 10.7±0.2°, or, 14.7±0.2°, 21.2±0.2°, 13.1±0.2°, 21.4±0.2°, 25.4±0.2°, 17.1±0.2°, 20.6±0.2°, 22.5±0.2°, 23.8±0.2° and 10.7±0.2°, or, 21.2±0.2°, 21.4±0.2°, 20.6±0.2°, 22.5±0.2°, 23.8±0.2°, 10.7±0.2°, 11.4±0.2°, 13.7±0.2°, 19.0±0.2 and 21.6±0.2°.

The characteristic X-ray diffraction peaks represented by the 2θ angle and the interplanar spacing d value by using Cu-Kα radiation are as shown in Table 8.

TABLE 8

| The XRPD data of crystal form A of methanesulfonate | | | | |
|---|---|---|---|---|
| No. | 2θ (±0.2°) | d value | Peak height | Proportion (I %) |
| 1 | 10.7 | 8.2988 | 540 | 20.7 |
| 2 | 11.4 | 7.7872 | 534 | 20.4 |
| 3 | 13.1 | 6.7431 | 636 | 24.3 |
| 4 | 13.7 | 6.4446 | 413 | 15.8 |
| 5 | 14.7 | 6.0018 | 1544 | 59.1 |
| 6 | 15.9 | 5.5616 | 319 | 12.2 |
| 7 | 17.1 | 5.1755 | 881 | 33.7 |
| 8 | 19.0 | 4.6774 | 450 | 17.2 |
| 9 | 20.1 | 4.4107 | 1066 | 40.8 |
| 10 | 20.3 | 4.3799 | 339 | 13 |
| 11 | 20.6 | 4.3078 | 583 | 22.3 |
| 12 | 21.2 | 4.185 | 2612 | 100 |
| 13 | 21.4 | 4.1574 | 1736 | 66.5 |
| 14 | 21.6 | 4.1191 | 443 | 17 |
| 15 | 22.5 | 3.9495 | 764 | 29.2 |
| 16 | 23.8 | 3.7379 | 620 | 23.7 |
| 17 | 25.4 | 3.4998 | 1521 | 58.2 |
| 18 | 26.4 | 3.3758 | 492 | 18.8 |
| 20 | 28.9 | 3.0873 | 355 | 13.6 |
| 21 | 30.6 | 2.9192 | 396 | 15.2 |

Provided is crystal form A of methanesulfonate of the compound according to the present invention, the X-ray powder diffraction pattern thereof is substantially as shown in FIG. 10, the DSC spectrum thereof is substantially as shown in FIG. 11.

In a further preferred embodiment of the present invention, provided is crystal form A of 1,5-naphthalenedisulfonate of the compound of Example 12A, the X-ray powder diffraction pattern thereof has a diffraction peak of 21.4±0.2°, or a diffraction peak of 18.0±0.2°, or a diffraction peak of 22.4±0.2°, or a diffraction peak of 24.1±0.2°, or a diffraction peak of 26.0±0.2°, or a diffraction peak of 10.5±0.2°, or a diffraction peak of 15.4±0.2°, or a diffraction peak of 15.6±0.2°, or a diffraction peak of 23.0±0.2°, or a diffraction peak of 17.8±0.2°; preferably comprises any 2 to 5, or 3 to 5, or 3 to 6, or 3 to 8, or 5 to 8, or 6 to 8 of the above diffraction peaks, more preferably comprises any 6, 7 or 8 of the above diffraction peaks;

preferably, the X-ray powder diffraction pattern of crystal form A of 1,5-naphthalenedisulfonate comprises at least one or more diffraction peaks at 2θ of 21.4±0.2°, 26.0±0.2°, 22.4±0.2° and 18.0±0.2°; preferably comprises 2 of the above diffraction peaks, more preferably comprises 3 of the above diffraction peaks; optionally further comprises at least one diffraction peaks at 2θ of 24.1±0.2°, 10.5±0.2°, 15.4±0.2°, 15.6±0.2° and 23.0±0.2°, preferably comprises 2, 3, 4 or 5 of the above diffraction peaks;

for example, the X-ray powder diffraction pattern of crystal form A of 1,5-naphthalenedisulfonate has diffraction peaks at 2θ of the following positions:

18.0±0.2° and 22.4±0.2°, or, 21.4±0.2° and 24.1±0.2°, or, 26.0±0.2° and 10.5±0.2°, or, 18.0±0.2°, 22.4±0.2° and 24.1±0.2°, or, 21.4±0.2°, 22.4±0.2° and 10.5±0.2°, or, 26.0±0.2°, 15.4±0.2° and 15.6±0.2°, or, 18.0±0.2°, 22.4±0.2°, 15.4±0.2° and 15.6±0.2°, or, 18.0±0.2°, 21.4±0.2°, 22.4±0.2° and 24.1±0.2°, or, 21.4±0.2°, 26.0±0.2°, 22.4±0.2° and 10.5±0.2°, or, 18.0±0.2°, 22.4±0.2°, 24.1±0.2°, 15.4±0.2° and 15.6±0.2°, or, 21.4±0.2°, 22.4±0.2°, 24.1±0.2°, 10.5±0.2° and 15.4±0.2°, or, 26.0±0.2°, 22.4±0.2°, 24.1±0.2°, 10.5±0.2° and 15.4±0.2°, or, 18.0±0.2°, 21.4±0.2°, 22.4±0.2°, 24.1±0.2°, 15.4±0.2° and 15.6±0.2°, or, 26.0±0.2°, 22.4±0.2°, 24.1±0.2°, 10.5±0.2°, 18.0±0.2° and 15.4±0.2°, or, 21.4±0.2°, 22.4±0.2°, 24.1±0.2°, 10.5±0.2°, 15.4±0.2° and 15.6±0.2°, or, 26.0±0.2°, 22.4±0.2°, 24.1±0.2°, 10.5±0.2°, 15.4±0.2° and 15.6±0.2°, or, 26.0±0.2°, 22.4±0.2°, 24.1±0.2°, 10.5±0.2°, 23.0±0.2°, 18.0±0.2° and 15.4±0.2°;

more preferably, the X-ray powder diffraction pattern of crystal form A of 1,5-naphthalenedisulfonate optionally also comprises at least one or more diffraction peaks at 2θ of 17.8±0.2°, 25.6±0.2°, 25.1±0.2°, 17.2±0.2°, 19.7±0.2°, 20.0±0.2° and 20.6±0.2°; preferably comprises any 2 to 3, or 4 to 5, or 6 to 7 of the above diffraction peaks; further preferably comprises any 2, 3, 4, 5, 6 or 7 of the above diffraction peaks;

for example, the X-ray powder diffraction pattern of crystal form A of 1,5-naphthalenedisulfonate has diffraction peaks at 2θ of the following positions:

18.0±0.2°, 21.4±0.2°, 26.0±0.2°, 22.4±0.2°, 24.1±0.2°, 10.5±0.2°, 15.6±0.2° and 23.0±0.2°, or, 18.0±0.2°, 21.4±0.2°, 26.0±0.2°, 22.4±0.2°, 24.1±0.2°, 10.5±0.2°, 15.6±0.2°, 23.0±0.2° and 17.8±0.2°, or, 18.0±0.2°, 21.4±0.2°, 26.0±0.2°, 22.4±0.2°, 24.1±0.2°, 10.5±0.2°, 15.6±0.2°, 23.0±0.2°, 17.8±0.2° and 19.7±0.2°;

further preferably, the X-ray powder diffraction pattern of crystal form A of 1,5-naphthalenedisulfonate comprises one or more diffraction peaks at 2θ of 21.4±0.2°, 22.4±0.2°, 24.1±0.2°, 18.0±0.2°, 26.0±0.2°, 10.5±0.2°, 15.4±0.2°, 15.6±0.2°, 23.0±0.2°, 17.2±0.2°, 17.8±0.2°, 19.7±0.2°, 20.0±0.2°, 20.6±0.2° and 25.1±0.2°; preferably comprises any 4, 5, 6, 8 or 10 of the above diffraction peaks;

for example, the X-ray powder diffraction pattern of crystal form A of 1,5-naphthalenedisulfonate has diffraction peaks at 2θ of the following positions:

18.0±0.2°, 21.4±0.2°, 26.0±0.2° and 22.4±0.2°, or, 18.0±0.2°, 21.4±0.2°, 24.1±0.2° and 10.5±0.2°, or, 18.0±0.2°, 21.4±0.2°, 26.0±0.2°, 22.4±0.2°, 24.1±0.2°, 10.5±0.2°, or, 21.4±0.2°, 22.4±0.2°, 24.1±0.2°, 15.4±0.2°, 15.6±0.2° and 23.0±0.2°, or, 18.0±0.2°, 21.4±0.2°, 26.0±0.2°, 22.4±0.2°, 24.1±0.2°, 10.5±0.2°, 15.4±0.2° and 15.6±0.2°, or, 18.0±0.2°, 26.0±0.2°, 24.1±0.2°, 10.5±0.2°, 15.4±0.2°, 15.6±0.2°, 23.0±0.20 and 17.8±0.2°, or, 18.0±0.2°, 21.4±0.2°, 26.0±0.2°, 22.4±0.2°, 24.1±0.2°, 10.5±0.2°, 15.4±0.2°, 15.6±0.2°, 23.0±0.20 and 17.8±0.2°, or, 21.4±0.2°, 22.4±0.2°, 15.4±0.2°, 15.6±0.2°, 23.0±0.2°, 17.2±0.2°, 17.8±0.2°, 19.7±0.2°, 20.0±0.2°, 20.6±0.20 and 25.1±0.2°.

The characteristic X-ray diffraction peaks represented by the 2θ angle and the interplanar spacing d value by using Cu-Kα radiation are as shown in Table 9.

TABLE 9

| The XRPD data of crystal form A of 1,5-naphthalenedisulfonate | | | | |
|---|---|---|---|---|
| No. | 2θ (±0.2°) | d value | Peak height | Proportion (I %) |
| 1 | 6.4 | 13.7 | 150 | 13.1 |
| 2 | 10.5 | 8.4 | 298 | 26 |
| 3 | 15.4 | 5.7659 | 350 | 30.5 |
| 4 | 15.6 | 5.663 | 325 | 28.4 |
| 5 | 16.6 | 5.3387 | 115 | 10 |
| 6 | 17.2 | 5.1557 | 256 | 22.3 |
| 7 | 17.8 | 4.9887 | 305 | 26.6 |
| 8 | 18.0 | 4.9168 | 467 | 40.8 |
| 9 | 19.7 | 4.5005 | 220 | 19.2 |
| 10 | 20.0 | 4.437 | 250 | 21.8 |
| 11 | 20.6 | 4.3108 | 174 | 15.2 |
| 12 | 21.4 | 4.1499 | 1146 | 100 |
| 13 | 22.4 | 3.9602 | 453 | 39.5 |
| 14 | 23.0 | 3.8573 | 321 | 28 |
| 15 | 24.1 | 3.694 | 416 | 36.3 |
| 16 | 24.8 | 3.5849 | 119 | 10.4 |
| 17 | 25.1 | 3.5442 | 263 | 22.9 |
| 18 | 25.6 | 3.4754 | 266 | 23.2 |
| 20 | 26.0 | 3.4297 | 458 | 40 |
| 21 | 28.6 | 3.115 | 117 | 10.2 |

Provided is crystal form A of hydrochloride of the compound according to the present invention, the X-ray powder diffraction pattern thereof is substantially as shown in FIG. 12, the DSC spectrum thereof is substantially as shown in FIG. 13.

In a further preferred embodiment of the present invention, provided is crystal form A of nitrate of the compound of Example 12A, the X-ray powder diffraction pattern thereof has a diffraction peak of 25.7±0.20, or a diffraction peak of 16.3±0.20, or a diffraction peak of 18.0±0.20, or a diffraction peak of 21.6±0.20, or a diffraction peak of 19.8±0.20, or a diffraction peak of 24.3±0.20, or a diffraction peak of 27.5±0.20, or a diffraction peak of 11.9±0.2°, or a diffraction peak of 23.6±0.2°, or a diffraction peak of 14.2±0.2°; preferably comprises any 2 to 5, or 3 to 5, or 3 to 6, or 3 to 8, or 5 to 8, or 6 to 8 of the above diffraction peaks, more preferably comprises any 6, 7 or 8 of the above diffraction peaks;

preferably, the X-ray powder diffraction pattern of crystal form A of nitrate comprises at least one or more diffraction peaks at 2θ of 25.7±0.2°, 18.0±0.2°, 21.6±0.2° and 16.3±0.2°; preferably comprises 2 of the above diffraction peaks, more preferably comprises 3 of the above diffraction peaks; optionally further comprises at least one diffraction peaks at 2θ of 19.8±0.2°, 24.3±0.2°, 27.5±0.2°, 11.9±0.2° and 23.6±0.2°, preferably comprises 2, 3, 4 or 5 of the above diffraction peaks;

for example, the X-ray powder diffraction pattern of crystal form A of nitrate has diffraction peaks at 2θ of the following positions:

16.3±0.2° and 18.0±0.2°, or, 25.7±0.2° and 21.6±0.2°, or, 19.8±0.2° and 24.3±0.2°, or, 16.3±0.2°, 18.0±0.2° and 21.6±0.2°, or, 25.7±0.2°, 18.0±0.2° and 24.3±0.2°, or, 19.8±0.2°, 27.5±0.2° and 11.9±0.2°, or, 16.3±0.2°, 18.0±0.2°, 27.5±0.2° and 11.9±0.2°, or, 16.3±0.2°, 25.7±0.2°, 18.0±0.2° and 21.6±0.2°, or, 25.7±0.2°, 19.8±0.2°, 18.0±0.2° and 24.3±0.2°, or, 16.3±0.2°, 18.0±0.2°, 21.6±0.2°, 27.5±0.2° and 11.9±0.2°, or, 25.7±0.2°, 18.0±0.2°, 21.6±0.2°, 24.3±0.2° and 27.5±0.2°, or, 19.8±0.2°, 18.0±0.2°, 21.6±0.2°, 24.3±0.2° and 27.5±0.2°, or, 16.3±0.2°, 25.7±0.2°, 18.0±0.2°, 21.6±0.2°, 27.5±0.2° and 11.9±0.2°, or, 19.8±0.2°, 18.0±0.2°, 21.6±0.2°, 24.3±0.2°, 14.2±0.2° and 27.5±0.2°, or, 25.7±0.2°, 18.0±0.2°, 21.6±0.2°, 24.3±0.2°, 27.5±0.2° and 11.9±0.2°, or, 19.8±0.2°, 18.0±0.2°, 21.6±0.2°, 24.3±0.2°, 27.5±0.2° and 11.9±0.2°, or, 19.8±0.2°, 18.0±0.2°, 21.6±0.2°, 24.3±0.2°, 23.6±0.2°, 14.2±0.2° and 27.5±0.2°;

more preferably, the X-ray powder diffraction pattern of crystal form A of nitrate optionally also comprises at least one or more diffraction peaks at 2θ of 14.2±0.2°, 12.8±0.2°, 13.5±0.2°, 22.6±0.2°, 21.0±0.2°, 24.6±0.2° and 25.2±0.2°; preferably comprises any 2 to 3, or 4 to 5, or 6 to 7 of the above diffraction peaks; further preferably comprises any 2, 3, 4, 5, 6 or 7 of the above diffraction peaks;

for example, the X-ray powder diffraction pattern of crystal form A of nitrate has diffraction peaks at 2θ of the following positions:

16.3±0.2°, 25.7±0.2°, 19.8±0.2°, 18.0±0.2°, 21.6±0.2°, 24.3±0.2°, 14.2±0.2° and 12.8±0.2°, or, 16.3±0.2°, 25.7±0.2°, 19.8±0.2°, 18.0±0.2°, 21.6±0.2°, 24.3±0.2°, 14.2±0.2°, 12.8±0.2° and 13.5±0.2°, or, 16.3±0.2°, 25.7±0.2°, 19.8±0.2°, 18.0±0.2°, 21.6±0.2°, 24.3±0.2°, 22.6±0.2°, 12.8±0.2°, 13.5±0.2° and 14.2±0.2°;

further preferably, the X-ray powder diffraction pattern of crystal form A of nitrate comprises one or more diffraction peaks at 2θ of 25.7±0.2°, 18.0±0.2°, 21.6±0.2°, 16.3±0.2°, 19.8±0.2°, 24.3±0.2°, 27.5±0.2°, 11.9±0.2°, 12.8±0.2°, 13.5±0.2°, 14.2±0.2°, 23.6±0.2°, 22.6±0.2°, 24.6±0.2° and 25.2±0.2°; preferably comprises any 4, 5, 6, 8 or 10 of the above diffraction peaks;

for example, the X-ray powder diffraction pattern of crystal form A of nitrate has diffraction peaks at 2θ of the following positions:

16.3±0.2°, 25.7±0.2°, 19.8±0.2° and 18.0±0.2°, or, 16.3±0.2°, 25.7±0.2°, 21.6±0.2° and 24.3±0.2°, or, 16.3±0.2°, 25.7±0.2°, 19.8±0.2°, 18.0±0.2°, 21.6±0.2°, 24.3±0.2°, or, 25.7±0.2°, 18.0±0.2°, 21.6±0.2°, 27.5±0.2°, 11.9±0.2° and 12.8±0.2°, or, 16.3±0.2°, 25.7±0.2°, 19.8±0.2°, 18.0±0.2°, 21.6±0.2°, 24.3±0.2°, 27.5±0.2° and 11.9±0.2°, or, 16.3±0.2°, 19.8±0.2°, 21.6±0.2°, 24.3±0.2°, 27.5±0.2°, 11.9±0.2°, 12.8±0.2° and 13.5±0.2°, or, 16.3±0.2°, 25.7±0.2°, 19.8±0.2°, 18.0±0.2°, 21.6±0.2°, 24.3±0.2°, 27.5±0.2°, 11.9±0.2°, 12.8±0.2° and 13.5±0.2°, or, 25.7±0.2°, 18.0±0.2°, 27.5±0.2°, 11.9±0.2°, 12.8±0.2°, 13.5±0.2°, 14.2±0.2°, 23.6±0.2°, 22.6±0.2°, 24.6±0.2° and 25.2±0.2°.

The characteristic X-ray diffraction peaks represented by the 2θ angle and the interplanar spacing d value by using Cu-Kα radiation are as shown in Table 10.

TABLE 10

The XRPD data of crystal form A of nitrate

| No. | 2θ (±0.2°) | d value | Peak height | Proportion (I %) |
|---|---|---|---|---|
| 1 | 11.9 | 7.4292 | 323 | 30.6 |
| 2 | 12.8 | 6.9331 | 282 | 26.7 |
| 3 | 13.5 | 6.5499 | 260 | 24.6 |
| 4 | 13.7 | 6.5 | 195 | 18.5 |
| 5 | 14.2 | 6.2257 | 291 | 27.6 |
| 6 | 16.3 | 5.4323 | 740 | 70.1 |
| 7 | 17.5 | 5.0676 | 212 | 20.1 |
| 8 | 18.0 | 4.9164 | 944 | 89.4 |
| 9 | 19.6 | 4.5312 | 270 | 25.6 |
| 10 | 19.8 | 4.4774 | 445 | 42.1 |
| 11 | 21.0 | 4.2314 | 233 | 22.1 |
| 12 | 21.6 | 4.1079 | 892 | 84.5 |
| 13 | 22.6 | 3.9289 | 252 | 23.9 |
| 14 | 23.6 | 3.7728 | 295 | 27.9 |
| 15 | 24.3 | 3.6602 | 518 | 49.1 |
| 16 | 24.6 | 3.6155 | 225 | 21.3 |
| 17 | 25.2 | 3.5 | 257 | 24.3 |
| 18 | 25.7 | 3.47 | 1056 | 100 |
| 20 | 27.5 | 3.236 | 469 | 44.4 |
| 21 | 28.3 | 3.1478 | 189 | 17.9 |
| 22 | 30.0 | 2.9732 | 177 | 16.8 |

Provided is crystal form A of nitrate of the compound according to the present invention, the X-ray powder diffraction pattern thereof is substantially as shown in FIG. 14, the DSC spectrum thereof is substantially as shown in FIG. 15.

In a further preferred embodiment of the present invention, provided is crystal form A of acetate of the compound of Example 12A, the X-ray powder diffraction pattern thereof has a diffraction peak of 11.2±0.2°, or a diffraction peak of 16.9±0.2°, or a diffraction peak of 20.8±0.2°, or a diffraction peak of 18.7±0.2°, or a diffraction peak of 13.5±0.2°, or a diffraction peak of 13.9±0.2°, or a diffraction peak of 22.3±0.2°, or a diffraction peak of 24.5±0.2°, or a diffraction peak of 22.7±0.2°, or a diffraction peak of 28.2±0.2°; preferably comprises any 2 to 5, or 3 to 5, or 3 to 6, or 3 to 8, or 5 to 8, or 6 to 8 of the above diffraction peaks, more preferably comprises any 6, 7 or 8 of the above diffraction peaks;

preferably, the X-ray powder diffraction pattern of crystal form A of acetate comprises at least one or more diffraction peaks at 2θ of 11.2±0.2°, 20.8±0.2°, 18.7±0.2° and 16.9±0.2°; preferably comprises 2 of the above diffraction peaks, more preferably comprises 3 of the above diffraction peaks; optionally further comprises at least one diffraction peaks at 2θ of 13.5±0.2°, 13.9±0.2°, 22.3±0.2°, 24.5±0.2° and 22.7±0.2°, preferably comprises 2, 3, 4 or 5 of the above diffraction peaks;

for example, the X-ray powder diffraction pattern of crystal form A of acetate has diffraction peaks at 2θ of the following positions:

16.9±0.2° and 20.8±0.2°, or, 11.2±0.2° and 18.7±0.2°, or, 13.5±0.2° and 13.9±0.2°, or, 16.9±0.2°, 20.8±0.2° and 18.7±0.2°, or, 11.2±0.2°, 20.8±0.2° and 13.9±0.2°, or, 13.5±0.2°, 22.3±0.2° and 24.5±0.2°, or, 16.9±0.2°, 20.8±0.2°, 22.3±0.2° and 24.5±0.2°, or, 16.9±0.2°, 11.2±0.2°, 20.8±0.2° and 18.7±0.2°, or, 11.2±0.2°, 13.5±0.2°, 20.8±0.2° and 13.9±0.2°, or, 16.9±0.2°, 20.8±0.2°, 18.7±0.2°, 22.3±0.2° and 24.5±0.2°, or, 11.2±0.2°, 20.8±0.2°, 18.7±0.2°, 13.9±0.2° and 22.3±0.2°, or, 13.5±0.2°, 20.8±0.2°, 18.7±0.2°, 13.9±0.2° and 22.3±0.2°, or, 16.9±0.2°, 11.2±0.2°, 20.8±0.2°, 18.7±0.2°, 22.3±0.2° and 24.5±0.2°, or, 13.5±0.2°, 20.8±0.2°, 18.7±0.2°, 13.9±0.2°, 24.5±0.2° and 22.3±0.2°, or, 11.2±0.2°, 20.8±0.2°, 18.7±0.2°, 13.9±0.2°, 22.3±0.2° and 24.5±0.2°, or, 13.5±0.2°, 20.8±0.2°, 18.7±0.2°, 13.9±0.2°, 22.3±0.2° and 24.5±0.2°, or, 13.5±0.2°, 20.8±0.2°, 18.7±0.2°, 13.9±0.2°, 22.7±0.2°, 24.5±0.2° and 22.3±0.2°;

more preferably, the X-ray powder diffraction pattern of crystal form A of acetate optionally also comprises at least one or more diffraction peaks at 2θ of 28.2±0.2°, 15.8±0.2°, 17.9±0.2°, 19.3±0.2°, 15.0±0.2°, 17.4±0.2° and 21.1±0.2°; preferably comprises any 2 to 3, or 4 to 5, or 6 to 7 of the above diffraction peaks; further preferably comprises any 2, 3, 4, 5, 6 or 7 of the above diffraction peaks;

for example, the X-ray powder diffraction pattern of crystal form A of acetate has diffraction peaks at 2θ of the following positions:

16.9±0.2°, 11.2±0.2°, 13.5±0.2°, 20.8±0.2°, 18.7±0.2°, 13.9±0.2°, 24.5±0.2° and 15.8±0.2°, or, 16.9±0.2°, 11.2±0.2°, 13.5±0.2°, 20.8±0.2°, 18.7±0.2°, 13.9±0.2°, 24.5±0.2°, 15.8±0.2° and 17.9±0.2°, or, 16.9±0.2°, 11.2±0.2°, 13.5±0.2°, 20.8±0.2°, 18.7±0.2°, 13.9±0.2°, 24.5±0.2°, 15.8±0.2°, 17.9±0.2° and 19.3±0.2°;

further preferably, the X-ray powder diffraction pattern of crystal form A of acetate comprises one or more diffraction peaks at 2θ of 11.2±0.2°, 20.8±0.2°, 18.7±0.2°, 16.9±0.2°, 13.5±0.2°, 13.9±0.2°, 22.3±0.2°, 24.5±0.2°, 15.8±0.2°, 17.9±0.2°, 19.3±0.2°, 22.7±0.2°, 28.2±0.2°, 17.4±0.2° and 21.1±0.2°; preferably comprises any 4, 5, 6, 8 or 10 of the above diffraction peaks;

for example, the X-ray powder diffraction pattern of crystal form A of acetate has diffraction peaks at 2θ of the following positions:

16.9±0.2°, 11.2±0.2°, 13.5±0.2° and 20.8±0.2°, or, 16.9±0.2°, 11.2±0.2°, 18.7±0.2° and 13.9±0.2°, or, 16.9±0.2°, 11.2±0.2°, 13.5±0.2°, 20.8±0.2°, 18.7±0.2°, 13.9±0.2°, or, 11.2±0.2°, 20.8±0.2°, 18.7±0.2°, 22.3±0.2°, 24.5±0.2° and 15.8±0.2°, or, 16.9±0.2°, 11.2±0.2°, 13.5±0.2°, 20.8±0.2°, 18.7±0.2°, 13.9±0.2°, 22.3±0.2° and 24.5±0.2°, or, 16.9±0.2°, 13.5±0.2°, 18.7±0.2°, 13.9±0.2°, 22.3±0.2°, 24.5±0.2°, 15.8±0.2° and 17.9±0.2°, or, 16.9±0.2°, 11.2±0.2°, 13.5±0.2°, 20.8±0.2°, 18.7±0.2°, 13.9±0.2°, 22.3±0.2°, 24.5±0.2°, 15.8±0.2° and 17.9±0.2°, or, 11.2±0.2°, 20.8±0.2°, 22.3±0.2°, 24.5±0.2°, 15.8±0.2°, 17.9±0.2°, 19.3±0.2°, 22.7±0.2°, 28.2±0.2°, 17.4±0.20 and 21.1±0.20.

The characteristic X-ray diffraction peaks represented by the 2θ angle and the interplanar spacing d value by using Cu-Kα radiation are as shown in Table 11.

TABLE 11

| | The XRPD data of crystal form A of acetate | | | |
|---|---|---|---|---|
| No. | 2θ (±0.2°) | d value | Peak height | Proportion (I %) |
| 1 | 11.2 | 7.865 | 420 | 61.8 |
| 2 | 13.5 | 6.566 | 235 | 34.6 |
| 3 | 13.9 | 6.3799 | 246 | 36.2 |
| 4 | 14.5 | 6.0878 | 65 | 9.6 |
| 5 | 15.0 | 5.892 | 68 | 10 |
| 6 | 15.3 | 5.797 | 65 | 9.6 |
| 7 | 15.8 | 5.6051 | 122 | 17.9 |
| 8 | 16.9 | 5.2501 | 283 | 41.6 |
| 9 | 17.4 | 5.1028 | 71 | 10.4 |
| 10 | 17.9 | 4.954 | 116 | 17.1 |
| 11 | 18.7 | 4.743 | 680 | 100 |
| 12 | 19.3 | 4.607 | 142 | 20.9 |
| 13 | 20.8 | 4.2655 | 292 | 42.9 |
| 14 | 21.1 | 4.2053 | 84 | 12.4 |
| 15 | 22.3 | 3.9857 | 230 | 33.8 |
| 16 | 22.5 | 3.9435 | 197 | 29 |
| 17 | 22.7 | 3.9188 | 184 | 27.1 |
| 18 | 24.1 | 3.6872 | 53 | 7.8 |
| 20 | 24.5 | 3.6283 | 208 | 30.6 |
| 21 | 28.2 | 3.1634 | 154 | 22.6 |
| 22 | 36.8 | 2.4386 | 68 | 10 |

Provided is crystal form A of acetate of the compound according to the present invention, the X-ray powder diffraction pattern thereof is substantially as shown in FIG. 16, the DSC spectrum thereof is substantially as shown in FIG. 17.

In a further preferred embodiment of the present invention, provided is crystal form A of fumarate of the compound of Example 12A, the X-ray powder diffraction pattern thereof has a diffraction peak of 17.8±0.20, or a diffraction peak of 18.6±0.20, or a diffraction peak of 21.7±0.20, or a diffraction peak of 22.7±0.20, or a diffraction peak of 16.9±0.20, or a diffraction peak of 20.8±0.20, or a diffraction peak of 24.3±0.20, or a diffraction peak of 24.7±0.20, or a diffraction peak of 22.3±0.20, or a diffraction peak of 15.8±0.20; preferably comprises any 2 to 5, or 3 to 5, or 3 to 6, or 3 to 8, or 5 to 8, or 6 to 8 of the above diffraction peaks, more preferably comprises any 6, 7 or 8 of the above diffraction peaks;

preferably, the X-ray powder diffraction pattern of crystal form A of fumarate comprises at least one or more diffraction peaks at 2θ of 17.8±0.2°, 21.7±0.2°, 22.7±0.2° and 18.6±0.2°; preferably comprises 2 of the above diffraction peaks, more preferably comprises 3 of the above diffraction peaks; optionally further comprises at least one diffraction peaks at 2θ of 16.9±0.2°, 20.8±0.2°, 24.3±0.2°, 24.7±0.2° and 15.8±0.2°, preferably comprises 2, 3, 4 or 5 of the above diffraction peaks;

for example, the X-ray powder diffraction pattern of crystal form A of fumarate has diffraction peaks at 2θ of the following positions:

18.6±0.2° and 21.7±0.2°, or, 17.8±0.2° and 22.7±0.2°, or, 16.9±0.2° and 20.8±0.2°, or, 18.6±0.2°, 21.7±0.2° and 22.7±0.2°, or, 17.8±0.2°, 21.7±0.2° and 20.8±0.2°, or, 16.9±0.2°, 24.3±0.2° and 24.7±0.2°, or, 18.6±0.2°, 21.7±0.2°, 24.3±0.2° and 24.7±0.2°, or, 18.6±0.2°, 17.8±0.2°, 21.7±0.2° and 22.7±0.2°, or, 17.8±0.2°, 16.9±0.2°, 21.7±0.2° and 20.8±0.2°, or, 18.6±0.2°, 21.7±0.2°, 22.7±0.2°, 24.3±0.2° and 24.7±0.2°, or, 17.8±0.2°, 21.7±0.2°, 22.7±0.2°, 20.8±0.2° and 24.3±0.2°, or, 16.9±0.2°, 21.7±0.2°, 22.7±0.2°, 20.8±0.2° and 24.3±0.2°, or, 18.6±0.2°, 17.8±0.2°, 21.7±0.2°, 22.7±0.2°, 24.3±0.2° and 24.7±0.2°, or, 16.9±0.2°, 21.7±0.2°, 22.7±0.2°, 20.8±0.2°, 15.8±0.2° and 24.3±0.2°, or, 17.8±0.2°, 21.7±0.2°, 22.7±0.2°, 20.8±0.2°, 24.3±0.2° and 24.7±0.2°, or, 16.9±0.2°, 21.7±0.2°, 22.7±0.2°, 20.8±0.2°, 24.3±0.2° and 24.7±0.2°, or, 16.9±0.2°, 21.7±0.2°, 22.7±0.2°, 20.8±0.2°, 22.3±0.2°, 15.8±0.2° and 24.3±0.2°;

more preferably, the X-ray powder diffraction pattern of crystal form A of fumarate optionally also comprises at least one or more diffraction peaks at 2θ of 22.3±0.2°, 23.7±0.2°, 13.6±0.2°, 17.4±0.2°, 16.1±0.2°, 18.3±0.2° and 19.6±0.2°; preferably comprises any 2 to 3, or 4 to 5, or 5 to 6 of the above diffraction peaks; further preferably comprises any 2, 3, 4, 5 or 6 of the above diffraction peaks;

for example, the X-ray powder diffraction pattern of crystal form A of fumarate has diffraction peaks at 2θ of the following positions:

18.6±0.2°, 17.8±0.2°, 16.9±0.2°, 21.7±0.2°, 22.7±0.2°, 20.8±0.2°, 24.7±0.2° and 13.6±0.2°, or, 118.6±0.2°, 17.8±0.2°, 16.9±0.2°, 21.7±0.2°, 22.7±0.2°, 20.8±0.2°, 24.7±0.2°, 13.6±0.2° and 15.8±0.2°, or, 18.6±0.2°, 17.8±0.2°, 16.9±0.2°, 21.7±0.2°, 22.7±0.2°, 20.8±0.2°, 24.7±0.2°, 13.6±0.2°, 15.8±0.2° and 22.3±0.2°;

further preferably, the X-ray powder diffraction pattern of crystal form A of fumarate comprises one or more diffraction peaks at 2θ of 17.8±0.2°, 21.7±0.2°, 22.7±0.2°, 18.6±0.2°, 16.9±0.2°, 20.8±0.2°, 24.3±0.2°, 24.7±0.2°, 13.6±0.2°, 15.8±0.2°, 16.1±0.2°, 22.3±0.2°, 23.7±0.2°, 17.4±0.2° and 18.3±0.2°; preferably comprises any 4, 5, 6, 8 or 10 of the above diffraction peaks;

for example, the X-ray powder diffraction pattern of crystal form A of fumarate has diffraction peaks at 2θ of the following positions:

18.6±0.2°, 17.8±0.2°, 16.9±0.2° and 21.7±0.2°, or, 18.6±0.2°, 17.8±0.2°, 22.7±0.2° and 20.8±0.2°, or, 18.6±0.2°, 17.8±0.2°, 16.9±0.2°, 21.7±0.2°, 22.7±0.2°, 20.8±0.2°, or, 17.8±0.2°, 21.7±0.2°, 22.7±0.2°, 24.3±0.2°, 24.7±0.2° and 13.6±0.2°, or, 18.6±0.2°, 17.8±0.2°, 16.9±0.2°, 21.7±0.2°, 22.7±0.2°, 20.8±0.2°, 24.3±0.2° and 24.7±0.2°, or, 18.6±0.2°, 16.9±0.2°, 22.7±0.2°, 20.8±0.2°, 24.3±0.2°, 24.7±0.2°, 13.6±0.2° and 15.8±0.2°, or, 18.6±0.2°, 17.8±0.2°, 16.9±0.2°, 21.7±0.2°, 22.7±0.2°, 20.8±0.2°, 24.3±0.2°, 24.7±0.2°, 13.6±0.2° and 15.8±0.2°, or, 17.8±0.2°, 21.7±0.2°, 24.3±0.2°, 24.7±0.2°, 13.6±0.2°, 15.8±0.2°, 16.1±0.2°, 22.3±0.2° and 23.7±0.2°.

The characteristic X-ray diffraction peaks represented by the 2θ angle and the interplanar spacing d value by using Cu-Kα radiation are as shown in Table 12.

TABLE 12

| | The XRPD data of crystal form A of fumarate | | | |
|---|---|---|---|---|
| No. | 2θ (±0.2°) | d value | Peak height | Proportion (I %) |
| 1 | 13.6 | 6.4927 | 220 | 14.3 |
| 2 | 15.8 | 5.5912 | 412 | 26.8 |
| 3 | 16.1 | 5.4928 | 275 | 17.9 |
| 4 | 16.9 | 5.2371 | 517 | 33.7 |
| 5 | 17.4 | 5.0934 | 198 | 12.9 |
| 6 | 17.8 | 4.983 | 1536 | 100 |
| 7 | 18.3 | 4.846 | 176 | 11.5 |
| 8 | 18.6 | 4.7783 | 629 | 41 |
| 9 | 19.6 | 4.5179 | 139 | 9 |
| 10 | 20.8 | 4.2581 | 601 | 39.1 |
| 11 | 21.7 | 4.0927 | 639 | 41.6 |
| 12 | 22.1 | 4.0257 | 250 | 16.3 |
| 13 | 22.3 | 3.9782 | 361 | 23.5 |
| 14 | 22.7 | 3.9187 | 925 | 60.2 |
| 15 | 23.7 | 3.757 | 296 | 19.3 |
| 16 | 24.3 | 3.6671 | 603 | 39.3 |
| 17 | 24.7 | 3.5956 | 460 | 29.9 |
| 18 | 26.0 | 3.4275 | 139 | 9 |
| 20 | 26.7 | 3.3394 | 133 | 8.7 |
| 21 | 27.7 | 3.2132 | 134 | 8.7 |
| 22 | 31.9 | 2.8016 | 138 | 9 |

Provided is crystal form A of fumarate of the compound according to the present invention, the X-ray powder diffraction pattern thereof is substantially as shown in FIG. 18, the DSC spectrum thereof is substantially as shown in FIG. 19.

The present invention also provides a method for preparing the acid salt of the compound of formula (I) or the stereoisomer thereof or the crystal form thereof, specifically comprising the following steps of:

1) weighing an appropriate amount of free base and dissolving it with a good solvent;
2) weighing an appropriate amount of counter ion acid and dissolving it with an organic solvent; the amount of counter ion acid is preferably 1.0 to 1.5 equivalent;
3) combining the above two solutions, stirring it to precipitate a solid or adding a poor solvent dropwise to precipitate a solid under stirring;
4) rapid centrifugation or standing blow-drying to obtain the target product;

wherein:

the good solvent is one or more selected from the group consisting of acetone, dichloromethane, tetrahydrofuran, ethyl formate, ethyl acetate, 2-methyl-tetrahydrofuran, 2-butanone, n-butanol, 1,4-dioxane, isobutanol, N,N-dimethylformamide, N,N-dimethylacetamide, n-propanol and tert-butanol; preferably one or more of 2-methyl-tetrahydrofuran, ethyl acetate, 2-butanone, acetone and ethyl formate;

the organic solvent is one or more selected from the group consisting of methanol, ethanol, ethyl acetate, dichloromethane, acetone, n-hexane, petroleum ether, benzene, toluene, chloroform, acetonitrile, carbon tetrachloride, dichloroethane, tetrahydrofuran, 2-methyltetrahydrofuran, 2-butanone, 3-pentanone, heptane, methyl tert-butyl ether, isopropyl ether, 1,4-dioxane, tert-butanol and N,N-dimethylformamide; preferably one or more of methanol, ethanol and acetonitrile;

the above good solvent and the organic solvent need to be miscible when used;

the poor solvent is one or more selected from the group consisting of heptane, water, methyl tert-butyl ether, cyclohexane, toluene, isopropyl ether, ethyl acetate, acetone and acetonitrile; preferably one or more of water, methyl tert-butyl ether and isopropyl ether;

the counter ion acid is one or more selected from the group consisting of hydrochloric acid, sulfuric acid, nitric acid, hydrobromic acid, hydrofluoric acid, hydroiodic acid, phosphoric acid, 2,5-dihydroxybenzoic acid, 1-hydroxy-2-naphthoic acid, acetic acid, dichloroacetic acid, trichloroacetic acid, acetohydroxamic acid, adipic acid, benzenesulfonic acid, 4-chlorobenzenesulfonic acid, benzoic acid, 4-acetamidobenzoic acid, 4-aminobenzoic acid, decanoic acid, caproic acid, caprylic acid, cinnamic acid, citric acid, cyclamic acid, camphorsulfonic acid, aspartic acid, camphoric acid, gluconic acid, glucuronic acid, glutamic acid, isoascorbic acid, lactic acid, malic acid, mandelic acid, pyroglutamic acid, tartaric acid, dodecyl sulfuric acid, dibenzoyl tartaric acid, ethane-1,2-disulfonic acid, ethanesulfonic acid, formic acid, fumaric acid, galactonic acid, gentisic acid, glutaric acid, 2-ketoglutaric acid, glycolic acid, hippuric acid, isethionic acid, lactobionic acid, ascorbic acid, aspartic acid, lauric acid, camphoric acid, maleic acid, malonic acid, methanesulfonic acid, 1,5-naphthalenedisulfonic acid, naphthalene-2-sulfonic acid, nicotinic acid, oleic acid, orotic acid, oxalic acid, palmitic acid, embonic acid, propionic acid, salicylic acid, 4-aminosalicylic acid, decanedioic acid, stearic acid, succinic acid, thiocyanic acid, pamoic acid, methanoic acid, undecylenic acid, trifluoroacetic acid, benzenesulfonic acid, p-toluenesulfonic acid and L-malic acid; preferably one or more of maleic acid, benzenesulfonic acid, isethionic acid, 1,5-naphthalenedisulfonic acid, tartaric acid, adipic acid, sulfuric acid, p-toluenesulfonic acid, hydrobromic acid, oxalic acid, fumaric acid, methanoic acid, hippuric acid, lauric acid and stearic acid; more preferably one or more of hydrochloric acid, p-toluenesulfonic acid, sulfuric acid, oxalic acid and hydrobromic acid.

The present invention also provides a method for preparing the acid salt of the compound of formula (I) or the stereoisomer thereof or the crystal form thereof, specifically comprising the following steps of:

1) weighing an appropriate amount of free base and suspending it with a poor solvent;
2) weighing an appropriate amount of counter ion acid and dissolving it with an organic solvent; the amount of counter ion acid is preferably 1.0 to 1.5 equivalent;
3) adding the above solution into the above suspension, and stirring for 2 hours;
4) rapid centrifugation or standing blow-drying to obtain the target product;

the poor solvent is one or more selected from the group consisting of ethanol, acetone, ethyl acetate, ethyl formate, isopropanol, isopropyl acetate, methyl tert-butyl ether, methanol, acetonitrile, chlorobenzene, benzene, toluene, n-butanol, isobutanol and 3-pentanone; preferably one or more of ethanol, ethyl acetate, isopropanol and isopropyl acetate;

the organic solvent is one or more selected from the group consisting of methanol, ethanol, ethyl acetate, dichloromethane, acetone, n-hexane, petroleum ether, benzene, toluene, chloroform, acetonitrile, carbon tetrachloride, dichloroethane, tetrahydrofuran, 2-methyltetrahydrofuran, 2-butanone, 3-pentanone, heptane, methyl tert-butyl ether, isopropyl ether, 1,4-dioxane, tert-butanol and N,N-dimethylformamide; preferably one or more of methanol, ethanol and acetonitrile;

the above poor solvent and the organic solvent need to be miscible when used;

the counter ion acid is one or more selected from the group consisting of hydrochloric acid, sulfuric acid, nitric acid, hydrobromic acid, hydrofluoric acid, hydroiodic acid, phosphoric acid, 2,5-dihydroxybenzoic acid, 1-hydroxy-2-naphthoic acid, acetic acid, dichloroacetic acid, trichloroacetic acid, acetohydroxamic acid, adipic acid, benzenesulfonic acid, 4-chlorobenzenesulfonic acid, benzoic acid, 4-acetamidobenzoic acid, 4-aminobenzoic acid, decanoic acid, caproic acid, caprylic acid, cinnamic acid, citric acid, cyclamic acid, camphorsulfonic acid, aspartic acid, camphoric acid, gluconic acid, glucuronic acid, glutamic acid, isoascorbic acid, lactic acid, malic acid, mandelic acid, pyroglutamic acid, tartaric acid, dodecyl sulfuric acid, dibenzoyl tartaric acid, ethane-1,2-disulfonic acid, ethanesulfonic acid, formic acid, fumaric acid, galactonic acid, gentisic acid, glutaric acid, 2-ketoglutaric acid, glycolic acid, hippuric acid, isethionic acid, lactobionic acid, ascorbic acid, aspartic acid, lauric acid, camphoric acid, maleic acid, malonic acid, methanesulfonic acid, 1,5-naphthalenedisulfonic acid, naphthalene-2-sulfonic acid, nicotinic acid, oleic acid, orotic acid, oxalic acid, palmitic acid, embonic acid, propionic acid, salicylic acid, 4-aminosalicylic acid, decanedioic acid, stearic acid, succinic acid, thiocyanic acid, pamoic acid, methanoic acid, undecylenic acid, trifluoroacetic acid, benzenesulfonic acid, p-toluenesulfonic acid and L-malic acid; preferably one or more of hydrochloric acid, p-toluenesulfonic acid, sulfuric acid, oxalic acid and hydrobromic acid.

The present invention also provides a method for preparing the acid salt of the compound of formula (I) or the stereoisomer thereof or the crystal form thereof, specifically comprising the following steps of:

1) weighing an appropriate amount of acid salt of compound, suspending it with a poor solvent, the suspension density is preferably 50 to 200 mg/mL;
2) shaking the suspension obtained above at a certain temperature for a certain time, the temperature is preferably 25 to 50° C., and the time is preferably 1 day to 15 days;
3) rapidly centrifuging the above suspension, removing the supernatant, and drying the remaining solid in a vacuum drying oven at 50° C. to a constant weight to obtain the target product;

wherein, the poor solvent is one or more selected from the group consisting of methanol, ethanol, dichloromethane, 1,4-dioxane, acetonitrile, chlorobenzene, benzene, toluene, acetone, ethyl acetate, water, 88% acetone, isopropyl acetate, 3-pentanone, ethyl formate, tetrahydrofuran, 2-methyl-tetrahydrofuran, isopropanol, n-butanol, isobutanol, n-propanol, methyl tert-butyl ether, n-heptane, tert-butanol and 2-butanone.

The objective of the present invention is also to provide a pharmaceutical composition comprising a therapeutically effective dose of the acid salt of any compound and the stereoisomer thereof or the crystal form of the acid salt as described above, and one or more pharmaceutically acceptable carriers, diluents or excipients.

The objective of the present invention is also to provide a use of the salt of the compound and the stereoisomer thereof or the crystal form of the salt, or the pharmaceutical composition as described above in the preparation of a G protein-coupled receptor modulator medicament, particularly a dopamine D3 receptor modulator medicament and 5-HT2A receptor modulator medicament.

The objective of the present invention is also to provide a use of the pharmaceutical composition as described above in the preparation of a medicament for treating or preventing a central nervous system disease and/or psychiatric disease or disorder, wherein the nervous system disease and/or psychiatric disease is preferably schizophrenia, sleep disorder, mood disorder, schizophrenia spectrum disorder, spastic disorder, memory disorder and/or cognitive disorder, movement disorder, personality disorder, autism spectrum disorder, pain, traumatic brain injury, vascular disease, substance abuse disorder and/or withdrawal syndrome, tinnitus, depression, autism, senile dementia, Alzheimer's disease, seizures, neuralgia, withdrawal symptom major depressive disorder, mania and the like.

DETAILED DESCRIPTION OF THE INVENTION

Figure 1:
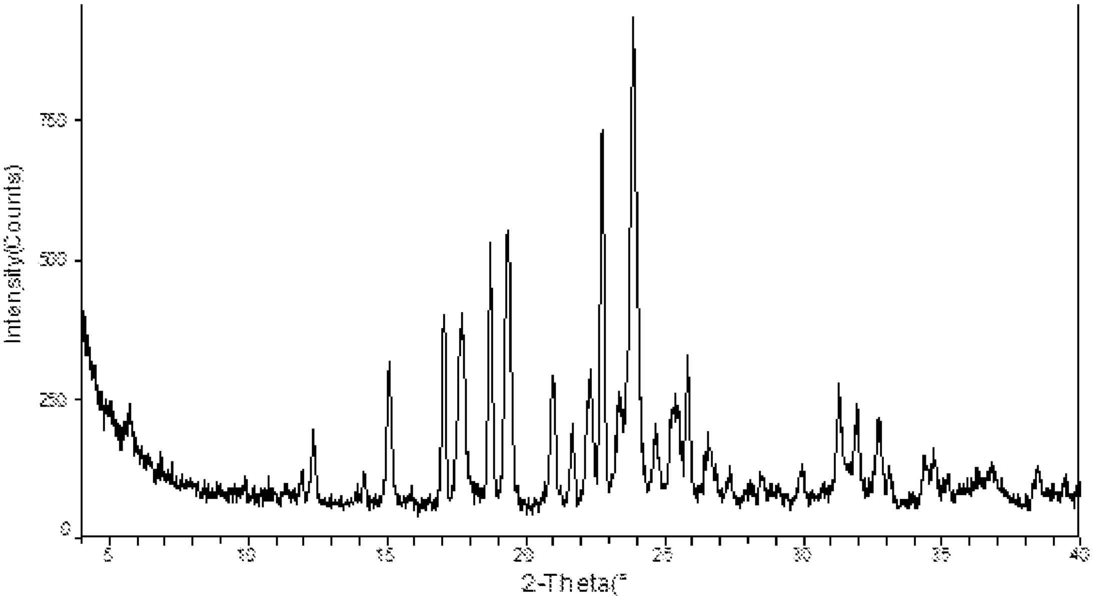
FIG. 1 is the XRPD pattern of crystal form A of hydrochloride of N-(trans-3-(2-(4-(2,3-dichlorophenyl)piperazin-1-yl)ethyl)cyclobutyl)oxazole-2-carboxamide.

Unless otherwise stated, the terms used in the specification and claims have the meanings described below.

The term "alkyl" refers to a saturated aliphatic hydrocarbon group, which is a straight or branched chain group comprising 1 to 20 carbon atoms, preferably an alkyl having 1 to 8 carbon atoms, more preferably an alkyl having 1 to 6 carbon atoms, and most preferably an alkyl having 1 to 3 carbon atoms. Non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl, n-nonyl, 2-methyl-2-ethylhexyl, 2-methyl-3-ethylhexyl, 2,2-diethylpentyl, n-decyl, 3,3-diethylhexyl, 2,2-diethylhexyl, and various branched isomers thereof. The alkyl group can be substituted or unsubstituted. When substituted, the substituent group(s) can be substituted at any available connection point. The substituent group(s) is preferably one or more group(s) independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio, heterocyclylthio, oxo, carboxy and alkoxycarbonyl. The alkyl of the present invention is preferably selected from the group consisting of methyl, ethyl, isopropyl, tert-butyl, haloalkyl, deuterated alkyl, alkoxy-substituted alkyl, hydroxy-substituted alkyl and cyano-substituted alkyl.

The term "cycloalkyl" refers to a saturated or partially unsaturated monocyclic or polycyclic hydrocarbon substituent group having 3 to 20 carbon atoms, preferably 3 to 8 carbon atoms, more preferably 3 to 6 carbon atoms. Non-limiting examples of monocyclic cycloalkyl include cyclopropyl, cyclobutyl, cyclopentyl, cyclopentenyl, cyclohexyl, cyclohexenyl, cyclohexadienyl, cycloheptyl, cycloheptatrienyl, cyclooctyl and the like. Polycyclic cycloalkyl includes a cycloalkyl having a spiro ring, fused ring or bridged ring. The cycloalkyl is preferably cyclopropyl, cyclobutyl, cyclohexyl, cyclopentyl and cycloheptyl. The cycloalkyl ring can be fused to the ring of aryl, heteroaryl or heterocyclyl, wherein the ring bound to the parent structure is cycloalkyl. Non-limiting examples include indanyl, tetrahydronaphthyl, benzocycloheptyl and the like. The cycloalkyl can be optionally substituted or unsubstituted. When substituted, the substituent group(s) is preferably one or more group(s) independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio, heterocyclylthio, oxo, carboxy and alkoxycarbonyl.

The term "heterocyclyl" refers to a 3 to 20 membered saturated or partially unsaturated monocyclic or polycyclic hydrocarbon group, wherein one or more ring atoms are heteroatoms selected from the group consisting of nitrogen, oxygen and $S(O)_m$ (wherein m is an integer of 0 to 2), but excluding —O—O—, —O—S— or —S—S— in the ring, with the remaining ring atoms being carbon atoms. Preferably, the heterocyclyl has 3 to 12 ring atoms wherein 1 to 4 atoms are heteroatoms; more preferably, 3 to 8 ring atoms; and most preferably 3 to 8 ring atoms. Non-limiting examples of monocyclic heterocyclyl include oxetanyl, pyrrolidinyl, pyrrolidonyl, imidazolidinyl, tetrahydrofuranyl, tetrahydrothienyl, dihydroimidazolyl, dihydrofuranyl, dihydropyrazolyl, dihydropyrrolyl, piperidinyl, piperazinyl, morpholinyl, thiomorpholinyl, homopiperazinyl, pyranyl and the like, preferably oxetanyl, pyrrolidonyl, tetrahydrofuranyl, pyrazolidinyl, morpholinyl, piperazinyl and pyranyl. Polycyclic heterocyclyl includes a heterocyclyl having a spiro ring, fused ring or bridged ring. The heterocyclyl having a spiro ring, fused ring or bridged ring is optionally bonded to other group via a single bond, or further bonded to other cycloalkyl, heterocyclyl, aryl and heteroaryl via any two or more atoms on the ring. The heterocyclyl can be optionally substituted or unsubstituted. When substituted, the substituent group(s) is preferably one or more group(s) independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio, heterocyclylthio, oxo, carboxy and alkoxycarbonyl.

The term "aryl" refers to a 6 to 14 membered all-carbon monocyclic ring or polycyclic fused ring (i.e. each ring in the system shares an adjacent pair of carbon atoms with another ring in the system) having a conjugated π-electron system, preferably a 6 to 10 membered aryl, for example, phenyl and naphthyl. The aryl is more preferably phenyl. The aryl ring can be fused to the ring of heteroaryl, heterocyclyl or cycloalkyl, wherein the ring bound to the parent structure is aryl ring. The aryl can be substituted or unsubstituted. When substituted, the substituent group(s) is preferably one or more group(s) independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio, heterocyclylthio, carboxy and alkoxycarbonyl.

The term "heteroaryl" refers to a 5 to 14 membered heteroaromatic system having 1 to 4 heteroatoms selected from the group consisting of oxygen, sulfur and nitrogen. The heteroaryl is preferably a 5 to 10 membered heteroaryl, more preferably a 5 or 6 membered heteroaryl, for example imidazolyl, furanyl, thienyl, thiazolyl, pyrazolyl, oxazolyl, pyrrolyl, triazolyl, tetrazolyl, pyridyl, pyrimidinyl, thiadiazolyl, oxadiazolyl, pyrazinyl and the like, preferably oxazolyl, oxadiazolyl, tetrazolyl, triazolyl, thienyl, imidazolyl, pyridyl, pyrazolyl, pyrimidinyl and thiazolyl, and more preferably oxazolyl, oxadiazolyl, tetrazolyl, triazolyl, thienyl, pyridyl, thiazolyl and pyrimidinyl. The heteroaryl ring can be fused to the ring of aryl, heterocyclyl or cycloalkyl, wherein the ring bound to the parent structure is heteroaryl ring. The heteroaryl can be optionally substituted or unsubstituted. When substituted, the substituent group(s) is preferably one or more group(s) independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio, heterocyclylthio, carboxy and alkoxycarbonyl.

The term "alkoxy" refers to an —O-(alkyl) or an —O-(unsubstituted cycloalkyl) group, wherein the alkyl is as defined above, preferably an alkoxy having 1 to 8 carbon atoms, more preferably an alkoxy having 1 to 6 carbon atoms, and most preferably an alkoxy having 1 to 3 carbon atoms. Non-limiting examples of alkoxy include methoxy, ethoxy, propoxy, butoxy, cyclopropyloxy, cyclobutyloxy, cyclopentyloxy and cyclohexyloxy. The alkoxy can be optionally substituted or unsubstituted. When substituted, the substituent group(s) is preferably one or more group(s) independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio, heterocyclylthio, carboxy and alkoxycarbonyl.

"Haloalkyl" refers to an alkyl group substituted by one or more halogen(s), wherein the alkyl is as defined above.

"Haloalkoxy" refers to an alkoxy group substituted by one or more halogen(s), wherein the alkoxy is as defined above.

"Hydroxyalkyl" refers to an alkyl group substituted by hydroxy(s), wherein the alkyl is as defined above.

"Alkenyl" refers to a chain alkenyl, also known as alkene group. The alkenyl can be further substituted by other related group, for example alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio, heterocyclylthio, carboxy or alkoxycarbonyl.

"Hydroxy" refers to an —OH group.

"Halogen" refers to fluorine, chlorine, bromine or iodine.

"Amino" refers to a $—NH_2$ group.

"Cyano" refers to a —CN group.

"Nitro" refers to a $—NO_2$ group.

"Carboxy" refers to a —C(O)OH group.

"THF" refers to tetrahydrofuran.

"EtOAc" refers to ethyl acetate.

"DMSO" refers to dimethyl sulfoxide.

"LDA" refers to lithium diisopropylamide.

"DMAP" refers to 4-dimethylaminopyridine.

"EtMgBr" refers to ethylmagnesium bromide.

"HOSu" refers to N-hydroxysuccinimide.

"EDCl" refers to 1-(3-dimethylaminopropyl)-3-ethylcarbodiimide hydrochloride.

"IPA" refers to isopropyl alcohol.

"MeOH" refers to methanol.

"EtOH" refers to ethanol.

"DMF" refers to N,N-dimethylformamide.

"DIPEA" refers to diisopropylethylamine.

"HEPES" refers to 4-hydroxyethylpiperazine ethanesulfonic acid.

Different expressions such as "X is selected from the group consisting of A, B or C", "X is selected from the group consisting of A, B and C", "X is A, B or C", "X is A, B and C" and the like, express the same meaning, that is, X can be any one or more of A, B and C.

"Optional" or "optionally" means that the event or circumstance described subsequently can, but need not, occur, and such a description includes the situation in which the event or circumstance does or does not occur.

"Substituted" refers to one or more hydrogen atoms in a group, preferably up to 5, and more preferably 1 to 3 hydrogen atoms, independently substituted by a corresponding number of substituents. It goes without saying that the substituents only exist in their possible chemical position. The person skilled in the art is able to determine whether the substitution is possible or impossible by experiments or theory without excessive efforts. For example, the combination of amino or hydroxy having free hydrogen and carbon atoms having unsaturated bonds (such as olefinic) may be unstable.

"Stereoisomerism" includes three categories of geometric isomerism (cis- and trans-isomerism), optical isomerism, and conformational isomerism.

The hydrogen atom described in the present invention may be substituted by its isotope deuterium, and any hydrogen atom in the example compound of the present invention may also be substituted by a deuterium atom.

A "pharmaceutical composition" refers to a mixture of one or more of the compounds according to the present invention or physiologically/pharmaceutically acceptable salts or prodrugs thereof with other chemical components, and other components such as physiologically/pharmaceutically acceptable carriers and excipients. The purpose of the pharmaceutical composition is to facilitate administration of a compound to an organism, which is conducive to the absorption of the active ingredient so as to exert biological activity.

X-ray powder diffraction (XRPD) pattern refers to the experimentally observed diffraction pattern or the parameters derived from it, and the X-ray powder diffraction pattern is characterized by peak position (abscissa) and peak intensity (ordinate). Those skilled in the art will appreciate that the experimental error therein depends on the conditions of the instrument, the preparation of the sample, and the purity of the sample. In particular, it is well known to those skilled in the art that X-ray diffraction pattern generally varies with the conditions of the instrument. Those skilled in the art will appreciate that suitable error tolerances for XRPD may be: $2\theta\pm0.5°$, $2\theta\pm0.4°$, $2\theta\pm0.3°$, $2\theta\pm0.2°$. In particular, it is important to point out that the relative intensity in X-ray diffraction pattern may vary with experimental conditions, so the order of peak intensity cannot be used as the sole or decisive factor. In addition, due to the influence of experimental factors such as the height of the sample, the overall deviation of the peak angle will occur, and a certain deviation is usually allowed. Therefore, those skilled in the art can understand that any crystal form having the same or similar characteristic peaks as the pattern of the present invention falls within the scope of the present invention.

"TGA" refers to thermogravimetric analysis (TGA) test.

"DSC" refers to differential scanning calorimetry (DSC) test.

"HPLC" refers to high performance liquid chromatography (HPLC) test.

"PK" refers to pharmacokinetic (PK) test.

The present invention will be further described with reference to the following examples, but the examples should not be considered as limiting the scope of the present invention.

I. Preparation of the Compounds

The structures of the compounds of the present invention are identified by nuclear magnetic resonance (NMR) and/or liquid chromatography-mass spectrometry (LC-MS). NMR shifts (δ) are given in parts per million (ppm). NMR is determined by a Bruker AVANCE-400 machine. The solvents for determination are deuterated-dimethyl sulfoxide (DMSO-$d_6$), deuterated-methanol ($CD_3OD$) and deuterated-chloroform ($CDCl_3$), and the internal standard is tetramethylsilane (TMS).

Liquid chromatography-mass spectrometry (LC-MS) is determined on an Agilent 1200 Infinity Series mass spectrometer. High performance liquid chromatography (HPLC) is determined on an Agilent 1200DAD high pressure liquid chromatograph (Sunfire C18 150×4.6 mm chromatographic column), and a Waters 2695-2996 high pressure liquid chromatograph (Gimini C18 150×4.6 mm chromatographic column).

Yantai Huanghai HSGF254 or Qingdao GF254 silica gel plate is used as the thin-layer silica gel chromatography (TLC) plate. The dimension of the silica gel plate used in TLC is 0.15 mm to 0.2 mm, and the dimension of the silica gel plate used in product purification is 0.4 mm to 0.5 mm. Yantai Huanghai 200 to 300 mesh silica gel is generally used as a carrier for column chromatography.

The raw materials used in the examples of the present invention are known and commercially available, or can be synthesized by adopting or according to known methods in the art.

Unless otherwise stated, all reactions of the present invention are carried out under continuous magnetic stirring under dry nitrogen or argon atmosphere. The solvent is dry, and the reaction temperature is in degrees celsius.

Compound a

3-(3-(2-(4-(2,3-Dichlorophenyl)piperazin-1-yl)ethyl) cyclobutyl)-1,1-dimethylurea

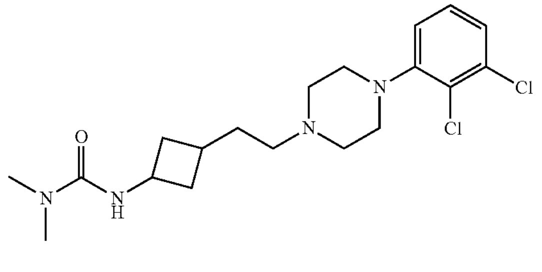 [SMILES: CN(C)C(=O)NC1CC(CCN2CCN(c3cccc(Cl)c3Cl)CC2)C1]

Step 1: Tert-butyl (3-oxocyclobutyl)carbamate

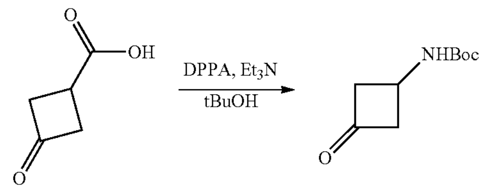 [SMILES: "tBuOH" ; O=C1CC(C(=O)O)C1 ; CC(C)(C)OC(=O)NC1CC(=O)C1]

3-Oxocyclobutane-1-carboxylic acid (1.5 g, 13.2 mmol), triethylamine (2.0 mL, 14.5 mmol) and toluene (30 mL) were added to a 100 mL eggplant-shaped flask successively. Diphenylphosphoryl azide (4.0 g, 14.5 mmol) was slowly added at −5° C. to 0° C. The reaction solution was stirred at 0° C. for 16 hours. The reaction solution was washed with saturated aqueous sodium bicarbonate solution (30 mL×1) and saturated aqueous sodium chloride solution (30 mL×1) at 0° C., and the organic phase was dried over anhydrous sodium sulfate. Tert-butanol (7.5 mL, 74.8 mmol) was added to the organic phase, and the reaction solution was heated to 100° C. and stirred for 16 hours. The reaction solution was concentrated to dryness by rotary evaporation to obtain a crude product. The crude product was purified by column chromatography (petroleum ether/ethyl acetate: 5/1) to obtain tert-butyl (3-oxocyclobutyl)carbamate (500 mg, yield: 20.5%).

$^1H$ NMR (400 MHz, $CDCl_3$) δ 4.86 (s, 1H), 4.27 (s, 1H), 3.50-3.33 (m, 2H), 3.11-2.97 (m, 2H), 1.46 (s, 9H).

Step 2: Methyl 2-(3-((tert-butoxycarbonyl)amino) cyclobutylidene)acetate

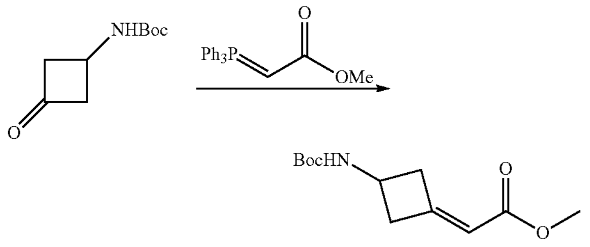

Tert-butyl (3-oxocyclobutyl)carbamate (450 mg, 2.43 mmol) and toluene (20 mL) were added to a 50 mL eggplant-shaped flask successively, followed by the slow addition of methyl (triphenylphosphoranylidene)acetate (1.22 g, 3.64 mmol). The reaction solution was refluxed under a nitrogen atmosphere for 16 hours, cooled, and concentrated to dryness by rotary evaporation to obtain a crude product. The crude product was purified by column chromatography (petroleum ether/ethyl acetate: 6/1) to obtain methyl 2-(3-((tert-butoxycarbonyl)amino)cyclobutylidene)acetate (450 mg, yield: 76.8%).

$^1H$ NMR (400 MHz, $CDCl_3$) δ 5.76-5.66 (m, 1H), 4.80 (br, 1H), 4.24 (s, 1H), 3.69 (s, 3H), 3.63-3.49 (m, 1H), 3.27-3.10 (m, 1H), 3.00-2.86 (m, 1H), 2.82-2.64 (m, 1H), 1.45 (s, 9H).

Step 3: Methyl 2-(3-((tert-butoxycarbonyl)amino) cyclobutyl)acetate

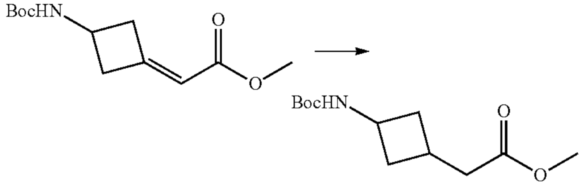

Methyl 2-(3-((tert-butoxycarbonyl)amino)cyclobutylidene)acetate (450 mg, 1.9 mmol) and methanol (10 mL) were added to a 50 mL eggplant-shaped flask successively. Pd/C (45 mg, containing 10% palladium and 50% water) were added slowly under a nitrogen atmosphere. The reaction solution was stirred under a hydrogen atmosphere (1 atm) for 5 hours, filtered, and concentrated to dryness by rotary evaporation to remove the solvent and obtain a crude product of methyl 2-(3-((tert-butoxycarbonyl)amino)cyclobutyl)acetate (450 mg), which was used directly in the next step.

MS m/z (ESI): 244.2 $[M+H]^+$.

Step 4: Tert-butyl (3-(2-hydroxyethyl)cyclobutyl)carbamate

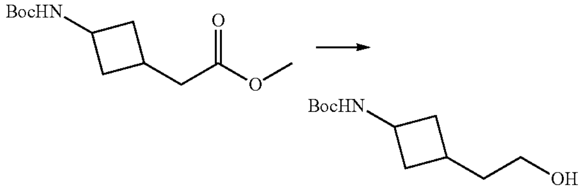

Methyl 2-(3-((tert-butoxycarbonyl)amino)cyclobutyl)acetate (450 mg, 1.9 mmol) and anhydrous tetrahydrofuran (10 mL) were added to a 50 mL eggplant-shaped flask successively. Lithium aluminum tetrahydride (210 mg, 5.6 mmol) was added slowly at 0° C. under a nitrogen atmosphere. The reaction solution was stirred at 0° C. for 2 hours, and the reaction was quenched by saturated aqueous sodium bicarbonate solution. The reaction solution was dried over anhydrous sodium sulfate directly, and stirred for 15 minutes. The organic phase was filtered, and concentrated to dryness by rotary evaporation to obtain a crude product of tert-butyl (3-(2-hydroxyethyl)cyclobutyl)carbamate (450 mg), which was used directly in the next step.

MS m/z (ESI): 216.2 $[M+H]^+$.

Step 5: 2-(3-((Tert-butoxycarbonyl)amino)cyclobutyl)ethyl 4-methylbenzenesulfonate

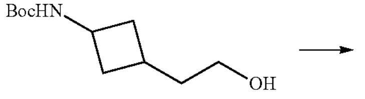

-continued

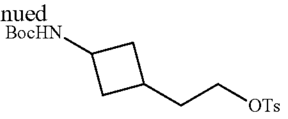

Tert-butyl (3-(2-hydroxyethyl)cyclobutyl)carbamate (450 mg, 2.1 mmol), triethylamine (634 mg, 6.3 mmol) and dichloromethane (10 mL) were added to a 50 mL eggplant-shaped flask successively, followed by the slow addition of 4-tosyl chloride (438 mg, 2.3 mmol). The reaction solution was stirred at room temperature overnight, followed by the addition of dichloromethane (20 mL), and washed with water (30 mL×1). The organic phase was dried and concentrated to dryness by rotary evaporation to obtain a crude product. The crude product was purified by column chromatography (petroleum ether/ethyl acetate: 5/1) to obtain 2-(3-((tert-butoxycarbonyl)amino)cyclobutyl)ethyl 4-methylbenzenesulfonate (710 mg, yield: 84%).

MS m/z (ESI): 370.2 $[M+H]^+$.

Step 6: Tert-butyl (3-(2-(4-(2,3-dichlorophenyl)piperazin-1-yl)ethyl)cyclobutyl)carbamate

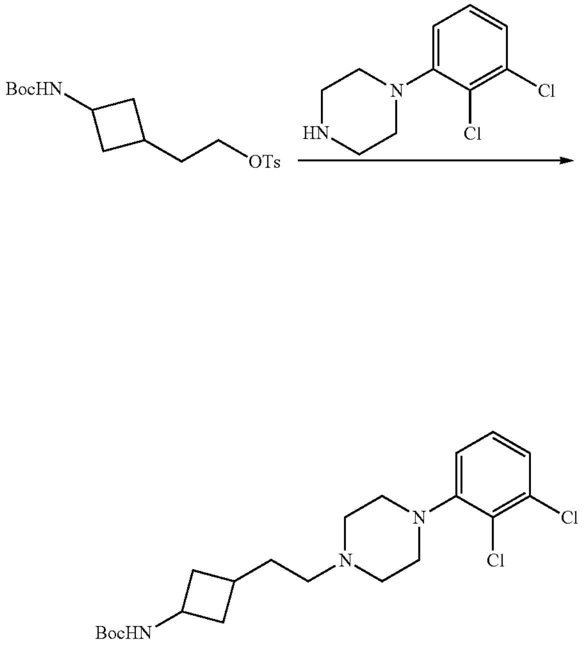

2-(3-((Tert-butoxycarbonyl)amino)cyclobutyl)ethyl 4-methylbenzenesulfonate (350 mg, 0.95 mmol), potassium carbonate (392 mg, 2.84 mmol) and acetonitrile (10 mL) were added to a 50 mL eggplant-shaped flask successively, followed by the slow addition of 1-(2,3-dichlorophenyl) piperazine (219 mg, 0.95 mmol). The reaction solution was refluxed overnight. The reaction solution was cooled, followed by the addition of dichloromethane (20 mL), and washed with water (30 mL×3). The organic phase was dried and concentrated to dryness by rotary evaporation to obtain a crude product. The crude product was purified by column chromatography (dichloromethane/methanol: 50/1) to obtain tert-butyl (3-(2-(4-(2,3-dichlorophenyl)piperazin-1-yl)ethyl)cyclobutyl)carbamate (310 mg, yield: 76%).

MS m/z (ESI): 428.2 $[M+H]^+$.

Step 7: 3-(2-(4-(2,3-Dichlorophenyl)piperazin-1-yl)ethyl)cyclobutan-1-amine hydrochloride

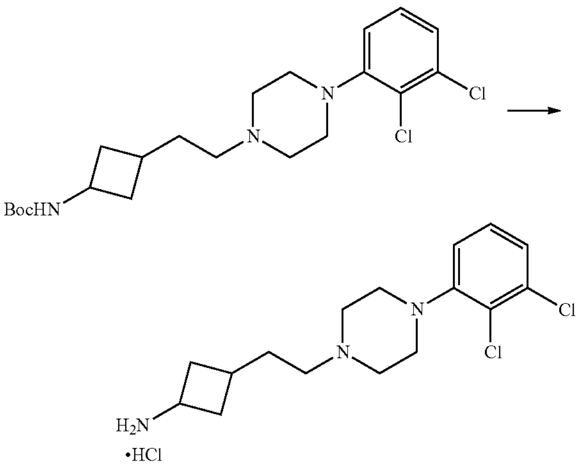

Tert-butyl (3-(2-(4-(2,3-dichlorophenyl)piperazin-1-yl)ethyl)cyclobutyl)carbamate (310 mg, 0.72 mmol) and ethyl acetate (2 mL) were added to a 25 mL eggplant-shaped flask successively, followed by the addition of hydrochloric acid in ethyl acetate (10 mL, 4M) at 0° C. The reaction solution was stirred at room temperature for 1 hour, and concentrated to dryness by rotary evaporation to remove the solvent and obtain a crude product of 3-(2-(4-(2,3-dichlorophenyl)piperazin-1-yl)ethyl)cyclobutan-1-amine hydrochloride (310 mg), which was used directly in the next step.

MS m/z (ESI): 328.1 $[M+H]^+$.

Step 8: 3-(3-(2-(4-(2,3-Dichlorophenyl)piperazin-1-yl)ethyl)cyclobutyl)-1,1-dimethylurea

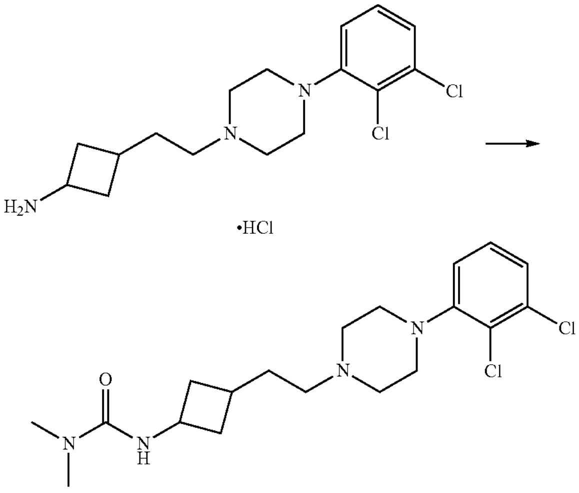

3-(2-(4-(2,3-Dichlorophenyl)piperazin-1-yl)ethyl)cyclobutan-1-amine hydrochloride (50 mg, 0.11 mmol), triethylamine (69 mg, 0.69 mmol) and dichloromethane (2 mL) were added to a 10 mL reaction flask successively, followed by the addition of dimethylcarbamoyl chloride (18.4 mg, 0.17 mmol) under stirring. The reaction solution was stirred at room temperature for 12 hours, and concentrated to dryness by rotary evaporation to remove the solvent and obtain a crude product. The crude product was purified by preparative HPLC to obtain 3-(3-(2-(4-(2,3-dichlorophenyl)piperazin-1-yl)ethyl)cyclobutyl)-1,1-dimethylurea (11 mg, yield: 24%).

$^1H$ NMR (400 MHz, $CDCl_3$) δ 7.23-7.10 (m, 2H), 7.08-6.91 (m, 1H), 4.61-3.93 (m, 2H), 3.56-3.02 (m, 4H), 3.03-2.64 (m, 8H), 2.65-2.31 (m, 3H), 2.31-1.21 (m, 7H).

MS m/z (ESI): 399.2$[M+H]^+$.

Compound b 1-Cyclopropyl-3-(3-(2-(4-(2,3-dichlorophenyl)piperazin-1-yl)ethyl)cyclobutyl)urea

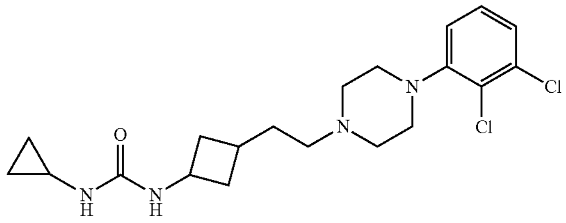 [SMILES: O=C(NC1CC1)NC1CC(CCN2CCN(c3cccc(Cl)c3Cl)CC2)C1]

Step 1: 1-Cyclopropyl-3-(3-(2-(4-(2,3-dichlorophenyl)piperazin-1-yl)ethyl)cyclobutyl)urea

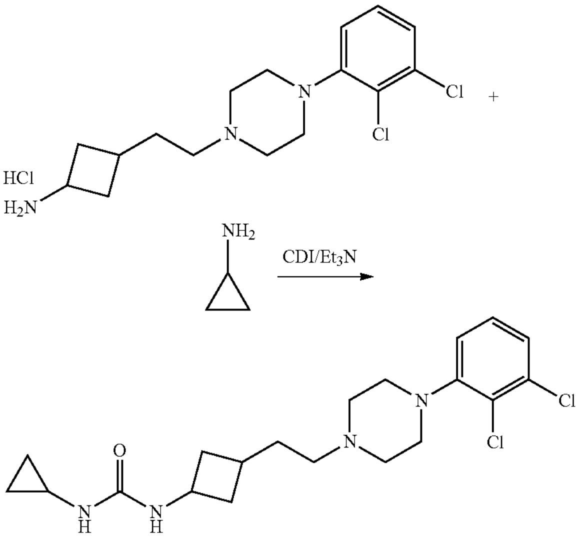

3-(2-(4-(2,3-Dichlorophenyl)piperazin-1-yl)ethyl)cyclobutan-1-amine hydrochloride (33 mg, 0.09 mmol), triethylamine (46 mg, 0.45 mmol) and N'N-carbonyldiimidazole (22 mg, 0.16 mmol) were dissolved in dichloromethane (2 mL). The reaction solution was stirred at room temperature for 2 hours, and the raw materials disappeared. Cyclopropylamine (10 mg, 0.18 mmol) was added, and the reaction solution was stirred at 35° C. for 48 hours. The reaction solution was concentrated to dryness by rotary evaporation, and the resulting crude product was purified by preparative HPLC to obtain 1-cyclopropyl-3-(3-(2-(4-(2,3-dichlorophenyl)piperazin-1-yl)ethyl)cyclobutyl)urea (12 mg, yield: 32.2%).

$^1$H NMR (400 MHz, $CDCl_3$) δ 7.20-7.12 (m, 2H), 6.97 (dd, J=7.0, 2.4 Hz, 1H), 5.08 (dd, J=28.8, 7.3 Hz, 1H), 4.64 (s, 1H), 4.43-4.09 (m, 1H), 3.14 (s, 4H), 2.73 (s, 4H), 2.56 (ddd, J=16.2, 7.4, 2.8 Hz, 2H), 2.43 (s, 3H), 2.05 (dddd, J=33.4, 24.1, 16.7, 8.5 Hz, 4H), 1.83-1.68 (m, 2H), 1.48 (dt, J=9.6, 6.0 Hz, 2H), 0.76 (q, J=6.3 Hz, 2H), 0.61-0.53 (m, 2H).

MS m/z (ESI): 411.2[M+H]$^+$.

Compound c N-(3-(2-(4-(2,3-Dichlorophenyl)piperazin-1-yl)ethyl)cyclobutyl)-1H-indole-2-carboxamide

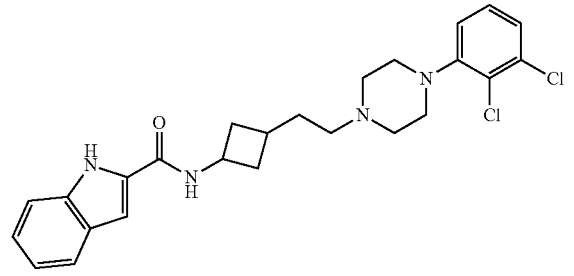 [SMILES: O=C(NC1CC(CCN2CCN(c3cccc(Cl)c3Cl)CC2)C1)c1cc2ccccc2[nH]1]

Step 1: N-(3-(2-(4-(2,3-Dichlorophenyl)piperazin-1-yl)ethyl)cyclobutyl)-1H-indole-2-carboxamide

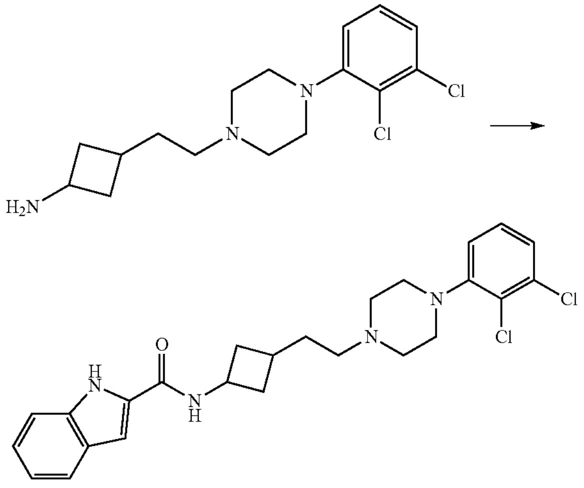

3-(2-(4-(2,3-Dichlorophenyl)piperazin-1-yl)ethyl)cyclobutan-1-amine (50 mg, 0.15 mmol) was dissolved in N,N-dimethylformamide (3 mL), followed by the addition of 1H-indole-2-carboxylic acid (30 mg, 0.18 mmol), HATU (86 mg, 0.23 mmol) and diisopropylethylamine (58 mg, 0.45 mmol). The reaction solution was stirred at room temperature overnight, and concentrated to dryness by rotary evaporation. The resulting crude product was purified by high performance liquid chromatography to obtain N-(3-(2-(4-(2,3-dichlorophenyl)piperazin-1-yl)ethyl)cyclobutyl)-1H-indole-2-carboxamide.

MS m/z (ESI): 471.2[M+H]$^+$.

Compound d 3-(3-(2-(4-(Benzo[b]thiophen-4-yl)piperazin-1-yl)ethyl)cyclobutyl)-1,1-dimethylurea

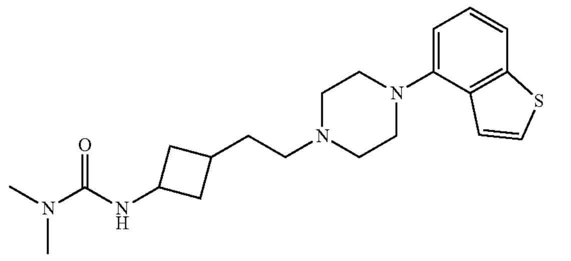 [SMILES: CN(C)C(=O)NC1CC(CCN2CCN(c3cccc4sccc34)CC2)C1]

Step 1: Tert-butyl (3-(2-(4-(benzo[b]thiophen-4-yl)piperazin-1-yl)ethyl)cyclobutyl)carbamate

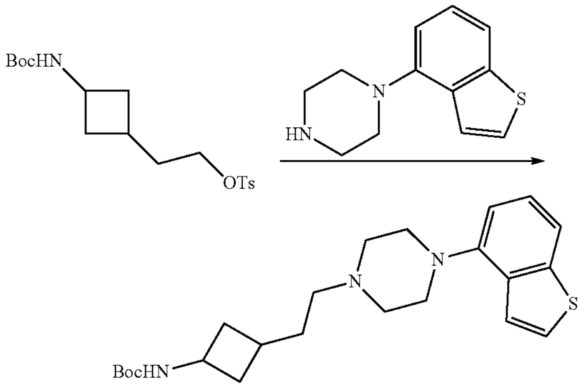

2-(3-((Tert-butoxycarbonyl)amino)cyclobutyl)ethyl 4-methylbenzenesulfonate (200 mg, 0.54 mmol), potassium carbonate (224 mg, 1.62 mmol) and acetonitrile (10 mL) were added to a 50 mL eggplant-shaped flask successively, followed by the slow addition of 1-(benzo[b]thiophen-4-yl)piperazine (118 mg, 0.54 mmol). The reaction solution was refluxed overnight. The reaction solution was cooled, followed by the addition of dichloromethane (20 mL), and washed with water (30 mL×3). The organic phase was dried and concentrated to dryness by rotary evaporation to obtain a crude product. The crude product was purified by column chromatography (dichloromethane/methanol: 50/1) to obtain tert-butyl (3-(2-(4-(benzo[b]thiophen-4-yl)piperazin-1-yl)ethyl)cyclobutyl)carbamate (120 mg, yield: 53%).

MS m/z (ESI): 416.2 [M+H]$^+$.

Step 2: 3-(2-(4-(Benzo[b]thiophen-4-yl)piperazin-1-yl)ethyl)cyclobutan-1-amine hydrochloride

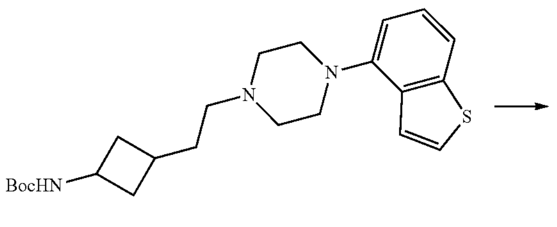

-continued

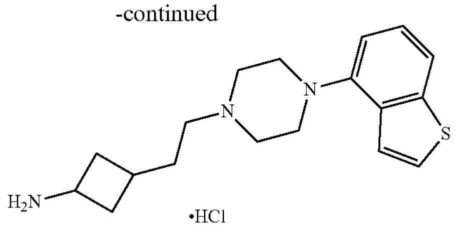

Tert-butyl (3-(2-(4-(benzo[b]thiophen-4-yl)piperazin-1-yl)ethyl)cyclobutyl)carbamate (120 mg, 0.29 mmol) and ethyl acetate (1 mL) were added to a 25 mL eggplant-shaped flask successively, followed by the addition of hydrochloric acid in ethyl acetate (6 mL, 4M) at 0° C. The reaction solution was stirred at room temperature for 1 hour, and concentrated to dryness by rotary evaporation to remove the solvent and obtain a crude hydrochloride (110 mg), which was used directly in the next step.

MS m/z (ESI): 316.1 $[M+H]^+$.

Step 3: 3-(3-(2-(4-(Benzo[b]thiophen-4-yl)piperazin-1-yl)ethyl)cyclobutyl)-1,1-dimethylurea

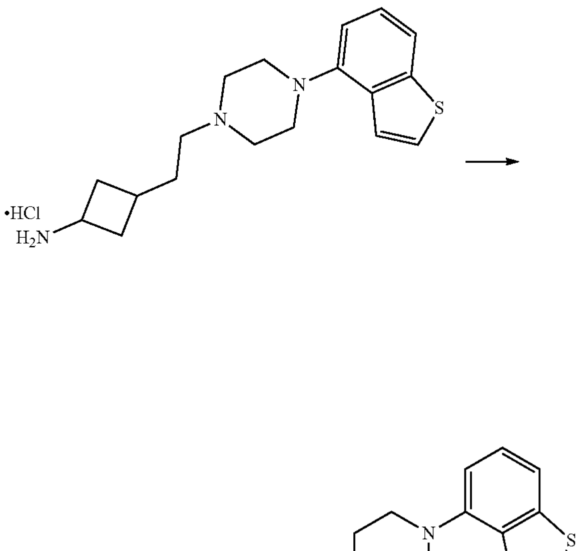

3-(2-(4-(Benzo[b]thiophen-4-yl)piperazin-1-yl)ethyl)cyclobutan-1-amine hydrochloride (50 mg, 0.12 mmol), triethylamine (71 mg, 0.70 mmol) and dichloromethane (2 mL) were added to a 10 mL reaction flask successively, followed by the addition of dimethylcarbamoyl chloride (19 mg, 0.18 mmol) under stirring. The reaction solution was stirred at room temperature for 12 hours, and concentrated to dryness by rotary evaporation to remove the solvent and obtain a crude product. The crude product was purified by preparative HPLC to obtain 3-(3-(2-(4-(benzo[b]thiophen-4-yl)piperazin-1-yl)ethyl)cyclobutyl)-1,1-dimethylurea (17 mg, yield: 37%).

MS m/z (ESI): 387.2 $[M+H]^+$.

Example 1

N-(3-(2-(4-(2,3-Dichlorophenyl)piperazin-1-yl)ethyl)cyclobutyl)-5-methylfuran-2-carb oxamide

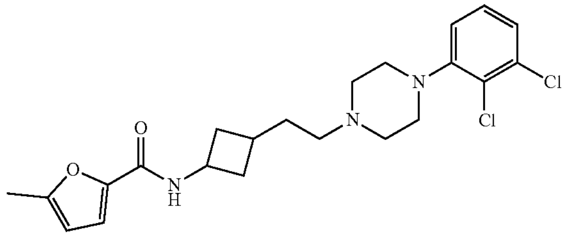 [SMILES: Cc1ccc(C(=O)NC2CC(CCN3CCN(c4cccc(Cl)c4Cl)CC3)C2)o1]

In accordance with Step 8 of Compound a, N-(3-(2-(4-(2,3-dichlorophenyl)piperazin-1-yl)ethyl)cyclobutyl)-5-methylfuran-2-carboxamide (23 mg, white solid, yield: 28.3%) was obtained.

$^1$H NMR (400 MHz, Chloroform-d) δ 7.21-7.12 (m, 2H), 7.01-6.96 (m, 2H), 6.39 (dd, J=34.1, 8.0 Hz, 1H), 6.11-6.06 (m, 1H), 4.52 (dq, J=84.5, 8.0 Hz, 1H), 3.23-3.05 (m, 4H), 2.76 (s, 4H), 2.59 (td, J=7.4, 6.8, 2.2 Hz, 1H), 2.48-2.46 (m, 1H), 2.35 (s, 3H), 2.24-2.13 (m, 2H), 2.04-1.97 (m, 1H), 1.84-1.75 (m, 2H), 1.62 (qd, J=9.1, 2.8 Hz, 2H).

MS m/z (ESI): 436.1 $[M+H]^+$.

Example 2

N-(3-(2-(4-(2,3-Dichlorophenyl)piperazin-1-yl)ethyl)cyclobutyl)-2-methoxyacetamide

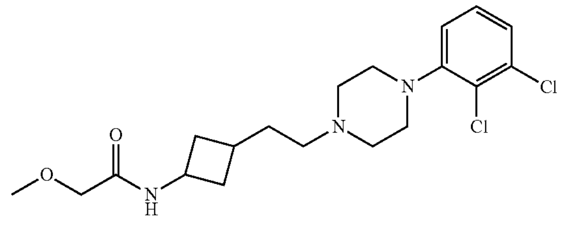 [SMILES: COCC(=O)NC1CC(CCN2CCN(c3cccc(Cl)c3Cl)CC2)C1]

In accordance with Step 8 of Compound a, N-(3-(2-(4-(2,3-dichlorophenyl)piperazin-1-yl)ethyl)cyclobutyl)-2-methoxyacetamide (29 mg, white solid, yield: 33%) was obtained.

$^1$H NMR (400 MHz, Chloroform-d) δ 7.19-7.12 (m, 2H), 6.97 (dd, J=7.0, 2.5 Hz, 1H), 6.63 (dd, J=42.2, 8.2 Hz, 1H), 4.42 (dq, J=87.5, 7.9 Hz, 1H), 3.86 (d, J=4.7 Hz, 2H), 3.42 (d, J=2.5 Hz, 3H), 3.22-3.06 (m, 4H), 2.81-2.61 (m, 4H), 2.58-2.52 (m, 1H), 2.45-2.32 (m, 2H), 2.21-2.03 (m, 2H), 2.02-1.91 (m, 1H), 1.79-1.73 (m, 1H), 1.70-1.67 (m, 1H), 1.57-1.49 (m, 1H).

MS m/z (ESI): 400.1 $[M+H]^+$.

Example 3

N-(3-(2-(4-(2,3-Dichlorophenyl)piperazin-1-yl)ethyl)cyclobutyl)nicotinamide

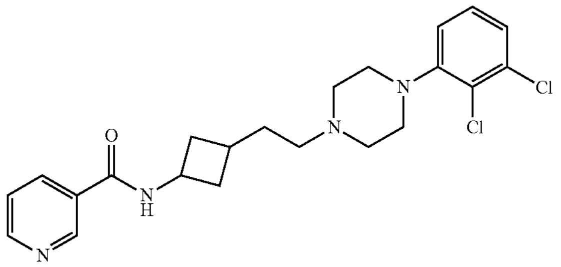 [SMILES: O=C(NC1CC(CCN2CCN(c3cccc(Cl)c3Cl)CC2)C1)c1cccnc1]

In accordance with Compound c, N-(3-(2-(4-(2,3-dichlorophenyl)piperazin-1-yl)ethyl)cyclobutyl)nicotinamide (25 mg, white solid, yield: 29%) was obtained.

$^1$H NMR (400 MHz, Chloroform-d) δ 8.97 (d, J=2.2 Hz, 1H), 8.72 (dd, J=4.8, 1.8 Hz, 1H), 8.12 (dq, J=8.0, 2.0 Hz, 1H), 7.44-7.34 (m, 1H), 7.19-7.12 (m, 2H), 6.97 (dt, J=7.0, 2.7 Hz, 1H), 6.41 (dd, J=14.4, 7.5 Hz, 1H), 4.85-4.34 (m, 1H), 3.12 (t, J=5.0 Hz, 4H), 2.78-2.66 (m, 4H), 2.46-2.39 (m, 2H), 2.27-2.16 (m, 2H), 2.13-2.02 (m, 1H), 1.87-1.79 (m, 1H), 1.79-1.57 (m, 3H).

MS m/z (ESI): 433.1 [M+H]$^+$.

Example 4

N-(3-(2-(4-(2,3-Dichlorophenyl)piperazin-1-yl)ethyl)cyclobutyl)-2-hydroxy-2-methylpropanamide

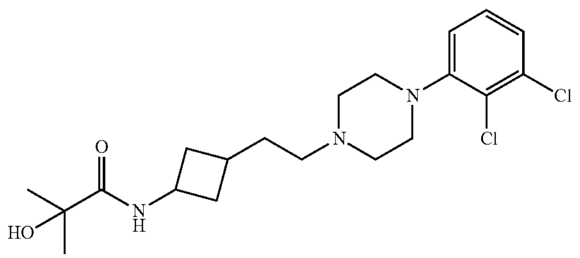 [SMILES: CC(C)(O)C(=O)NC1CC(CCN2CCN(c3cccc(Cl)c3Cl)CC2)C1]

In accordance with Compound c, N-(3-(2-(4-(2,3-dichlorophenyl)piperazin-1-yl)ethyl)cyclobutyl)-2-hydroxy-2-methylpropanamide (32 mg, white solid, yield: 30%) was obtained.

MS m/z (ESI): 414.1 [M+H]$^+$.

Example 5

N-(3-(2-(4-(2,3-Dichlorophenyl)piperazin-1-yl)ethyl)cyclobutyl)-3-methoxyazetidine-1-carboxamide

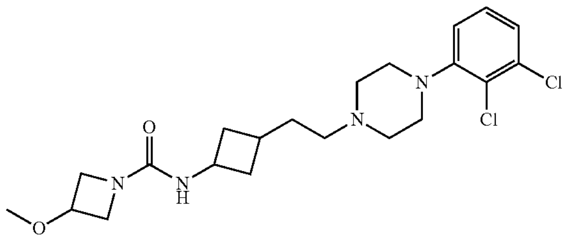 [SMILES: COC1CN(C(=O)OC2CC(CCN3CCN(c4cccc(Cl)c4Cl)CC3)C2)C1]

In accordance with Compound b, N-(3-(2-(4-(2,3-dichlorophenyl)piperazin-1-yl)ethyl)cyclobutyl)-3-methoxyazetidine-1-carboxamide (22 mg, white solid, yield: 23%) was obtained.

$^1$H NMR (400 MHz, Chloroform-d) δ 7.18-7.12 (m, 2H), 6.96 (dd, J=7.1, 2.6 Hz, 1H), 4.41-4.22 (m, 1H), 4.21-4.15 (m, 2H), 4.11-4.06 (m, 2H), 3.85-3.78 (m, 2H), 3.29 (s, 3H), 3.16-3.08 (m, 4H), 2.69 (s, 4H), 2.55-2.49 (m, 1H), 2.42-2.35 (m, 2H), 2.11 (ddd, J=11.5, 7.3, 2.9 Hz, 1H), 2.04-1.85 (m, 2H), 1.71 (dq, J=32.8, 7.8 Hz, 2H), 1.44 (td, J=9.2, 2.9 Hz, 1H).

MS m/z (ESI): 441.1 [M+H]$^+$.

Example 6

N-(3-(2-(4-(2,3-Dichlorophenyl)piperazin-1-yl)ethyl)cyclobutyl)-1-hydroxycyclopropane-1-carboxamide

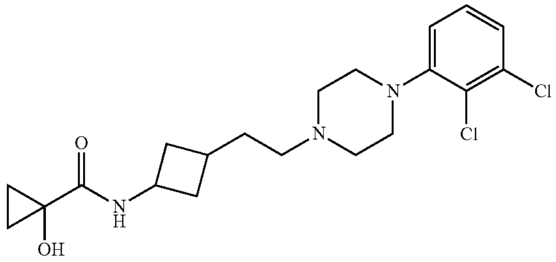

Step 1: N-(3-(2-(4-(2,3-Dichlorophenyl)piperazin-1-yl)ethyl)cyclobutyl)-1-hydroxycyclopropane-1-carboxamide

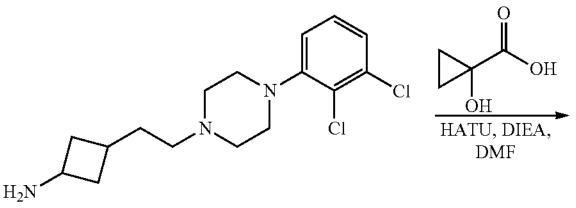

-continued

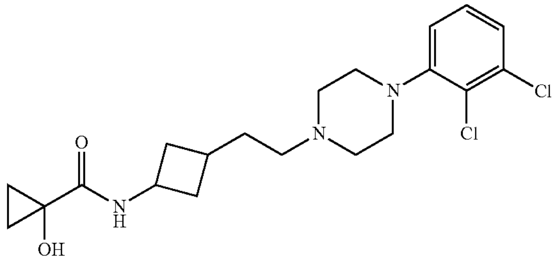 [SMILES: O=C(NC1CC(CCN2CCN(c3cccc(Cl)c3Cl)CC2)C1)C1(O)CC1]

3-(2-(4-(2,3-Dichlorophenyl)piperazin-1-yl)ethyl)cyclobutan-1-amine (50 mg, 0.15 mmol) was dissolved in N,N-dimethylformamide (3 mL), followed by the addition of 1-hydroxycyclopropane-1-carboxylic acid (18 mg, 0.18 mmol), HATU (86 mg, 0.23 mmol) and diisopropylethylamine (58 mg, 0.45 mmol). The reaction solution was stirred at room temperature overnight, and concentrated to dryness by rotary evaporation. The resulting crude product was purified by high performance liquid chromatography to obtain N-(3-(2-(4-(2,3-dichlorophenyl)piperazin-1-yl)ethyl)cyclobutyl)-1-hydroxycyclopropane-1-carboxamide (13 mg, white solid, yield: 21%).

$^{1}$H NMR (400 MHz, Chloroform-d) δ 7.20-7.12 (m, 2H), 7.07 (dd, J=28.3, 8.0 Hz, 1H), 6.96 (dd, J=7.1, 2.5 Hz, 1H), 4.38 (dq, J=87.6, 7.9 Hz, 1H), 3.20-3.05 (m, 4H), 2.72 (s, 4H), 2.56 (dd, J=8.9, 2.9 Hz, 1H), 2.41 (dd, J=9.5, 6.3 Hz, 2H), 2.25 (d, J=8.4 Hz, 1H), 2.19-2.06 (m, 2H), 1.99 (dd, J=14.2, 6.4 Hz, 1H), 1.82-1.69 (m, 2H), 1.55 (dd, J=9.1, 2.9 Hz, 1H), 1.35-1.30 (m, 2H), 1.01 (q, J=4.6 Hz, 2H).

MS m/z (ESI): 412.1 [M+H]$^{+}$.

Example 6A

N-(Trans-3-(2-(4-(2,3-dichlorophenyl)piperazin-1-yl)ethyl)cyclobutyl)-1-hydroxycyclopropane-1-carboxamide

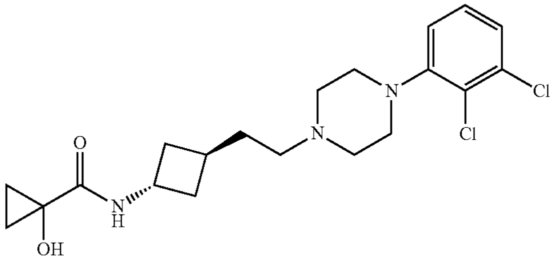 [SMILES: O=C(N[C@H]1C[C@H](CCN2CCN(c3cccc(Cl)c3Cl)CC2)C1)C1(O)CC1]

Step 1: N-(Trans-3-(2-(4-(2,3-dichlorophenyl)piperazin-1-yl)ethyl)cyclobutyl)-1-hydroxycyclopropane-1-carboxamide

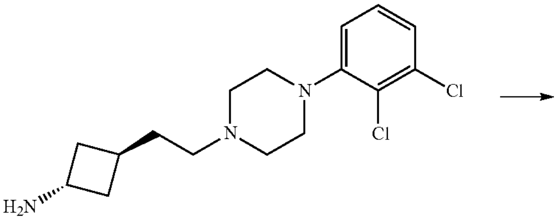

1-1

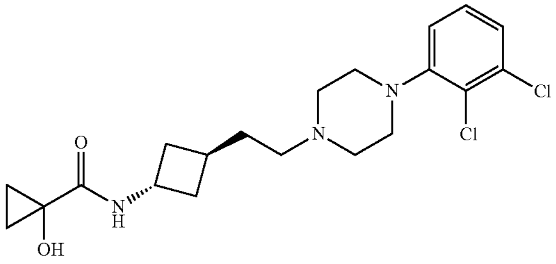

In accordance with the reaction conditions of Example 6, N-(Trans-3-(2-(4-(2,3-dichlorophenyl)piperazin-1-yl)ethyl)cyclobutyl)-1-hydroxycyclopropane-1-carboxamide was obtained with intermediate 1-1 as starting material.

$^{1}$H NMR (400 MHz, Chloroform-d) δ 7.20-7.13 (m, 2H), 7.07 (d, J=8.0 Hz, 1H), 6.97 (dd, J=7.0, 2.6 Hz, 1H), 4.56-4.44 (m, 1H), 3.22-3.07 (m, 4H), 2.86-2.66 (m, 4H), 2.50-2.41 (m, 2H), 2.32-2.24 (m, 1H), 2.20-2.05 (m, 5H), 1.84-1.76 (m, 2H), 1.38-1.32 (m, 2H), 1.06-1.00 (m, 2H).

MS m/z (ESI): 412.1 [M+H]$^{+}$.

Example 6B

N-(Cis-3-(2-(4-(2,3-dichlorophenyl)piperazin-1-yl)ethyl)cyclobutyl)-1-hydroxycyclopropane-1-carboxamide

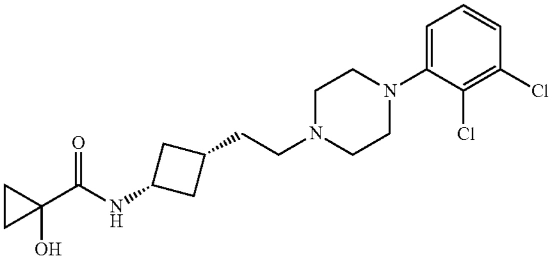 [SMILES: O=C(N[C@H]1C[C@@H](CCN2CCN(c3cccc(Cl)c3Cl)CC2)C1)C1(O)CC1]

Step 1: N-(Cis-3-(2-(4-(2,3-dichlorophenyl)piperazin-1-yl)ethyl)cyclobutyl)-1-hydroxycyclopropane-1-carboxamide

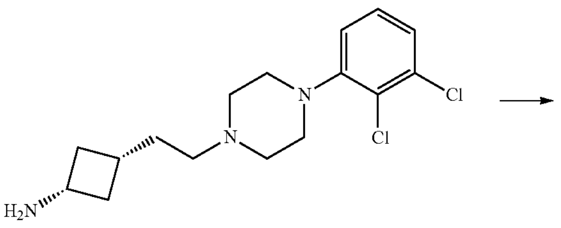

1-2

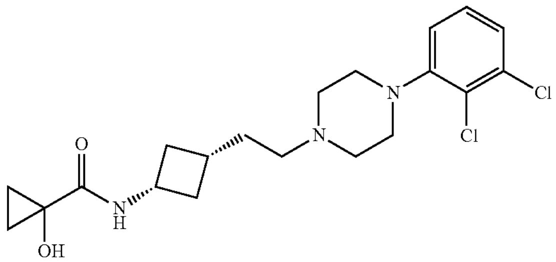

In accordance with the reaction conditions of Example 6, N-(cis-3-(2-(4-(2,3-dichlorophenyl)piperazin-1-yl)ethyl)cyclobutyl)-1-hydroxycyclopropane-1-carboxamide was obtained with intermediate 1-2 as starting material.

MS m/z (ESI): 412.1 $[M+H]^+$.

$^1$H NMR (400 MHz, Chloroform-d) δ 7.24-7.15 (m, 2H), 7.09 (d, J=7.8 Hz, 1H), 7.02-6.98 (m, 1H), 4.36-4.25 (m, 1H), 3.33 (s, 4H), 3.18-2.95 (m, 3H), 2.73-2.65 (m, 2H), 2.63-2.54 (m, 2H), 2.05-1.89 (m, 4H), 1.71-1.59 (m, 3H), 1.36-1.30 (m, 2H), 1.06-1.00 (m, 2H).

Example 7

N-(3-(2-(4-(2,3-Dichlorophenyl)piperazin-1-yl)ethyl)cyclobutyl)thiazole-2-carboxamide

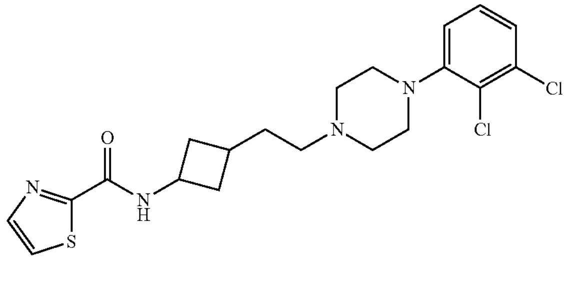 [SMILES: O=C(NC1CC(CCN2CCN(c3cccc(Cl)c3Cl)CC2)C1)c1nccs1]

Step 1: N-(3-(2-(4-(2,3-Dichlorophenyl)piperazin-1-yl)ethyl)cyclobutyl)thiazole-2-carboxamide

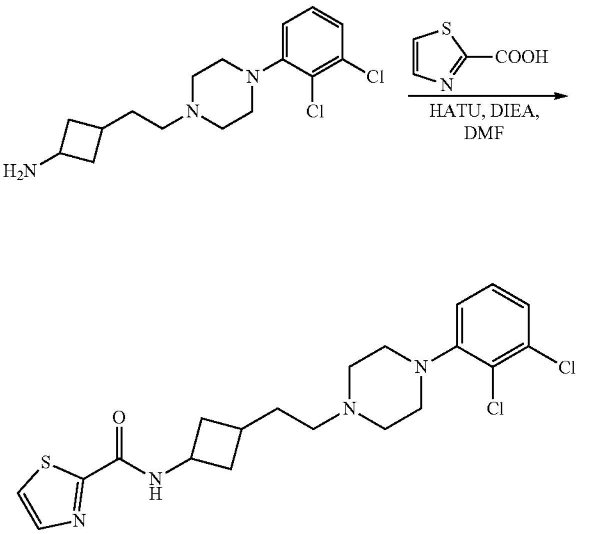

3-(2-(4-(2,3-Dichlorophenyl)piperazin-1-yl)ethyl)cyclobutan-1-amine (50 mg, 0.15 mmol) was dissolved in N,N-dimethylformamide (3 mL), followed by the addition of thiazole-2-carboxylic acid (23 mg, 0.18 mmol), HATU (86 mg, 0.23 mmol) and diisopropylethylamine (58 mg, 0.45 mmol). The reaction solution was stirred at room temperature overnight, and concentrated to dryness by rotary evaporation. The resulting crude product was purified by high performance liquid chromatography to obtain N-(3-(2-(4-(2,3-dichlorophenyl)piperazin-1-yl)ethyl)cyclobutyl)thiazole-2-carboxamide (21 mg, white solid, yield: 32%).

$^1$H NMR (400 MHz, Chloroform-d) δ 7.86 (dd, J=3.1, 1.5 Hz, 1H), 7.57 (d, J=3.1 Hz, 1H), 7.40 (dd, J=42.4, 8.2 Hz, 1H), 7.20-7.12 (m, 2H), 7.01-6.93 (m, 1H), 4.73- 4.28 (m, 1H), 3.18-3.03 (m, 4H), 2.78-2.54 (m, 6H), 2.44-2.35 (m, 2H), 2.24-2.19 (m, 1H), 2.10-1.98 (m, 1H), 1.81-1.75 (m, 1H), 1.71-1.65 (m, 2H).

MS m/z (ESI): 439.1 $[M+H]^+$.

Example 7A

N-(Trans-3-(2-(4-(2,3-dichlorophenyl)piperazin-1-yl)ethyl)cyclobutyl)thiazole-2-carboxamide

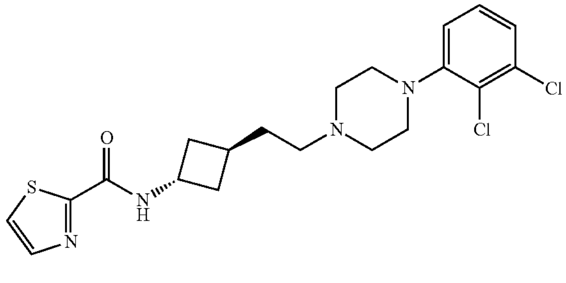 [SMILES: O=C(N[C@H]1C[C@H](CCN2CCN(c3cccc(Cl)c3Cl)CC2)C1)c1nccs1]

Step 1: N-(Trans-3-(2-(4-(2,3-dichlorophenyl)piperazin-1-yl)ethyl)cyclobutyl)thiazole-2-carboxamide

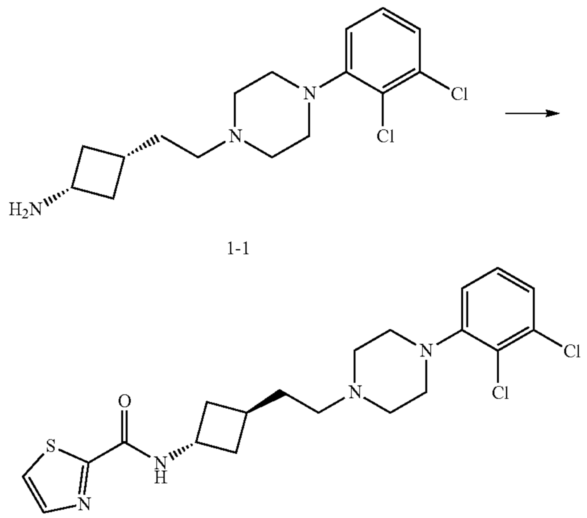

1-1

In accordance with the reaction conditions of Example 7, N-(Trans-3-(2-(4-(2,3-dichlorophenyl)piperazin-1-yl)ethyl)cyclobutyl)thiazole-2-carboxamide (21 mg, white solid, yield: 32%) was obtained with intermediate 1-1 as starting material.

$^1$H NMR (400 MHz, Chloroform-d) δ 7.86 (d, J=3.1 Hz, 1H), 7.57 (d, J=3.1 Hz, 1H), 7.45 (d, J=8.0 Hz, 1H), 7.21-7.13 (m, 2H), 7.00-6.95 (m, 1H), 4.74-4.59 (m, 1H), 3.18-3.02 (m, 4H), 2.79-2.58 (m, 4H), 2.47-2.38 (m, 2H), 2.35-2.27 (m, 1H), 2.25-2.18 (m, 4H), 1.87-1.77 (m, 2H).

MS m/z (ESI): 439.1 $[M+H]^+$.

Example 8

N-(3-(2-(4-(2,3-Dichlorophenyl)piperazin-1-yl)ethyl)cyclobutyl)-3-hydroxy-3-methylbutanamide

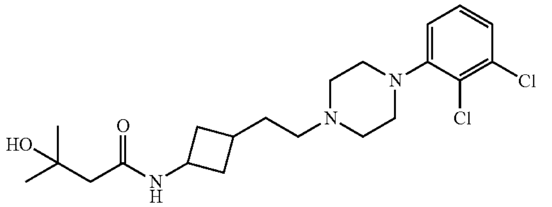 [SMILES: CC(C)(O)CC(=O)NC1CC(CCN2CCN(c3cccc(Cl)c3Cl)CC2)C1]

In accordance with Compound C, N-(3-(2-(4-(2,3-dichlorophenyl)piperazin-1-yl)ethyl)cyclobutyl)-3-hydroxy-3-methylbutan amide (21 mg, white solid, yield: 20%) was obtained.

$^1$H NMR (400 MHz, Chloroform-d) δ 7.21-7.13 (m, 2H), 6.96 (dd, J=7.0, 2.7 Hz, 1H), 6.08 (dd, J=21.6, 7.5 Hz, 1H), 4.51-4.19 (m, 2H), 3.10 (d, J=6.2 Hz, 4H), 2.76-2.62 (m, 4H), 2.56 (ddd, J=8.9, 5.9, 2.7 Hz, 1H), 2.42-2.36 (m, 2H), 2.29 (d, J=6.4 Hz, 2H), 2.05-1.96 (m, 3H), 1.72 (dq, J=28.0, 7.6 Hz, 2H), 1.51 (td, J=9.1, 2.8 Hz, 1H), 1.27 (d, J=2.2 Hz, 6H).

MS m/z (ESI): 428.1 $[M+H]^+$.

Example 9

N-(3-(2-(4-(2,3-Dichlorophenyl)piperazin-1-yl)ethyl)cyclobutyl)-2-(5-methyloxazol-2-yl)acetamide

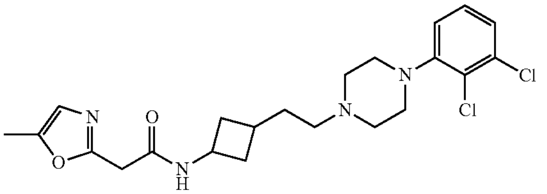 [SMILES: Cc1cnc(CC(=O)NC2CC(CCN3CCN(c4cccc(Cl)c4Cl)CC3)C2)o1]

In accordance with Compound c, N-(3-(2-(4-(2,3-dichlorophenyl)piperazin-1-yl)ethyl)cyclobutyl)-2-(5-methyloxazol-2-yl)acetamide (15 mg, white solid, yield: 16%) was obtained.

MS m/z (ESI): 451.1 $[M+H]^+$.

Example 10

N-(3-(2-(4-(2,3-Dichlorophenyl)piperazin-1-yl)ethyl)cyclobutyl)-2-(3-methylisoxazol-5-yl)acetamide

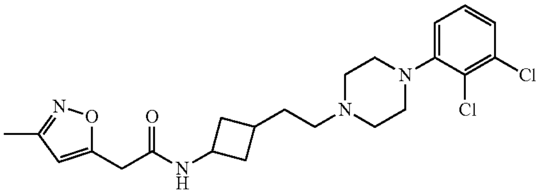 [SMILES: Cc1cc(CC(=O)NC2CC(CCN3CCN(c4cccc(Cl)c4Cl)CC3)C2)on1]

In accordance with Compound c, N-(3-(2-(4-(2,3-dichlorophenyl)piperazin-1-yl)ethyl)cyclobutyl)-2-(3-methylisoxazol-5-yl) acetamide (26 mg, white solid, yield: 28%) was obtained.

MS m/z (ESI): 451.1 $[M+H]^+$.

Example 11

N-(3-(2-(4-(2,3-Dichlorophenyl)piperazin-1-yl)ethyl)cyclobutyl)cyclopropanesulfonamide

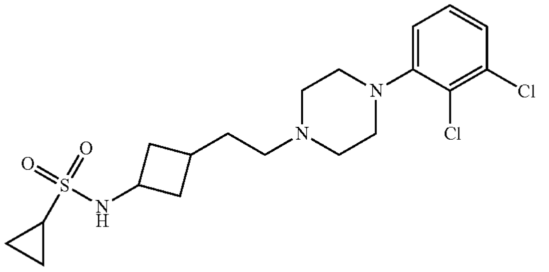 [SMILES: O=S(=O)(NC1CC(CCN2CCN(c3cccc(Cl)c3Cl)CC2)C1)C1CC1]

Step 1: N-(3-(2-(4-(2,3-Dichlorophenyl)piperazin-1-yl)ethyl)cyclobutyl)cyclopropanesulfonamide

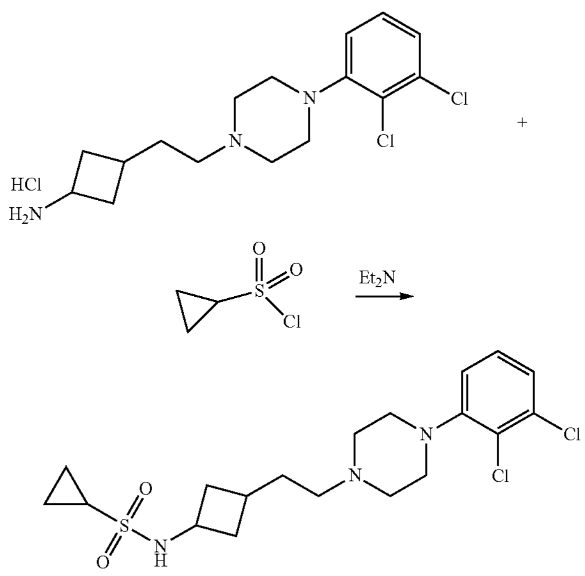

3-(2-(4-(2,3-Dichlorophenyl)piperazin-1-yl)ethyl)cyclobutan-1-amine hydrochloride (40 mg, 0.11 mmol), triethylamine (44 mg, 0.44 mmol) and cyclopropanesulfonyl chloride (31 mg, 0.22 mmol) were dissolved in dichloromethane (2 mL). The reaction solution was stirred at room temperature for 12 hours, and concentrated to dryness by rotary evaporation to remove the solvent. The resulting crude product was purified by preparative HPLC to obtain N-(3-(2-(4-(2,3-dichlorophenyl)piperazin-1-yl)ethyl)cyclobutyl)cyclopropanesulfonamide (15 mg, yield: 31.6%).

$^1$H NMR (400 MHz, $CDCl_3$) δ 7.20-7.10 (m, 2H), 7.00-6.92 (m, 1H), 4.75-4.60 (m, 1H), 4.14-3.73 (m, 1H), 3.09 (s, 4H), 2.67 (s, 4H), 2.62-2.49 (m, 2H), 2.42-2.29 (m, 3H), 2.25-1.89 (m, 5H), 1.79-1.54 (m, 4H), 1.16 (d, J=4.8 Hz, 2H), 0.99 (q, J=6.8 Hz, 2H).

MS m/z (ESI): 432.0 $[M+H]^+$.

Example 12

N-(3-(2-(4-(2,3-Dichlorophenyl)piperazin-1-yl)ethyl)cyclobutyl)oxazole-2-carboxamide

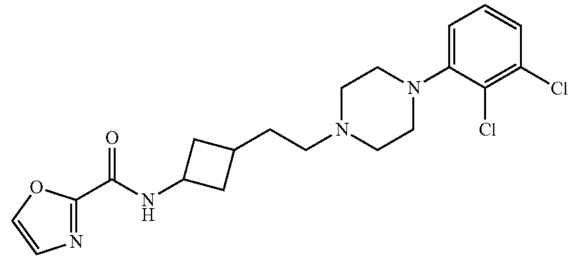 [SMILES: O=C(NC1CC(CCN2CCN(c3cccc(Cl)c3Cl)CC2)C1)c1ncco1]

Step 1: N-(3-(2-(4-(2,3-dichlorophenyl)piperazin-1-yl)ethyl)cyclobutyl)oxazole-2-carboxamide

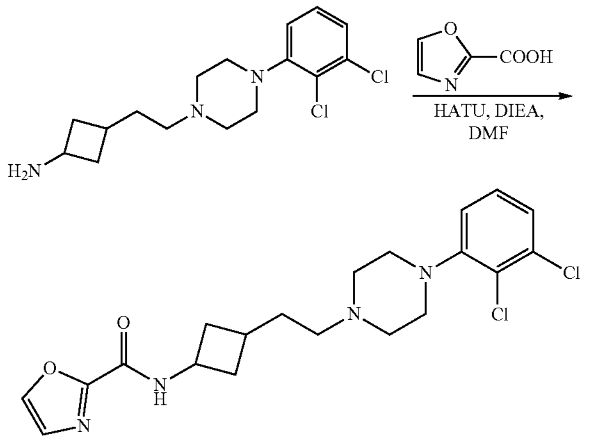

3-(2-(4-(2,3-Dichlorophenyl)piperazin-1-yl)ethyl)cyclobutan-1-amine (50 mg, 0.15 mmol) was dissolved in N,N-dimethylformamide (3 mL), followed by the addition of oxazole-2-carboxylic acid (20 mg, 0.18 mmol), HATU (86 mg, 0.23 mmol) and diisopropylethylamine (58 mg, 0.45 mmol). The reaction solution was stirred at room temperature overnight, and concentrated to dryness by rotary evaporation. The resulting crude product was purified by high performance liquid chromatography to obtain N-(3-(2-(4-(2,3-dichlorophenyl)piperazin-1-yl)ethyl)cyclobutyl)oxazole-2-carboxamide (13 mg, white solid, yield: 21%).

$^1$H NMR (400 MHz, Chloroform-d) δ 7.79 (d, J=1.9 Hz, 1H), 7.24-7.14 (m, 4H), 6.98 (m, 2.0 Hz, 1H), 4.68-4.59 (m, 0.4H), 4.48-4.38 (m, 0.7H), 3.26-3.15 (m, 4H), 2.98-2.81 (m, 3H), 2.64-2.56 (m, 3H), 2.22 (t, J=7.0 Hz, 2H), 2.07-1.99 (m, 1H), 1.89-1.80 (m, 2H), 1.75-1.67 (m, 2H).

MS m/z (ESI): 423.1 $M+H]^+$.

Example 12A and Example 12B

N-(Trans-3-(2-(4-(2,3-dichlorophenyl)piperazin-1-yl)ethyl)cyclobutyl)oxazole-2-carboxamide (12A)

N-(Cis-3-(2-(4-(2,3-dichlorophenyl)piperazin-1-yl)ethyl)cyclobutyl)oxazole-2-carboxamide (12B)

12A

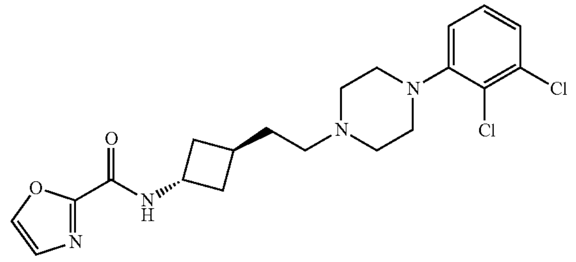

-continued

12B

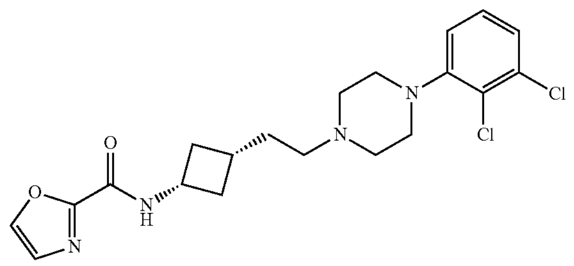

The compound of Example 12 was resolved to obtain N-(trans-3-(2-(4-(2,3-dichlorophenyl)piperazin-1-yl)ethyl) cyclobutyl)oxazole-2-carboxamide (12A) and N-(cis-3-(2-(4-(2,3-dichlorophenyl)piperazin-1-yl)ethyl)cyclobutyl) oxazole-2-carboxamide (12B).

Chiral Preparation Conditions:

| | |
|---|---|
| Instrument | SFC-80 (Thar, Waters) |
| Column type | AD 20*250 mm, 10 um (Daicel) |
| Column pressure | 100 bar |
| Mobile phase | $CO_2$/EtOH(1% Methanol Ammonia) = 50/50 |
| Flow rate | 80 g/min |
| Detection wavelength | UV 214 nm |
| Column temperature | 35° C. |

Example 12A: $t_R$=2.473 min $^1$H NMR (400 MHz, Chloroform-d) δ 7.79 (s, 1H), 7.24-7.20 (m, 2H), 7.17-7.11 (m, 2H), 6.97 (dd, J=6.4, 3.1 Hz, 1H), 4.69-4.58 (m, 1H), 3.16-3.02 (m, 4H), 2.76-2.58 (m, 4H), 2.41-2.36 (m, 2H), 2.36-2.28 (m, 1H), 2.24-2.17 (m, 4H), 1.82-1.73 (m, 2H).

MS m/z (ESI): 423.1 M+H]$^+$.

Example 12B: $t_R$=1.782 min $^1$H NMR (400 MHz, Chloroform-d) δ 7.79 (s, 1H), 7.22 (s, 1H), 7.19-7.10 (m, 3H), 6.97 (dd, J=7.0, 2.5 Hz, 1H), 4.49-4.37 (m, 1H), 3.28-3.03 (m, 4H), 2.84-2.67 (m, 3H), 2.67-2.54 (m, 3H), 2.53-2.35 (m, 2H), 2.15-2.02 (m, 1H), 1.75-1.63 (m, 4H).

MS m/z (ESI): 423.1 M+H]$^+$.

Example 13

N-(3-(2-(4-(2,3-Dichlorophenyl)piperazin-1-yl) ethyl)cyclobutyl)-4-methylisoxazole-5-carboxamide

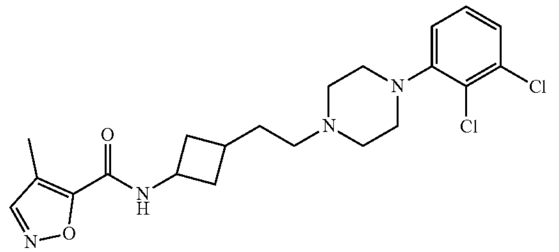 [SMILES: Cc1cnoc1C(=O)NC1CC(CCN2CCN(c3cccc(Cl)c3Cl)CC2)C1]

In accordance with Compound c, N-(3-(2-(4-(2,3-dichlorophenyl)piperazin-1-yl)ethyl)cyclobutyl)-4-methylisoxazole-5-carb oxamide was obtained.

$^1$H NMR (400 MHz, Chloroform-d) δ 8.16 (s, 1H), 7.23-7.09 (m, 2H), 7.05-6.91 (m, 1H), 6.75-6.51 (m, 1H), 4.70-4.33 (m, 1H), 3.41-3.00 (m, 4H), 2.90-2.54 (m, 4H), 2.54-2.40 (m, 2H), 2.34 (s, 3H), 2.26-2.02 (m, 3H), 1.91-1.58 (m, 4H).

MS m/z (ESI): 437.1[M+H]$^+$.

Example 13A

N-(Trans-3-(2-(4-(2,3-dichlorophenyl)piperazin-1-yl)ethyl)cyclobutyl)-4-methylisoxazole-5-carboxamide

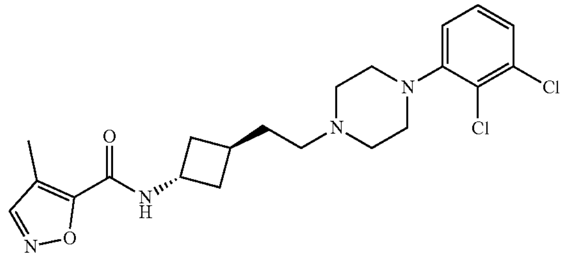

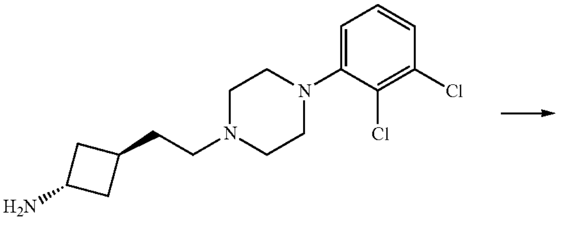

1-1

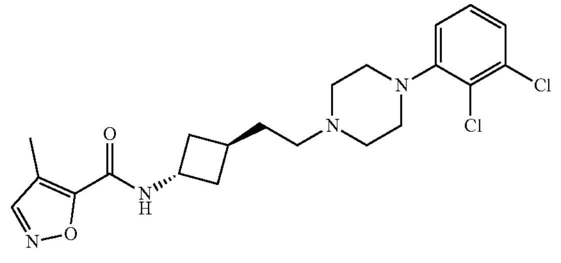

In accordance with the reaction conditions of Compound c, N-(trans-3-(2-(4-(2,3-dichlorophenyl)piperazin-1-yl) ethyl)cyclobutyl)-4-methylisoxazole-5-carboxamide (13A) (21 mg, white solid, yield: 25%) was obtained with intermediate 1-1 as starting material.

$^1$H NMR (400 MHz, Chloroform-d) δ 8.17 (s, 1H), 7.22-7.09 (m, 2H), 7.02-6.90 (m, 1H), 6.71 (d, J=7.5 Hz, 1H), 4.69-4.54 (m, 1H), 3.30-3.00 (m, 4H), 2.86-2.58 (m, 4H), 2.53-2.39 (m, 2H), 2.34 (s, 3H), 2.33-2.27 (m, 1H), 2.26-2.12 (m, 4H), 1.91- 1.72 (m, 2H).

MS m/z (ESI): 437.1[M+H]$^+$.

Example 13B

N-(Cis-3-(2-(4-(2,3-dichlorophenyl)piperazin-1-yl)ethyl)cyclobutyl)-4-methylisoxazole-5-carboxamide

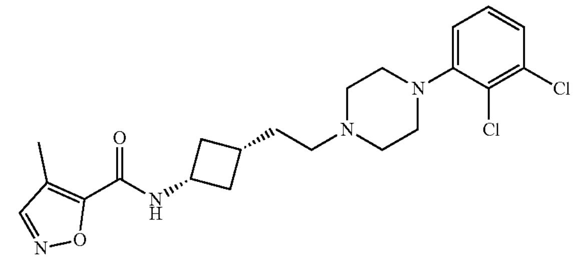

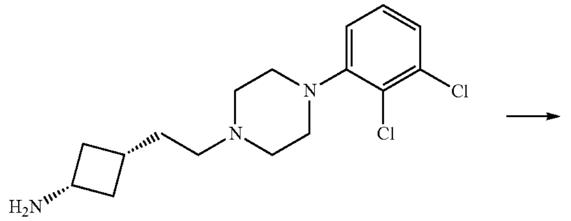

1-2

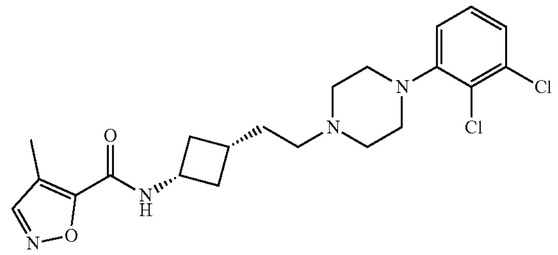

In accordance with the reaction conditions of Compound c, N-(cis-3-(2-(4-(2,3-dichlorophenyl)piperazin-1-yl)ethyl)cyclobutyl)-4-methylisoxazole-5-carboxamide (35B) was obtained with intermediate 1-2 as starting material.

MS m/z (ESI): 437.1[M+H]$^+$.

Example 14

N-(3-(2-(4-(2,3-Dichlorophenyl)piperazin-1-yl)ethyl)cyclobutyl)-3-methylisoxazole-5-carboxamide

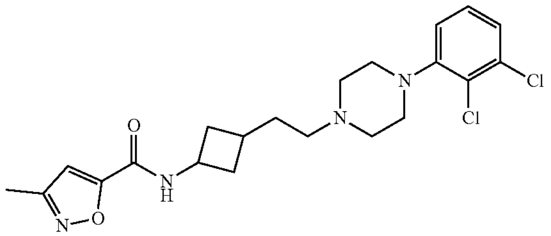 [SMILES: Cc1cc(C(=O)NC2CC(CCN3CCN(c4cccc(Cl)c4Cl)CC3)C2)on1]

In accordance with Compound C, N-(3-(2-(4-(2,3-dichlorophenyl)piperazin-1-yl)ethyl)cyclobutyl)-3-methylisoxazole-5-carb oxamide (21 mg, white solid, yield: 32%) was obtained.

$^1$H NMR (400 MHz, Chloroform-d) δ 7.21-7.11 (m, 2H), 7.02-6.93 (m, 1H), 6.77-6.57 (m, 2H), 4.69-4.33 (m, 1H), 3.30-3.01 (m, 4H), 2.89-2.56 (m, 5H), 2.49-2.38 (m, 2H), 2.36 (s, 3H), 2.27-2.15 (m, 1H), 2.10-1.99 (m, 1H), 1.87-1.57 (m, 4H).

MS m/z (ESI): 437.0 [M+H]$^+$.

Example 15

N-(3-(2-(4-(2,3-Dichlorophenyl)piperazin-1-yl)ethyl)cyclobutyl)isoxazole-5-carboxamide

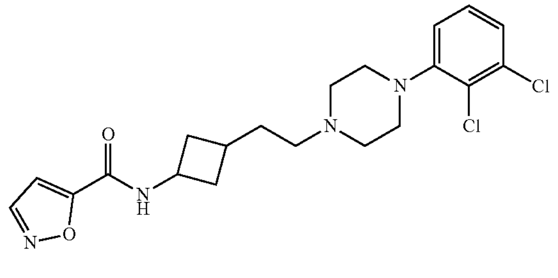 [SMILES: O=C(NC1CC(CCN2CCN(c3cccc(Cl)c3Cl)CC2)C1)c1ccno1]

In accordance with Compound c, N-(3-(2-(4-(2,3-dichlorophenyl)piperazin-1-yl)ethyl)cyclobutyl)isoxazole-5-carboxamide (14 mg, white solid, yield: 22%) was obtained.

$^1$H NMR (400 MHz, Chloroform-d) δ 8.46 (d, J=1.6 Hz, 1H), 7.21-7.11 (m, 2H), 7.06-6.87 (m, 2H), 6.84-6.77 (m, 1H), 4.70-4.34 (m, 1H), 3.24-3.01 (m, 4H), 2.76-2.57 (m, 5H), 2.46-2.35 (m, 2H), 2.34-2.14 (m, 2H), 2.11-1.99 (m, 1H), 1.83-1.59 (m, 3H).

MS m/z (ESI): 423.0 [M+H]$^+$.

Example 15A

N-(Trans-3-(2-(4-(2,3-dichlorophenyl)piperazin-1-yl)ethyl)cyclobutyl)isoxazole-5-carboxamide

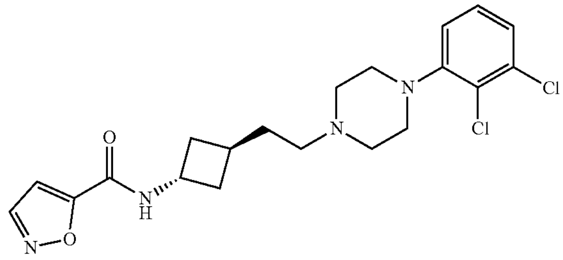

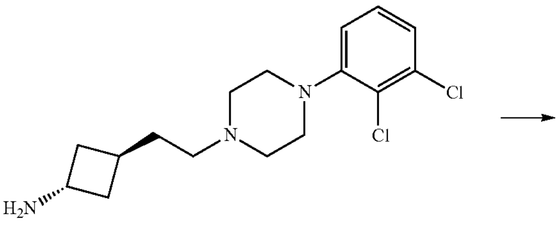

1-1

-continued

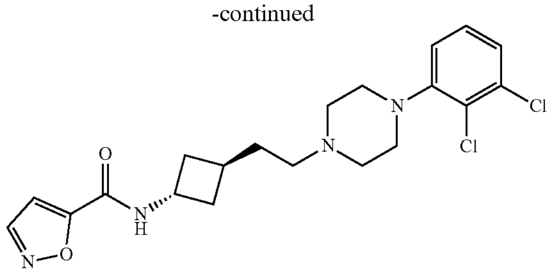

In accordance with the reaction conditions of Compound c, N-(trans-3-(2-(4-(2,3-dichlorophenyl)piperazin-1-yl) ethyl)cyclobutyl)isoxazole-5-carboxamide (37A) (white solid) was obtained with intermediate 1-1 as starting material.

$^1$H NMR (400 MHz, Chloroform-d) δ 8.34 (d, J=1.8 Hz, 1H), 7.22-7.11 (m, 2H), 6.98 (dd, J=6.7, 2.9 Hz, 1H), 6.91 (d, J=1.9 Hz, 1H), 6.78 (d, J=7.6 Hz, 1H), 4.70-4.57 (m, 1H), 3.28-3.02 (m, 4H), 2.86-2.56 (m, 4H), 2.50-2.39 (m, 2H), 2.39-2.30 (m, 1H), 2.28-2.14 (m, 4H), 1.88-1.76 (m, 2H).

MS m/z (ESI): 423.2 [M+H]$^+$.

Example 16

N-(3-(2-(4-(2,3-Dichlorophenyl)piperazin-1-yl) ethyl)cyclobutyl)-2-methyloxazole-5-carboxamide

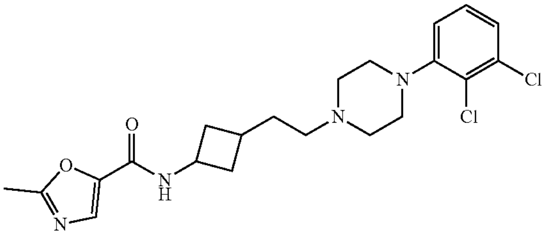 [SMILES: Cc1ncc(C(=O)NC2CC(CCN3CCN(c4cccc(Cl)c4Cl)CC3)C2)o1]

In accordance with Compound c, N-(3-(2-(4-(2,3-dichlorophenyl)piperazin-1-yl)ethyl)cyclobutyl)-2-methyloxazole-5-carboxamide was obtained.

$^1$H NMR (400 MHz, $CDCl_3$) δ 7.55 (s, 1H), 7.16 (dd, J=7.2, 4.3 Hz, 2H), 6.96 (dd, J=6.6, 2.8 Hz, 1H), 6.28 (d, J=7.7 Hz, 1H), 4.47-4.32 (m, 1H), 3.09 (s, 4H), 2.68-2.58 (m, 7H), 2.41-2.33 (m, 2H), 2.18 (td, J=20.3, 12.2 Hz, 2H), 2.02 (dd, J=15.7, 8.3 Hz, 1H), 1.78 (dd, J=15.3, 7.6 Hz, 1H), 1.71-1.55 (m, 3H).

MS m/z (ESI): 437.1 [M+H]$^+$.

Example 17

N-(3-(2-(4-(2,3-Dichlorophenyl)piperazin-1-yl) ethyl)cyclobutyl)isoxazole-3-carboxamide

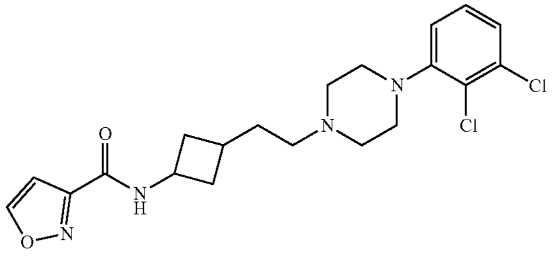 [SMILES: O=C(NC1CC(CCN2CCN(c3cccc(Cl)c3Cl)CC2)C1)c1ccon1]

In accordance with Compound c, N-(3-(2-(4-(2,3-dichlorophenyl)piperazin-1-yl)ethyl)cyclobutyl)isoxazole-3-carboxamide was obtained.

$^1$H NMR (400 MHz, $CDCl_3$) δ 8.33 (d, J=1.7 Hz, 1H), 7.19-7.14 (m, 2H), 7.02-6.93 (m, 1H), 6.91 (d, J=1.6 Hz, 1H), 4.48-4.64 (m, 1H), 3.29-3.11 (m, 4H), 2.79-2.60 (m, 4H), 2.45-2.39 (m, 2H), 2.26-2.22 (m, 2H), 2.05-2.01 (m, 1H), 1.76-1.60 (m, 4H).

MS m/z (ESI): 423.1 [M+H]$^+$.

Example 17A

N-(Trans-3-(2-(4-(2,3-dichlorophenyl)piperazin-1-yl)ethyl)cyclobutyl)isoxazole-3-carboxamide

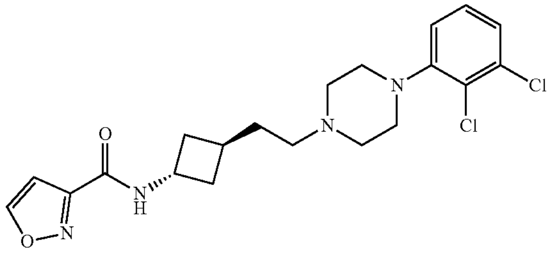

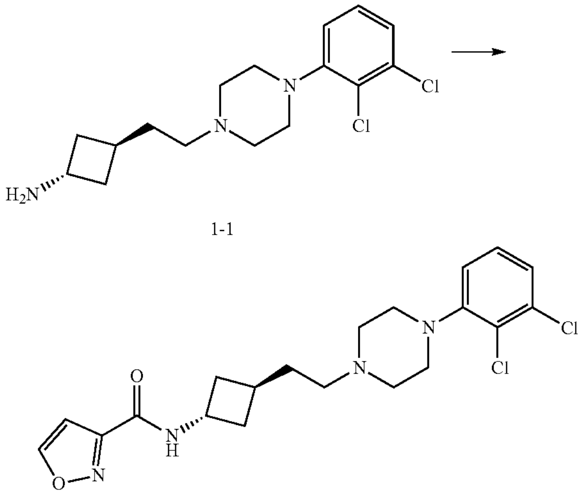
1-1

In accordance with the reaction conditions of Compound c, N-(trans-3-(2-(4-(2,3-dichlorophenyl)piperazin-1-yl)

ethyl)cyclobutyl)isoxazole-3-carboxamide was obtained with intermediate 1-1 as starting material.

$^1$H NMR (400 MHz, $CDCl_3$) δ 8.46 (d, J=1.4 Hz, 1H), 7.22-7.17 (m, 2H), 7.00 (d, J=6.8 Hz, 2H), 6.81 (d, J=1.4 Hz, 1H), 4.64 (dd, J=15.1, 7.5 Hz, 1H), 3.29 (s, 4H), 2.79-2.77 (m, 4H), 2.36 (s, 2H), 2.24 (d, J=7.0 Hz, 2H), 2.01 (s, 1H), 1.60 (s, 4H).

MS m/z (ESI): 423.1 $[M+H]^+$.

Example 18

N-(3-(2-(4-(2,3-Dichlorophenyl)piperazin-1-yl)ethyl)cyclobutyl)-2-methyloxazole-4-carboxamide

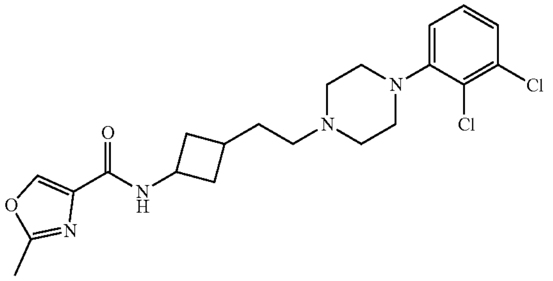 [SMILES: Cc1nc(C(=O)NC2CC(CCN3CCN(c4cccc(Cl)c4Cl)CC3)C2)co1]

In accordance with Compound c, N-(3-(2-(4-(2,3-dichlorophenyl)piperazin-1-yl)ethyl)cyclobutyl)-2-methyloxazole-4-carboxamide (white solid) was obtained.

$^1$H NMR (400 MHz, Chloroform-d) δ 8.06 (d, J=1.6 Hz, 1H), 7.17-7.13 (m, 2H), 7.05-6.90 (m, 2H), 4.66-4.36 (m, 1H), 3.19-3.05 (m, 4H), 2.74-2.63 (m, 3H), 2.64-2.53 (m, 2H), 2.50-2.46 (m, 3H), 2.42-2.34 (m, 2H), 2.21-2.13 (m, 1H), 2.08-1.94 (m, 1H), 1.68-1.60 (m, 4H).

MS m/z (ESI): 437.1 $M+H]^+$.

Example 18A

N-(Trans-3-(2-(4-(2,3-dichlorophenyl)piperazin-1-yl)ethyl)cyclobutyl)-2-methyloxazole-4-carboxamide

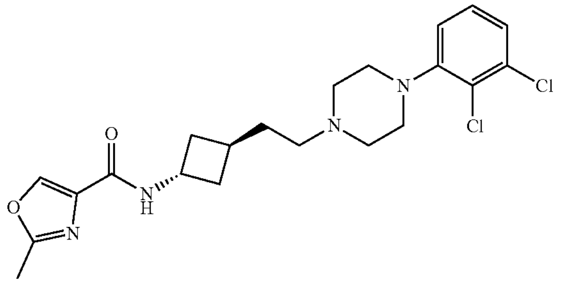

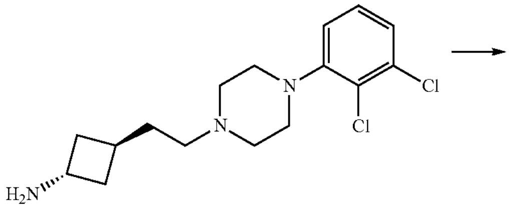

1-1

-continued

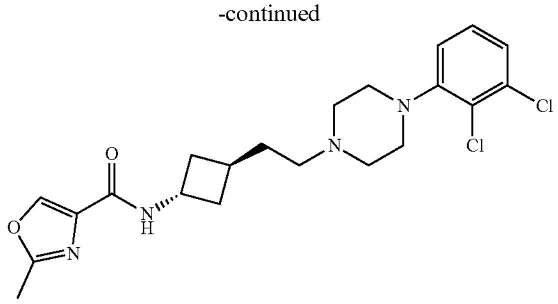

In accordance with the reaction conditions of Compound c, N-(trans-3-(2-(4-(2,3-dichlorophenyl)piperazin-1-yl)ethyl)cyclobutyl)-2-methyloxazole-4-carboxamide was obtained with intermediate 1-1 as starting material.

$^1$H NMR (400 MHz, Chloroform-d) δ 8.06 (s, 1H), 7.20-7.11 (m, 2H), 7.05-6.92 (m, 2H), 4.67-4.54 (m, 1H), 3.19-3.06 (m, 4H), 2.76-2.63 (m, 4H), 2.48 (s, 3H), 2.44-2.41 (m, 2H), 2.21-2.11 (m, 5H), 1.84-1.75 (m, 2H).

MS m/z (ESI): 437.1 $M+H]^+$.

Example 19

N-(3-(2-(4-(2,3-Dichlorophenyl)piperazin-1-yl)ethyl)cyclobutyl)quinoline-5-carboxamide

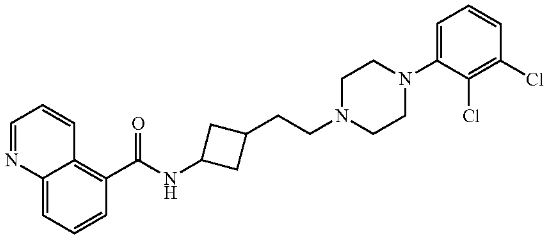 [SMILES: O=C(NC1CC(CCN2CCN(c3cccc(Cl)c3Cl)CC2)C1)c1cccc2ncccc12]

In accordance with Step 1 of Compound c, N-(3-(2-(4-(2,3-dichlorophenyl)piperazin-1-yl)ethyl)cyclobutyl)quinoline-5-carboxamide (35 mg, white solid) was obtained.

$^1$H NMR (400 MHz, Chloroform-d) δ 8.96 (dd, J=4.2, 1.7 Hz, 1H), 8.76 (d, J=8.7 Hz, 1H), 8.25-8.16 (m, 1H), 7.75-7.67 (m, 2H), 7.51-7.45 (m, 1H), 7.16 (dd, J=7.0, 2.0 Hz, 2H), 7.03-6.95 (m, 1H), 6.29-6.15 (m, 1H), 4.84-4.52 (m, 1H), 3.23-3.05 (m, 4H), 2.80-2.67 (m, 4H), 2.52-2.41 (m, 2H), 2.35-2.04 (m, 3H), 1.70-1.57 (m, 4H).

MS m/z (ESI): 483.1 $M+H]^+$.

Example 19A

N-(Trans-3-(2-(4-(2,3-dichlorophenyl)piperazin-1-yl)ethyl)cyclobutyl)quinoline-5-carb oxamide

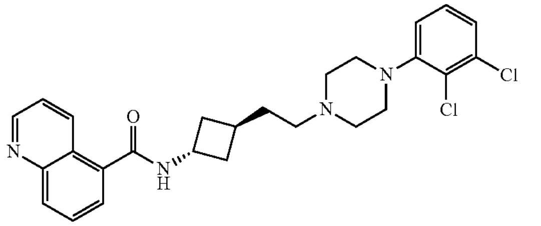

-continued

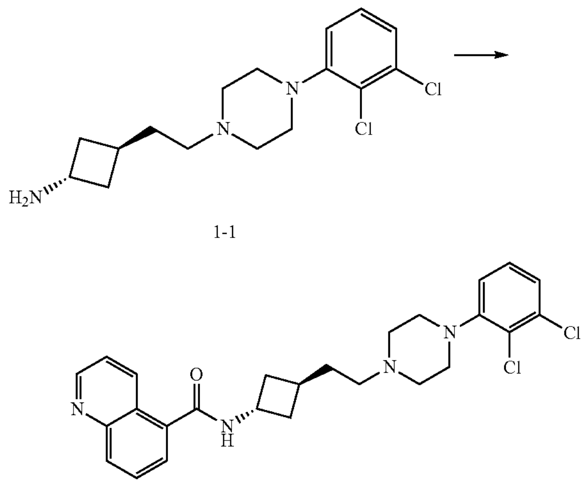

1-1

In accordance with the reaction conditions of Compound c, N-(trans-3-(2-(4-(2,3-dichlorophenyl)piperazin-1-yl) ethyl)cyclobutyl)quinoline-5-carboxamide was obtained with intermediate 1-1 as starting material.

$^1$H NMR (400 MHz, Chloroform-d) δ 8.96 (dd, J=4.3, 1.7 Hz, 1H), 8.76 (d, J=8.6 Hz, 1H), 8.25-8.14 (m, 1H), 7.69 (d, J=5.0 Hz, 2H), 7.47 (dd, J=8.6, 4.2 Hz, 1H), 7.19-7.14 (m, 2H), 6.98 (dd, J=7.2, 2.4 Hz, 1H), 6.29 (d, J=7.5 Hz, 1H), 4.84-4.71 (m, 1H), 3.22-3.14 (m, 4H), 2.94-2.88 (m, 1H), 2.86-2.74 (m, 4H), 2.56-2.50 (m, 2H), 2.32-2.26 (m, 2H), 2.25-2.18 (m, 2H), 1.93-1.84 (m, 2H).

MS m/z (ESI): 483.1 M+H]$^+$.

Example 20

1-Cyclopropyl-3-(3-(2-(4-(2,3-dichlorophenyl)piperazin-1-yl)ethyl)cyclobutyl)-1-methylurea

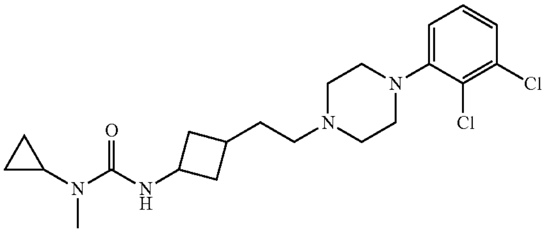 [SMILES: CN(C(=O)NC1CC(CCN2CCN(c3cccc(Cl)c3Cl)CC2)C1)C1CC1]

In accordance with Step 8 of Compound a, 1-cyclopropyl-3-(3-(2-(4-(2,3-dichlorophenyl)piperazin-1-yl)ethyl)cyclobutyl)-1-methylurea (43 mg, white solid, yield: 33%) was obtained.

$^1$H NMR (400 MHz, Chloroform-d) δ 7.22-7.11 (m, 2H), 7.03-6.92 (m, 1H), 5.32 (dd, J=36.5, 7.6 Hz, 1H), 4.45-4.10 (m, 1H), 3.25-3.02 (m, 4H), 2.88 (d, J=1.7 Hz, 3H), 2.82-2.57 (m, 4H), 2.57-2.51 (m, 1H), 2.47-2.32 (m, 3H), 2.24-2.10 (m, 1H), 2.08-1.90 (m, 1H), 2.06-1.75 (m, 2H), 1.50-1.39 (m, 1H), 0.88-0.78 (m, 2H), 0.75-0.67 (m, 2H).

MS m/z (ESI): 425.1 [M+H]$^+$.

Example 21

1-Cyano-N-(3-(2-(4-(2,3-dichlorophenyl)piperazin-1-yl)ethyl)cyclobutyl)cyclopropane-1-carboxamide

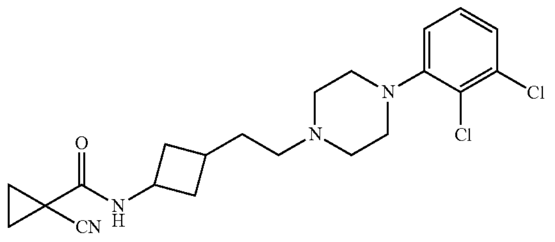 [SMILES: N#CC1(C(=O)NC2CC(CCN3CCN(c4cccc(Cl)c4Cl)CC3)C2)CC1]

In accordance with Step 1 of Compound c, 1-cyano-N-(3-(2-(4-(2,3-dichlorophenyl)piperazin-1-yl)ethyl)cyclobutyl)cyclopropane-1-carboxamide (31 mg, white solid) was obtained.

$^1$H NMR (400 MHz, Chloroform-d) δ 7.19-7.12 (m, 2H), 7.00-6.94 (m, 1H), 6.56-6.36 (m, 1H), 4.54-4.17 (m, 1H), 3.21-3.02 (m, 4H), 2.79-2.60 (m, 4H), 2.57-2.53 (m, 1H), 2.43-2.36 (m, 2H), 2.18-2.12 (m, 1H), 2.06-1.95 (m, 1H), 1.68-1.65 (m, 3H), 1.63-1.56 (m, 3H), 1.51-1.45 (m, 2H).

MS m/z (ESI): 421.1 M+H]$^+$.

Example 22

(R)—N-(3-(2-(4-(2,3-Dichlorophenyl)-3-methylpiperazin-1-yl)ethyl)cyclobutyl)-2-hydroxy-2-methylpropanamide

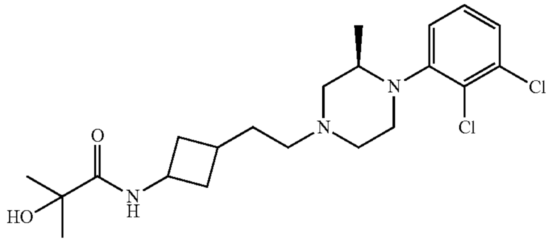 [SMILES: C[C@@H]1CN(CCC2CC(NC(=O)C(C)(C)O)C2)CCN1c1cccc(Cl)c1Cl]

Step 1: Tert-butyl (R)-4-(2,3-dichlorophenyl)-3-methylpiperazine-1-carboxylate

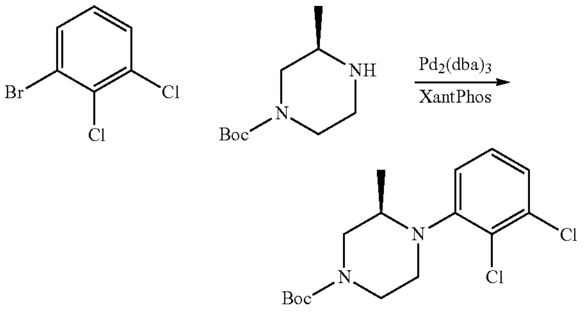

In accordance with Step 1 of Compound a, tert-butyl (R)-4-(2,3-dichlorophenyl)-3-methylpiperazine-1-carboxylate (600 mg, yellow solid, yield: 32.6%) was obtained with 1-bromo-2,3-dichlorobenzene and tert-butyl (R)-3-methylpiperazine-1-carboxylate as starting materials.

MS m/z (ESI): 345.1 $[M+H]^+$.

$^1H$ NMR (400 MHz, Chloroform-d) δ 7.26-7.21 (m, 1H), 7.21-7.11 (m, 1H), 7.11-6.94 (m, 1H), 3.99-3.00 (m, 7H), 1.49 (s, 9H), 0.91 (d, J=6.3 Hz, 3H).

Step 2: (R)-1-(2,3-Dichlorophenyl)-2-methylpiperazine

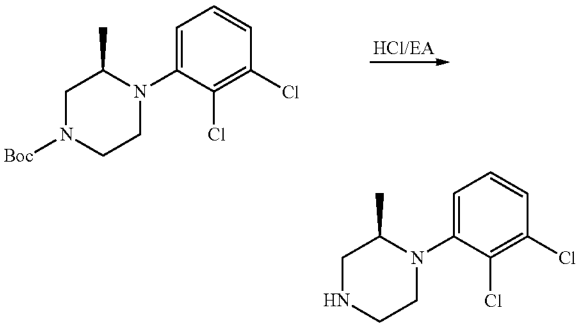

In accordance with Step 2 of Compound a, (R)-1-(2,3-dichlorophenyl)-2-methylpiperazine (420 mg, yellow solid, yield: 98.8%) was obtained with tert-butyl (R)-4-(2,3-dichlorophenyl)-3-methylpiperazine-1-carboxylate as starting material.

MS m/z (ESI): 245.1 $[M+H]^+$.

$^1H$ NMR (400 MHz, Methanol-d4) δ 7.36-7.29 (m, 1H), 7.27-7.16 (m, 2H), 3.60-3.44 (m, 1H), 3.42-3.27 (m, 2H), 3.21-3.13 (m, 2H), 3.02-2.81 (m, 2H), 0.88 (d, J=6.3 Hz, 3H).

Step 3: (R)-3-(2-(4-(2,3-Dichlorophenyl)-3-methylpiperazin-1-yl)ethyl)cyclobutan-1-amine

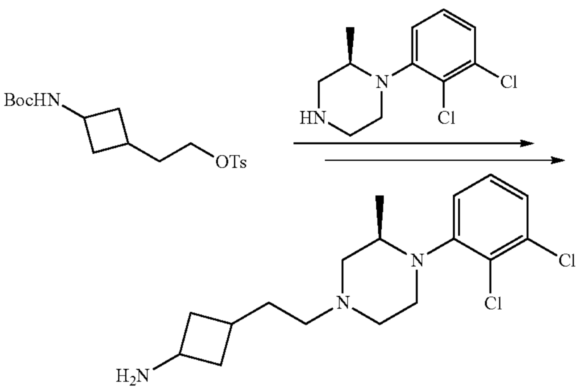

In accordance with Steps 6 and 7 of Compound a, (R)-3-(2-(4-(2,3-dichlorophenyl)-3-methylpiperazin-1-yl)ethyl)cyclobutan-1-amine (280 mg) was obtained.

MS m/z (ESI): 342.1 $[M+H]^+$.

Step 4: (R)—N-(3-(2-(4-(2,3-Dichlorophenyl)-3-methylpiperazin-1-yl)ethyl)cyclobutyl)-2-hydroxy-2-methylpropanamide

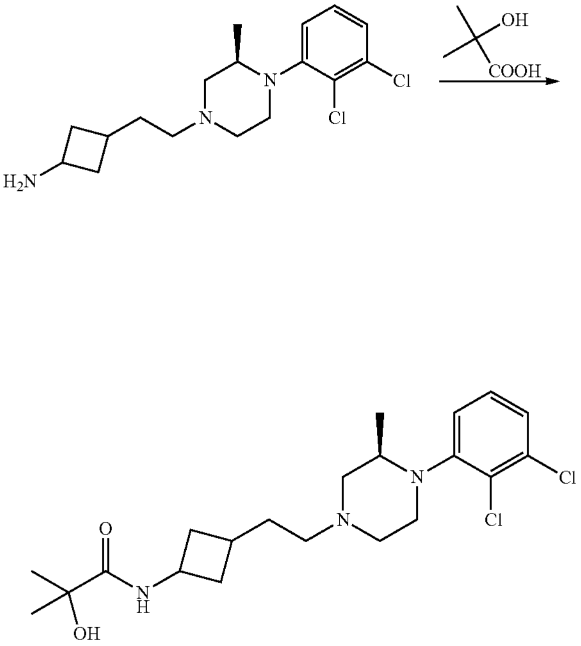

In accordance with Example 4, (R)—N-(3-(2-(4-(2,3-dichlorophenyl)-3-methylpiperazin-1-yl)ethyl)cyclobutyl)-2-hydroxy-2-methylpropanamide (18 mg) was obtained.

$^1H$ NMR (400 MHz, Chloroform-d) δ 7.25-7.20 (m, 1H), 7.16 (t, J=7.9 Hz, 1H), 7.10-7.04 (m, 1H), 6.91-6.75 (m, 1H), 4.49-4.14 (m, 1H), 3.47-3.34 (m, 1H), 3.21-3.13 (m, 1H), 2.91-2.82 (m, 1H), 2.83-2.68 (m, 2H), 2.59-2.48 (m, 2H), 2.38-2.31 (m, 2H), 2.24-2.12 (m, 2H), 2.11-1.93 (m, 2H), 1.82-1.73 (m, 1H), 1.70-1.65 (m, 1H), 1.56-1.46 (m, 2H), 1.44 (d, J=2.4 Hz, 6H), 0.90 (d, J=6.2 Hz, 3H).

MS m/z (ESI): 428.1 $[M+H]^+$.

Example 23

Tert-butyl (R)-(3-(2-(4-(2,3-dichlorophenyl)-3-methylpiperazin-1-yl)ethyl)cyclobutyl)carbamate

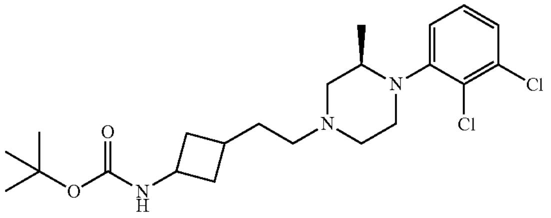 [SMILES: C[C@@H]1CN(CCC2CC(NC(=O)OC(C)(C)C)C2)CCN1c1cccc(Cl)c1Cl]

In accordance with Example 22, tert-butyl (R)-(3-(2-(4-(2,3-dichlorophenyl)-3-methylpiperazin-1-yl)ethyl)cyclobutyl)carbamate was obtained.

MS m/z (ESI): 441.3 $[M+H]^+$.

Example 24

3-(3-(2-(4-(Benzo[b]thiophen-4-yl)piperazin-1-yl)ethyl)cyclobutyl)-1-ethyl-1-methylurea

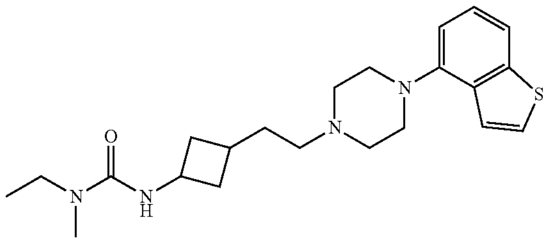 [SMILES: CCN(C)C(=O)NC1CC(CCN2CCN(c3cccc4sccc34)CC2)C1]

In accordance with Compound d, 3-(3-(2-(4-(benzo[b]thiophen-4-yl)piperazin-1-yl)ethyl)cyclobutyl)-1-ethyl-1-methylurea was obtained with 1-(benzo[b]thiophen-4-yl)piperazine as starting material.

$^1$H NMR (400 MHz, Chloroform-d) δ 7.55 (d, J=8.0 Hz, 1H), 7.40 (d, J=3.7 Hz, 2H), 7.31-7.26 (m, 1H), 6.90 (d, J=7.6 Hz, 1H), 4.54-4.09 (m, 2H), 3.41-3.15 (m, 6H), 2.85 (d, J=4.0 Hz, 3H), 2.82-2.63 (m, 4H), 2.59-2.51 (m, 1H), 2.48-2.35 (m, 2H), 2.28-2.07 (m, 1H), 2.07-1.87 (m, 2H), 1.85-1.62 (m, 2H), 1.53-1.40 (m, 1H), 1.22-1.02 (m, 3H).

MS m/z (ESI): 401.2 $[M+H]^+$.

Example 25

N-(3-(2-(4-(2,3-Dichlorophenyl)-1,4-diazepan-1-yl)ethyl)cyclobutyl)furan-2-carboxamide

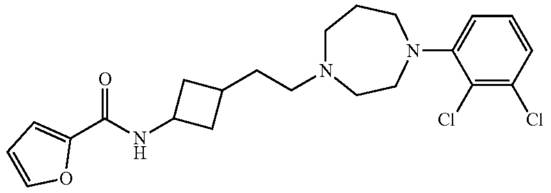 [SMILES: O=C(NC1CC(CCN2CCCN(c3cccc(Cl)c3Cl)CC2)C1)c1ccco1]

The compound of Example 25 was prepared by referring to Example 12.

MS m/z (ESI): 436.2$[M+H]^+$.

II. Biological Assay and Evaluation

The present invention is further described below in combination with the following test examples, which are not intended to limit the scope of the present invention.

(I). Radioligand-Receptor Binding Assay

Test Example 1. Determination of the Binding Ability of the Compounds of the Present Invention to Dopamine D3 Receptor 1. Experimental Objective The objective of this test example is to determine the affinity of the compounds for dopamine D3 receptor.

2. Experimental Instruments and Reagents 2.1 Experimental Instruments

Vortex mixer (IKA; MS3 basic)

Electric heating constant temperature incubator (Shanghai Yiheng Scientific Instruments Co., Ltd; DHP-9032)

Microplate shaker (VWR; 12620-928)

TopCount (PerkinElmer; NTX)

Universal Harvester (PerkinElmer; UNIFILTER-96).

2.2 Experimental Reagents and Consumables

[$^3$H]-methylspiperone (PerkinElmer; NET856250UC)

Human Dopamine D3 Receptor membrane (PerkinElmer; ES-173-M400UA)

GR 103691 (Sigma; 162408-66-4)

ULTIMA GOLD (Perkin Elmer; 77-16061)

96 round deep well plate 1.1 mL (Perkin Elmer; P-DW-11-C)

UNIFILTER-96 GF/B filter plate (PerkinElmer; 6005174)

Polyethyleneimine branched (Sigma; 408727)

Centrifuge tubes (BD, 352096; 352070)

Loading slot (JET BIOFIL; LTT001050)

Pipette tips (Axygen; T-300-R-S, T-200-Y-R-S, T-1000-B-R-S)

Magnesium chloride (Sigma, 7786-30-3)

Tris-base (Sigma, 77-86-1)

HCl (Beijing XingJing Precision Chemical Technology CO., LTD)

3. Experimental Method

Experimental buffer: 50 mM Tris-HCl pH 7.4, 10 mm $MgCl_2$; washing liquor: 50 mM Tris-HCl pH 7.4, stored at 4° C.; 0.5% PEI solution: 0.5 g PEI dissolved in 100 mL $ddH_2O$, 4° C. storage of spare.

5 μL of the test compounds (0.005 nM to 100 nM, 10 concentrations in total) and 100 μL of buffer were added to a 96-well assay plate. 1 μL of cell membrane and 300 μL of buffer were added to each well, and the plate was shaken at 600 rpm for 5 minutes. 100 μL of a mixed solution of buffer and [3H]-methylspiperone (final concentration of 0.5 nM) was added to the reaction system per well, and the plate was shaken at 600 rpm for 5 minutes and incubated at 27° C. for 30 min. The UNIFILTER-96 GF/B filter plate pre-incubated with 0.5% PEI for 1 h was washed twice with the buffer (1 mL/well). The cell membrane suspension was added to the UNIFILTER-96 GF/B filter plate, washed 4 times, and incubated at 55° C. for 10 min. 40 μL of ULTIMA GOLD was added to each well, and liquid scintillation counting was carried out.

4. Experimental Data Processing Method

The CPM (Counts per minute) values were determined by TopCount. The percent inhibition rate of [$^3$H]-methylspiperone binding was calculated from the values of the High control (DMSO control) experimental group and Low control (100 nM positive compound) experimental group {% inhibition rate=$(CPM_{sample}-CPM_{low\ control})/(CPM_{high\ control}-CPM_{low\ control})\times100$}. The 10 concentrations of the compound were from 100 nM to 0.005 nM after 3-fold dilution of the reaction system. The percent inhibition rate and ten-point concentration data were fitted to the parametric nonlinear logistic equation by using GraphPad prism to calculate the $IC_{50}$ values of the compound.

5. Experimental Results

The binding activity of the compounds of the present invention to D3 was determined by the above assay, and the resulting $IC_{50}$ values are shown in Table 13.

TABLE 13

| IC$_{50}$ of the binding activity of the compounds of the present invention to D3 | |
|---|---|
| Example No. | D3 Binding IC$_{50}$ (nM) |
| Cariprazine | 0.89 |
| 4A | 0.95 |
| 6A | 0.75 |
| 6B | 4.37 |
| 7A | 0.44 |
| 11 | 0.62 |
| 12A | 0.37 |
| 12B | 2.54 |
| 13A | 1.36 |
| 14A | 0.34 |
| 15A | 0.31 |
| 16A | 0.33 |
| 17A | 0.30 |
| 18A | 0.42 |
| 19A | 0.40 |
| 20 | 1.99 |
| 22 | 2.78 |
| 24 | 1.13 |
| 25 | 0.79 |

6. Experimental Conclusion

The compounds of the present invention have good affinity for dopamine receptor D3.

Test Example 2. Determination of the Binding Ability of the Compounds of the Present Invention to 5-HT2A Receptor 1. Experimental Objective The objective of this test example is to determine the affinity of the compounds for 5-HT2A receptor.

2. Experimental Instruments and Reagents 2.1 Instruments

Vortex mixer (IKA; MS3 basic)

Electric heating constant temperature incubator (Shanghai Yiheng Scientific Instruments Co., Ltd; DHP-9032)

Microplate shaker (VWR; 12620-928)

TopCount (PerkinElmer; NTX)

Universal Harvester (PerkinElmer; UNIFILTER-96).

2.2 Experimental Reagents and Consumables

[$^3$H]-Ketanserin (PerkinElmer NET791)

Human Dopamine 5-HT2A Receptor membrane (PerkinElmer)

ULTIMA GOLD (Perkin Elmer; 77-16061)

96 round deep well plate 1.1 mL (Perkin Elmer; P-DW-11-C)

UNIFILTER-96 GF/B filter plate (PerkinElmer; 6005174)

Polyethyleneimine, branched (Sigma; 408727)

Centrifuge tubes (BD, 352096; 352070)

Loading slot (JET BIOFIL; LTT001050)

Pipette tips (Axygen; T-300-R-S, T-200-Y-R-S, T-1000-B-R-S)

Magnesium chloride (Sigma, 7786-30-3)

Calcium chloride (Sigma)

Tris-base (Sigma, 77-86-1)

HCl (Beijing XingJing Precision Chemical Technology CO., LTD)

L-Ascorbic acid (Tianjin Guangfu)

3. Experimental Method

Experimental buffer: 50 mM Tris-HCl pH 7.4, 4 mM $CaCl_2$); washing liquor: 50 mM Tris-HCl pH 7.4, stored at 4° C.; 0.5% PEI solution: 0.5 g PEI dissolved in 100 mL $ddH_2O$, 4° C. storage of spare.

5 µL of the test compounds (0.005 nM to 100 nM, 10 concentrations in total) and 100 µL of buffer were added to a 96-well assay plate. 1.5 µL of cell membrane and 300 µL of buffer were added to each well, and the plate was shaken at 600 rpm for 5 minutes. 100 µL of a mixed solution of buffer and [3H]-Ketanserin (final concentration of 2 nM) was added to the reaction system per well, and the plate was shaken at 600 rpm for 5 minutes and incubated at 27° C. for 30 min. The UNIFILTER-96 GF/B filter plate pre-incubated with 0.5% PEI for 1 h was washed twice with the buffer (1 mL/well). The cell membrane suspension was added to the UNIFILTER-96 GF/B filter plate, washed 4 times, and incubated at 55° C. for 10 min. 40 µL of ULTIMA GOLD was added to each well, and liquid scintillation counting was carried out.

4. Experimental Data Processing Method

The CPM (Counts per minute) values were determined by TopCount. The percent inhibition rate of [$^3$H]-Ketanserin binding was calculated from the values of the High control (DMSO control) experimental group and Low control (100 nM positive compound) experimental group {% inhibition rate=$(CPM_{sample}-CPM_{low\ control})/(CPM_{high\ control}-CPM_{low\ control})\times 100$}. The 10 concentrations of the compound were from 100 nM to 0.005 nM after 3-fold dilution of the reaction system. The percent inhibition rate and ten-point concentration data were fitted to the parametric nonlinear logistic equation by using GraphPad prism to calculate the IC$_{50}$ values of the compound.

5. Experimental Results

The binding activity of the compounds of the present invention to 5-HT2A was determined by the above assay, and the resulting IC$_{50}$ values are shown in Table 14.

TABLE 14

| IC$_{50}$ of the binding ability of the compounds of the present invention to 5-HT2A | |
|---|---|
| Example No. | 5HT-2A Binding IC$_{50}$ (nM) |
| Cariprazine | 191.28 |
| 4A | 41.5 |
| 6A | 5.77 |
| 6B | 48.45 |
| 7A | 0.79 |
| 11 | 43.97 |
| 12A | 4.19 |
| 12B | 8.73 |
| 13A | 1.81 |
| 14A | 1.35 |
| 15A | 0.98 |
| 16A | 1.80 |
| 17A | 1.92 |
| 18A | 1.37 |
| 19A | 1.89 |
| 20 | 19.08 |
| 22 | 9.63 |
| 24 | 6.39 |
| 25 | 6.35 |

6. Experimental Conclusion

The above data show that the compounds of the present invention have good affinity for 5-HT2A.

(II). Cell Function Assay

Test Example 1. Determination of the Effect of the Compounds of the Present Invention on cAMP Content in Cells Stably Expressing D3 Receptors 1. Experimental objective To determine the activation effect of the compounds on D3 receptor.

2. Experimental Instruments and Reagents 2.1 Instruments 384-well assay plate (Perkin Elmer; 6007680)

96-well conical btm PP Plt nature RNASE/Dnase-free plate (ThermoFisher; 249944)

EnVision (Perkin Elmer).

2.2 Reagents

Fetal Bovine Serum (Gibco, 10999141)

Ham's F-12K (Kaighn's) Medium (Hyclone; SH30526.01)

Penicillin-Streptomycin, Liquid (Gibco; 15140122)

G418 (invitrogen; 0131-027)

Forskolin (Selleck, S2449)

BSA stabilizer (Perkin Elmer; CR84-100)

cAMP kit (Cisbio; 62AM4PEC)

IBMX (Sigma; 15879)

HEPES (Gibco; 15630080)

HBSS (Gibco; 14025076)

TrypLE (ThermoFisher; 12604021).

3. Experimental Method:

1. Preparation of the buffer: 1*HBSS+20 mM HEPES+0.1% BSA+500 μM IBMX.

Complete medium: Ham's F12K+10% fetal bovine serum+1*penicillin-streptomycin+400 μg/mL G418.

2. CHO-D3 cells were cultured in the complete medium at 37° C., 5% $CO_2$. After TrypLE digestion, the cells were resuspended in the experimental buffer, and seeded into a 384-well cell culture plate at a seeding density of 8000 cells per well.

3. The experimental buffer (1*HBSS, 0.1% BSA, 20 mM HEPES and 500 μM IBMX) was prepared. The compound was diluted with the buffer. 2.5 μL of the compound solution was added to each well, and the plate was incubated at 37° C. for 10 minutes. The forskolin was diluted to 8 μM (8*) with the experimental buffer. 2.5 μL of the diluted 8*forskolin was added, and the plate was incubated at 37° C. for 30 minutes. cAMP-d2 and Anti-cAMP-$Eu^{3+}$ were thawed, and diluted by 20-fold with the lysis buffer. 10 μL of cAMP-d2 was added to the experimental well, followed by the addition of 10 μL of Anti-cAMP-$Eu^{3+}$. The reaction plate was centrifuged at 200 g for 30 s at room temperature, and left to stand at 25° C. for 1 h. Data was collected using Envision.

Experimental Data Processing Method:

$$Z' \text{ factor} = 1 - 3 * (SDMax + SDMin)/(MeanMax - MeanMin); \quad 1)$$

$$CVMax = (SDMax/MeanMax) * 100\%; \quad 2)$$

$$CVMin = (SDMin/MeanMin) * 100\%; \quad 3)$$

$$S/B = \text{Signal/Background}; \quad 4)$$

5) $EC_{50}$ of the compound was calculated using the GraphPad nonlinear fitting equation:

$$Y = \text{Bottom} + (\text{Top} - \text{Bottom})/(1 + 10\hat{}((LogEC_{50} - X) * HillSlope))$$

X: log value of compound concentration; Y: Activation %

4. Experimental Results:

TABLE 15

$EC_{50}$ values of the compounds on cAMP content in cells stably expressing D3 receptors

| Example No. | $EC_{50}$ (nM) |
|---|---|
| Cariprazine | 1.69 |
| 1 | 3.5 |
| 2 | 2.2 |
| 3 | 1.2 |
| 4A | 0.4 |
| 5 | 2.4 |
| 6 | 2.9 |
| 6A | 0.6 |
| 7 | 2.8 |
| 7A | 1.0 |
| 10 | 1.2 |
| 12 | 1.7 |
| 12A | 0.6 |
| 12B | 0.7 |
| 13 | 3.4 |
| 13A | 1.1 |
| 14 | 1.2 |
| 14A | 0.9 |
| 15 | 1.7 |
| 15A | 0.7 |
| 16 | 0.7 |
| 16A | 1.7 |
| 17 | 3.1 |
| 17A | 1.1 |
| 18 | 3.9 |
| 18A | 1.4 |
| 19 | 1.0 |
| 19A | 1.6 |
| 20 | 1.0 |
| 21 | 3.3 |
| 22 | 0.4 |
| 24 | 0.9 |

5. Experimental Conclusion

It can be seen from the data in the table that the compounds of the Examples of the present invention show good agonistic activity in the cAMP content effect assay in cells stably expressing D3 receptors.

Test Example 2. Determination of the Effect of the Compounds of the Present Invention on Calcium Ion Mobility in Cells Stably Expressing 5-HT2A Receptors 1. Experimental Objective To determine the inhibitory effect of the compounds on 5-HT2A receptor.

2. Experimental Instruments and Reagents 2.1 Instruments 384-well assay plate (Corning; 3712);

FLIPR (Molecular Devices).

2.2 Reagents

DMEM (Invitrogen; 11965);

Fetal bovine serum (Biowest; S1810-500);

Dialysis serum (S-FBS-AU-065; Serana);

Penicillin-Streptomycin (Biowest; L0022-100);

Hygromycin B (CABIOCHEM, 400052);

Matrigel (BD; 354230);
DMSO (Sigma; D2650);
HBSS (Invitrogen; 14065);
HEPES (Invitrogen; 15630080);
Probenecid (Sigma; P8761);
BSA (renview; FA016);
TrypLE (ThermoFisher; 12604021).

3. Experimental Method

1) Preparation of the buffer: 1×HBSS, 20 mM HEPES, 2.5 mM probenecid (probenecid was 400 mM stock in 1 M NaOH), 0.1% BSA. Probenecid and BSA were added fresh on the day of the experiment. Experimental buffers include dye buffer and compound dilution buffer.

2) Cell culture medium: Ham's F-12K+10% fetal bovine serum+600 μg/ml hygromycin B+1*penicillin-streptomycin. Seeding medium: Ham's F-12K+10% dialysis serum; Assay buffer: 1×HBSS+20 mM HEPES; Cell line: Flp-In-CHO-5HT2A stable pool.

3) The cells were cultured in the complete medium at 37° C., 5% $CO_2$ to 70%-90% confluency. The cells were digested with TrypLE, seeded to the 384-well assay plate at a density of $1\times10^4$ cells/well, and incubated for 16 to 24 hours (at least overnight).

4) 20× Component A was thawed to room temperature, diluted to 2× working concentration (containing 5 mM Probenecid) with the assay buffer, and placed at room temperature for later use.

5) The cell culture plate was taken out and left to stand at room temperature for 10 min. FBS was diluted to a concentration of 0.03% with Apricot and the assay buffer, and 20 μL of the solution was finally remained in the 3764 culture plate. 20 μL of 2× Component A (containing 5 mM Probenecid) was added to each experimental well, centrifuged at 200 g and RT for 3 to 5 sec, and incubated at 37° C. for 2 hr.

6) The working solution of the positive control compound and the test compound (6×) were formulated with DMSO.

7) The cell culture plate was taken out and left to stand at room temperature for 10 minutes; 10 μL of 6× compound working solution in step 5 was added to the corresponding experimental well of the 384-well cell culture plate, and incubated for 30 min at room temperature.

8) 5HT was diluted to 6 nM (6×) with experimental buffer, 50 μL was transferred to a 384-well plate (Corning, 3657), which was left to stand at room temperature. 10 μl of diluted 5HT was add to each experimental well using FLIPR Tetra, and the values were read.

4. Experimental Data Processing Method

The calcium signal values were determined by FLIPR. The calculated output for each sampling time point in the experiment was the ratio of the 340/510 nm wavelength signals to 380/510 nm wavelength signals. The maximum minus minimum calculation was derived from the ratio signal curve. The percent inhibition rate and ten-point concentration data were fitted to the parametric nonlinear logistic equation by using GraphPad prism to calculate the $IC_{50}$ values of the compound.

5. Experimental Results

TABLE 16

$IC_{50}$ values of the compounds on calcium ion mobility in cells stably expressing 5-HT2A receptors

| Example No. | $IC_{50}$ (nM) |
|---|---|
| Cariprazine | 551.0 |
| 1 | 8.08 |
| 2 | 16.68 |
| 3 | 48.01 |
| 4A | 38.98 |
| 5 | 22.08 |
| 6 | 13.05 |
| 6A | 3.07 |
| 6B | 38.95 |
| 7 | 6.44 |
| 7A | 2.74 |
| 10 | 8.90 |
| 12 | 5.20 |
| 12A | 2.21 |
| 12B | 11.60 |
| 13 | 10.86 |
| 13A | 11.73 |
| 14 | 13.35 |
| 14A | 4.37 |
| 15 | 8.06 |
| 15A | 3.14 |
| 16 | 5.78 |
| 16A | 4.28 |
| 17 | 8.92 |
| 17A | 20.79 |
| 18 | 6.40 |
| 18A | 6.44 |
| 19 | 7.37 |
| 19A | 7.67 |
| 20 | 11.59 |
| 21 | 33.54 |

6. Experimental Conclusion

It can be seen from the data in the table that the compounds of the Examples of the present invention show good inhibitory activity in the calcium ion mobility assay in cells stably expressing 5-HT2A receptors.

(III). Pharmacokinetic Assay in Balb/c Mice

1. Study Objective

Balb/c mice were used as test animals. The pharmacokinetic behavior in mouse body (plasma and brain tissue) of the compounds of Examples of the present invention was studied at an oral administration dose of 5 mg/kg.

2. Experimental Protocol 2.1 Test Compounds

Compounds of the Examples of the present invention, prepared by the applicant.

2.2 Test Animals

Male Balb/c mice (12 mice per group), purchased from Shanghai Jiesijie Laboratory Animal Co., LTD, with Certificate No.: SCXK (Shanghai) 2013-0006 N0.311620400001794.

2.3 Formulation of the Preparation

The test compound was dissolved in 0.5% CMC-Na (1% Tween80) by sonication to formulate a clear solution or homogeneous suspension.

2.4 Administration

After an overnight fast, male Balb/c mice (12 mice per group) were administered p.o. with the test compound at an administration dose of 5 mg/kg and an administration volume of 10 mL/kg.

2.5 Sample Collection 0.2 mL of blood was taken from the heart of the mouse before administration and at 1, 2, 4, 8 and 24 hours after administration, and the mice were sacrificed with $CO_2$. The samples were stored in EDTA-$K_2$ tubes, and centrifuged for 6 minutes at 4° C., 6000 rpm to separate the plasma. The plasma samples were stored at −80° C. Whole brain tissue was taken out, weighed, placed in a 2 mL centrifuge tube, and stored at −80° C.

2.6 Sample Process 1) 160 μL of acetonitrile was added to 40 μL of the plasma sample for precipitation, and then the mixture was centrifuged for 5 to 20 minutes at 3500×g.

2) 90 μL of acetonitrile containing internal standard (100 ng/mL) was added to 30 μL of the plasma and brain homogenate sample for precipitation, and then the mixture was centrifuged for 8 minutes at 13000 rpm.

3) 70 μL of water was added to 70 μL of the treated supernatant and mixed by vortex for 10 minutes. 20 μL of the supernatant was taken to analyze the concentration of the test compound by LC/MS/MS. LC/MS/MS analytical instrument: AB Sciex API 4000 Qtrap.

2.7 Liquid Chromatography Analysis:

Liquid chromatography condition: Shimadzu LC-20AD pump

Chromatographic column: Agilent ZORBAX XDB-C18 (50×2.1 mm, 3.5 μm); Mobile phase: Eluent A was 0.1% formic acid in water, and Eluent B was acetonitrile Flow rate: 0.4 mL/min Elution time: 0-4.0 minutes, the eluent is as follows:

| Time/minute | Eluent A | Eluent B |
|---|---|---|
| 0.01 | 90% | 10% |
| 0.5 | 90% | 10% |
| 0.8 | 5% | 95% |
| 2.4 | 5% | 95% |
| 2.5 | 90% | 10% |
| 4.0 | Stop | |

3. Experimental Results and Analysis

The main parameters of pharmacokinetics were calculated by WinNonlin 6.1. The results of pharmacokinetic test in mice are shown in the following Table 17.

TABLE 17

Experimental results of pharmacokinetic assay in mice

| Example No. | Pharmacokinetic test (5 mg/kg) Peak time $t_{max}$ (ng/mL) | Plasma concentration $C_{max}$ (ng/mL) | Area under curve $AUC_{0-t}$ (ng/mL × h) | Area under curve $AUC_{0-\infty}$ (ng/mL × h) | Half life $t_{1/2}$ (h) | Average residence time MRT (h) |
|---|---|---|---|---|---|---|
| 6 Plasma | 0.5 | 864.7 | 2326.5 | 2462.4 | 1.9 | 2.8 |
| 6 Brain | 1.0 | 464.0 | 1972.6 | NA | NA | NA |
| 6A Plasma | 0.5 | 745.0 | 1423 | 1444.0 | 1.3 | 1.8 |
| 6A Brain | 1.0 | 321.0 | 1081 | NA | NA | NA |
| 6B Plasma | 0.5 | 961.0 | 2250 | 2325.0 | 1.6 | 2.3 |
| 6B Brain | 1.0 | 361.0 | 900 | NA | NA | NA |
| 7 Plasma | 0.5 | 254.0 | 503.0 | 540.9 | 2.1 | 2.8 |
| 7 Brain | 1.0 | 569.3 | 2077.8 | NA | NA | NA |
| 7A Plasma | 1.0 | 102.0 | 395 | 501.0 | 3.7 | 5.3 |
| 7A Brain | 1.0 | 179.0 | 1346 | NA | NA | NA |
| 12 Plasma | 0.5 | 391.0 | 1038.9 | 1227.3 | 2.8 | 3.9 |
| 12 Brain | 1.0 | 1196.0 | 4830.1 | 4881.3 | NA | NA |
| 12A Plasma | 0.5 | 673.0 | 1844.0 | 1970.0 | 1.9 | 3.1 |
| 12A Brain | 1.0 | 1763.0 | 8130.0 | NA | NA | NA |
| 12B Plasma | 0.5 | 715.0 | 1624.0 | 1711.0 | 1.8 | 2.4 |
| 12B Brain | 1.0 | 1871.0 | 5204.0 | NA | NA | NA |
| 19A Plasma | 0.5 | 349.0 | 456 | 471.0 | 1.7 | 1.8 |
| 19A Brain | 1.0 | 372.0 | 1236 | NA | NA | NA |
| 24 Plasma | 0.5 | 368.7 | 1475.7 | 2001.3 | 3.4 | 5.7 |
| 24 Brain | 1.0 | 338.7 | 2187.7 | 2305.1 | NA | NA |
| 25 Plasma | 1.0 | 49.7 | 239.5 | 297.3 | 3.25 | 5.1 |
| 25 Brain | 1.0 | 161.9 | 1535.5 | 1653.4 | NA | NA |

4. Experimental Conclusion

It can be seen from the experimental results of pharmacokinetic assay in mice that the compounds of the Examples of the present invention showed good pharmacokinetic properties, both the exposure AUC and maximum plasma concentration $C_{max}$ were good.

(IV). Pharmacodynamic Model of Active Escape Experiment in Rats

1. Experimental Objective

To evaluate the anti-schizophrenic effect of the compounds using the pharmacodynamic model of the active escape experiment in rats.

2. Experimental Instruments and Reagents 2.1 Instruments

| No. | Instrument name | Instrument model | Source | Manufacturer |
|---|---|---|---|---|
| 1 | Active and passive shuttle device | MED-APA-D1R | Imported | Med Associates, Inc. |
| 2 | Thermostatic magnetic stirrer | 85-2 | Domestic | Shanghai Sile Instrument Co., Ltd. |
| 3 | Vortex mixer | H-101 | Domestic | Shanghai Kanghe Photoelectric Instrument Co., Ltd. |
| 4 | Ultrasonic cleaner | KQ3200DE | Domestic | Kunshan Ultrasonic Instruments Co., Ltd |

2.2 Reagents

| No. | Name | Purity | Batch number | Storage condition | Manufacturer |
|---|---|---|---|---|---|
| 1 | CMC-Na | 100% | SLBV9664 | RT | Sigma |
| 2 | Tween 80 | 100% | BCBV8843 | RT | Sigma |

2.3 Test Compounds

Compounds of the Examples of the present invention, prepared by the applicant.

3. Test Animals

| Species | Strain | Age | Gender | Supplier |
|---|---|---|---|---|
| Rats | F344 | 6-8 weeks | Male | Beijing Vital River Laboratory Animal Technology Co., Ltd. |

4. Formulation of the Vehicle and Compounds 4.1 Vehicle (0.5% CMC-Na+1% Tween80)

A certain mass (such as 1.0 g) of CMC-Na was weighed into a glass bottle. A certain volume (such as 200 mL) of purified water was added. The resulting mixture was stirred to disperse evenly. 1% (v/v) Tween 80 was added according to the solution volume, and the resulting mixture was stirred overnight to obtain a homogeneous clear solution, which was stored at 2 to 8° C. for later use.

4.2 Formulation of the Compounds

A prescription amount of the compound was weighed, followed by the addition of a prescription volume of 0.5% CMC-Na+1% Tween 80 solution. The compound solution was formulated before the administration, stored at 2 to 8° C., and used within 4 days.

The actual sample amount needs to be calculated during the formulation and administration of the compound solution. The calculation equation is as follows: the actual sample amount of the compound=theoretical weighing sample amount*purity/salt coefficient.

5. Experimental Operation

After arriving at the experimental facility, the animals were acclimatized for one week before starting the experiment.

5.1 Establishment of the Pharmacodynamic Model:

5.1.1 The animal was put into the shuttle box and adapted for 5 seconds, followed by subjecting to 10 seconds of sound and light stimulation;

5.1.2 If the animal avoided to the other side during the 10 seconds of sound and light stimulation, then no electric shock would be given, this would be recorded as avoids, and the single training ended;

5.1.3 If the animal failed to move to the other side after the 10 seconds of sound and light stimulation, then an electric shock would be given. The current intensity was 0.6 mA and the duration was 10 seconds. If the animal avoided to the other side during the 10 seconds of electric shock, then the electric shock would stop. This would be recorded as escapes, and the single training ended;

5.1.4 If the animal failed to avoid during the 10 seconds of electric shock, then the electric shock would stop. This would be recorded as escape failures, and the single training ended;

5.1.5 Each animal was trained 30 times a day for a total of 6 days, and returned to the cage after the training.

5.2 Baseline Test and Grouping

The day before the compound screening test, a baseline test was performed. The test process was the same as 5.1.1 to 5.1.3, and the number of the baseline test was 20. The animals whose number of avoids reached 16 (80%) were grouped according to the number of avoids, 10 animals per group. The first group was administered with the vehicle orally, and the other groups were administered with the corresponding test compounds according to the experimental design.

5.3 Compound Screening Test

The compound was administered orally (5 mL/kg) one hour before the test.

The test process was the same as 5.1.1 to 5.1.4, and the number of the test was 20.

6. Data Process

The following data was collected by the software for data analysis:

Number of avoids of the animal;

Number of escape failures of the animal;

Escape latency of the animal;

All measurement data were expressed as mean±standard error (Mean±SEM), and analyzed by Graphpad 6 statistical software. The difference was considered to be significant when $p<0.05$.

7. Experimental Results

TABLE 18

| Example No. | CAR value | Dose (mg/kg) |
|---|---|---|
| Vehicle | 91-98% | — |
| 12 | 30% | 1 |
| 12A | 18.5% | 1 |

8. Experimental Conclusion

It can be seen from the above data that the compounds of the Examples of the present invention show good effects in the pharmacodynamic model of the active escape experiment in rats, indicating that they have anti-schizophrenia effect.

III. Study on the Salt of Compound and the Crystal Form of Salt

As those skilled in the art are well known, when the above example compounds are shown to have pharmacological activity that significantly inhibits D3/5HT2A binding, their pharmaceutically acceptable salts tend to have the same pharmacological activity. On this basis, the inventor further studied physical and chemical properties of salt form and crystal form of the corresponding compound, but the preparation and characterization of the following specific salt form or crystal form does not represent a limitation of the protection scope of the present invention, and those skilled in the art may obtain more salt forms and crystals of the compounds of the present invention by conventional salt forming or crystallization means based on the present invention, and these salt forms and crystals are the technical solutions protected by the present invention. The details are as follows.

1. Experimental Instruments 1.1 Some Parameters of Physical and Chemical Testing Instruments

| | | |
|---|---|---|
| XRPD | Instrument model | BRUKER D8 ADVANCE |
| | Diffraction ray | CuK (40 kV, 25 mA) |
| | Scan rate | 0.02°/S (2θ value) |
| | Scan range | 4° to 40° (2θ value) |
| DSC | Instrument model | NETZSCH DSC 214 polyma |
| | Purge gas | Nitrogen |
| | Purge speed | 40 mL/min |
| | Heating rate | 10° C./min |
| | Temperature range | 25 to 300° C. |
| | Plate type | Aluminum plate |
| TGA | Instrument model | NETZSCH TG 209 Tarsus |
| | Purge gas | Nitrogen |
| | Purge speed | 40 mL/min |
| | Heating rate | 10° C. /min |
| | Temperature range | 35° C. to 350° C. |
| | Plate type | $Al_2O_3$ |

1.2 Instruments and Liquid Phase Analysis Conditions 1.2.1 Instruments and Devices

| Instrument name | Model |
|---|---|
| Analytical Balance | METTLER TOLEDO XA105 |
| Water purifier | Milli-Q Plus, Millipore |
| High performance liquid chromatograph | Agilent1260 |
| Pump | Agilent G1311B |
| Injector | G1329B |
| Column oven | G1316A |
| Detector | G1315D |

1.2.2 Chromatography Conditions

Chromatographic column: ZORBAX (SB-C8, 3.5 μm, 4.6*75 mm)

Flow rate: 1.5 mL/min

Column temperature: 40° C.

Detection wavelength: 251 nm

Injection volume: 5.0 μL

Running time: 15 min

Diluent: DMSO

Mobile phase: A: water (0.05% trifluoroacetic acid); B: acetonitrile (0.05% trifluoroacetic acid)

| T(min) | A(%) | B(%) |
|---|---|---|
| 0.00 | 90 | 10 |
| 8.00 | 40 | 60 |
| 12.00 | 10 | 90 |
| 12.01 | 90 | 10 |
| 15.00 | 90 | 10 |

2. Study on the Salt Form of Compound

2.1 Study on the Salt Form of Compound N-(trans-3-(2-(4-(2,3-dichlorophenyl)piperazin-1-yl)ethyl) cyclobutyl)oxazole-2-carboxamide (Example 12A)

2.1.1 Experimental Objective

To identify which counter ion acids can form salts with the compound by selecting different counter ion acids.

2.1.2 Experimental Steps

1) Instruments

| Name | Model | Source |
|---|---|---|
| Analytical Balance | BSA224S-CW | Sartorius |
| Ultrasonic cleaner | SK5200LHC | Shanghai Kudos Ultrasonic Instrument |
| Pipettes | Eppendorf (50 mL, 1000 μL) | Eppendorf |

2) Operating Procedures

Salt Forming by Volatilization Method 10 mg of free base was weighed. 200 μL of tetrahydrofuran was added. Different counter ion acids were added separately at room temperature, and the solvent was volatilized to dry. If a solid was precipitated during the reaction, the suspension was centrifuged, and the resulting solid was vacuum dried at 50° C. If the product obtained in the volatilization salt screening experiment was an oil or gel, 200 μL of ethyl acetate was added thereto and then stirred for 4 hours at room temperature. The resulting suspension was centrifuged and the supernatant was removed. The solid was dried in vacuum at 50° C. The results are shown in Table 19 below.

TABLE 19

| Acid | Amount of acid added | Phenomenon after the addition of acid | Product | Pulping by ethyl acetate |
|---|---|---|---|---|
| HCl (1 mol/L in MeOH) | 36 μL | Clear, no solid precipitation | Gel | Salt forming |
| HBr (1 mol/L in MeOH) | 36 μL | Clear, no solid precipitation | Gel | Salt forming |
| $H_2SO_4$ (1 mol/L in MeOH) | 36 μL | Clear, no solid precipitation | Gel | Salt forming |
| p-Toluenesulfonic acid (1 mol/L in MeOH) | 36 μL | Clear, no solid precipitation | Salt forming | / |
| Oxalic acid (1 mol/L in MeOH) | 36 μL | Clear, no solid precipitation | Gel | Salt forming |

Preparation of Salt Form by Volatilization and Suspension Method 10 mg of free base was weighed, and 200 μL of acetone was added. Different counter ion acids were added separately at room temperature, and the solvent was volatilized to dry. If a solid was precipitated, the resulting solid was dried in vacuum overnight at 50° C. If the product obtained in the volatilization salt screening experiment was an oil or gel, 200 μL of other solvent was added thereto, and stirred for 4 hours at room temperature. The resulting suspension was centrifuged, and the supernatant was removed. The solid was dried in vacuum at 50° C. The results are shown in Table 20 below.

TABLE 20

| Acid solution | Phenomenon | Pro-duct | After adding 200 μL of ethyl acetate | After adding 200 μL of methanol |
|---|---|---|---|---|
| Nitric acid (1 mol/L in EtOH) | Clear, no solid precipitation | Gel | Gel | Salt forming |
| Methanesulfonic acid (1 mol/L in EtOH) | Clear, no solid precipitation | Gel | Gel | Salt forming |
| 1,5-Naphthalene-disulfonic acid (0.125 mol/L in EtOH) | Clear, no solid precipitation | Salt forming | Gel | Gel |

Suspension Reaction Crystallization Method for Salt Form Study 10 mg of free base compound was weighed, and 100 μL of organic solvent was added to the suspension state. The corresponding acid was added according to the molar ratio of 1:1.2 at room temperature, and the reaction was stirred for 4d. The reaction was centrifuged, and the resulting solid was dried in vacuum at 50° C. The results are shown in Table 21 below.

TABLE 21

| Solvent | Acid | Phenomenon after the addition of acid | Product |
|---|---|---|---|
| Isopropanol | Acetic acid | muddy | Salt forming |
| Isopropanol | Fumaric acid | muddy | Salt forming |
| | Acetic acid | muddy | Salt forming |

2.1.3 Stability Study of Salt

Hydrochloride and p-toluenesulfonate of N-(trans-3-(2-(4-(2,3-dichlorophenyl)piperazin-1-yl)ethyl)cyclobutyl) oxazole-2-carboxamide were weighed about 1 mg, respectively, and then placed under light (5000 lux), high temperature (60° C.), high humidity (92.50 RH), high temperature and high humidity (50° C. and 75% RH) for 5 days and 10 days, then a diluent DMSO was added to prepare a solution with salt concentration of about 1 mg/mL.

The chromatographic peak area normalization method was used to calculate the changes of related substances. The determination method of related substances by HPLC is shown in the following table. The stability results are shown in the table below.

| | |
|---|---|
| Column | Waters XBridge C8 (4.6*150 mm, 3.5 um) |
| Mobile phase | A: 0.05% TFA in $H_2O$, B: 0.05% TFA in ACN |
| Column temperature | 40° C. |
| Flow rate | 1.5 ml/min |
| Sample temperature | 37° C. |
| Injection volume | 5 μL |
| Wavelength | 251 nm |

| Gradient | Time | A(%) | A(%) |
|---|---|---|---|
| | 0 | 90 | 10 |
| | 8 | 40 | 60 |
| | 12 | 10 | 90 |
| | 12.01 | 90 | 10 |
| | 15 | 90 | 10 |

Stability results are shown in Table 22 and Table 23 below.

TABLE 22

Stability test results of p-toluenesulfonate

| | RRT/Area % | 0.190 | 0.210 | 0.890 | 1.000 | 1.050 | 1.190 | 1.540 | total |
|---|---|---|---|---|---|---|---|---|---|
| p-Toluenesulfonate | 0 d | 0.317% | 0.073% | \ | 99.217% | 0.149% | 0.178% | 0.067% | 0.783% |
| | GZ-5 d | 0.266% | 0.072% | 0.130% | 99.184% | 0.101% | 0.171% | 0.075% | 0.816% |
| | GW-5 d | 0.163% | 0.072% | \ | 99.400% | 0.121% | 0.175% | 0.068% | 0.600% |
| | GS-5 d | 0.213% | 0.074% | \ | 99.310% | 0.145% | 0.177% | 0.080% | 0.690% |
| | GWGS-5 d | 0.348% | 0.072% | \ | 99.204% | 0.137% | 0.170% | 0.070% | 0.796% |
| | GZ-10 d | 0.324% | 0.073% | 0.232% | 99.028% | 0.115% | 0.162% | 0.066% | 0.972% |
| | GW-10 d | 0.224% | 0.075% | \ | 99.319% | 0.131% | 0.178% | 0.073% | 0.681% |
| | GS-10 d | 0.233% | 0.075% | \ | 99.298% | 0.143% | 0.180% | 0.071% | 0.702% |
| | GWGS-10 d | 0.319% | 0.074% | \ | 99.246% | 0.128% | 0.168% | 0.065% | 0.754% |

Stability test results of hydrochloride

| | RRT/Area % | 0.220 | 1.000 | 1.050 | 1.200 | 1.550 | total |
|---|---|---|---|---|---|---|---|
| Hydrochloride | 0 d | \ | 99.619% | 0.153% | 0.163% | 0.065% | 0.381% |
| | GZ-5 d | \ | 99.617% | 0.148% | 0.160% | 0.075% | 0.383% |
| | GW-5 d | \ | 99.604% | 0.164% | 0.163% | 0.068% | 0.396% |
| | GS-5 d | 0.055% | 99.556% | 0.160% | 0.161% | 0.069% | 0.444% |
| | GWGS-5 d | \ | 99.603% | 0.144% | 0.165% | 0.088% | 0.397% |
| | GZ-10 d | \ | 99.604% | 0.162% | 0.158% | 0.077% | 0.396% |
| | GW-10 d | \ | 99.590% | 0.170% | 0.163% | 0.077% | 0.410% |
| | GS-10 d | \ | 99.619% | 0.153% | 0.163% | 0.065% | 0.381% |
| | GWGS-10 d | \ | 99.614% | 0.157% | 0.161% | 0.067% | 0.386% |

The stability results showed that N-(trans-3-(2-(4-(2,3-dichlorophenyl)piperazin-1-yl)ethyl)cyclobutyl)oxazole-2-carboxamide hydrochloride had good stability under high temperature, light, high humidity, high temperature and high humidity experimental conditions, no significant growth of impurities, and p-toluenesulfonate had no significant changes in impurities under high temperature, high humidity, and high temperature and high humidity conditions.

2.1.4 Hygroscopicity Study of Salt

The hygroscopicity of a drug refers to the characteristics of the drug's ability or degree of water absorption at a certain temperature and humidity. Dynamic Sorption Sorption (DVS) was used to characterize the ability of drugs to absorb water under different humidity conditions. The instrument parameters are detailed in the table below.

| | |
|---|---|
| Instrument mode | SMS Intrinsic |
| Experimental temperature | 25° C. |
| Drying time | 0% RH 120 min |
| Balanced dm/dt | 0.02%/min (min. 10 min, max. 180 min) |
| RH(%) step size of measurement | 10% |
| Gradient of measurement | 0-95-0% |
| Number of cycles | 1 |

Figure 20:
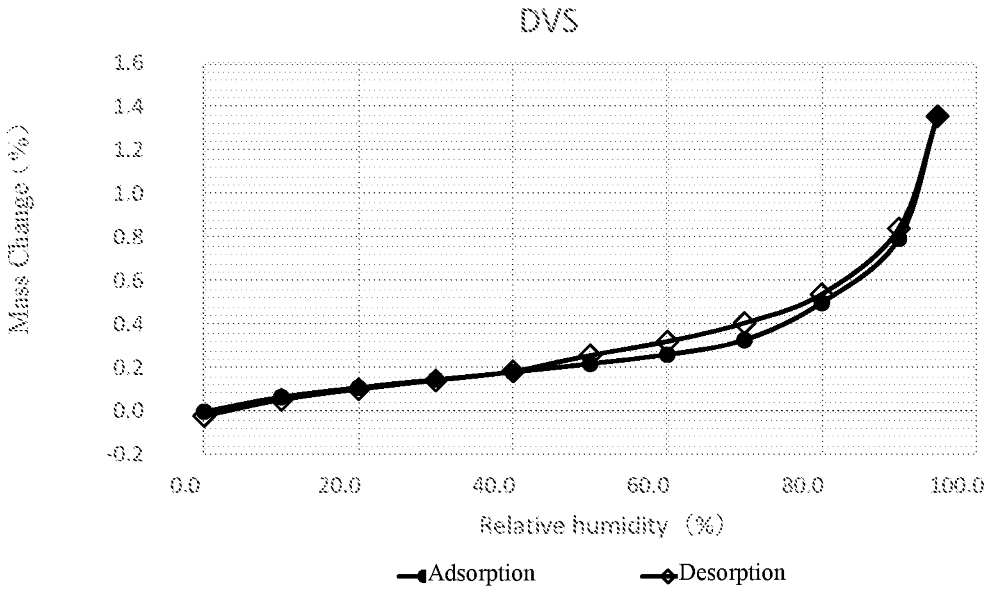
FIG. 20 is the DVS spectrum of hydrochloride of N-(trans-3-(2-(4-(2,3-dichlorophenyl)piperazin-1-yl)ethyl)cyclobutyl)oxazole-2-carboxamide.

The hygroscopicity test results of N-(trans-3-(2-(4-(2,3-dichlorophenyl)piperazin-1-yl)ethyl)cyclobutyl)oxazole-2-carboxamide hydrochloride are shown in FIG. 20.

The experimental results showed that N-(trans-3-(2-(4-(2,3-dichlorophenyl)piperazin-1-yl)ethyl)cyclobutyl)oxazole-2-carboxamide hydrochloride was slightly hygroscopic.

2.1.5 Solubility of Hydrochloride in Different Media 1.0 mg of compound was weighed into a 2 mL glass bottle, then 1 mL of dissolving medium was added respectively. The glass bottle was shaken overnight on an electrothermal constant temperature shaking tank, and the temperature was set to 37° C. After 24 hours, the sample solution was filtered with a 0.45 μm mixed water fiber filter membrane, and the subsequent filtrate was taken to test its content by HPLC. HPLC detection methods are described in "Stability Study Conditions".

The solubility of hydrochloride in different buffer media is shown in Table 24 below.

TABLE 24

Solubility of hydrochloride and free base in different pH buffers

| Buffer | Free base | Hydrochloride |
|---|---|---|
| pH 1 | >1 | >1 |
| pH 2 | >1 | >1 |
| pH 3 | >1 | >1 |
| pH 4 | >1 | >1 |
| pH 5 | >1 | 0.863 |
| pH 6 | 0.388 | 0.187 |
| pH 7 | 0.044 | 0.014 |
| pH 8 | 0.002 | 0.001 |
| $H_2O$ | 0.125 | >1 |
| FaSSGF | 0.154 | 0.117 |
| FaSSIF | >1 | >1 |
| FeSSIF | >1 | >1 |
| FaSSCoF | >1 | >1 |
| FeSSCoF | >1 | >1 |

The results show that the solubility of N-(trans-3-(2-(4-(2,3-dichlorophenyl)piperazin-1-yl)ethyl)cyclobutyl)oxazole-2-carboxamide hydrochloride is pH-dependent, with better solubility under acidic conditions, poor solubility under neutral or alkaline conditions, and is almost insolubility. After forming salt, the solubility in water was greatly improved than that of free base.

3. Study on the Crystal Form of Salt of Compound 3.1 Study on the Crystal Form of Salt of Compound N-(trans-3-(2-(4-(2,3-dichlorophenyl)piperazin-1-yl)ethyl)cyclobutyl)oxazole-2-carboxamide (Example 12A)

3.1.1 Experimental Objective

To identify which counter ion acids can form crystal form of salt of compound by selecting different counter ion acids according to suitable crystallization methods.

3.1.2 Experimental Steps

1) Instruments and Devices

| Name | Model | Source |
|---|---|---|
| Analytical Balance | XA105 | METTLER TOLEDO |
| Ultrasonic cleaner | SK5200LHC | Shanghai Kudos Ultrasonic Instrument |
| Pipettes | Eppendorf (50 mL, 1000 μL) | Eppendorf |

2) Preparation of Crystal Form B of Free Base

Figure 21:
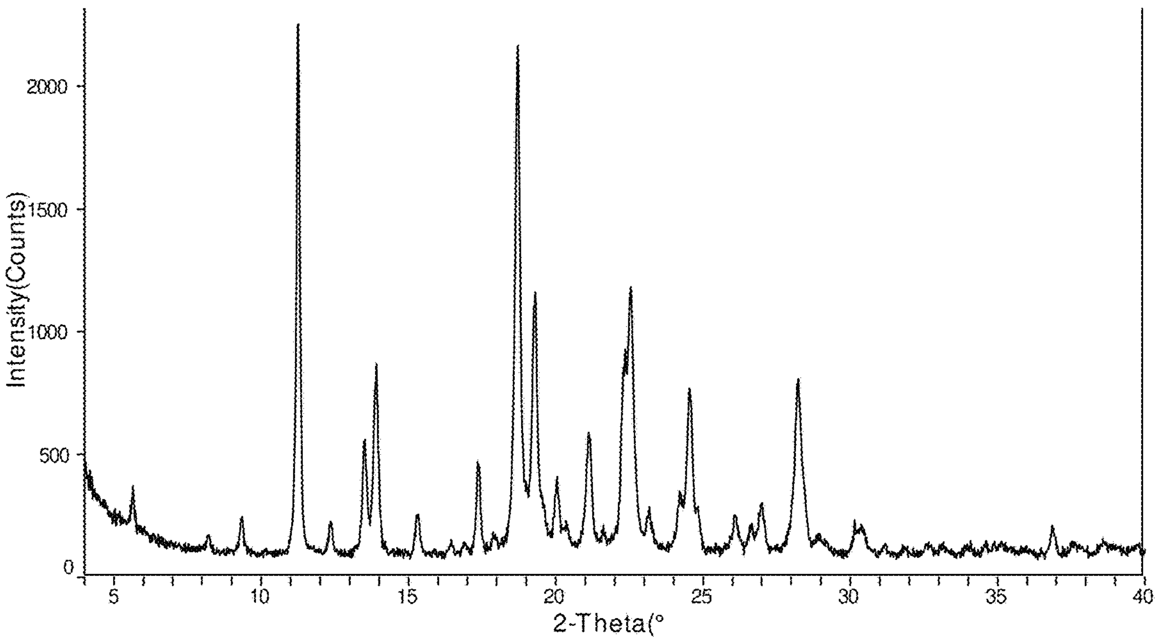
FIG. 21 is the XRPD pattern of crystal form B of free base of N-(trans-3-(2-(4-(2,3-dichlorophenyl)piperazin-1-yl)ethyl)cyclobutyl)oxazole-2-carboxamide.
Figure 22:
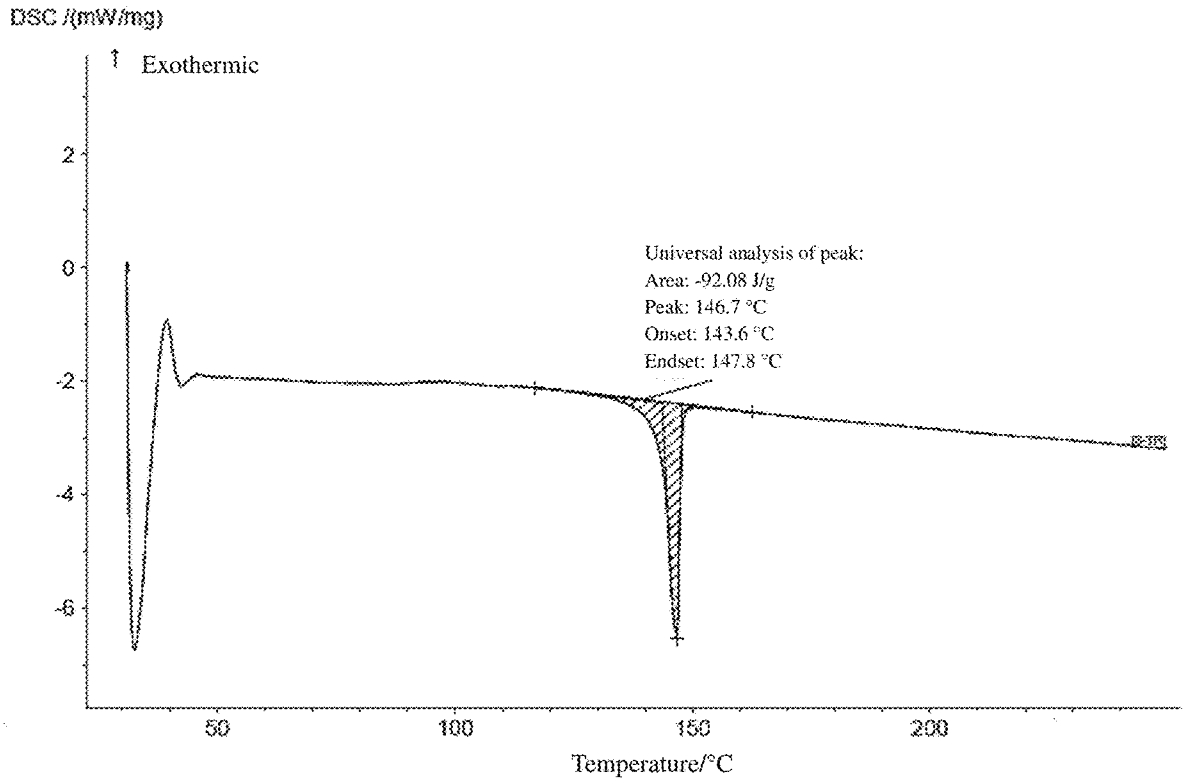
FIG. 22 is the DSC spectrum of crystal form B of free base of N-(trans-3-(2-(4-(2,3-dichlorophenyl)piperazin-1-yl)ethyl)cyclobutyl)oxazole-2-carboxamide.
Figure 23:
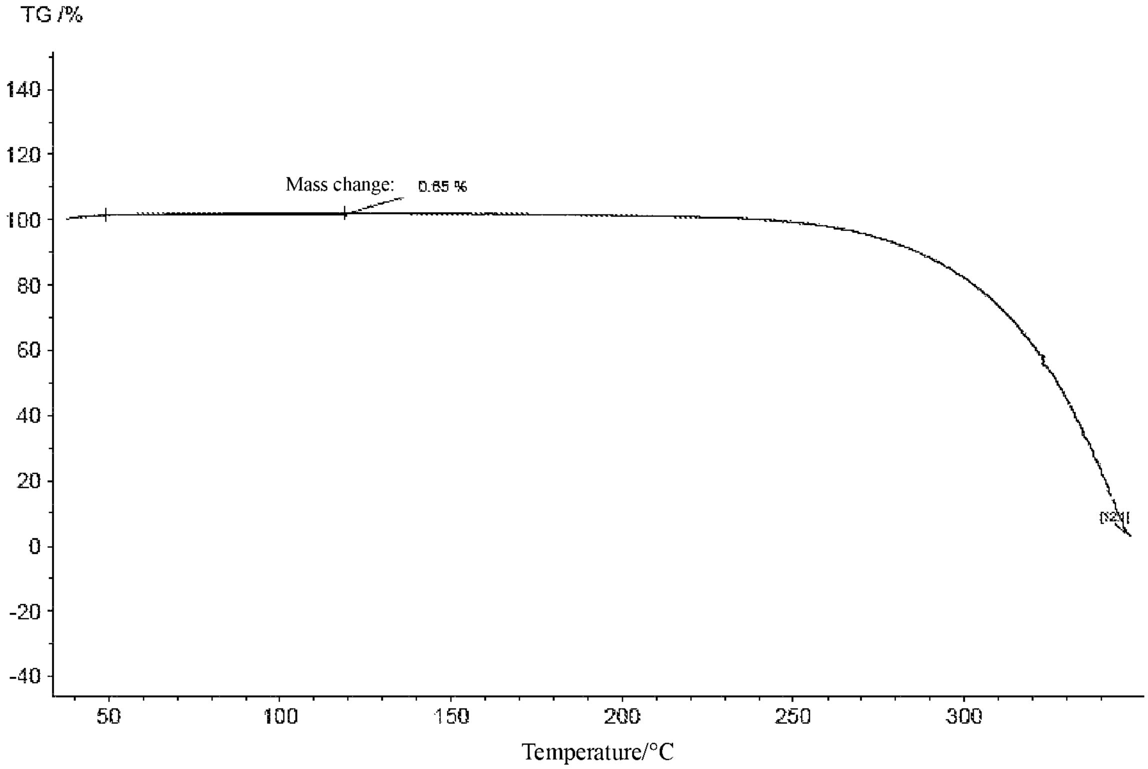
FIG. 23 is the TGA spectrum of crystal form B of free base of N-(trans-3-(2-(4-(2,3-dichlorophenyl)piperazin-1-yl)ethyl)cyclobutyl)oxazole-2-carboxamide.

The compound N-(trans-3-(2-(4-(2,3-dichlorophenyl)piperazin-1-yl)ethyl)cyclobutyl)oxazole-2-carboxamide was subjected to column chromatography (mobile phase: DCM/MeOH=10:1) and freeze-dried to obtain crystal form B. After detection and analysis, it has the following XRPD pattern as shown in FIG. 21, DSC spectrum as shown in FIG. 22, and TGA spectrum as shown in FIG. 23.

3) Crystal Form Study of Salt

I Volatilization Method 228 mg of crystal form B of free base was weighed, and dissolved in 18 mL of tetrahydrofuran solvent to produce a clear solution. 1 mL of the solution was taken into a glass bottle, and different counter ion acids (molar reaction ratio of base:acid=1:1.2) were added, and then the glass bottle was opened at room temperature to volatile solvent. The amorphous or oily was pulped with 200 μL of ethyl acetate. The results are shown in Table below.

TABLE 25

| No. | Acid | Phenomenon after the addition of acid | Results | Ethyl acetate pulping results |
|---|---|---|---|---|
| 1 | 1.0M hydrochloric acid (in methanol) | Clear | Oil or gel | Crystal form |
| 2 | 1.0M hydrobromic acid (in methanol) | Clear | Oil or gel | Crystal form |
| 3 | 1.0M sulfuric acid (in methanol) | Clear | Oil or gel | Crystal form |
| 4 | 1.0M p-toluenesulfonic acid (in methanol) | Clear | Crystal form | N/A |
| 5 | 1.0M methanesulfonic acid (in ethanol) | Clear | Oil or gel | Crystal form |
| 6 | 1.0M oxalic acid (in methanol) | Clear | Oil or gel | Crystal form |
| 7 | 0.25M oxalic acid (in methanol) | Clear | Oil or gel | Crystal form |
| 8 | 0.125M 1,5-naphthalenedisulfonic acid (in ethanol) | Crystal form | / | / |

TABLE 25-continued

| No. | Acid | Phenomenon after the addition of acid | Results | Ethyl acetate pulping results |
|---|---|---|---|---|
| 9 | 1.0M nitric acid (in ethanol) | Clear | Oil or gel | Crystal form |
| 10 | 1.0M acetic acid (in methanol) | Clear | Oil or gel | Crystal form |

II Salt Forming Crystallization by Precipitating or Suspending in Different Solvents 1) 10 mg of crystal form B of free base was weighed, and 200 μL of methanol solvent was added, and counter ion acid (molar reaction ratio of base:acid=1:1.2) was added respectively at 25° C. The results are shown in Table 26 below.

TABLE 26

| Solvent | Acid | Phenomenon | Results |
|---|---|---|---|
| Ethyl acetate | 1.0M hydrochloric acid (in methanol) | Suspension | Crystal form |
| Acetone | | Suspension | Crystal form |
| Ethanol | | Clear | Crystal form |
| Ethyl formate | | Precipitation | Crystal form |
| 2-Methyl-tetrahydrofuran | | Suspension | Crystal form |
| 2-Butanone | | Clear | Crystal form |
| Isopropanol | | Suspension | Crystal form |
| Isopropyl acetate | | Suspension | Crystal form |
| Methyl tert-butyl ether | | Suspension | Crystal form |
| Isopropanol | 1M acetic acid in methanol | Turbid | Crystal form |
| Isopropyl ether | 0.25M fumaric acid in ethanol | Turbid | Crystal form |
| | 1M acetic acid in methanol | Turbid | Crystal form |

2) 85 mg of crystal form B of free base was weighed, and ethyl acetate was added to produce a clear solution. Different counter ion acids (molar reaction ratio of base:acid=1:1.2) were added respectively at 25° C. The results are shown in Table 27 below.

TABLE 27

| No. | Acid | Phenomenon | Results |
|---|---|---|---|
| 1 | 1.0M hydrochloric acid (in methanol) | Add acid and precipitate solids at the same time | Crystal form |
| 2 | 1.0M p-toluenesulfonic acid (in methanol) | Add acid and precipitate solids at the same time | Crystal form |

3.1.3 Experimental Results

The crystalline salts of compound N-(trans-3-(2-(4-(2,3-dichlorophenyl)piperazin-1-yl)ethyl)cyclobutyl)oxazole-2-carboxamide obtained by different crystallization methods are hydrochloride, p-toluenesulfonate, hydrobromide, oxalate, sulfate, methanesulfonate, 1,5-naphthalenedisulfonate, nitrate, acetate and fumarate. They are named as crystal form A of hydrochloride, crystal form B of hydrochloride, crystal form A of p-toluenesulfonate, crystal form B of p-toluenesulfonate, crystal form A of hydrobromide, crystal form A of oxalate, crystal form A of sulfate, crystal form A of methanesulfonate, crystal form A of 1,5-naphthalenedisulfonate, crystal form A of nitrate, crystal form A of acetate and crystal form A of fumarate.

3.2 Polycrystalline Screening of Salts of Compound N-(trans-3-(2-(4-(2,3-dichlorophenyl)piperazin-1-yl)ethyl)cyclobutyl)oxazole-2-carboxamide (Example 12A)

3.2.1 Experimental Objective

According to the results of salt form screening, different crystal forms of salt were screened by selecting appropriate crystallization method.

3.1.2 Experimental Steps

1) Instruments and Devices

| Name | Model | Source |
|---|---|---|
| Analytical Balance | XA105 | METTLER TOLEDO |
| Ultrasonic cleaner | SK5200LHC | Shanghai Kudos Ultrasonic Instrument |
| Pipettes | Eppendorf (50 mL, 1000 μL) | Eppendorf |

2) Operating Procedures

I. Preparation of Crystal Form of Hydrochloride

Figure 2:
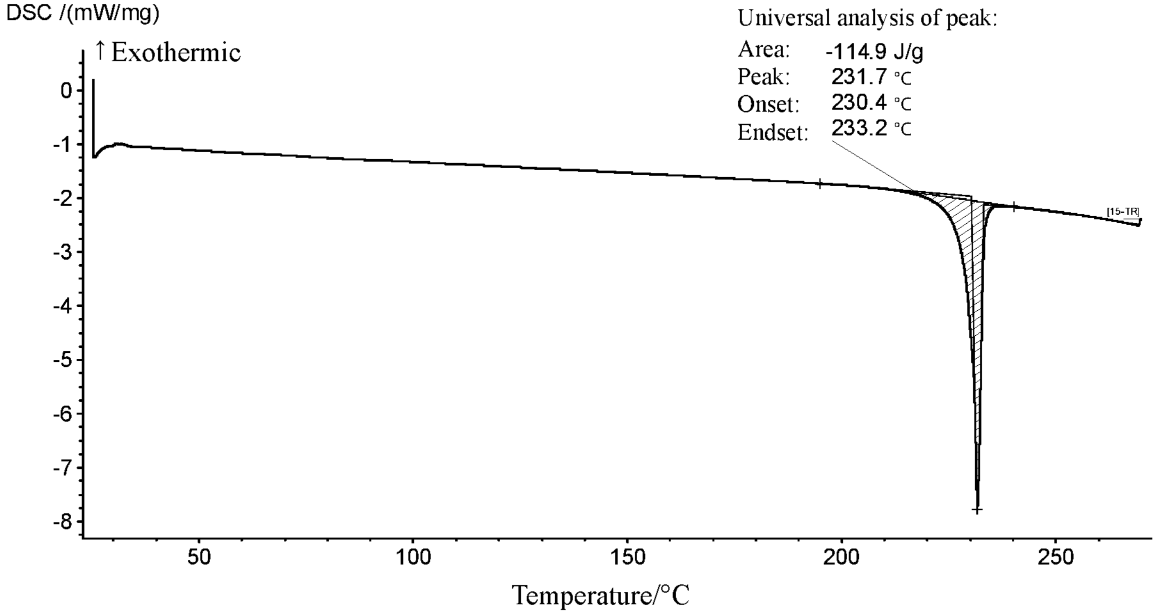
FIG. 2 is the DSC spectrum of crystal form A of hydrochloride of N-(trans-3-(2-(4-(2,3-dichlorophenyl)piperazin-1-yl)ethyl)cyclobutyl)oxazole-2-carboxamide.
Figure 3:
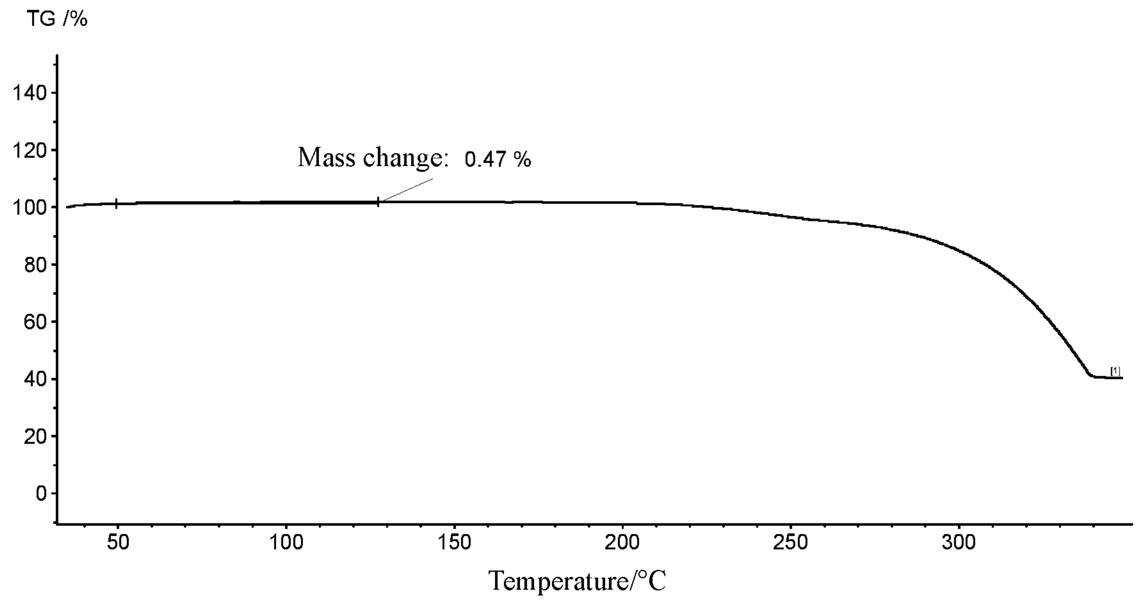
FIG. 3 is the TGA spectrum of crystal form A of hydrochloride of N-(trans-3-(2-(4-(2,3-dichlorophenyl)piperazin-1-yl)ethyl)cyclobutyl)oxazole-2-carboxamide.

Preparation of Crystal Form A of Hydrochloride:

300 mg of crystal form B of free base was weighed. 6 mL of methanol was added. The mixture was heated and stirred at 50° C. to produce a clear solution. 851 μL of LOM hydrochloric acid in methanol was slowly added to the system. A large amount of white solid was precipitated while acid was added. The solid was filtered and dried in vacuum to obtain crystal form A of hydrochloride. After detection and analysis, it has the XRPD pattern as shown in FIG. 1, the DSC spectrum as shown in FIG. 2, and the TGA spectrum as shown in FIG. 3.

Figure 4:
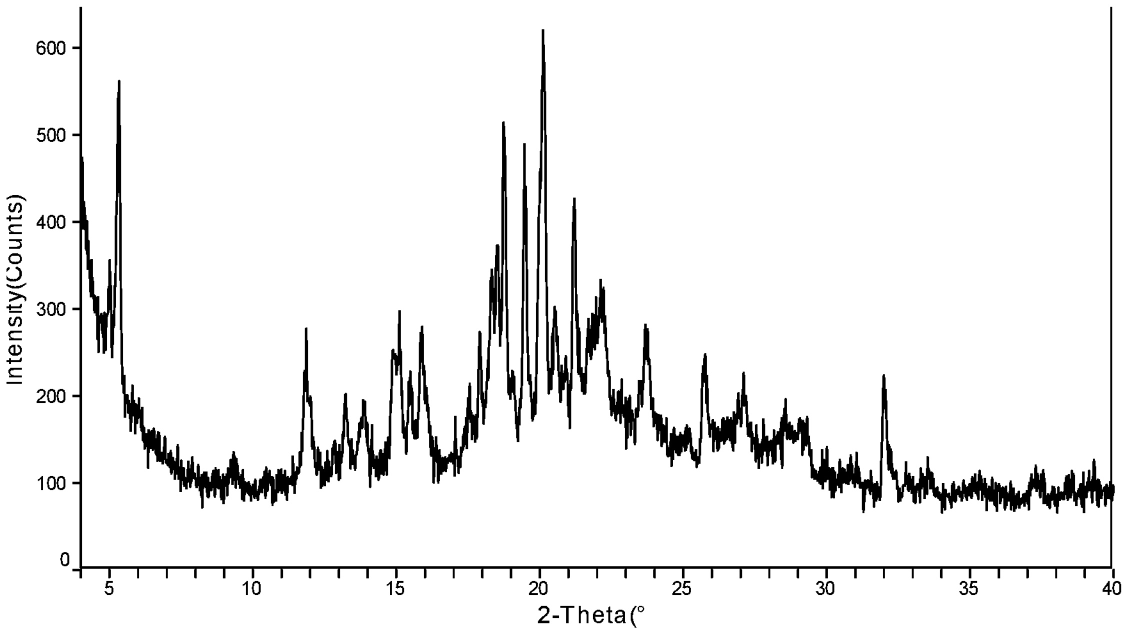
FIG. 4 is the XRPD pattern of crystal form B of hydrochloride of N-(trans-3-(2-(4-(2,3-dichlorophenyl)piperazin-1-yl)ethyl)cyclobutyl)oxazole-2-carboxamide.

Preparation of Crystal Form B of Hydrochloride 300 mg of crystal form B of free base was weighed. 4 mL of ethyl acetate was added. The mixture was warmed up to 50° C., and 6 mol/L hydrochloric acid in ethanol was added thereto according to 1:1.2 mole ratio. A white solid was precipitated. It was cooled to room temperature and stirred for 1 hour and filtered. The solid was dried in vacuum overnight at 50° C. Crystal form B of hydrochloride was obtained by detecting the PXRD of the solid. After detection and analysis, it has the XRPD pattern as shown in FIG. 4.

II. Preparation of Crystal Form of p-Toluenesulfonate

Figure 5:
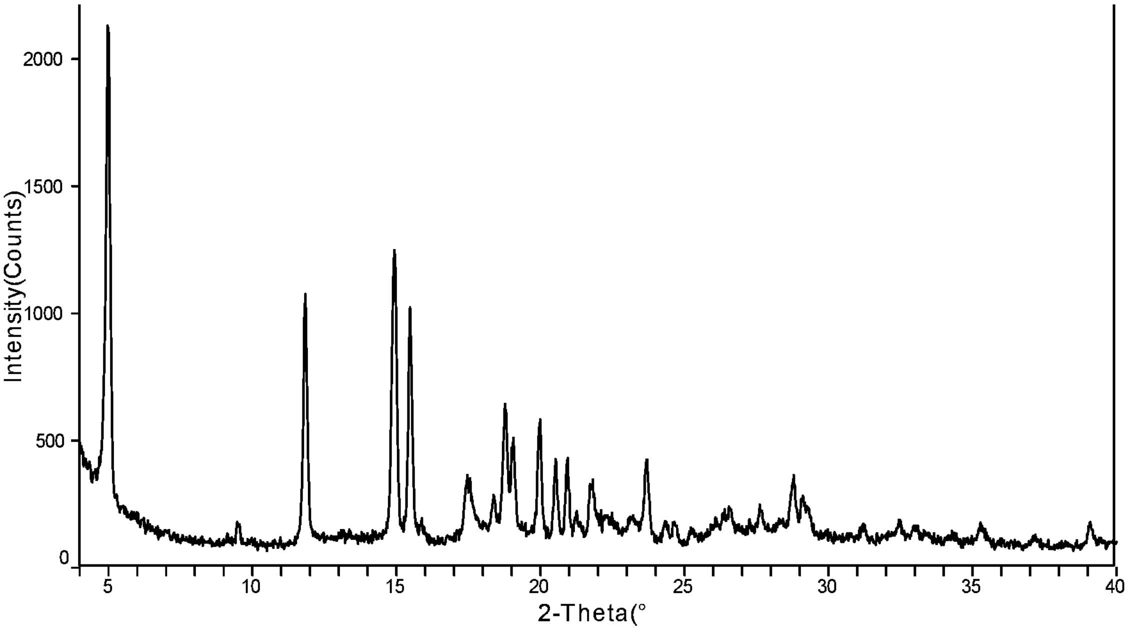
FIG. 5 is the XRPD pattern of crystal form A of p-toluenesulfonate of N-(trans-3-(2-(4-(2,3-dichlorophenyl)piperazin-1-yl)ethyl)cyclobutyl)oxazole-2-carboxamide.

Preparation of Crystal Form a of p-Toluenesulfonate 228 mg of crystal form B of free base was weighed. 18 mL of tetrahydrofuran solvent was added to produce a clear solution. 1 mL of the solution was taken into a glass bottle, and 36 μL of 1.0M p-toluenesulfonic acid in methanol was slowly add to the system, and then the glass bottle was opened to volatile solvent at room temperature to obtain crystal form A of p-toluenesulfonate. After detection and analysis, it has the XRPD pattern as shown in FIG. 5.

Figure 6:
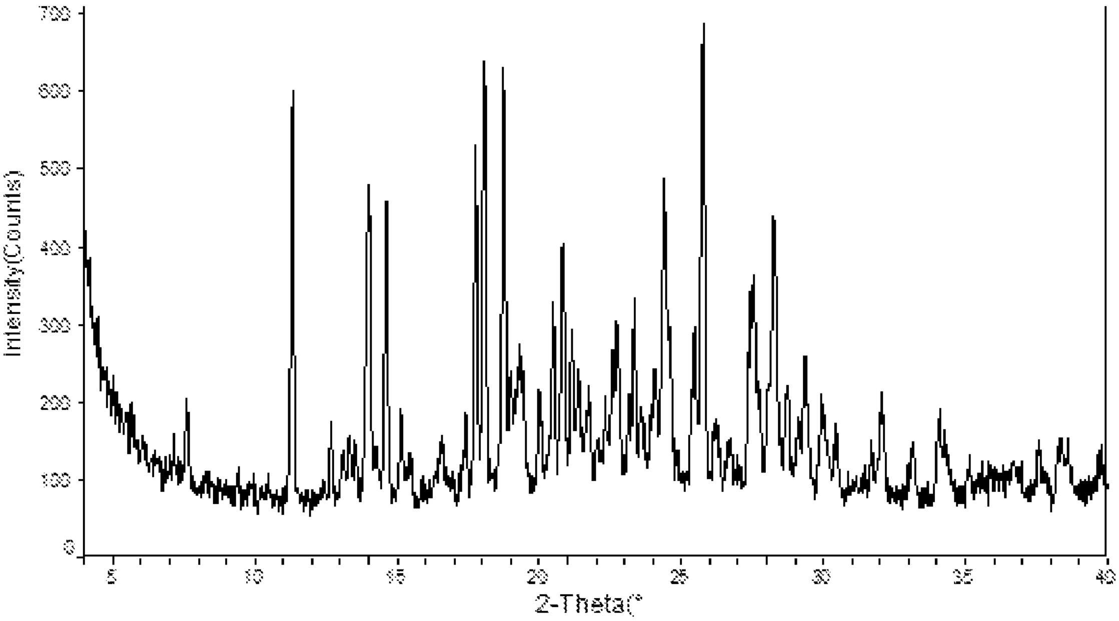
FIG. 6 is the XRPD pattern of crystal form B of p-toluenesulfonate of N-(trans-3-(2-(4-(2,3-dichlorophenyl)piperazin-1-yl)ethyl)cyclobutyl)oxazole-2-carboxamide.

Preparation of Crystal Form B of p-Toluenesulfonate 85 mg of crystal form B of free base was weighed. 3 mL of ethyl acetate solvent was added to produce a clear solution. 240 μL of 1.0M p-toluenesulfonic acid in methanol was slowly added to the system. A large amount of white solid was precipitated while acid was added. The solid was filtered and dried in vacuum to obtain crystal form B of p-toluenesulfonate. After detection and analysis, it has the XRPD pattern as shown in FIG. 6.

Figure 7:
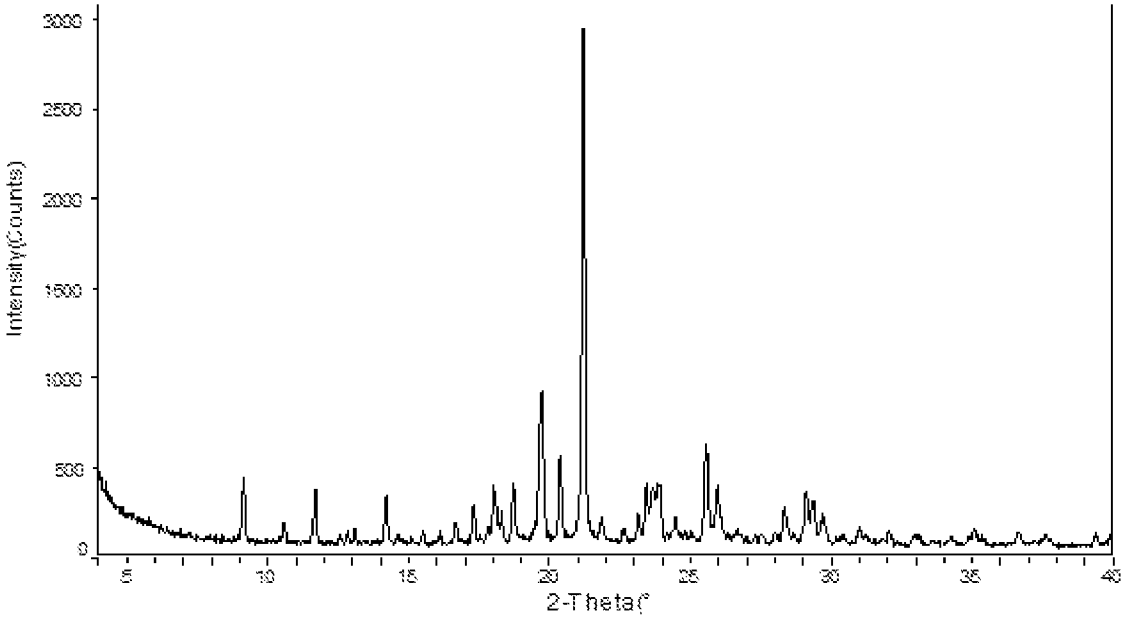
FIG. 7 is the XRPD pattern of crystal form A of hydrobromide of N-(trans-3-(2-(4-(2,3-dichlorophenyl)piperazin-1-yl)ethyl)cyclobutyl)oxazole-2-carboxamide.

III. Preparation of Crystal Form A of Hydrobromide 228 mg of crystal form B of free base was weighed. 18 mL of tetrahydrofuran solvent was added to produce a clear solution. 1 mL of the solution was taken into a glass bottle. 36 μL of 1.0M hydrobromic acid in methanol was slowly added to the system, and then the glass bottle was opened to volatile solvent at room temperature to obtain an oil or gel. 200 μL ethyl acetate was added for pulping for 4 h to precipitate a solid, which was centrifuged and dried in vacuum to obtain crystal form A of hydrobromide. After detection and analysis, it has the XRPD pattern as shown in FIG. 7.

Figure 8:
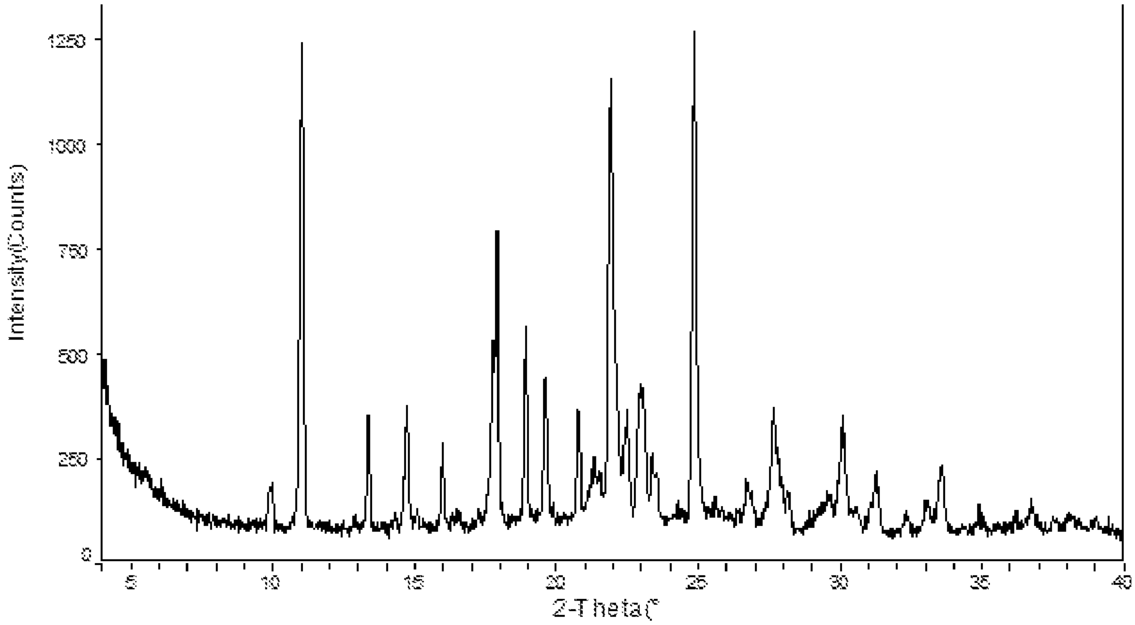
FIG. 8 is the XRPD pattern of crystal form A of oxalate of N-(trans-3-(2-(4-(2,3-dichlorophenyl)piperazin-1-yl)ethyl)cyclobutyl)oxazole-2-carboxamide.

IV. Preparation of Crystal Form A of Oxalate 228 mg of crystal form B of free base was weighed. 18 mL of tetrahydrofuran solvent was added to produce a clear solution. 1 mL of the solution was taken into a glass bottle, and 36 μL of 1.0M oxalic acid in methanol was slowly added to the system, and then the glass bottle was opened to volatile solvent at room temperature to obtain an oil or gel. 200 μL ethyl acetate was added for pulping for 4 h to precipitate a solid, which was centrifuged and dried in vacuum to obtain crystal form A of oxalate. After detection and analysis, it has the XRPD pattern as shown in FIG. 8.

Figure 9:
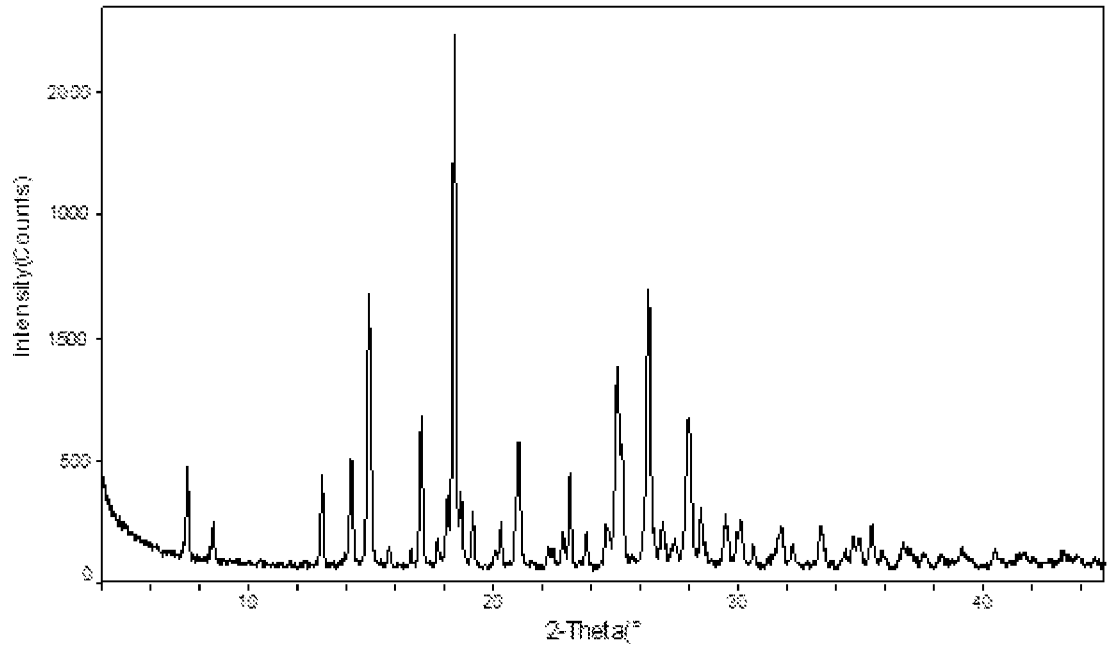
FIG. 9 is the XRPD pattern of crystal form A of sulfate of N-(trans-3-(2-(4-(2,3-dichlorophenyl)piperazin-1-yl)ethyl)cyclobutyl)oxazole-2-carboxamide.

V). Preparation of Crystal Form A of Sulfate 228 mg of crystal form B of free base was weighed. 18 mL of tetrahydrofuran solvent was added to produce a clear solution. 1 mL of the solution was taken into a glass bottle, and 36 μL of 1.0M sulfuric acid in methanol was slowly added to the system, and then the glass bottle was opened to volatile solvent at room temperature to obtain an oil or gel. 200 μL ethyl acetate was added for pulping for 4 h to precipitate a solid, which was centrifuged and dried in vacuum to obtain crystal form A of sulfate. After detection and analysis, it has the following XRPD diagram as shown in FIG. 9.

Figure 10:
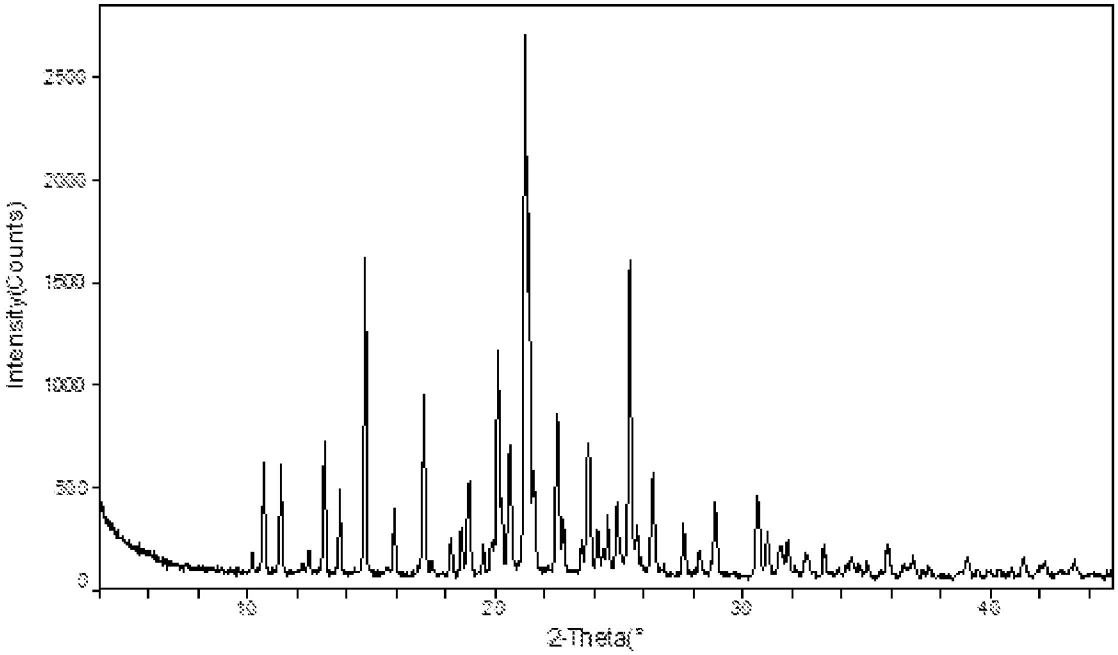
FIG. 10 is the XRPD pattern of crystal form A of methanesulfonate of N-(trans-3-(2-(4-(2,3-dichlorophenyl)piperazin-1-yl)ethyl)cyclobutyl)oxazole-2-carboxamide.
Figure 11:
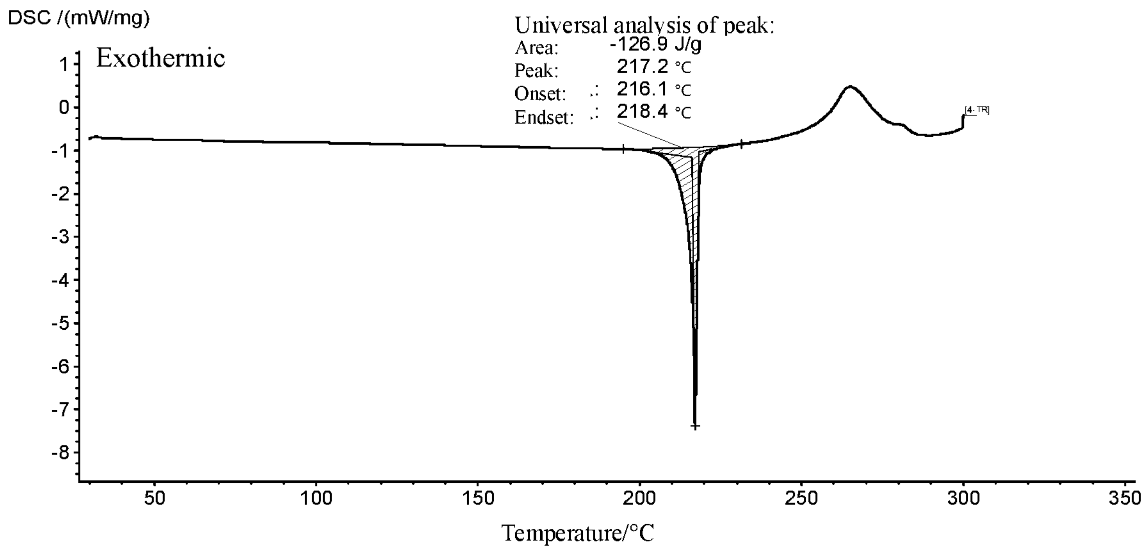
FIG. 11 is the DSC spectrum of crystal form A of methanesulfonate of N-(trans-3-(2-(4-(2,3-dichlorophenyl)piperazin-1-yl)ethyl)cyclobutyl)oxazole-2-carboxamide.

VI. Preparation of Crystal Form A of Methanesulfonate 250 mg of crystal form B of free base was weighed. 5 mL of acetone was added to produce a clear solution at room temperature. 200 μL of the solution was taken into a 2 mL sample vial, and 28.3 μL of 1M methanesulfonic acid in ethanol was added according to the molar reaction ratio of base:acid=1:1.2. The resulting clear solution was opened to volatile solvent at room temperature to obtain a gel. 200 μL ethyl acetate was added thereto to produce a clear solution, and the solvent is continued to volatilize. The resulting oil was added to 100 μL of methanol, and dissolved at 50° C. 400 μL of isopropyl ether was added thereto. The resulting solid was dried in vacuum at room temperature for 48 h. After detection and analysis, it has the XRPD pattern as shown in FIG. 10 and the DSC spectrum as shown in FIG. 11.

Figure 12:
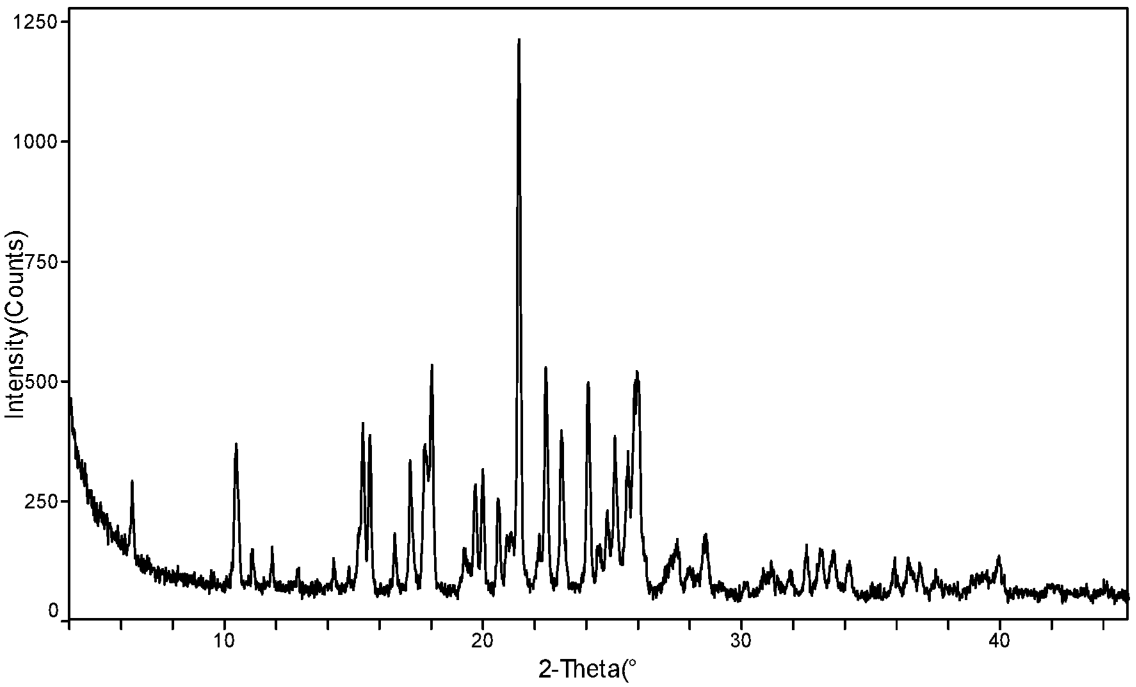
FIG. 12 is the XRPD pattern of crystal form A of 1,5-naphthalenedisulfonate of N-(trans-3-(2-(4-(2,3-dichlorophenyl)piperazin-1-yl)ethyl)cyclobutyl)oxazole-2-carboxamide.
Figure 13:
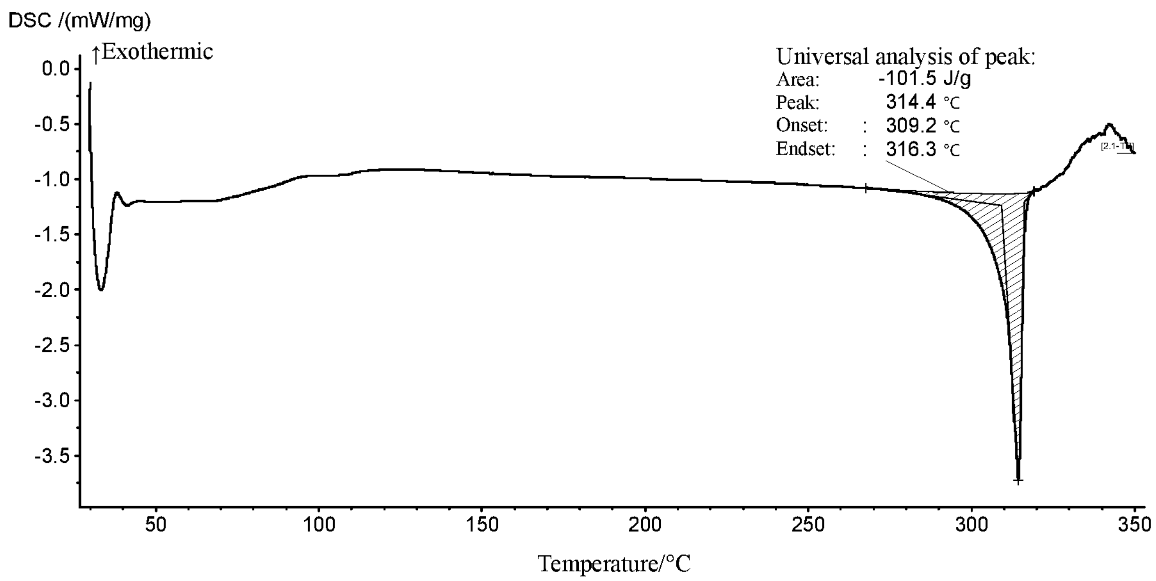
FIG. 13 is the DSC spectrum of crystal form A of 1,5-naphthalenedisulfonate of N-(trans-3-(2-(4-(2,3-dichlorophenyl)piperazin-1-yl)ethyl)cyclobutyl)oxazole-2-carboxamide.

VII. Preparation of Crystal Form A of 1,5-Naphthalenedisulfonate 250 mg of crystal form B of free base was weighed. 5 mL of acetone was added to produce a clear solution at room temperature. 200 μL of the solution was taken into a 2 mL sample vial, and 226 μL of 0.125M 1,5-naphthalenedisulfonic acid in ethanol was added at room temperature. The resulting suspension was stirred for 1 h and filtered. The resulting solid was dried in vacuum at room temperature for 48 h to obtain crystal form A of 1,5-naphthalenedisulfonate. After detection and analysis, it has the XRPD pattern as shown in FIG. 12 and the DSC spectrum as shown in FIG. 13.

Figure 14:
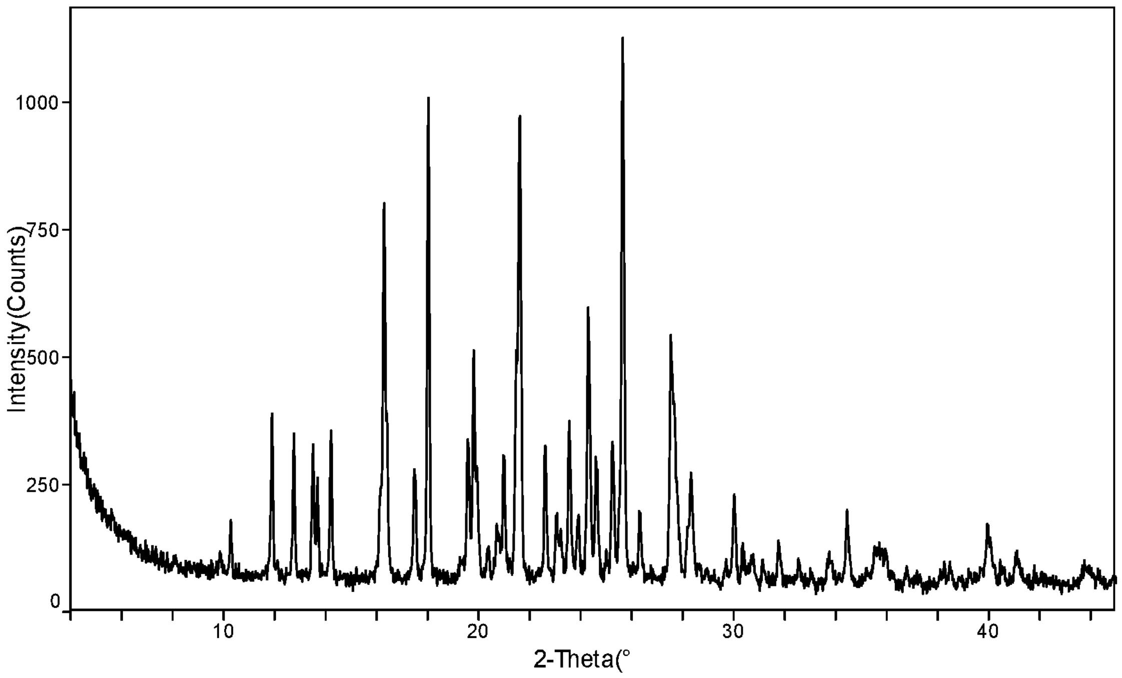
FIG. 14 is the XRPD pattern of crystal form A of nitrate of N-(trans-3-(2-(4-(2,3-dichlorophenyl)piperazin-1-yl)ethyl)cyclobutyl)oxazole-2-carboxamide.
Figure 15:
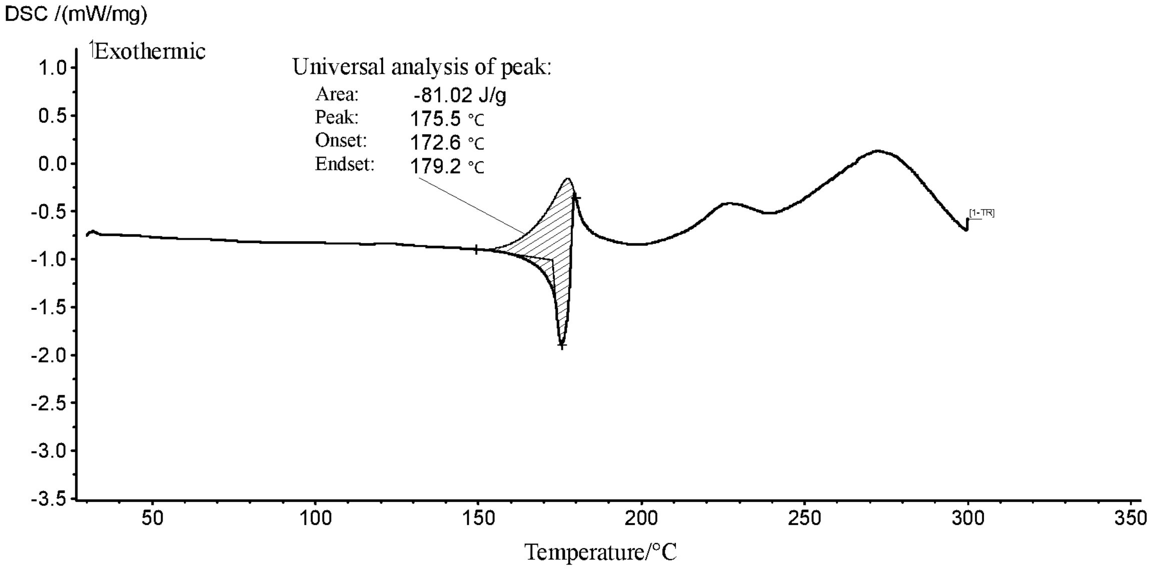
FIG. 15 is the DSC spectrum of crystal form A of nitrate of N-(trans-3-(2-(4-(2,3-dichlorophenyl)piperazin-1-yl)ethyl)cyclobutyl)oxazole-2-carboxamide.

VIII. Preparation of Crystal Form A of Nitrate 250 mg of crystal form B of free base was weighed. 5 mL of acetone was added to produce a clear solution at room temperature. 200 μL of the solution was taken into a 2 mL sample vial, and 28.3 μL of 1M nitric acid in ethanol was added according to the molar reaction ratio of base:acid=1:1.2. The resulting clear solution was opened to volatile solvent at room temperature to obtain a gel. 200 μL ethyl acetate was added thereto to produce a clear solution, and the solvent is continued to volatilize. The resulting oil was added to 100 μL of methanol and dissolved at 50° C., and 400 μL of isopropyl ether was added thereto. The resulting solid was dried in vacuum at room temperature for 48 h. After detection and analysis, it has the XRPD pattern as shown in FIG. 14 and the DSC spectrum as shown in FIG. 15.

Figure 16:
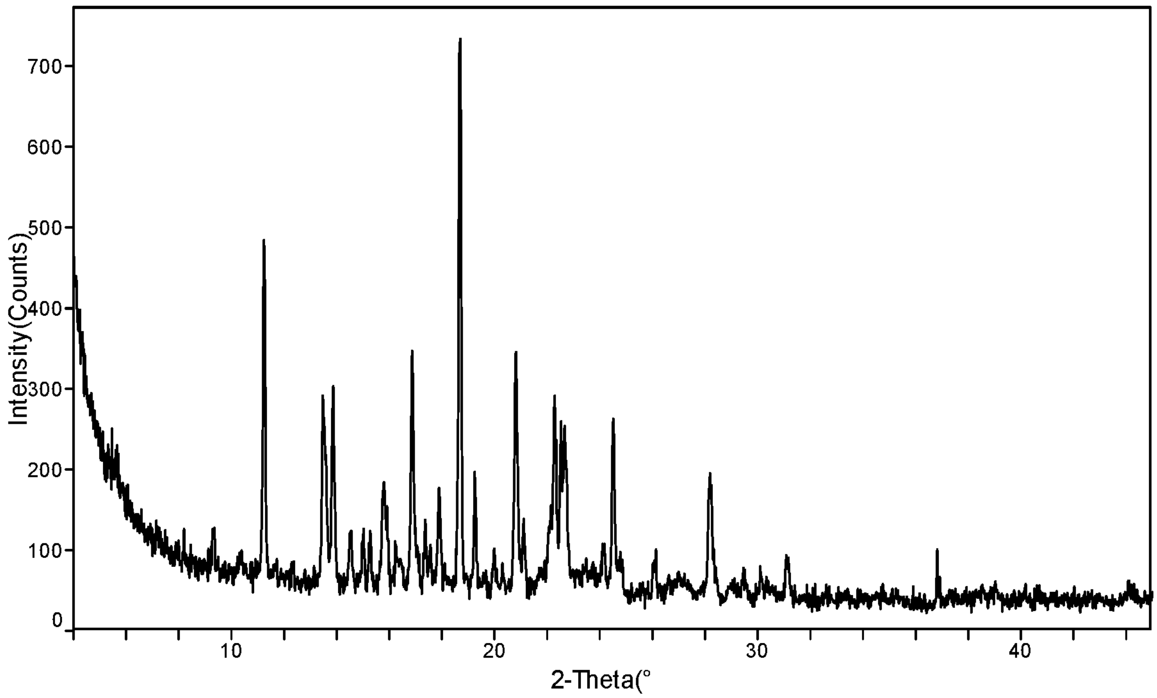
FIG. 16 is the XRPD pattern of crystal form A of acetate of N-(trans-3-(2-(4-(2,3-dichlorophenyl)piperazin-1-yl)ethyl)cyclobutyl)oxazole-2-carboxamide.
Figure 17:
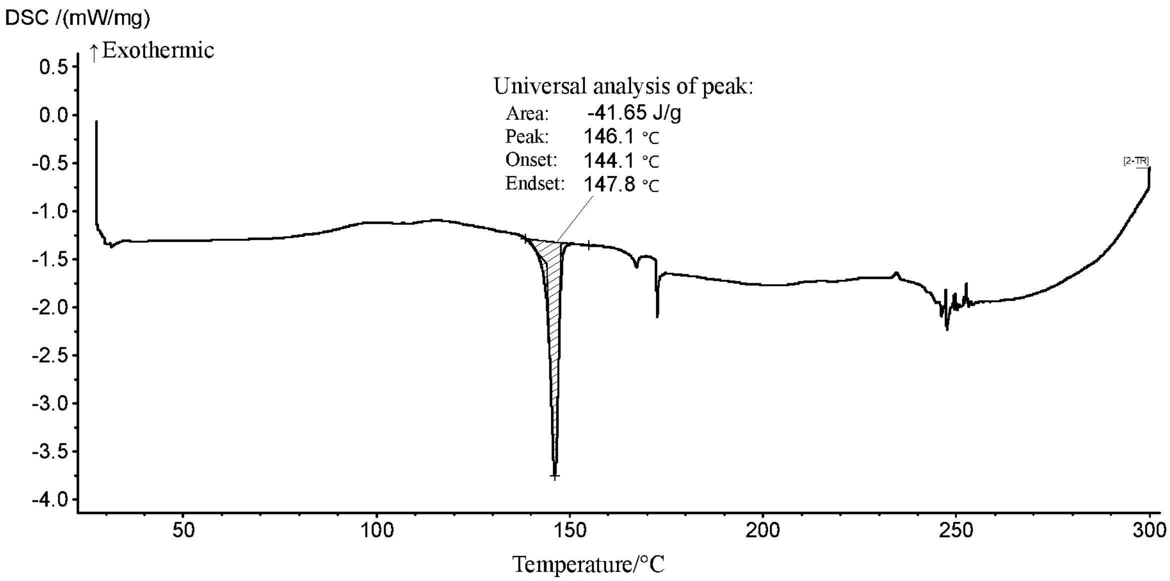
FIG. 17 is the DSC spectrum of crystal form A of acetate of N-(trans-3-(2-(4-(2,3-dichlorophenyl)piperazin-1-yl)ethyl)cyclobutyl)oxazole-2-carboxamide.

IX. Preparation of Crystal Form A of Acetate 10 mg of crystal form B of free base was weighed. 100 μL of isopropanol or isopropyl ether was added to produce a suspension. 28.3 μL of 1M acetic acid in methanol was added at room temperature according to a molar ratio of 1:1.2. The mixture was stirred for 4d and centrifuged, and the solid was vacuum dried at 50° C. After detection and analysis, it has the XRPD pattern as shown in FIG. 16 and the DSC spectrum as shown in FIG. 17.

Figure 18:
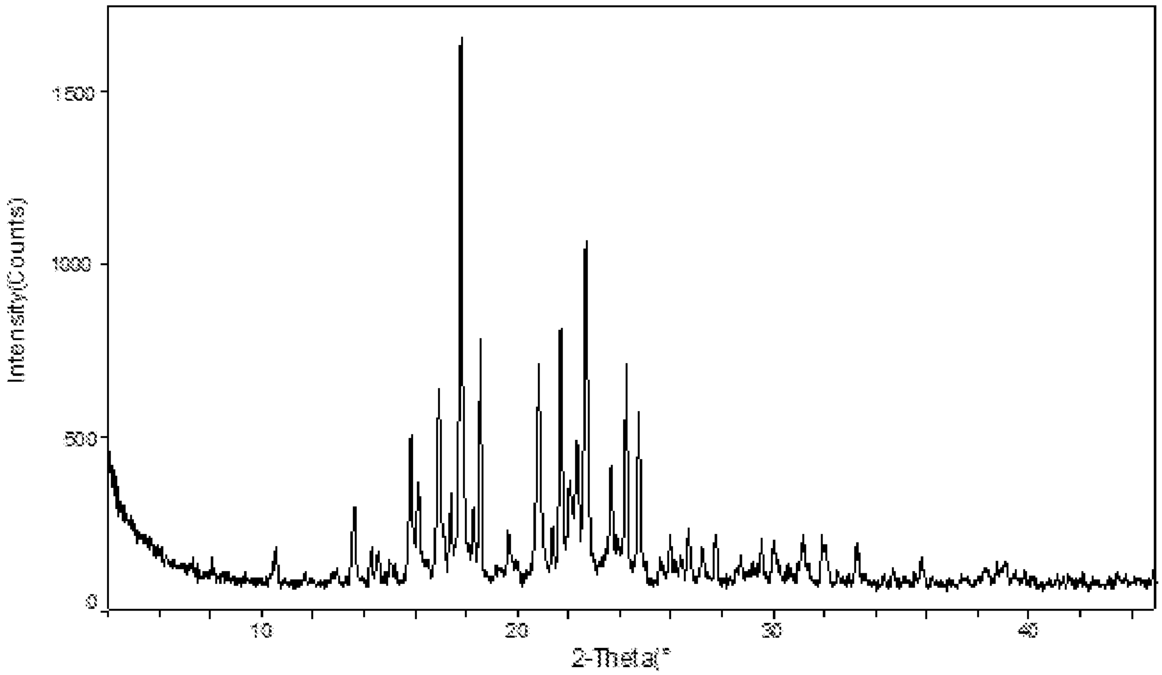
FIG. 18 is the XRPD pattern of crystal form A of fumarate of N-(trans-3-(2-(4-(2,3-dichlorophenyl)piperazin-1-yl)ethyl)cyclobutyl)oxazole-2-carboxamide.
Figure 19:
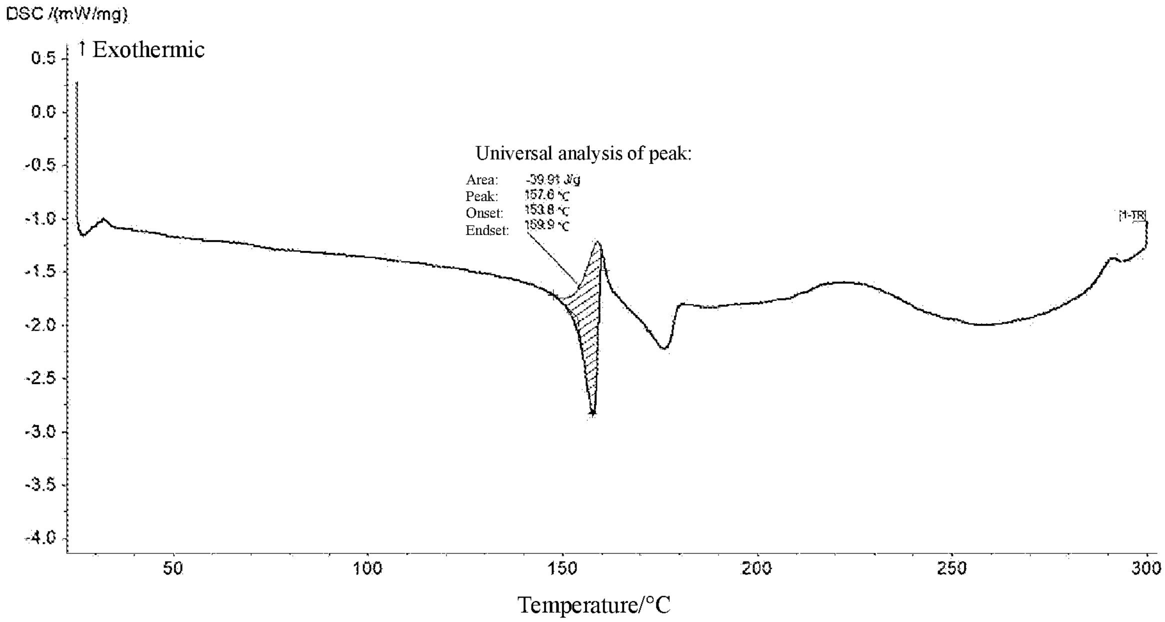
FIG. 19 is the DSC spectrum of crystal form A of fumarate of N-(trans-3-(2-(4-(2,3-dichlorophenyl)piperazin-1-yl)ethyl)cyclobutyl)oxazole-2-carboxamide.

X. Preparation of Fumarate Crystal Form A 10 mg of crystal form B of free base was weighed. 100 μL of isopropyl ether was added to produce a suspension. 0.25M of 28.3 μL fumaric acid in ethanol was added at room temperature according to a molar ratio of 1:1.2. The mixture was stirred for 4d, centrifuged, and the solid was dried in vacuum at 50° C. After detection and analysis, it has the XRPD pattern as shown in FIG. 18 and the DSC spectrum as shown in FIG. 19.

4. Solid Stability Experiment 4.1 Experimental Objective

The physicochemical stability of crystal form of salt of compound N-(trans-3-(2-(4-(2,3-dichlorophenyl)piperazin-1-yl)ethyl)cyclobutyl)oxazole-2-carboxamide under the conditions of light 50001×, high temperature 60° C., high humidity 92.5% RH and high temperature and high humidity 50° C. 75% RH was investigated, which provided a basis for crystal form screening and compound crystal form storage.

4.2 Experimental Protocol

About 1 mg of different crystal forms of salt were taken and placed under the conditions of light 50001×, high temperature 60° C., high humidity 92.5% RH, high temperature and high humidity 50° C. 75% RH for 5 days and 10 days. The salt content was determined by HPLC and external standard method, and the change of relevant substances was calculated by chromatographic peak area normalization method.

4.3 Experimental Results

1) The physicochemical stability results of crystal form of salt of N-(trans-3-(2-(4-(2,3-dichlorophenyl)piperazin-1-yl)ethyl)cyclobutyl)oxazole-2-carboxamide are shown in Table 28 below:

TABLE 28

| | | Stability results of salt form | | | | | | | |
|---|---|---|---|---|---|---|---|---|---|
| | | Condition | | | | | | | |
| | | Light | | High temperature | | High humidity | | High temperature and high humidity | |
| | | Time | | | | | | | |
| No. | | 5 Days | 10 Days | 5 Days | 10 Days | 5 Days | 10 Days | 5 Days | 10 Days |
| Crystal form A of hydrochloride | Total impurity increase % | <0.02 | <0.02 | <0.02 | 0.03 | 0.06 | <0.02 | <0.02 | <0.02 |
| | Maximum single impurity increase % | <0.02 | <0.02 | <0.02 | <0.02 | 0.06 | <0.02 | <0.02 | <0.02 |
| Crystal form B of p-toluene sulfonate | Total impurity increase % | 0.03 | 0.19 | <0.02 | <0.02 | <0.02 | <0.02 | <0.02 | <0.02 |
| | Maximum single impurity increase % | 0.13 | 0.13 | <0.02 | <0.02 | <0.02 | <0.02 | <0.02 | <0.02 |

4.4 Experimental Conclusion

The stability results show that the crystal form stability of different salts is different, and crystal form A of hydrochloride is stable under all conditions, and impurities are not significantly increased. As for crystal form B of p-toluenesulfonate, single impurity increases significantly under light conditions, but it is stable under other conditions.

4.5 Pressure Crystal Transformation Test

An appropriate amount of crystal form A of hydrochloride was taken. The tablet press was adjusted to the maximum pressure. It was pressed into a tablet and then was subjected to PXRD characterization. The results show that crystal form A didn't undergo crystal transformation before and after pressure.

4.6 Grinding Crystal Transformation Test

An appropriate amount of crystal form A of hydrochloride was taken and ground in a mortar for 5 min, and then was subjected to PXRD characterization. The results show that crystal form A didn't undergo crystal transformation before and after grinding.

5 Hygroscopicity Experiment 5.1 Experimental Objective

The hygroscopicity of crystal form A of hydrochloride of N-(trans-3-(2-(4-(2,3-dichlorophenyl)piperazin-1-yl)ethyl)cyclobutyl)oxazole-2-carboxamide under different relative humidity conditions was investigated, which provided a basis for the screening and storage of crystal form of compound.

5.2 Experimental Protocol

Crystal form A of hydrochloride of compound was placed in saturated water vapor with different relative humidity to achieve dynamic equilibrium between the compound and water vapor, and the percentage of hygroscopic weight gain of the compound after equilibrium was calculated.

5.3 Experimental Results 5.3.1 Hygroscopicity of Crystal Form a of Hydrochloride of Compound.

Crystal form A of hydrochloride has a hygroscopic weight gain of 0.509% under the condition of RH 80%. After 2 cycles of humidification and dehumidification under 0 to 95% relative humidity condition, the XRPD pattern of crystal form A of hydrochloride does not change, that is, the crystal form does not transform.

5.4 Experimental Conclusion

Crystal form A of hydrochloride is slightly hygroscopic, but stable in humid environments.

6. Thermodynamic Stability Experiment of Crystal Form 6.1 Experimental Objective Through polycrystalline screening and crystal form competitive test, the thermodynamically stable crystal form of salt was found.

6.2 Experimental Protocol

An organic solvent with a certain solubility was selected. Crystal form A of hydrochloride of N-(trans-3-(2-(4-(2,3-dichlorophenyl)piperazin-1-yl)ethyl)cyclobutyl)oxazole-2-carboxamide was suspended in the solvent system, stirred and pulped for 1 week at room temperature and 50° C. respectively, and then centrifuged. The supernatant was discarded, and the solid was dried in vacuum (−0.1 Mpa) overnight at 50° C. The XRPD of the solid was determined and compared with XRPD of raw compound salt.

6.3 Experimental Results

The results after pulping crystal form A of hydrochloride are shown in Table 29.

TABLE 29

| No. | Solvent | Results |
|---|---|---|
| 1 | Methanol | Crystal form A |
| 2 | Ethanol | Crystal form A |
| 3 | Acetone | Crystal form A |
| 4 | Acetonitrile | Crystal form A |
| 5 | Tetrahydrofuran | Crystal form A |
| 6 | 2-Methyl-tetrahydrofuran | Crystal form A |
| 7 | Ethyl acetate | Crystal form A |
| 8 | Ethyl formate | Crystal form A |
| 9 | Dichloromethane | Crystal form A |
| 10 | 1,4-Dioxane | Crystal form A |
| 11 | Methyl tert-butyl ether | Crystal form A |
| 12 | n-Heptane | Crystal form A |
| 13 | Isopropanol | Crystal form A |
| 14 | 2-Butanone | Crystal form A |
| 15 | Toluene | Crystal form A |

6.4 Experimental Conclusion

As for crystal form A of hydrochloride, the crystal form does not change after being pulped by different solvents, therefore, crystal form A of hydrochloride is a thermodynamically stable crystal form.

7. Salt Form Quantification 7.1 Experimental Objective

The number of acids binding in the salt form was quantified by HPLC-ELSD test.

7.2 Experimental Protocol

An appropriate amount of NaCl was weighed, and a series of linear solutions of different concentrations with the diluent acetonitrile-water (50:50) was prepared. Different batches of appropriate amounts of crystal form A of hydrochloride of N-(trans-3-(2-(4-(2,3-dichlorophenyl)piperazin-1-yl)ethyl)cyclobutyl)oxazole-2-carboxamide were weighed, and solutions containing 2 mg/mL hydrochloride were prepared with the diluent acetonitrile-water (50:50).

The above linear solution and hydrochloride samples solution was taken to filter. After filtration, it was injected into HPLC-ELSD, and the ELSD method was shown in the following table.

| | |
|---|---|
| Dilutent | ACN + $H_2O$ (1:1) |
| Column | ZIC-HILIC(150*4.6 mm, 5 μm) |
| Mobile phase | 75 mnol/L Ammonium acetate solution (pH 4.8): acetonitrile = 30:70 |
| Injection volume | 10 μL |
| Flow rate | 1.0 ml/min |
| ELSD column Temperature | 80° C. |
| Time | 7 min |

7.3 Experimental results: The content of hydrochloric acid in hydrochloride was calculated according to the external standard method, and the quantitative results of hydrochloride are shown in Table 30.

TABLE 30

| Content/Batch | Batch 1 | Batch 2 |
|---|---|---|
| Determination of Cl-percentage content in hydrochloride | 7.82% | 7.90% |
| Theoretical value of Cl-percent content, bound with 1 hydrochloric acid | 7.94% | |
| Theoretical value of Cl-percent content, bound with 2 hydrochloric acid | 14.72% | |
| Conclusion | The number of hydrochloric acid binding in crystal form A of hydrochloride is 1 | |

8. Pharmacokinetics Study in Rats 8.1 Experimental Objective

Through animal PK studies, pharmacokinetic parameters of crystal form B of free base and crystal form A of hydrochloride of N-(trans-3-(2-(4-(2,3-dichlorophenyl)piperazin-1-yl)ethyl)cyclobutyl)oxazole-2-carboxamide were compared in rats.

8.2 Experimental Instruments and Reagents 8.2.1 Instruments

| Instrument | Manufacturer | Model |
|---|---|---|
| Analytical Balances | Sartorius Scientific Instruments (Beijing) Co., Ltd. | QVINTIX35-ICN |
| Centrifuge | EPPENDORF | Centrifuge 5415R |
| Ultrasonic cleaner | Kun Shan Ultrasonic Instruments Co., Ltd. | KQ-100B |
| Pipette | Eppendorf Lab Technologies (Shanghai) Co., Ltd. | YE5K655563(1000 uL)<br>YE5A592012(200 uL)<br>YE4A298094(100 uL)<br>YE4A405553(10 uL) |
| Triple quadrupole mass spectrometry | Thermo Fisher Scientific Inc. | Thermo TSQ Ultra |
| High performance liquid chromatography | Agilent Technologies, Inc. | Agilent 1100 |
| Ultrasonic cell disruptor | Nanjing Shunma Instrument Equipment Co., Ltd. | SM-650D |
| 4° C. refrigerator | Hefei Meiling Co., Ltd. | SC-316 |
| −20° C. refrigerator | Zhongke Meiling Cryogenics Co., Ltd. | DW-YL450 |

8.2.2 Reagents

| Reagents | Suppliers | Batch number |
|---|---|---|
| DMSO | Vetech | WXBD0293V |
| Acetonitrile | Sigma-Aldrich | WXBD0232V |
| Methyl Alcohol | Sigma-Aldrich | WXBC6573V |
| Formic Acid | Fisher Scientific | 193497 |
| Dexamethasone | Solarbio | 822A0523 |
| HP-β-CD | Shandong Binzhou Zhiyuan Biotechnology Co., Ltd. | 20190517 |
| HPMC K4M | Damas-beta | P1575251 |

8.3 Test Animals

| Species | Strain | Age | Gender | Supplier |
|---|---|---|---|---|
| Rats | SD | 7 weeks old, body weight 200 g | Male | JOINN (Suzhou) Laboratories Co., Ltd. |

8.4 Test Compounds

Crystal form B of free base and crystal form A of hydrochloride of N-(trans-3-(2-(4-(2,3-dichlorophenyl)piperazin-1-yl)ethyl)cyclobutyl)oxazole-2-carboxamide.

8.5 Experimental Protocol

Crystal form B of free base and crystal form A of hydrochloride were evenly suspended with an aqueous solution containing 0.5% HPMC (hydroxypropyl methylcellulose) K4M. Rats were administered by gavage with three rats in parallel. The dose was crystal form B of free base: 30 mg/kg, crystal form A of hydrochloride: 30 mg/kg, 100 mg/kg. The amount of compound was all converted into the same amount of free base.

8.6 Experimental Results

The results of the PK experiments of crystal form B of free base and crystal form A of hydrochloride in rats are shown in Table 31.

TABLE 31

Pharmacokinetic parameters of free base and crystal form A of hydrochloride in rats

| | Dose (oral) | | |
|---|---|---|---|
| Parameters | 30 mg/kg Crystal form B of free base | 30 mg/kg Crystal form A of hydrochloride | 100 mg/kg Crystal form A of hydrochloride |
| $t_{max}$(h) | 1.0 | 1.0 | 2.0 |
| $C_{max}$(ng/mL) | 3569.0 | 5576.2 | 16791.5 |
| $AUC_{0-24}$(ng/mL*h) | 50791.0 | 63058.2 | 242606.7 |

TABLE 31-continued

| Pharmacokinetic parameters of free base and crystal form A of hydrochloride in rats | | | |
|---|---|---|---|
| | Dose (oral) | | |
| Parameters | 30 mg/kg Crystal form B of free base | 30 mg/kg Crystal form A of hydrochloride | 100 mg/kg Crystal form A of hydrochloride |
| $t_{1/2}$(h) | 16.3 | 7.1 | 10.7 |
| $MRT_{0-\infty}$(h) | 9.0 | 7.0 | 8.3 |
| Formulation | | 0.5% HPMC | |

8.7 Experimental Conclusion

Compared with crystal form B of free base, the in vivo exposure of crystal form A of hydrochloride is increased in rats, and the exposure in rats is dose-related at a dose of 100 mg/kg and 30 mg/kg.

9. Crystal Form Stability Study of Hydrochloride for 30 Days

The 30 days stability of hydrochloride of N-(trans-3-(2-(4-(2,3-dichlorophenyl)piperazin-1-yl)ethyl)cyclobutyl) oxazole-2-carboxamide under four conditions of 60° C. (closed), 40° C. & RH 75% (open), 25° C./RH 92.5% (open) and light (5000±500 Lux) was detected, which provided scientific basis for the production, packaging, storage and transportation conditions of drugs.

About 2 mg of crystal form A of hydrochloride was weighed and placed for 30 days under light (5000 lux), high temperature (60° C.), high humidity (92.5% RH), high temperature and high humidity (40° C. & 75% RH). The diluent 80% methanol solution was added to prepare a solution containing about 0.5 mg/mL hydrochloride. The mixture was sonicated for 30 min to produce a clear solution. 1 mL of the solution was filtered and measured by HPLC. See "2.3.4" for the HPLC analysis method. The content of related substances was calculated according to the peak area normalization method, and the results are shown in Table 32 below.

TABLE 32

HPLC data of hydrochloride in stability experimental conditions for 30 days

| RRT/Area % | 1.00 | 1.07 | 1.93 | 2.43 |
|---|---|---|---|---|
| 0 d | 99.44 | 0.07 | 0.42 | 0.07 |
| GW-30 d | 99.51 | 0.08 | 0.41 | / |
| GS-30 d | 99.43 | 0.11 | 0.39 | 0.07 |
| GZ-30 d | 99.43 | 0.09 | 0.41 | 0.08 |
| WS-30 d | 99.46 | 0.09 | 0.38 | 0.07 |

According to the results of HPLC and PXRD, crystal form A of hydrochloride does not undergo crystal form change within 30 days, and impurities do not increase significantly, indicating that crystal form A of hydrochloride has good stability for 30 days.

What is claimed is:

1. An acid salt of a compound of formula (III) or a stereoisomer thereof, (III)

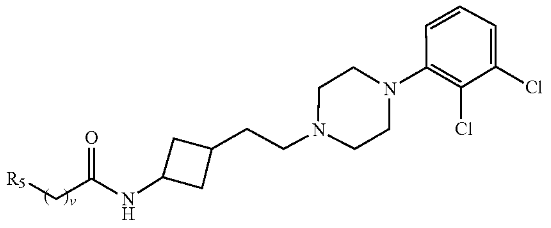

wherein:

$R_5$ is selected from the group consisting of hydrogen, amino, $C_{1-3}$ alkyl, $C_{1-3}$ alkoxy, $C_{1-3}$ hydroxyalkyl, $C_{3-8}$ cycloalkyl, phenyl, oxiranyl, thiiranyl, aziridinyl, oxetanyl, azetidinyl, thietanyl, tetrahydrofuryl, tetrahydrothienyl, furyl, thienyl, pyrrolyl, pyrazolyl, imidazolyl, oxazolyl, isoxazolyl, thiazolyl, isothiazolyl, pyridyl, pyridazinyl, pyrimidinyl, pyrazinyl, 1,3,5-triazinyl, benzofuryl, benzothienyl, indolyl, benzimidazolyl, indazolyl, benzoxazolyl, benzotriazolyl, quinolinyl and isoquinolyl, the amino, $C_{1-3}$ alkyl, $C_{1-3}$ alkoxy, $C_{1-3}$ hydroxyalkyl, $C_{3-8}$ cycloalkyl, phenyl, oxiranyl, thiiranyl, aziridinyl, oxetanyl, azetidinyl, thietanyl, tetrahydrofuryl, tetrahydrothienyl, furyl, thienyl, pyrrolyl, pyrazolyl, imidazolyl, oxazolyl, isoxazolyl, thiazolyl, isothiazolyl, pyridyl, pyridazinyl, pyrimidinyl, pyrazinyl, 1,3,5-triazinyl, benzofuryl, benzothienyl, indolyl, benzimidazolyl, indazolyl, benzoxazolyl, benzotriazolyl, quinolinyl and isoquinolyl are each optionally further substituted by one or more substituents selected from the group consisting of deuterium, halogen, hydroxy, cyano, oxo, $C_{1-3}$ alkyl, $C_{1-3}$ alkoxy and $C_{1-3}$ hydroxyalkyl;

the acid in the acid salt is an inorganic acid or an organic acid; wherein, the inorganic acid is selected from the group consisting of hydrochloric acid, sulfuric acid, nitric acid, hydrobromic acid, hydrofluoric acid, hydroiodic acid and phosphoric acid; the organic acid is selected from the group consisting of 2,5-dihydroxybenzoic acid, 1-hydroxy-2-naphthoic acid, acetic acid, dichloroacetic acid, trichloroacetic acid, acetohydroxamic acid, adipic acid, benzenesulfonic acid, 4-chlorobenzenesulfonic acid, benzoic acid, 4-acetamidobenzoic acid, 4-aminobenzoic acid, decanoic acid, caproic acid, caprylic acid, cinnamic acid, citric acid, cyclamic acid, camphorsulfonic acid, aspartic acid, camphoric acid, gluconic acid, glucuronic acid, glutamic acid, isoascorbic acid, lactic acid, malic acid, mandelic acid, pyroglutamic acid, tartaric acid, dodecyl sulfuric acid, dibenzoyl tartaric acid, ethane-1,2-disulfonic acid, ethanesulfonic acid, formic acid, fumaric acid, galactonic acid, gentisic acid, glutaric acid, 2-ketoglutaric acid, glycolic acid, hippuric acid, isethionic acid, lactobionic acid, ascorbic acid, aspartic acid, lauric acid, camphoric acid, maleic acid, malonic acid, methanesulfonic acid, 1,5-naphthalenedisulfonic acid, naphthalene-2-sulfonic acid, nicotinic acid, oleic acid, orotic acid, oxalic acid, palmitic acid, embonic acid, propionic acid, salicylic acid, 4-aminosalicylic acid, decanedioic acid, stearic acid, succinic acid, thiocyanic acid, pamoic acid, methanoic acid, undecylenic acid, trifluoroacetic acid, benzenesulfonic acid, p-toluenesulfonic acid and L-malic acid; and V is 0 or 1.

2. The acid salt according to claim 1, wherein formula (III) is further as shown in formula (IIIa) or formula (IIIb):
(IIIa)
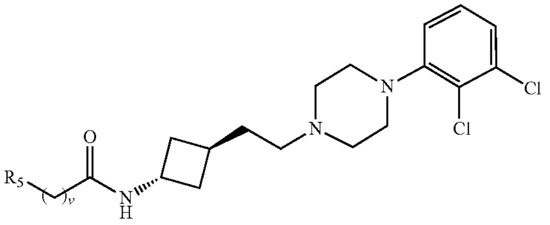
(IIIb)
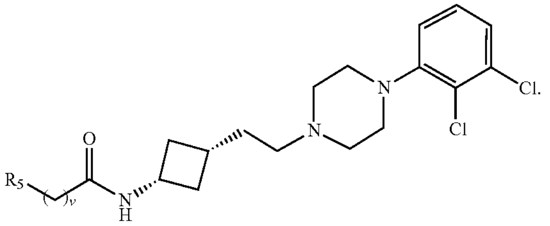
3. The acid salt according to claim 1, wherein formula (III) is selected from the group consisting of:
1
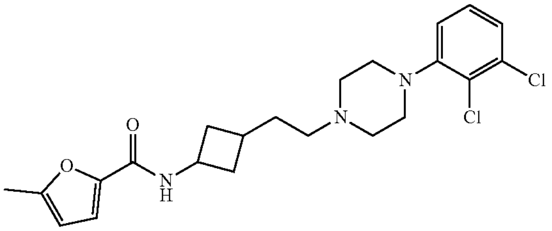
1A
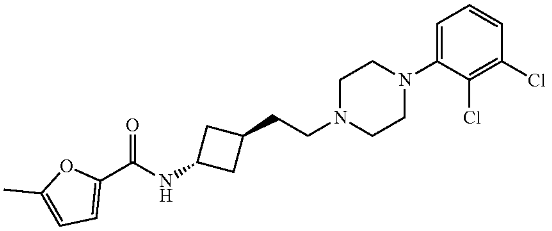
1B
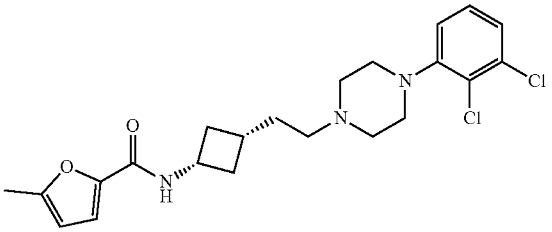
-continued
2
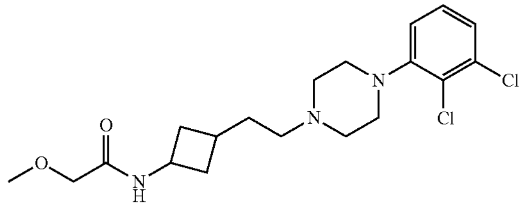
2A
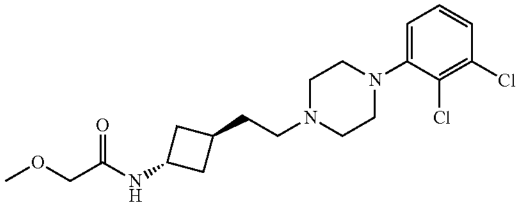
2B
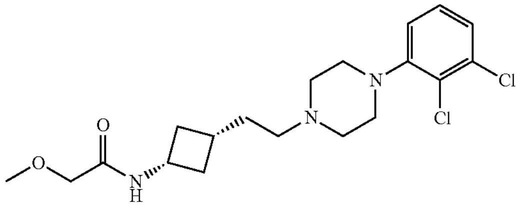
3
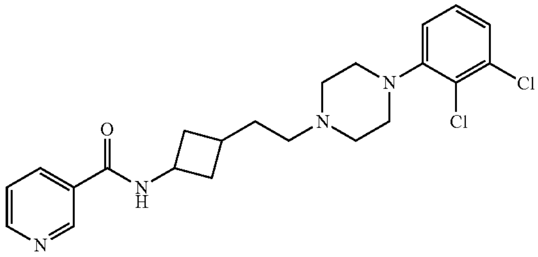
3A
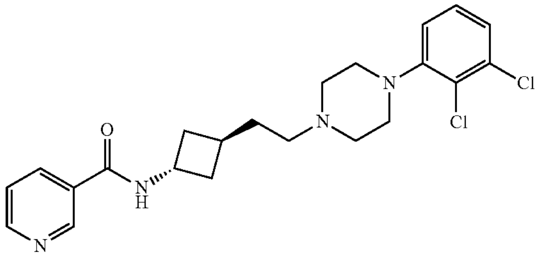
3B
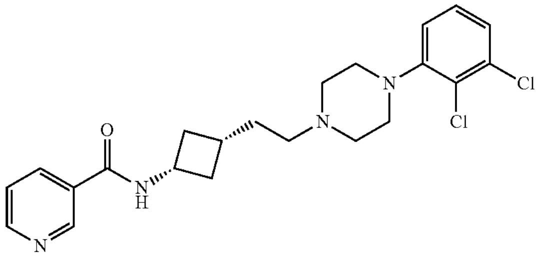

-continued
4
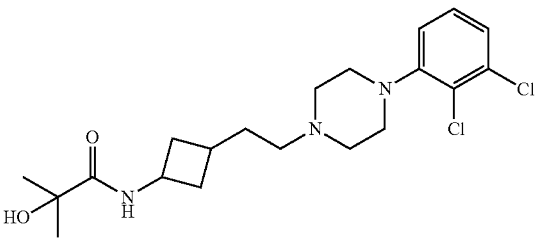
4A
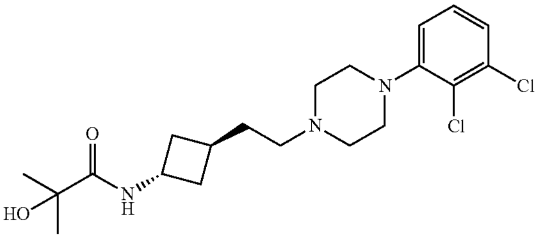
4B
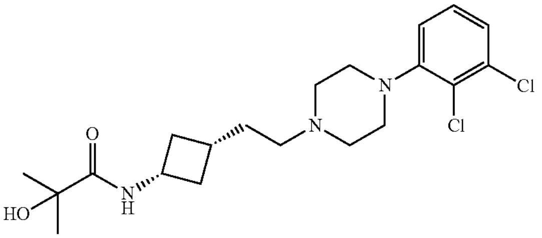
5
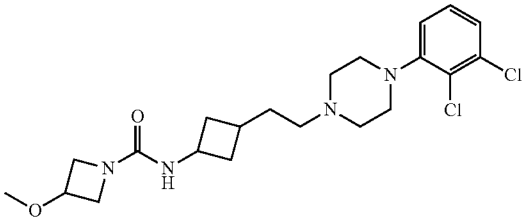
5A
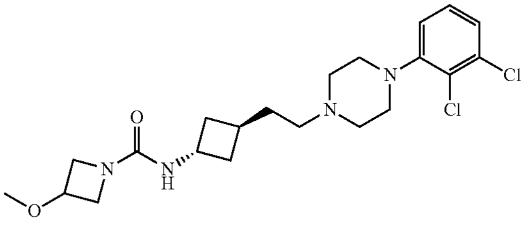
5B
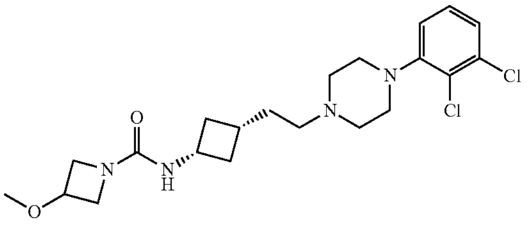
-continued
6
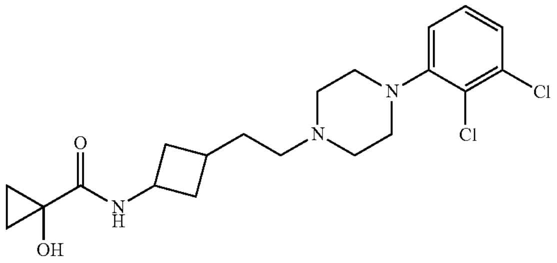
6A
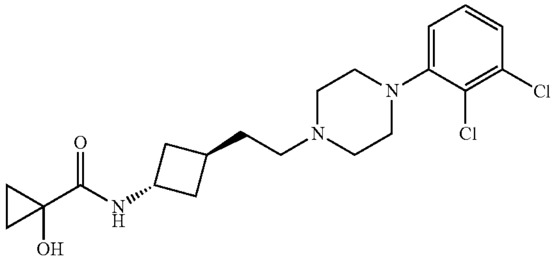
6B
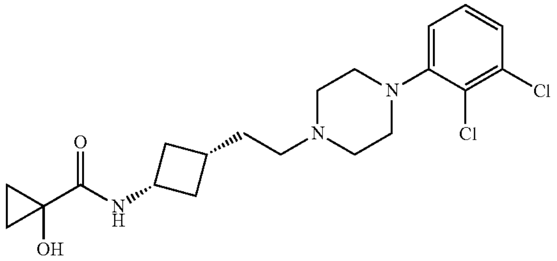
7
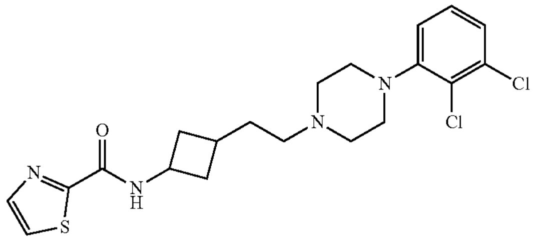
7A
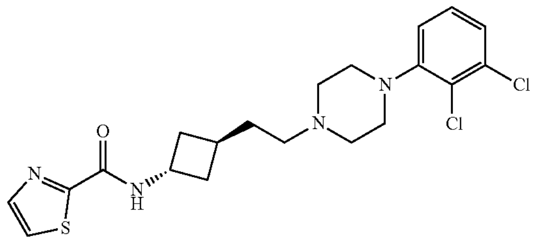
7B
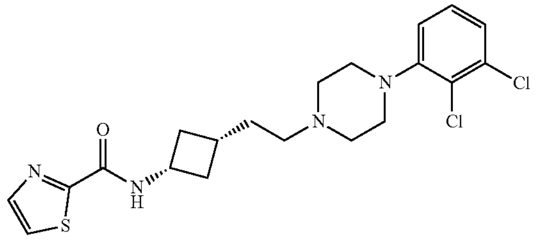

-continued
8
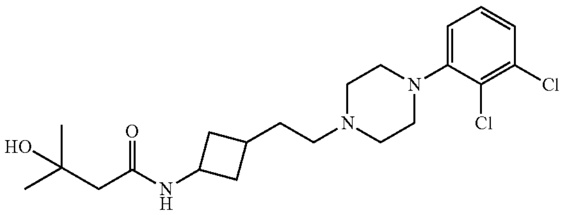
8A
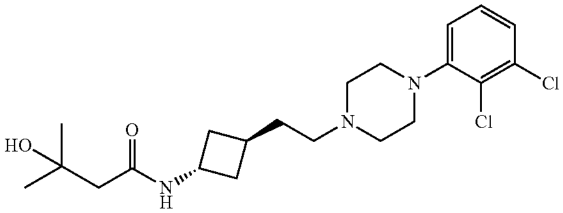
8B
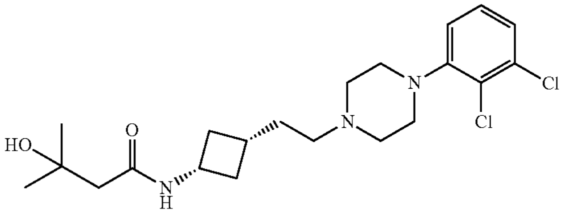
9
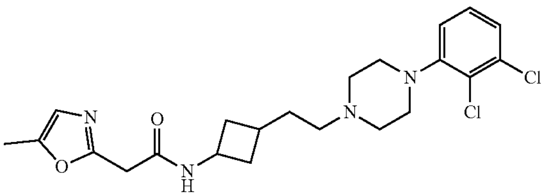
9A
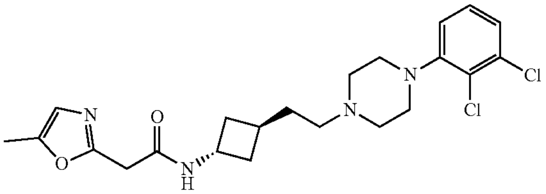
9B
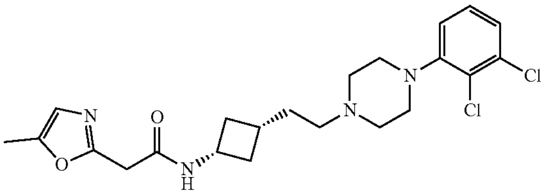
10
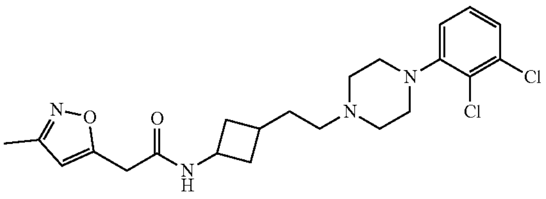
-continued
10A
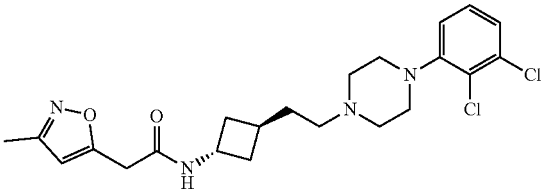
10B
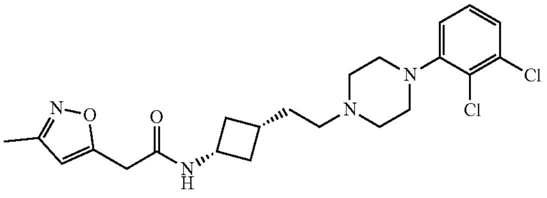
11
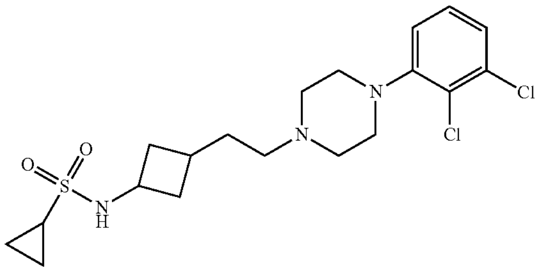
11A
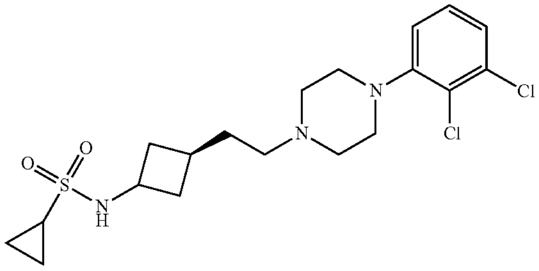
11B
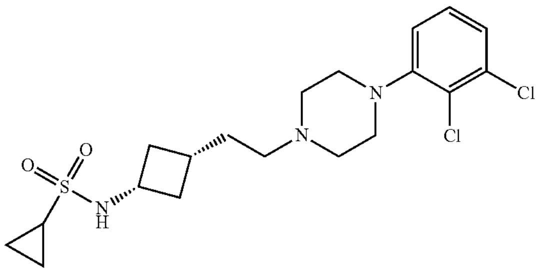
12
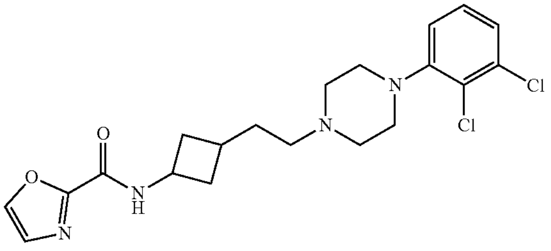

-continued
12A
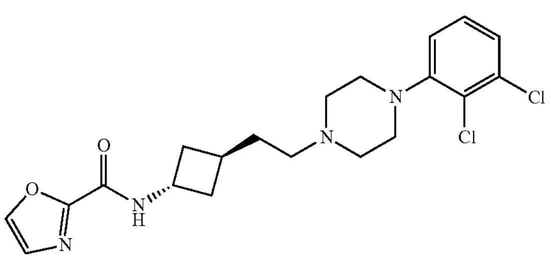
12B
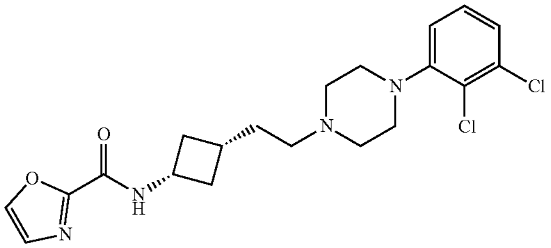
13
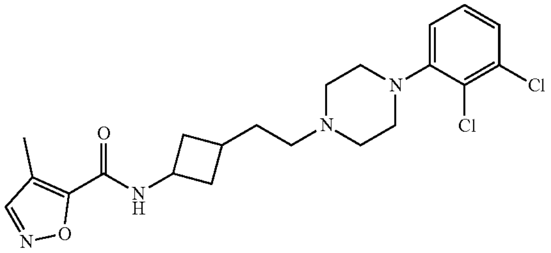
13A
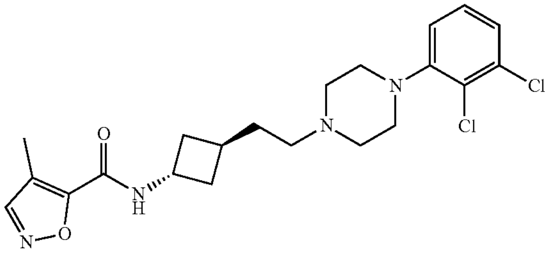
13B
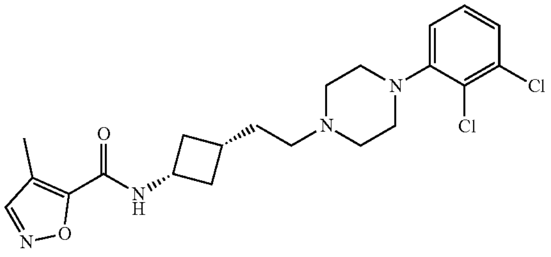
14
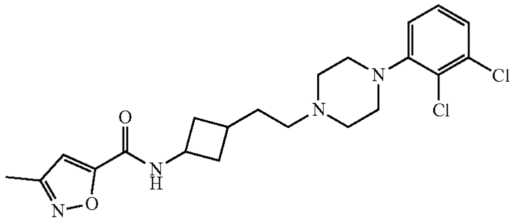
-continued
14A
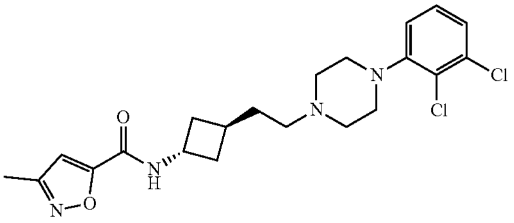
14B
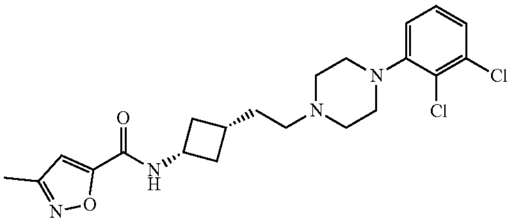
15
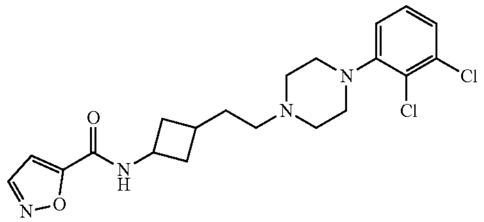
15A
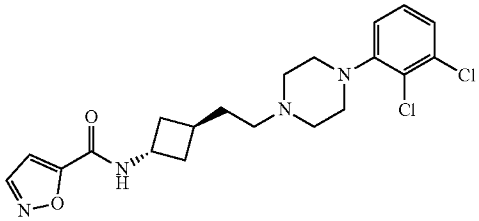
15B
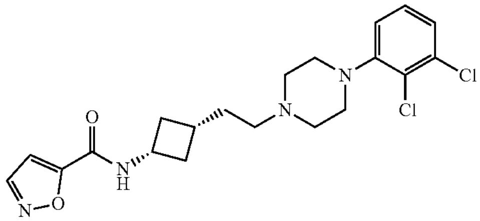
16
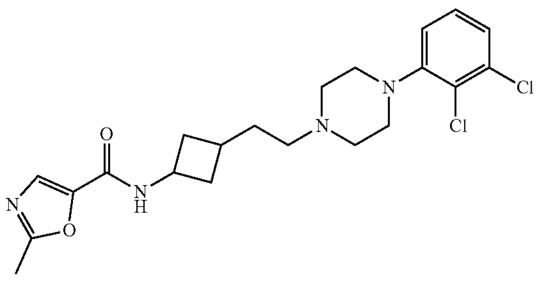

-continued
16A
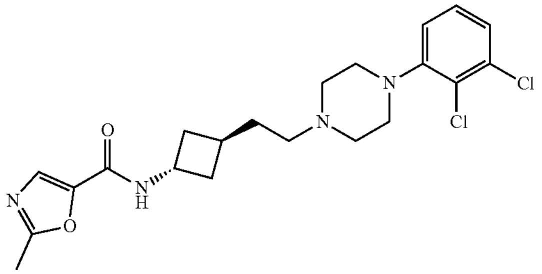
16B
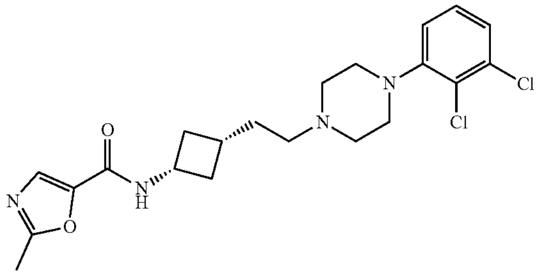
17
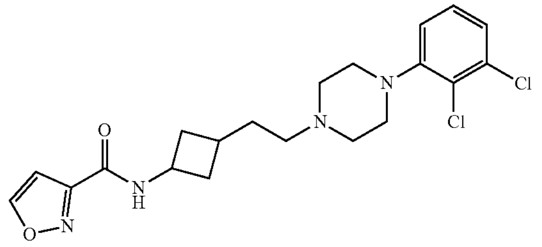
17A
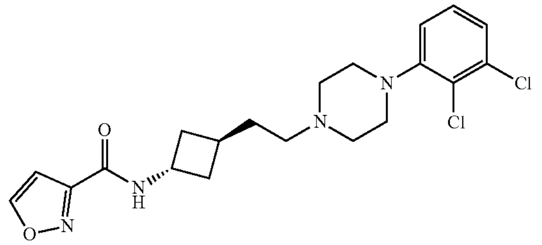
17B
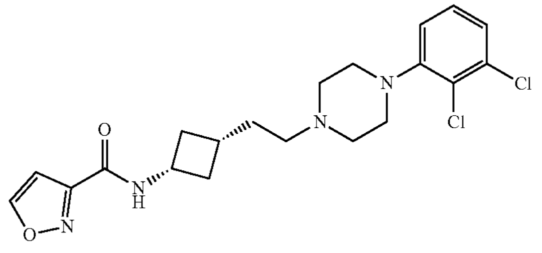
-continued
18
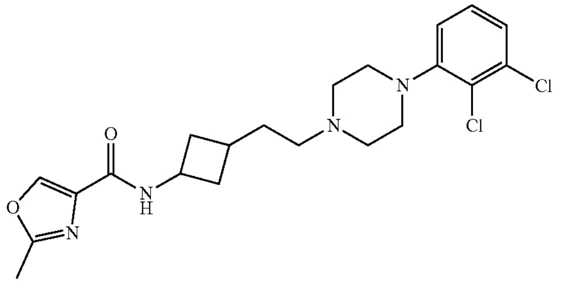
18A
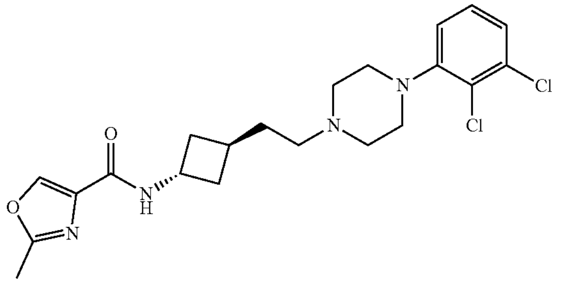
18B
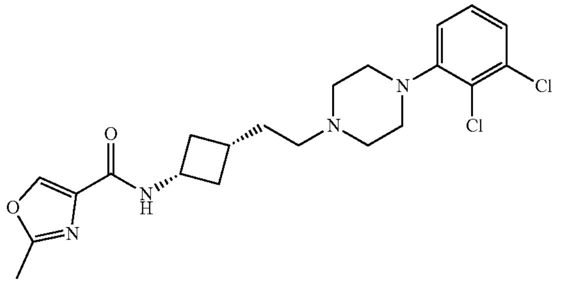
19
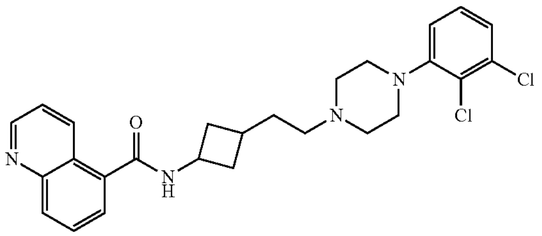
19A
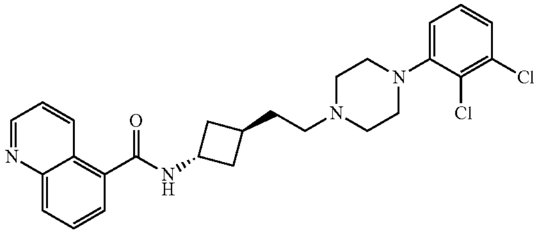

-continued
19B
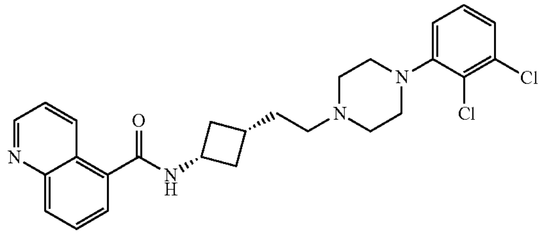
20
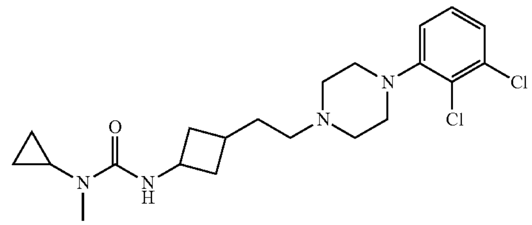
20A
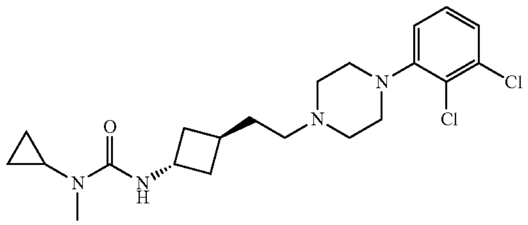
20B
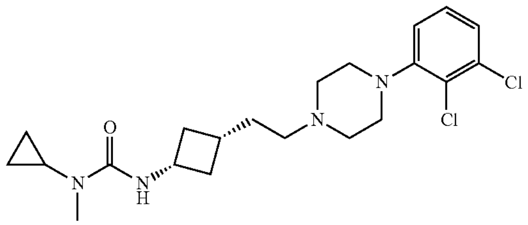
21
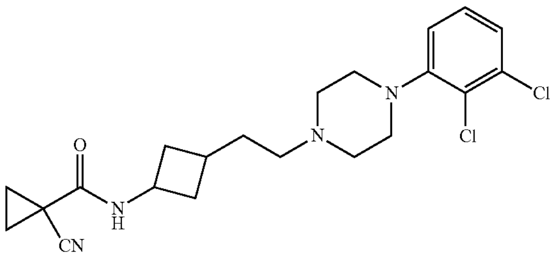
21A
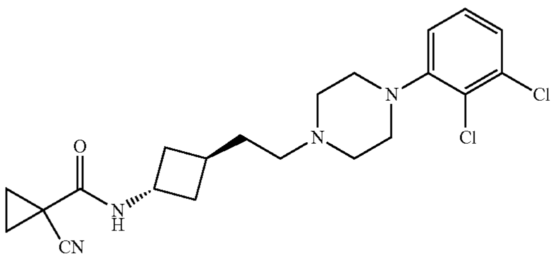
-continued
21B
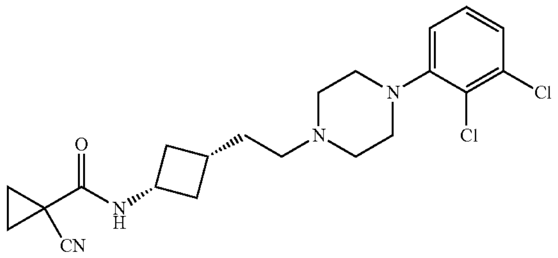
22
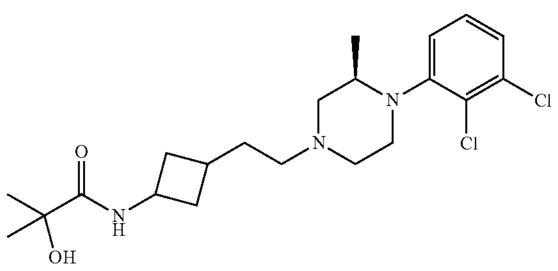
22A
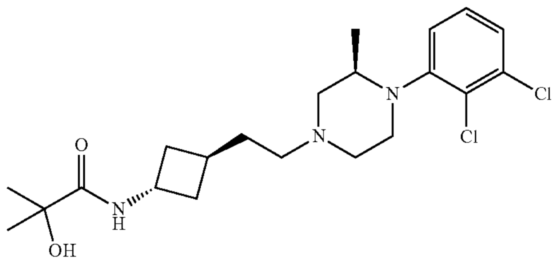
22B
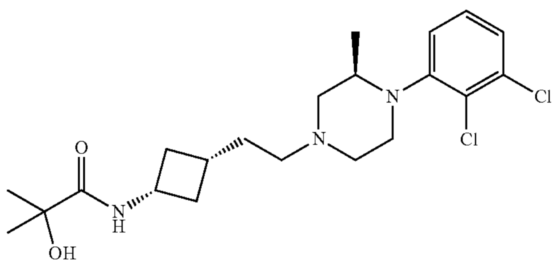
23
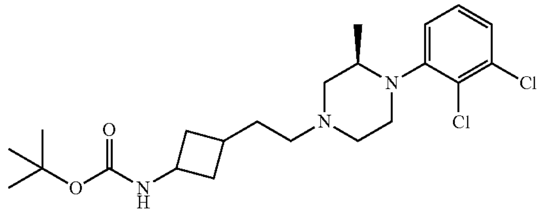
23A
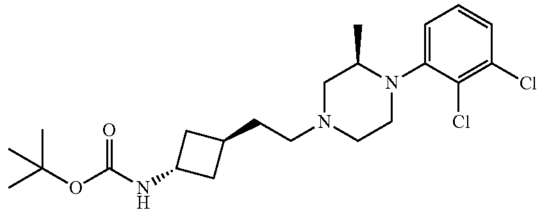

-continued

23B

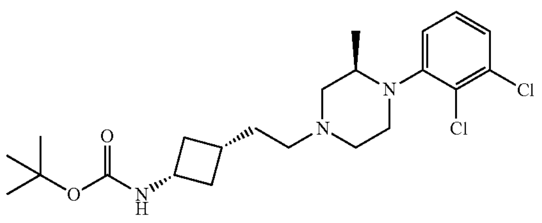

24

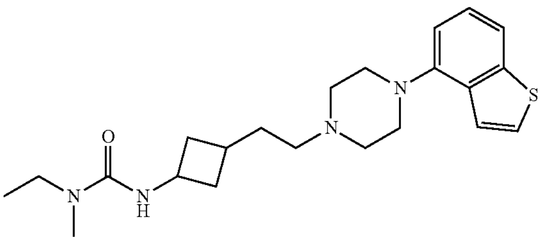

24A

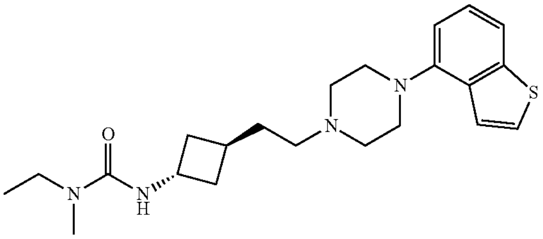

24B

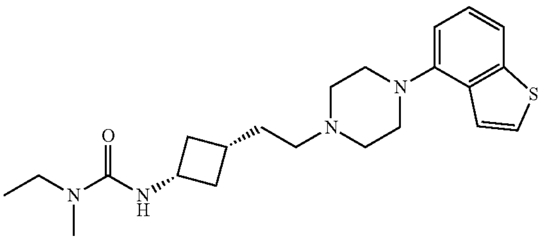

25

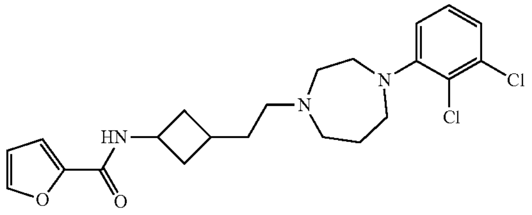

25A

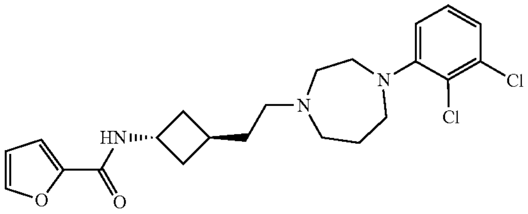

and

-continued

25B

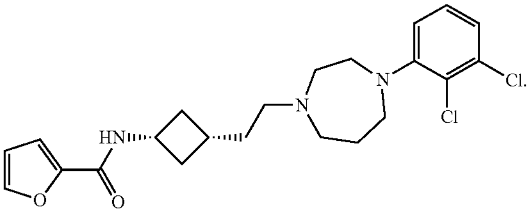

4. The acid salt according to claim 1, wherein it is an acid salt of N-(trans-3-(2-(4-(2,3-dichlorophenyl)piperazin-1-yl)ethyl)cyclobutyl)oxazole-2-carboxamide, wherein the acid in the acid salt is selected from the group consisting of nitric acid, hydrochloric acid, sulfuric acid, p-toluenesulfonic acid, methanesulfonic acid, oxalic acid, sulfuric acid, hydrobromic acid, phosphoric acid, succinic acid, acetic acid, ethanesulfonic acid, benzoic acid, pamoic acid, malonic acid, malic acid, maleic acid, benzenesulfonic acid, fumaric acid, hippuric acid, isethionic acid, 1,5-naphthalenedisulfonic acid, tartaric acid and adipic acid.

5. The acid salt according to claim 1, wherein the number of equivalents of acid is 0.5 to 2.

6. The acid salt according to claim 1, wherein the acid salt is hydrochloride, and the number of hydrochloric acid is 1.

7. The acid salt according to claim 1, wherein the acid salt is a crystal form, the crystal form is a hydrate or anhydrate; and when the crystal is a hydrate the number of equivalents of water is 0.5 to 3.

8. The acid salt according to claim 7, wherein it is a crystal form of an acid salt of N-(trans-3-(2-(4-(2,3-dichlorophenyl)piperazin-1-yl)ethyl)cyclobutyl)oxazole-2-carboxamide comprising crystal form A of hydrochloride, crystal form B of hydrochloride, crystal form A of p-toluenesulfonate, crystal form B of p-toluenesulfonate, crystal form A of hydrobromide, crystal form A of oxalate, crystal form A of sulfate, crystal form A of methanesulfonate, crystal form A of 1,5-naphthalenedisulfonate, crystal form A of nitrate, crystal form A of acetate and crystal form A of fumarate, wherein:

the X-ray powder diffraction pattern of crystal form A of hydrochloride has a diffraction peak of 23.9±0.2°, or a diffraction peak of 19.3±0.2°, or a diffraction peak of 22.8±0.2°, or a diffraction peak of 18.7±0.2°, or a diffraction peak of 17.1±0.2°, or a diffraction peak of 17.7±0.2°, or a diffraction peak of 15.1±0.2°, or a diffraction peak of 25.8±0.2°, or a diffraction peak of 21.0±0.2°, or a diffraction peak of 22.3±0.2°; the X-ray powder diffraction pattern of crystal form B of hydrochloride has a diffraction peak of 18.4±0.2°, or a diffraction peak of 14.9±0.2°, or a diffraction peak of 26.4±0.2°, or a diffraction peak of 17.1±0.2°, or a diffraction peak of 21.1±0.2°, or a diffraction peak of 25.1±0.2°, or a diffraction peak of 28.0±0.2°, or a diffraction peak of 7.5±0.2°, or a diffraction peak of 14.2±0.2°, or a diffraction peak of 13.0±0.2°; the X-ray powder diffraction pattern of crystal form A of p-toluenesulfonate has a diffraction peak of 20.1±0.2°, or a diffraction peak of 18.7±0.2°, or a diffraction peak of 19.5±0.2°, or a diffraction peak of 5.3±0.2°, or a diffraction peak of 21.2±0.2°, or a diffraction peak of 18.3±0.2°, or a diffraction peak of 11.9±0.2°, or a diffraction peak of 15.1±0.2°, or a diffraction peak of 15.9±0.2°, or a diffraction peak of 32.0±0.2°; the X-ray powder diffraction pattern of crystal form B of p-toluenesulfonate has a diffraction peak of 5.0±0.2°, or a diffraction peak of 11.8±0.2°, or a diffraction peak of 14.9±0.2°, or a diffraction peak of 15.5±0.2°, or a diffraction peak of 18.8±0.2°, or a diffraction peak of 20.0±0.2°, or a diffraction peak of 19.1±0.2°, or a diffraction peak of 23.7±0.2°, or a diffraction peak of 20.9±0.2°, or a diffraction peak of 20.5±0.2°; the X-ray powder diffraction pattern of crystal form A of hydrobromide has a diffraction peak of 25.8±0.2°, or a diffraction peak of 18.1±0.2°, or a diffraction peak of 18.7±0.2°, or a diffraction peak of 11.3±0.2°, or a diffraction peak of 17.8±0.2°, or a diffraction peak of 14.0±0.2°, or a diffraction peak of 14.6±0.2°, or a diffraction peak of 24.4±0.2°, or a diffraction peak of 28.3±0.2°, or a diffraction peak of 20.8±0.2°; the X-ray powder diffraction pattern of crystal form A of oxalate has a diffraction peak of 21.2±0.2°, or a diffraction peak of 19.7±0.2°, or a diffraction peak of 25.6±0.2°, or a diffraction peak of 20.4±0.2°, or a diffraction peak of 9.1±0.2°, or a diffraction peak of 18.7±0.2°, or a diffraction peak of 18.0±0.2°, or a diffraction peak of 26.0±0.2°, or a diffraction peak of 11.7±0.2°, or a diffraction peak of 23.4±0.2°; the X-ray powder diffraction pattern of crystal form A of sulfate has a diffraction peak of 11.0±0.2°, or a diffraction peak of 17.9±0.2°, or a diffraction peak of 21.9±0.2°, or a diffraction peak of 24.9±0.2°, or a diffraction peak of 18.9±0.2°, or a diffraction peak of 19.6±0.2°, or a diffraction peak of 23.0±0.2°, or a diffraction peak of 14.7±0.2°, or a diffraction peak of 27.6±0.2°, or a diffraction peak of 13.4±0.2°; the X-ray powder diffraction pattern of crystal form A of methanesulfonate has a diffraction peak of 21.2±0.2°, or a diffraction peak of 14.7±0.2°, or a diffraction peak of 21.4±0.2°, or a diffraction peak of 25.4±0.2°, or a diffraction peak of 20.1±0.2°, or a diffraction peak of 17.1±0.2°, or a diffraction peak of 22.5±0.2°, or a diffraction peak of 13.1±0.2°, or a diffraction peak of 23.8±0.2°, or a diffraction peak of 20.6±0.2°; the X-ray powder diffraction pattern of crystal form A of 1,5-naphthalenedisulfonate has a diffraction peak of 21.4±0.2°, or a diffraction peak of 18.0±0.2°, or a diffraction peak of 22.4±0.2°, or a diffraction peak of 24.1±0.2°, or a diffraction peak of 26.0±0.2°, or a diffraction peak of 10.5±0.2°, or a diffraction peak of 15.4±0.2°, or a diffraction peak of 15.6±0.2°, or a diffraction peak of 23.0±0.2°, or a diffraction peak of 17.8±0.2°; the X-ray powder diffraction pattern of crystal form A of nitrate has a diffraction peak of 25.7±0.2°, or a diffraction peak of 16.3±0.2°, or a diffraction peak of 18.0±0.2°, or a diffraction peak of 21.6±0.2°, or a diffraction peak of 19.8±0.2°, or a diffraction peak of 24.3±0.2°, or a diffraction peak of 27.5±0.2°, or a diffraction peak of 11.9±0.2°, or a diffraction peak of 23.6±0.2°, or a diffraction peak of 14.2±0.2°; the X-ray powder diffraction pattern of crystal form A of acetate has a diffraction peak of 11.2±0.2°, or a diffraction peak of 16.9±0.2°, or a diffraction peak of 20.8±0.2°, or a diffraction peak of 18.7±0.2°, or a diffraction peak of 13.5±0.2°, or a diffraction peak of 13.9±0.2°, or a diffraction peak of 22.3±0.2°, or a diffraction peak of 24.5±0.2°, or a diffraction peak of 22.7±0.2°, or a diffraction peak of 28.2±0.2°; the X-ray powder diffraction pattern of crystal form A of fumarate has a diffraction peak of 17.8±0.2°, or a diffraction peak of 18.6±0.2°, or a diffraction peak of 21.7±0.2°, or a diffraction peak of 22.7±0.2°, or a diffraction peak of 16.9±0.2°, or a diffraction peak of 20.8±0.2°, or a diffraction peak of 24.3±0.2°, or a diffraction peak of 24.7±0.2°, or a diffraction peak of 22.3±0.2°, or a diffraction peak of 15.8±0.2°.

9. A method for preparing the acid salt according to claim 1, specifically comprising the following steps of:

1) weighing an appropriate amount of free base and dissolving it with a good solvent;
2) weighing an appropriate amount of counter ion acid and dissolving it with an organic solvent;
3) combining the above two solutions, stirring it to precipitate a solid or dropwise adding a poor solvent to precipitate a solid under stirring;
4) rapid centrifugation or standing blow-drying to obtain the target product;

wherein the good solvent is one or more selected from the group consisting of acetone, dichloromethane, tetrahydrofuran, ethyl formate, ethyl acetate, 2-methyl-tetrahydrofuran, 2-butanone, n-butanol, 1,4-dioxane, isobutanol, N,N-dimethylformamide, N,N-dimethylacetamide, n-propanol and tert-butanol; the organic solvent is one or more selected from the group consisting of methanol, ethanol, ethyl acetate, dichloromethane, acetone, n-hexane, petroleum ether, benzene, toluene, chloroform, acetonitrile, carbon tetrachloride, dichloroethane, tetrahydrofuran, 2-methyltetrahydrofuran, 2-butanone, 3-pentanone, heptane, methyl tert-butyl ether, isopropyl ether, 1,4-dioxane, tert-butanol and N,N-dimethylformamide; the above good solvent and the organic solvent need to be miscible when used;

the poor solvent is one or more selected from the group consisting of heptane, water, methyl tert-butyl ether, cyclohexane, toluene, isopropyl ether, ethyl acetate, acetone and acetonitrile; or, specifically comprising the following steps of:

1) weighing an appropriate amount of free base and suspending it with a poor solvent;
2) weighing an appropriate amount of counter ion acid and dissolving it with an organic solvent;
3) adding the above solution into the above suspension, and stirring;
4) rapid centrifugation or standing blow-drying to obtain the target product;

the poor solvent is one or more selected from the group consisting of ethanol, acetone, ethyl acetate, ethyl formate, isopropanol, isopropyl acetate, methyl tert-butyl ether, methanol, acetonitrile, chlorobenzene, benzene, toluene, n-butanol, isobutanol and 3-pentanone; the organic solvent is one or more selected from the group consisting of methanol, ethanol, ethyl acetate, dichloromethane, acetone, n-hexane, petroleum ether, benzene, toluene, chloroform, acetonitrile, carbon tetrachloride, dichloroethane, tetrahydrofuran, 2-methyltetrahydrofuran, 2-butanone, 3-pentanone, heptane, methyl tert-butyl ether, isopropyl ether, 1,4-dioxane, tert-butanol and N,N-dimethylformamide; the above good solvent and the organic solvent need to be miscible when used;

or, specifically comprising the following steps of:

1) weighing an appropriate amount of acid salt of compound, suspending it with a poor solvent, and shaking;
2) rapidly centrifuging the above suspension, removing the supernatant, and drying the remaining solid to obtain the target product;

wherein the poor solvent is one or more selected from the group consisting of methanol, ethanol, dichloromethane, 1,4-dioxane, acetonitrile, chlorobenzene, benzene, toluene, acetone, ethyl acetate, water, 88% acetone, isopropyl acetate, 3-pentanone, ethyl formate, tetrahydrofuran, 2-methyl-tetrahydrofuran, isopropanol, n-butanol, isobutanol, n-propanol, methyl tert-butyl ether, n-heptane, tert-butanol and 2-butanone;

the counter ion acid or the acid in the acid salt is one or more selected from the group consisting of hydrochloric acid, sulfuric acid, nitric acid, hydrobromic acid, hydrofluoric acid, hydroiodic acid, phosphoric acid, 2,5-dihydroxybenzoic acid, 1-hydroxy-2-naphthoic acid, acetic acid, dichloroacetic acid, trichloroacetic acid, acetohydroxamic acid, adipic acid, benzenesulfonic acid, 4-chlorobenzenesulfonic acid, benzoic acid, 4-acetamidobenzoic acid, 4-aminobenzoic acid, decanoic acid, caproic acid, caprylic acid, cinnamic acid, citric acid, cyclamic acid, camphorsulfonic acid, aspartic acid, camphoric acid, gluconic acid, glucuronic acid, glutamic acid, isoascorbic acid, lactic acid, malic acid, mandelic acid, pyroglutamic acid, tartaric acid, dodecyl sulfuric acid, dibenzoyl tartaric acid, ethane-1,2-disulfonic acid, ethanesulfonic acid, formic acid, fumaric acid, galactonic acid, gentisic acid, glutaric acid, 2-ketoglutaric acid, glycolic acid, hippuric acid, isethionic acid, lactobionic acid, ascorbic acid, aspartic acid, lauric acid, camphoric acid, maleic acid, malonic acid, methanesulfonic acid, 1,5-naphthalenedisulfonic acid, naphthalene-2-sulfonic acid, nicotinic acid, oleic acid, orotic acid, oxalic acid, palmitic acid, embonic acid, propionic acid, salicylic acid, 4-aminosalicylic acid, decanedioic acid, stearic acid, succinic acid, thiocyanic acid, pamoic acid, methanoic acid, undecylenic acid, trifluoroacetic acid, benzenesulfonic acid, p-toluenesulfonic acid and L-malic acid.

10. A pharmaceutical composition comprising a therapeutically effective dose of the acid salt according to claim 1, and one or more pharmaceutically acceptable carriers, diluents or excipients.

11. A method for treating or preventing a central nervous system disease and/or psychiatric disease or disorder in a patient in need thereof, the method comprising administering to the patient a therapeutically effective dose of the acid salt according to claim 1, wherein the central nervous system disease and/or psychiatric disease or disorder is schizophrenia, sleep disorder, mood disorder, schizophrenia spectrum disorder, spastic disorder, memory disorder and/or cognitive disorder, movement disorder, personality disorder, autism spectrum disorder, pain, traumatic brain injury, vascular disease, substance abuse disorder and/or withdrawal syndrome, tinnitus, depression, autism, senile dementia, Alzheimer's disease, seizures, neuralgia, detoxification, symptomatic major depressive disorder, or mania.

12. The acid salt according to claim 1, wherein, $R_5$ is selected from the group consisting of:

H—, $(CH_3)_2N$—, $CH_3NH$—, $CH_3$—, $CH_3O$—, $CH_3CH_2$—, $CH_3CH_2NH$—, $CH_3CH_2N(CH_3)$—, $(CH_3)_2C(OH)$—, $(CH_3)_2C(OH)CH_2$—, $CH_3OCH_2$—,

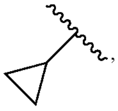, 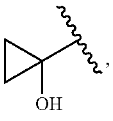, 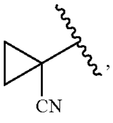, 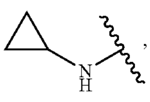,

-continued

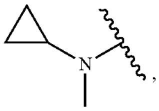, 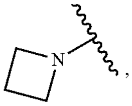, 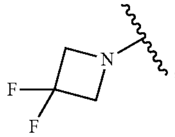,

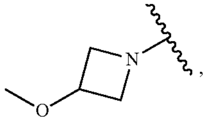, 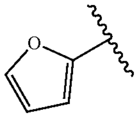, 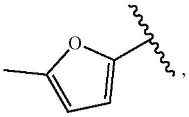,

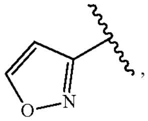, 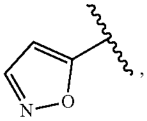, 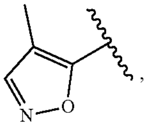,

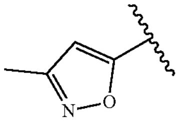, 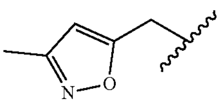,

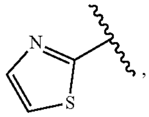, 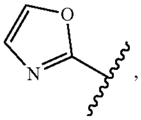, 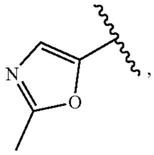,

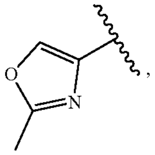, 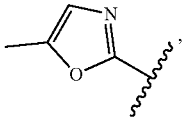, 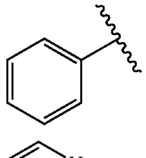,

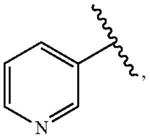, 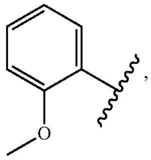, 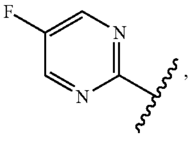,

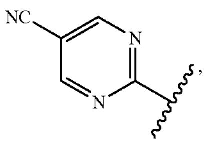, 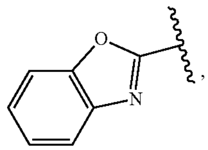,

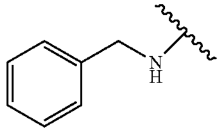, 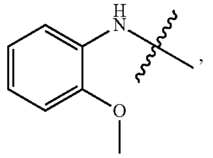,

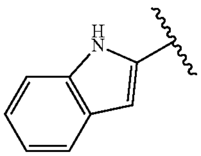 and 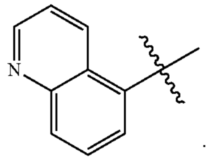.

13. The acid salt according to claim 8, wherein the X-ray powder diffraction pattern of crystal form A of hydrochloride comprises any 2 to 5, or 3 to 5, or 3 to 6, or 3 to 8, or 5 to 8, or 6 to 8 of the above diffraction peaks;

the X-ray powder diffraction pattern of crystal form B of hydrochloride comprises any 2 to 5, or 3 to 5, or 3 to 6, or 3 to 8, or 5 to 8, or 6 to 8 of the above diffraction peaks;

the X-ray powder diffraction pattern of crystal form A of p-toluenesulfonate comprises any 2 to 5, or 3 to 5, or 3 to 6, or 3 to 8, or 5 to 8, or 6 to 8 of the above diffraction peaks;

the X-ray powder diffraction pattern of crystal form B of p-toluenesulfonate comprises any 2 to 5, or 3 to 5, or 3 to 6, or 3 to 8, or 5 to 8, or 6 to 8 of the above diffraction peaks;

the X-ray powder diffraction pattern of crystal form A of hydrobromide comprises any 2 to 5, or 3 to 5, or 3 to 6, or 3 to 8, or 5 to 8, or 6 to 8 of the above diffraction peaks;

the X-ray powder diffraction pattern of crystal form A of oxalate comprises any 2 to 5, or 3 to 5, or 3 to 6, or 3 to 8, or 5 to 8, or 6 to 8 of the above diffraction peaks;

the X-ray powder diffraction pattern of crystal form A of sulfate comprises any 2 to 5, or 3 to 5, or 3 to 6, or 3 to 8, or 5 to 8, or 6 to 8 of the above diffraction peaks;

the X-ray powder diffraction pattern of crystal form A of methanesulfonate comprises any 2 to 5, or 3 to 5, or 3 to 6, or 3 to 8, or 5 to 8, or 6 to 8 of the above diffraction peaks;

the X-ray powder diffraction pattern of crystal form A of 1,5-naphthalenedisulfonate comprises any 2 to 5, or 3 to 5, or 3 to 6, or 3 to 8, or 5 to 8, or 6 to 8 of the above diffraction peaks;

the X-ray powder diffraction pattern of crystal form A of nitrate comprises any 2 to 5, or 3 to 5, or 3 to 6, or 3 to 8, or 5 to 8, or 6 to 8 of the above diffraction peaks;

the X-ray powder diffraction pattern of crystal form A of acetate comprises any 2 to 5, or 3 to 5, or 3 to 6, or 3 to 8, or 5 to 8, or 6 to 8 of the above diffraction peaks; and the X-ray powder diffraction pattern of crystal form A of fumarate comprises any 2 to 5, or 3 to 5, or 3 to 6, or 3 to 8, or 5 to 8, or 6 to 8 of the above diffraction peaks.

14. The acid salt according to claim 8, wherein the X-ray powder diffraction pattern of crystal form A of hydrochloride comprises at least one or more diffraction peaks at 2θ of 23.9±0.2°, 22.8±0.2°, 19.3±0.2° and 18.7±0.2°;

the X-ray powder diffraction pattern of crystal form B of hydrochloride comprises at least one or more diffraction peaks at 2θ of 18.4±0.2°, 26.4±0.2°, 25.1±0.2° and 14.9±0.2°;

the X-ray powder diffraction pattern of crystal form A of p-toluenesulfonate comprises at least one or more diffraction peaks at 2θ of 20.1±0.2°, 18.7±0.2°, 19.5±0.2° and 5.3±0.2°;

the X-ray powder diffraction pattern of crystal form B of p-toluenesulfonate comprises at least one or more diffraction peaks at 2θ of 5.0±0.2°, 14.9±0.2°, 15.5±0.2° and 11.8±0.2°;

the X-ray powder diffraction pattern of crystal form A of hydrobromide comprises at least one or more diffraction peaks at 2θ of 25.8±0.2°, 18.1±0.2°, 18.7±0.2° and 11.3±0.2°;

the X-ray powder diffraction pattern of crystal form A of oxalate comprises at least one or more diffraction peaks at 2θ of 21.2±0.2°, 25.6±0.2°, 20.4±0.2° and 19.7±0.2°;

the X-ray powder diffraction pattern of crystal form A of sulfate comprises at least one or more diffraction peaks at 2θ of 11.0±0.2°, 21.9±0.2°, 24.9±0.2° and 17.9±0.2°;

the X-ray powder diffraction pattern of crystal form A of methanesulfonate comprises at least one or more diffraction peaks at 2θ of 21.2±0.2°, 21.4±0.2°, 25.4±0.2° and 14.7±0.2°;

the X-ray powder diffraction pattern of crystal form A of 1,5-naphthalenedisulfonate comprises at least one or more diffraction peaks at 2θ of 21.4±0.2°, 26.0±0.2°, 22.4±0.2° and 18.0±0.2°;

the X-ray powder diffraction pattern of crystal form A of nitrate comprises at least one or more diffraction peaks at 2θ of 25.7±0.2°, 18.0±0.2°, 21.6±0.2° and 16.3±0.2°;

the X-ray powder diffraction pattern of crystal form A of acetate comprises at least one or more diffraction peaks at 2θ of 11.2±0.2°, 20.8±0.2°, 18.7±0.2° and 16.9±0.2°; and the X-ray powder diffraction pattern of crystal form A of fumarate comprises at least one or more diffraction peaks at 2θ of 17.8±0.2°, 21.7±0.2°, 22.7±0.2° and 18.6±0.2°.

15. The acid salt according to claim 14, wherein the X-ray powder diffraction pattern of crystal form A of hydrochloride optionally further comprises at least one diffraction peak at 2θ of 17.1±0.2°, 17.7±0.2°, 15.1±0.2°, 25.8±0.2° and 21.0±0.2°;

the X-ray powder diffraction pattern of crystal form B of hydrochloride optionally further comprises at least one diffraction peak at 2θ of 17.1±0.2°, 21.1±0.2°, 28.0±0.2°, 14.2±0.2° and 13.0±0.2°;

the X-ray powder diffraction pattern of crystal form A of p-toluenesulfonate optionally further comprises at least one diffraction peak at 2θ of 21.2±0.2°, 18.3±0.2°, 11.9±0.2°, 15.1±0.2° and 15.9±0.2°;

the X-ray powder diffraction pattern of crystal form B of p-toluenesulfonate optionally further comprises at least one diffraction peak at 2θ of 18.8±0.2°, 20.0±0.2°, 19.1±0.2°, 23.7±0.2° and 20.9±0.2°;

the X-ray powder diffraction pattern of crystal form A of hydrobromide optionally further comprises at least one diffraction peak at 2θ of 17.8±0.2°, 14.0±0.2°, 14.6±0.2°, 24.4±0.2° and 28.3±0.2°;

the X-ray powder diffraction pattern of crystal form A of oxalate optionally further comprises at least one diffraction peak at 2θ of 9.1±0.2°, 18.7±0.2°, 18.0±0.2°, 26.0±0.2° and 23.4±0.2°;

the X-ray powder diffraction pattern of crystal form A of sulfate optionally further comprises at least one diffraction peak at 2θ of 14.7±0.2°, 18.9±0.2°, 19.6±0.2°, 23.0±0.2° and 27.6±0.2°;

the X-ray powder diffraction pattern of crystal form A of methanesulfonate optionally further comprises at least one diffraction peak at 2θ of 20.1±0.2°, 17.1±0.2°, 22.5±0.2°, 13.1±0.2° and 23.8±0.2°;

the X-ray powder diffraction pattern of crystal form A of 1,5-naphthalenedisulfonate optionally further comprises at least one diffraction peak at 2θ of 24.1±0.2°, 10.5±0.2°, 15.4±0.2°, 15.6±0.2° and 23.0±0.2°;

the X-ray powder diffraction pattern of crystal form A of nitrate optionally further comprises at least one diffraction peak at 2θ of 19.8±0.2°, 24.3±0.2°, 27.5±0.2°, 11.9±0.2° and 23.6±0.2°;

the X-ray powder diffraction pattern of crystal form A of acetate optionally further comprises at least one diffraction peak at 2θ of 13.5±0.2°, 13.9±0.2°, 22.3±0.2°, 24.5±0.2° and 22.7±0.2°; and the X-ray powder diffraction pattern of crystal form A of fumarate optionally further comprises at least one diffraction peak at 2θ of 16.9±0.2°, 20.8±0.2°, 24.3±0.2°, 24.7±0.2° and 15.8±0.2°.

16. The acid salt according to claim 8, wherein the X-ray powder diffraction pattern of crystal form A of hydrochloride has diffraction peaks at 2θ of the following positions:

23.9±0.2° and 19.3±0.2°, or, 17.7±0.2° and 22.8±0.2°, or, 18.7±0.2° and 17.1±0.2°, or, 23.9±0.2°, 19.3±0.2° and 22.8±0.2°, or, 17.7±0.2°, 19.3±0.2° and 18.7±0.2°, or, 23.9±0.2°, 18.7±0.2° and 15.1±0.2°, or, 23.9±0.2°, 19.3±0.2°, 17.1±0.2° and 15.1±0.2°, or, 23.9±0.2°, 17.7±0.2°, 19.3±0.2° and 22.8±0.2°, or, 22.8±0.2°, 19.3±0.2°, 25.8±0.2° and 21.0±0.2°, or, 23.9±0.2°, 19.3±0.2°, 22.8±0.2°, 25.8±0.2° and 21.0±0.2°, or, 23.9±0.2°, 19.3±0.2°, 22.8±0.2°, 17.1±0.2° and 25.8±0.2°, or, 18.7±0.2°, 19.3±0.2°, 22.8±0.2°, 17.1±0.2° and 17.7±0.2°, or, 23.9±0.2°, 22.8±0.2°, 19.3±0.2°, 18.7±0.2°, 17.1±0.2° and 15.1±0.2°, or, 18.7±0.2°, 19.3±0.2°, 22.8±0.2°, 17.1±0.2°, 17.7±0.2° and 15.1±0.2°, or, 19.3±0.2°, 22.8±0.2°, 17.1±0.2°, 17.7±0.2°, 25.8±0.2° and 15.1±0.2°, or, 23.9±0.2°, 19.3±0.2°, 22.8±0.2°, 18.7±0.2°, 17.1±0.2° and 15.1±0.2°, or, 18.7±0.2°, 19.3±0.2°, 22.8±0.2°, 17.1±0.2°, 15.1±0.2°, 21.0±0.2° and 25.8±0.2°;

23.9±0.2°, 22.8±0.2°, 19.3±0.2°, 17.7±0.2°, 22.3±0.2°, 31.3±0.2°, 25.4±0.2° and 23.4±0.2°, or, 23.9±0.2°, 18.7±0.2°, 19.3±0.2°, 22.8±0.2°, 17.1±0.2°, 17.7±0.2°, 15.1±0.2°, 23.4±0.2° and 21.7±0.2°, or, 23.9±0.2°, 18.7±0.2°, 19.3±0.2°, 22.8±0.2°, 17.1±0.2°, 17.7±0.2°, 15.1±0.2°, 23.4±0.2°, 22.3±0.2° and 21.7±0.2°;

or, 23.9±0.2°, 22.8±0.2°, 19.3±0.2° and 18.7±0.2°, or, 23.9±0.2°, 22.8±0.2°, 17.1±0.2° and 17.7±0.2°, or, 23.9±0.2°, 22.8±0.2°, 19.3±0.2°, 18.7±0.2°, 17.1±0.2° and 17.7±0.2°, or, 22.8±0.2°, 19.3±0.2°, 18.7±0.2°, 17.7±0.2°, 15.1±0.2° and 25.8±0.2°, or, 23.9±0.2°, 22.8±0.2°, 19.3±0.2°, 18.7±0.2°, 17.1±0.2°, 17.7±0.2°, 15.1±0.2° and 25.8±0.2°, or, 19.3±0.2°, 18.7±0.2°, 17.1±0.2°, 17.7±0.2°, 15.1±0.2°, 25.8±0.2°, 21.0±0.2° and 22.3±0.2°, or, 23.9±0.2°, 22.8±0.2°, 19.3±0.2°, 18.7±0.2°, 17.1±0.2°, 17.7±0.2°, 15.1±0.2°, 25.8±0.2°, 21.0±0.2° and 22.3±0.2°, or, 22.8±0.2°, 19.3±0.2°, 18.7±0.2°, 17.1±0.2°, 17.7±0.2°, 15.1±0.2°, 25.8±0.2°, 21.0±0.2°, 22.3±0.2° and 31.3±0.2°;

the X-ray powder diffraction pattern of crystal form B of hydrochloride has diffraction peaks at 2θ of the following positions:

14.9±0.2° and 26.4±0.2°, or, 18.4±0.2° and 17.1±0.2°, or, 21.1±0.2° and 25.1±0.2°, or, 14.9±0.2°, 26.4±0.2° and 17.1±0.2°, or, 18.4±0.2°, 26.4±0.2° and 25.1±0.2°, or, 21.1±0.2°, 28.0±0.2° and 14.2±0.2°, or, 14.9±0.2°, 26.4±0.2°, 28.0±0.2° and 14.2±0.2°, or, 14.9±0.2°, 18.4±0.2°, 26.4±0.2° and 17.1±0.2°, or, 18.4±0.2°, 21.1±0.2°, 26.4±0.2° and 25.1±0.2°, or, 14.9±0.2°, 26.4±0.2°, 17.1±0.2°, 28.0±0.2° and 14.2±0.2°, or, 18.4±0.2°, 26.4±0.2°, 17.1±0.2°, 25.1±0.2° and 28.0±0.2°, or, 21.1±0.2°, 26.4±0.2°, 17.1±0.2°, 25.1±0.2° and 28.0±0.2°, or, 14.9±0.2°, 18.4±0.2°, 26.4±0.2°, 17.1±0.2°, 28.0±0.2° and 14.2±0.2°, or, 21.1±0.2°, 26.4±0.2°, 17.1±0.2°, 25.1±0.2°, 13.0±0.2° and 28.0±0.2°, or, 18.4±0.2°, 26.4±0.2°, 17.1±0.2°, 25.1±0.2°, 28.0±0.2° and 14.2±0.2°, or, 21.1±0.2°, 26.4±0.2°, 17.1±0.2°, 25.1±0.2°, 28.0±0.2° and 14.2±0.2°, or, 21.1±0.2°, 26.4±0.2°, 17.1±0.2°, 25.1±0.2°, 14.2±0.2°, 13.0±0.2° and 28.0±0.2°;

or, 14.9±0.2°, 18.4±0.2°, 21.1±0.2°, 26.3±0.2°, 17.1±0.2°, 25.1±0.2°, 7.5±0.2° and 8.5±0.2°, or, 14.9±0.2°, 18.4±0.2°, 21.1±0.2°, 26.3±0.2°, 17.1±0.2°, 25.1±0.2°, 7.5±0.2°, 8.5±0.2° and 13.0±0.2°, or, 14.9±0.2°, 18.4±0.2°, 21.1±0.2°, 26.3±0.2°, 17.1±0.2°, 25.1±0.2°, 7.5±0.2°, 8.5±0.2°, 13.0±0.2° and 14.2±0.2°;

or, 14.9±0.2°, 18.4±0.2°, 21.1±0.2° and 26.4±0.2°, or, 14.9±0.2°, 18.4±0.2°, 17.1±0.2° and 25.1±0.2°, or, 14.9±0.2°, 18.4±0.2°, 21.1±0.2°, 26.4±0.2°, 17.1±0.2°, 25.1±0.2°, or, 18.4±0.2°, 26.4±0.2°, 17.1±0.2°, 28.0±0.2°, 7.5±0.2° and 8.5±0.2°, or, 14.9±0.2°, 18.4±0.2°, 21.1±0.2°, 26.4±0.2°, 17.1±0.2°, 25.1±0.2°, 28.0±0.2° and 7.5±0.2°, or, 14.9±0.2°, 21.1±0.2°, 17.1±0.2°, 25.1±0.2°, 28.0±0.2°, 7.5±0.2°, 8.5±0.2° and 13.0±0.2°, or, 14.9±0.2°, 18.4±0.2°, 21.1±0.2°, 26.4±0.2°, 17.1±0.2°, 25.1±0.2°, 28.0±0.2°, 7.5±0.2°, 8.5±0.2° and 13.0±0.2°, or, 18.4±0.2°, 26.4±0.2°, 28.0±0.2°, 7.5±0.2°, 8.5±0.2°, 13.0±0.2°, 14.2±0.2°, 18.1±0.2°, 18.7±0.2°, 23.1±0.2° and 25.3±0.2°;

the X-ray powder diffraction pattern of crystal form A of p-toluenesulfonate has diffraction peaks at 2θ of the following positions:

18.7±0.2° and 20.1±0.2°, or, 18.7±0.2° and 21.2±0.2°, or, 20.1±0.2° and 18.3±0.2°, or, 18.7±0.2°, 20.1±0.2° and 21.2±0.2°, or, 18.3±0.2°, 20.1±0.2° and 18.7±0.2°, or, 20.1±0.2°, 19.5±0.2° and 11.9±0.2°, or, 18.7±0.2°, 20.1±0.2°, 21.2±0.2° and 11.9±0.2°, or, 18.7±0.2°, 18.3±0.2°, 20.1±0.2° and 21.2±0.2°, or, 18.3±0.2°, 21.2±0.2°, 20.1±0.2° and 5.3±0.2°, or, 18.7±0.2°, 20.1±0.2°, 21.2±0.2°, 18.3±0.2° and 11.9±0.2°, or, 18.7±0.2°, 20.1±0.2°, 21.2±0.2°, 18.3±0.2° and 15.1±0.2°, or, 20.1±0.2°, 18.7±0.2°, 19.5±0.2°, 5.3±0.2° and 21.2±0.2°, or, 18.7±0.2°, 18.3±0.2°, 20.1±0.2°, 21.2±0.2°, 15.1±0.2° and 11.9±0.2°, or, 20.1±0.2°, 19.5±0.2°, 5.3±0.2°, 21.2±0.2°, 15.1±0.20 and 15.9±0.2°, or, 20.1±0.2°, 18.7±0.2°, 19.5±0.2°, 5.3±0.2°, 21.2±0.2° and 18.3±0.2°, or, 20.1±0.2°, 18.7±0.2°, 21.2±0.2°, 18.3±0.2°, 15.1±0.2° and 15.9±0.2°, or, 19.5±0.2°, 5.3±0.2°, 21.2±0.2°, 18.3±0.2°, 11.9±0.2° and 15.1±0.2°;

or, 18.7±0.2°, 18.3±0.2°, 22.2±0.2°, 20.1±0.2°, 21.7±0.2°, 23.7±0.2°, 11.9±0.2° and 19.5±0.2°, or, 18.7±0.2°, 18.3±0.2°, 22.2±0.2°, 20.1±0.2°, 21.7±0.2°, 23.7±0.2°, 11.9±0.2°, 19.5±0.2° and 15.9±0.2°, or, 18.7±0.2°, 18.3±0.2°, 22.2±0.2°, 20.1±0.2°, 21.7±0.2°, 23.7±0.2°, 11.9±0.2°, 19.5±0.2°, 15.9±0.2° and 32.0±0.2°;

or, 18.7±0.2°, 18.3±0.2°, 21.2±0.2° and 20.1±0.2°, or, 18.7±0.2°, 18.3±0.2°, 21.2±0.2° and 25.8±0.2°, or, 18.7±0.2°, 18.3±0.2°, 21.2±0.2°, 20.1±0.2°, 22.2±0.2°, 25.8±0.2°, or, 20.1±0.2°, 18.7±0.2°, 19.5±0.2°, 5.3±0.2°, 21.2±0.2° and 18.3±0.2°, or, 20.1±0.2°, 18.7±0.2°, 19.5±0.2°, 5.3±0.2°, 21.2±0.2°, 18.3±0.2°, 11.9±0.2° and 15.9±0.2°, or, 18.7±0.2°, 19.5±0.2°, 5.3±0.2°, 21.2±0.2°, 18.3±0.2°, 11.9±0.2°, 15.9±0.2° and 15.1±0.2°, or, 20.1±0.2°, 18.7±0.2°, 19.5±0.2°, 5.3±0.2°, 21.2±0.2°, 18.3±0.2°, 11.9±0.2°, 15.9±0.2°, 15.1±0.2° and 32.0±0.2°, or, 18.7±0.2°, 19.5±0.2°, 5.3±0.2°, 21.2±0.2°, 18.3±0.2°, 11.9±0.2°, 15.9±0.2°, 15.1±0.2°, 32.0±0.2°, 22.2±0.2°, 25.8±0.2° and 15.5±0.2°;

the X-ray powder diffraction pattern of crystal form B of p-toluenesulfonate has diffraction peaks at 2θ of the following positions:

11.8±0.2° and 14.9±0.2°, or, 5.0±0.2° and 15.5±0.2°, or, 20.0±0.2° and 19.1±0.2°, or, 11.8±0.2°, 14.9±0.2° and 15.5±0.2°, or, 5.0±0.2°, 14.9±0.2° and 19.1±0.2°, or, 20.0±0.2°, 23.7±0.2° and 18.8±0.2°, or, 11.8±0.2°, 14.9±0.2°, 23.7±0.2° and 18.8±0.2°, or, 11.8±0.2°, 5.0±0.2°, 14.9±0.2° and 15.5±0.2°, or, 5.0±0.2°, 20.0±0.2°, 14.9±0.2° and 19.1±0.2°, or, 11.8±0.2°, 14.9±0.2°, 15.5±0.2°, 23.7±0.2° and 18.8±0.2°, or, 5.0±0.2°, 14.9±0.2°, 15.5±0.2°, 19.1±0.2° and 23.7±0.2°, or, 20.0±0.2°, 14.9±0.2°, 15.5±0.2°, 19.1±0.2° and 23.7±0.2°, or, 11.8±0.2°, 5.0±0.2°, 14.9±0.2°, 15.5±0.2°, 23.7±0.2° and 18.8±0.2°, or, 20.0±0.2°, 14.9±0.2°, 15.5±0.2°, 19.1±0.2°, 20.9±0.2° and 23.7±0.2°, or, 5.0±0.2°, 14.9±0.2°, 15.5±0.2°, 19.1±0.2°, 23.7±0.2° and 18.8±0.2°, or, 20.0±0.2°, 14.9±0.2°, 15.5±0.2°, 19.1±0.2°, 23.7±0.2° and 18.8±0.2°, or, 20.0±0.2°, 14.9±0.2°, 15.5±0.2°, 19.1±0.2°, 18.8±0.2°, 20.9±0.2° and 23.7±0.2°;

or, 11.8±0.2°, 5.0±0.2°, 20.0±0.2°, 14.9±0.2°, 15.5±0.2°, 19.1±0.2°, 18.8±0.2° and 28.8±0.2°, or, 11.8±0.2°, 5.0±0.2°, 20.0±0.2°, 14.9±0.2°, 15.5±0.2°, 19.1±0.2°, 18.8±0.2°, 28.8±0.2° and 29.1±0.2°, or, 11.8±0.2°, 5.0±0.2°, 20.0±0.2°, 14.9±0.2°, 15.5±0.2°, 19.1±0.2°, 18.8±0.2°, 28.8±0.2° 29.1±0.2° and 26.5±0.2°;

or, 11.8±0.2°, 5.0±0.2°, 20.0±0.2° and 14.9±0.2°, or, 11.8±0.2°, 5.0±0.2°, 15.5±0.2° and 19.1±0.2°, or, 11.8±0.2°, 5.0±0.2°, 20.0±0.2°, 14.9±0.2°, 15.5±0.2°, 19.1±0.2°, or, 5.0±0.2°, 14.9±0.2°, 15.5±0.2°, 23.7±0.2°, 18.8±0.2° and 28.8±0.2°, or, 11.8±0.2°, 5.0±0.2°, 20.0±0.2°, 14.9±0.2°, 15.5±0.2°, 19.1±0.2°, 23.7±0.2° and 18.8±0.2°, or, 11.8±0.2°, 20.0±0.2°, 15.5±0.2°, 19.1±0.2°, 23.7±0.2°, 18.8±0.2°, 28.8±0.2° and 29.1±0.2°, or, 11.8±0.2°, 5.0±0.2°, 20.0±0.2°, 14.9±0.2°, 15.5±0.2°, 19.1±0.2°, 23.7±0.2°, 18.8±0.2°, 28.8±0.2° and 29.1±0.2°, or, 5.0±0.2°, 14.9±0.2° 15.5±0.2°, 11.8±0.2°, 18.8±0.2°, 20.0±0.2°, 19.1±0.2°, 23.7±0.2°, 20.9±0.2° 20.5±0.2° and 17.5±0.2°;

the X-ray powder diffraction pattern of crystal form A of hydrobromide has diffraction peaks at 2θ of the following positions:

25.8±0.2° and 18.1±0.2°, or, 18.1±0.2° and 11.3±0.2°, or, 18.1±0.2° and 18.7±0.2°, or, 14.0±0.2°, 14.6±0.2° and 25.8±0.2°, or, 11.3±0.2°, 14.6±0.2° and 18.7±0.2°, or, 18.1±0.2°, 11.3±0.2° and 17.8±0.2°, or, 14.0±0.2°, 14.6±0.2°, 11.3±0.2° and 17.8±0.2°, or, 14.0±0.2°, 11.3±0.2°, 14.6±0.2° and 25.8±0.2°, or, 11.3±0.2°, 18.1±0.2°, 14.6±0.2° and 18.7±0.2°, or, 14.0±0.2°, 14.6±0.2°, 25.8±0.2°, 11.3±0.2° and 17.8±0.2°, or, 11.3±0.2°, 14.6±0.2°, 25.8±0.2°, 18.7±0.2° and 28.3±0.2°, or, 18.1±0.2°, 14.6±0.2°, 25.8±0.2°, 18.7±0.2° and 28.3±0.2°, or, 14.0±0.2°, 11.3±0.2°, 14.6±0.2°, 25.8±0.2°, 28.3±0.2° and 17.8±0.2°, or, 18.1±0.2°, 14.6±0.2°, 25.8±0.2°, 18.7±0.2°, 24.4±0.2° and 28.3±0.2°, or, 11.3±0.2°, 14.6±0.2°, 25.8±0.2°, 18.7±0.2°, 18.1±0.2° and 17.8±0.2°, or, 18.1±0.2°, 14.6±0.2°, 25.8±0.2°, 18.7±0.2°, 11.3±0.2° and 17.8±0.2°, or, 18.1±0.2°, 14.6±0.2°, 25.8±0.2°, 18.7±0.2°, 17.8±0.2°, 24.4±0.2° and 28.3±0.2°;

or, 25.8±0.2°, 18.1±0.2°, 18.7±0.2°, 11.3±0.2°, 17.8±0.2°, 14.0±0.2°, 14.6±0.2° and 27.5±0.2°, or, 25.8±0.2°, 18.1±0.2°, 18.7±0.2°, 17.8±0.2°, 14.0±0.2°, 27.5±0.2°, 23.4±0.2°, 25.5±0.2° and 22.7±0.2°, or, 18.1±0.2°, 18.7±0.2° and 11.3±0.2°, 24.4±0.2°, 28.3±0.2°, 25.5±0.2°, 22.7±0.2°, 19.3±0.2°, 21.2±0.2° and 29.4±0.2°;

or, 14.0±0.2°, 11.3±0.2°, 18.1±0.2° and 14.6±0.2°, or, 14.0±0.2°, 11.3±0.2°, 25.8±0.2° and 18.7±0.2°, or, 14.0±0.2°, 11.3±0.2°, 18.1±0.2°, 14.6±0.2°, 25.8±0.2°, 18.7±0.2°, or, 11.3±0.2°, 14.6±0.2°, 25.8±0.2°, 19.3±0.2°, 17.8±0.2° and 20.8±0.2°, or, 14.0±0.2°, 11.3±0.2°, 18.1±0.2°, 14.6±0.2°, 25.8±0.2°, 18.7±0.2°, 19.3±0.2° and 17.8±0.2°, or, 14.0±0.2°, 18.1±0.2°, 25.8±0.2°, 18.7±0.2°, 19.3±0.2°, 17.8±0.2°, 20.8±0.2° and 22.7±0.2°, or, 14.0±0.2°, 11.3±0.2°, 18.1±0.2°, 14.6±0.2°, 25.8±0.2°, 18.7±0.2°, 19.3±0.2°, 17.8±0.2°, 20.8±0.2° and 22.7±0.2°, or, 25.8±0.2°, 18.1±0.2°, 18.7±0.2°, 11.3±0.2°, 17.8±0.2°, 14.6±0.2°, 14.0±0.2°, 24.4±0.2°, 28.3±0.2°, 20.8±0.2° and 27.5±0.2°;

the X-ray powder diffraction pattern of crystal form A of oxalate has diffraction peaks at 2θ of the following positions:

19.7±0.2° and 21.2±0.2°, or, 9.1±0.2° and 20.4±0.2°, or, 25.6±0.2° and 18.7±0.2°, or, 19.7±0.2°, 21.2±0.2° and 20.4±0.2°, or, 9.1±0.2°, 21.2±0.2° and 18.7±0.2°, or, 25.6±0.2°, 20.4±0.2° and 9.1±0.2°, or, 19.7±0.2°, 21.2±0.2°, 20.4±0.2° and 18.7±0.2°, or, 19.7±0.2°, 9.1±0.2°, 21.2±0.2° and 20.4±0.2°, or, 9.1±0.2°, 25.6±0.2°, 21.2±0.2° and 18.7±0.2°, or, 19.7±0.2°, 21.2±0.2°, 20.4±0.2°, 18.7±0.2° and 18.0±0.2°,
or, 9.1±0.2°, 21.2±0.2°, 20.4±0.2°, 18.7±0.2° and 18.0±0.2°,
or, 25.6±0.2°, 21.2±0.2°, 20.4±0.2°, 18.7±0.2° and 26.0±0.2°,
or, 19.7±0.2°, 9.1±0.2°, 21.2±0.2°, 20.4±0.2°, 18.7±0.2° and 18.0±0.2°,
or, 25.6±0.2°, 21.2±0.2°, 20.4±0.2°, 18.7±0.2°, 23.4±0.2° and 19.7±0.2°,
or, 9.1±0.2°, 21.2±0.2°, 20.4±0.2°, 18.7±0.2°, 19.7±0.2° and 23.4±0.2°,
or, 25.6±0.2°, 21.2±0.2°, 20.4±0.2°, 18.7±0.2°, 19.7±0.2° and 9.1±0.2°,
or, 25.6±0.2°, 21.2±0.2°, 20.4±0.2°, 18.7±0.2°, 18.0±0.2°, 23.4±0.2° and 19.7±0.2°;
or, 19.7±0.2°, 9.1±0.2°, 25.6±0.2°, 21.2±0.2°, 20.4±0.2°, 18.7±0.2°, 14.2±0.2° and 29.4±0.2°,
or, 19.7±0.2°, 9.1±0°, 25.6±0.2°, 21.2±0.2°, 20.4±0.2°, 18.7±0.2°, 14.2±0.2°, 11.7±0.2° and 23.9±0.2°,
or, 19.7±0.2°, 9.1±0.2°, 25.6±0.2°, 21.2±0.2°, 20.4±0.2°, 18.7±0.2°, 14.2±0.2°, 11.7±0.2° 29.4±0.2° and 23.9±0.2°;
or, 19.7±0.2°, 9.1±0.2°, 25.6±0.2° and 21.2±0.2°,
or, 19.7±0.2°, 9.1±0.2°, 20.4±0.2° and 18.7±0.2°,
or, 19.7±0.2°, 9.1±0.2°, 25.6±0.2°, 21.2±0.2°, 20.4±0.2°, 18.7±0.2°,
or, 9.1±0.2°, 21.2±0.2°, 20.4±0.2°, 11.7±0.2°, 14.2±0.2° and 18.0±0.2°,
or, 19.7±0.2°, 9.1±0.2°, 25.6±0.2°, 21.2±0.2°, 20.4±0.2°, 18.7±0.2°, 11.7±0.2° and 14.2±0.2°,
or, 19.7±0.2°, 25.6±0.2°, 20.4±0.2°, 18.7±0.2°, 11.7±0.2°, 14.2±0.2°, 18.0±0.2° and 23.4±0.2°,
or, 19.7±0.2°, 9.1±0.2°, 25.6±0.2°, 21.2±0.2°, 20.4±0.2°, 18.7±0.2°, 11.7±0.2°, 14.2±0.2°, 18.0±0.2° and 23.4±0.2°,
or, 9.1±0.2°, 21.2±0.2°, 11.7±0.2°, 14.2±0.2°, 18.0±0.2°, 23.4±0.2°, 23.9±0.2°, 26.0±0.2°, 29.1±0.2° and 29.4±0.2°;

the X-ray powder diffraction pattern of crystal form A of sulfate has diffraction peaks at 2θ of the following positions:

17.9±0.2° and 21.9±0.2°,
or, 11.0±0.2° and 24.9±0.2°,
or, 14.7±0.2° and 18.9±0.2°,
or, 17.9±0.2°, 21.9±0.2° and 24.9±0.2°,
or, 11.0±0.2°, 21.9±0.2° and 18.9±0.2°,
or, 14.7±0.2°, 19.6±0.2° and 11.0±0.2°,
or, 17.9±0.2°, 21.9±0.2°, 19.6±0.2° and 11.0±0.2°,
or, 17.9±0.2°, 11.0±0.2°, 21.9±0.2° and 24.9±0.2°,
or, 11.0±0.2°, 14.7±0.2°, 21.9±0.2° and 18.9±0.2°,
or, 17.9±0.2°, 21.9±0.2°, 24.9±0.2°, 19.6±0.2° and 11.0±0.2°,
or, 11.0±0.2°, 21.9±0.2°, 24.9±0.2°, 18.9±0.2° and 19.6±0.2°,
or, 14.7±0.2°, 21.9±0.2°, 24.9±0.2°, 18.9±0.2° and 19.6±0.2°,
or, 17.9±0.2°, 11.0±0.2°, 21.9±0.2°, 24.9±0.2°, 19.6±0.2° and 11.0±0.2°,
or, 14.7±0.2°, 21.9±0.2°, 24.9±0.2°, 18.9±0.2°, 23.0±0.2° and 19.6±0.2°,
or, 11.0±0.2°, 21.9±0.2°, 24.9±0.2°, 18.9±0.2°, 19.6±0.2° and 14.7±0.2°,
or, 14.7±0.2°, 21.9±0.2°, 24.9±0.2°, 18.9±0.2°, 19.6±0.2° and 23.0±0.2°,
or, 14.7±0.2°, 21.9±0.2°, 24.9±0.2°, 18.9±0.2°, 23.0±0.2°, 27.6±0.2° and 19.6±0.2°;
or, 17.9±0.2°, 11.0±0.2°, 14.7±0.2°, 21.9±0.2°, 24.9±0.2°, 18.9±0.2°, 16.0±0.2° and 13.4±0.2°,
or, 17.9±0.2°, 11.0±0.2°, 14.7±0.2°, 21.9±0.2°, 24.9±0.2°, 18.9±0.2°, 16.0±0.2°, 13.4±0.2° and 20.8±0.2°,
or, 17.9±0.2°, 11.0±0.2°, 14.7±0.2°, 21.9±0.2°, 24.9±0.2°, 18.9±0.2°, 19.6±0.2°, 13.4±0.2°, 20.8±0.2° and 16.0±0.2°;
or, 17.9±0.2°, 11.0±0.2°, 14.7±0.2° and 21.9±0.2°,
or, 17.9±0.2°, 11.0±0.2°, 24.9±0.2° and 18.9±0.2°,
or, 17.9±0.2°, 11.0±0.2°, 14.7±0.2°, 21.9±0.2°, 24.9±0.2°, 18.9±0.2°,
or, 11.0±0.2°, 21.9±0.2°, 24.9±0.2°, 19.6±0.2°, 16.0±0.2° and 13.4±0.2°,
or, 17.9±0.2°, 11.0±0.2°, 14.7±0.2°, 21.9±0.2°, 24.9±0.2°, 18.9±0.2°, 19.6±0.2° and 16.0±0.2°,
or, 17.9±0.2°, 14.7±0.2°, 24.9±0.2°, 18.9±0.2°, 19.6±0.2°, 16.0±0.2°, 13.4±0.2° and 20.8±0.2°,
or, 17.9±0.2°, 11.0±0.2°, 14.7±0.2°, 21.9±0.2°, 24.9±0.2°, 18.9±0.2°, 19.6±0.2°, 16.0±0.2°, 13.4±0.2° and 20.8±0.2°,
or, 11.0±0.2°, 21.9±0.2°, 19.6±0.2°, 14.7±0.2°, 13.4±0.2°, 20.8±0.2°, 16.0±0.2°, 23.0±0.2°, 27.6±0.2° and 30.1±0.2°;

the X-ray powder diffraction pattern of crystal form A of methanesulfonate has diffraction peaks at 2θ of the following positions:

14.7±0.2° and 21.4±0.2°,
or, 21.2±0.2° and 25.4±0.2°,
or, 13.1±0.2° and 17.1±0.2°,
or, 14.7±0.2°, 21.4±0.2° and 25.4±0.2°,
or, 21.2±0.2°, 21.4±0.2° and 17.1±0.2°,
or, 13.1±0.2°, 20.1±0.2° and 22.5±0.2°,
or, 14.7±0.2°, 21.4±0.2°, 20.1±0.2° and 22.5±0.2°,
or, 14.7±0.2°, 21.2±0.2°, 21.4±0.2° and 25.4±0.2°,
or, 21.2±0.2°, 13.1±0.2°, 21.4±0.2° and 17.1±0.2°,
or, 14.7±0.2°, 21.4±0.2°, 25.4±0.2°, 20.1±0.2° and 22.5±0.2°,
or, 21.2±0.2°, 21.4±0.2°, 25.4±0.2°, 17.1±0.2° and 20.1±0.2°,
or, 13.1±0.2°, 21.4±0.2°, 25.4±0.2°, 17.1±0.2° and 20.1±0.2°,
or, 14.7±0.2°, 21.2±0.2°, 21.4±0.2°, 25.4±0.2°, 20.1±0.2° and 22.5±0.2°,
or, 13.1±0.2°, 21.4±0.2°, 25.4±0.2°, 17.1±0.2°, 14.7±0.2° and 20.1±0.2°,
or, 21.2±0.2°, 21.4±0.2°, 25.4±0.2°, 17.1±0.2°, 20.1±0.2° and 22.5±0.2°,
or, 13.1±0.2°, 21.4±0.2°, 25.4±0.2°, 17.1±0.2°, 20.1±0.2° and 22.5±0.2°,
or, 13.1±0.2°, 21.4±0.2°, 25.4±0.2°, 17.1±0.2°, 23.8±0.2°, 14.7±0.2° and 20.1±0.2°;
or, 14.7±0.2°, 21.2±0.2°, 13.1±0.2°, 21.4±0.2°, 25.4±0.2°, 17.1±0.2°, 20.6±0.2° and 10.7±0.2°,
or, 14.7±0.2°, 21.2±0.2°, 13.1±0.2°, 21.4±0.2°, 25.4±0.2°, 20.6±0.2°, 10.7±0.2°, 11.4±0.2° and 26.4±0.2°,
or, 14.7±0.2°, 21.2±0.2°, 13.1±0.2°, 21.4±0.2°, 25.4±0.2°, 17.1±0.2°, 26.4±0.2°, 19.0±0.2°, 21.6±0.2° and 13.7±0.2°;
or, 14.7±0.2°, 21.2±0.2°, 13.1±0.2° and 21.4±0.2°,
or, 14.7±0.2°, 21.2±0.2°, 25.4±0.2° and 17.1±0.2°,
or, 14.7±0.2°, 21.2±0.2°, 13.1±0.2°, 21.4±0.2° and 17.1±0.2°,
or, 21.2±0.2°, 21.4±0.2°, 25.4±0.2°, 20.6±0.2°, 22.5±0.2° and 23.8±0.2°,
or, 14.7±0.2°, 21.2±0.2°, 13.1±0.2°, 21.4±0.2°, 25.4±0.2°, 17.1±0.2°, 20.6±0.2° and 22.5±0.2°, or, 14.7±0.2°, 13.1±0.2°, 25.4±0.2°, 17.1±0.2°, 20.6±0.2°, 22.5±0.2°, 23.8±0.2° and 10.7±0.2°,
or, 14.7±0.2°, 21.2±0.2°, 13.1±0.2°, 21.4±0.2°, 25.4±0.2°, 17.1±0.2°, 20.6±0.2°, 22.5±0.2°, 23.8±0.2° and 10.7±0.2°,
or, 21.2±0.2°, 21.4±0.2°, 20.6±0.2°, 22.5±0.2°, 23.8±0.2°, 10.7±0.2°, 11.4±0.2°, 13.7±0.2°, 19.0±0.2° and 21.6±0.2°;
the X-ray powder diffraction pattern of crystal form A of 1,5-naphthalenedisulfonate has diffraction peaks at 2θ of the following positions:
18.0±0.2° and 22.4±0.2°,
or, 21.4±0.2° and 24.1±0.2°,
or, 26.0±0.2° and 10.5±0.2°,
or, 18.0±0.2°, 22.4±0.2° and 24.1±0.2°,
or, 21.4±0.2°, 22.4±0.2° and 10.5±0.2°,
or, 26.0±0.2°, 15.4±0.2° and 15.6±0.2°,
or, 18.0±0.2°, 22.4±0.2°, 15.4±0.2° and 15.6±0.2°,
or, 18.0±0.2°, 21.4±0.2°, 22.4±0.2° and 24.1±0.2°,
or, 21.4±0.2°, 26.0±0.2°, 22.4±0.2° and 10.5±0.2°,
or, 18.0±0.2°, 22.4±0.2°, 24.1±0.2°, 15.4±0.2° and 15.6±0.2°,
or, 21.4±0.2°, 22.4±0.2°, 24.1±0.2°, 10.5±0.2° and 15.4±0.2°,
or, 26.0±0.2°, 22.4±0.2°, 24.1±0.2°, 10.5±0.2° and 15.4±0.2°,
or, 18.0±0.2°, 21.4±0.2°, 22.4±0.2°, 24.1±0.2°, 15.4±0.2° and 15.6±0.2°,
or, 26.0±0.2°, 22.4±0.2°, 24.1±0.2°, 10.5±0.2°, 18.0±0.2° and 15.4±0.2°,
or, 21.4±0.2°, 22.4±0.2°, 24.1±0.2°, 10.5±0.2°, 15.4±0.2° and 15.6±0.2°,
or, 26.0±0.2°, 22.4±0.2°, 24.1±0.2°, 10.5±0.2°, 15.4±0.2° and 15.6±0.2°,
or, 26.0±0.2°, 22.4±0.2°, 24.1±0.2°, 10.5±0.2°, 23.0±0.2°, 18.0±0.2° and 15.4±0.2°;
or, 18.0±0.2°, 21.4±0.2°, 26.0±0.2°, 22.4±0.2°, 24.1±0.2°, 10.5±0.2°, 15.6±0.2° and 23.0±0.2°,
or, 18.0±0.2°, 21.4±0.2°, 26.0±0.2°, 22.4±0.2°, 24.1±0.2°, 10.5±0.2°, 15.6±0.2°, 23.0±0.2° and 17.8±0.2°,
or, 18.0±0.2°, 21.4±0.2°, 26.0±0.2°, 22.4±0.2°, 24.1±0.2°, 10.5±0.2°, 15.6±0.2°, 23.0±0.2°, 17.8±0.2° and 19.7±0.2°;
or, 18.0±0.2°, 21.4±0.2°, 26.0±0.2° and 22.4±0.2°,
or, 18.0±0.2°, 21.4±0.2°, 24.1±0.2° and 10.5±0.2°,
or, 18.0±0.2°, 21.4±0.2°, 26.0±0.2°, 22.4±0.2°, 24.1±0.2°, 10.5±0.2°, or, 21.4±0.2°, 22.4±0.2°, 24.1±0.2°, 15.4±0.2°, 15.6±0.2° and 23.0±0.2°,
or, 18.0±0.2°, 21.4±0.2°, 26.0±0.2°, 22.4±0.2°, 24.1±0.2°, 10.5±0.2°, 15.4±0.2° and 15.6±0.2°,
or, 18.0±0.2°, 26.0±0.2°, 24.1±0.2°, 10.5±0.2°, 15.4±0.2°, 15.6±0.2°, 23.0±0.2° and 17.8±0.2°,
or, 18.0±0.2°, 21.4±0.2°, 26.0±0.2°, 22.4±0.2°, 24.1±0.2°, 10.5±0.2°, 15.4±0.2°, 15.6±0.2°, 23.0±0.2° and 17.8±0.2°,
or, 21.4±0.2°, 22.4±0.2°, 15.4±0.2°, 15.6±0.2°, 23.0±0.2°, 17.2±0.2°, 17.8±0.2°, 19.7±0.2°, 20.0±0.2°, 20.6±0.2° and 25.1±0.2°;
the X-ray powder diffraction pattern of crystal form A of nitrate has diffraction peaks at 2θ of the following positions:
16.3±0.2° and 18.0±0.2°,
or, 25.7±0.2° and 21.6±0.2°,
or, 19.8±0.2° and 24.3±0.2°,
or, 16.3±0.2°, 18.0±0.2° and 21.6±0.2°,
or, 25.7±0.2°, 18.0±0.2° and 24.3±0.2°,
or, 19.8±0.2°, 27.5±0.2° and 11.9±0.2°,
or, 16.3±0.2°, 18.0±0.2°, 27.5±0.2° and 11.9±0.2°,
or, 16.3±0.2°, 25.7±0.2°, 18.0±0.2° and 21.6±0.2°,
or, 25.7±0.2°, 19.8±0.2°, 18.0±0.2° and 24.3±0.2°,
or, 16.3±0.2°, 18.0±0.2°, 21.6±0.2°, 27.5±0.2° and 11.9±0.2°,
or, 25.7±0.2°, 18.0±0.2°, 21.6±0.2°, 24.3±0.2° and 27.5±0.2°,
or, 19.8±0.2°, 18.0±0.2°, 21.6±0.2°, 24.3±0.2° and 27.5±0.2°,
or, 16.3±0.2°, 25.7±0.2°, 18.0±0.2°, 21.6±0.2°, 27.5±0.2° and 11.9±0.2°,
or, 19.8±0.2°, 18.0±0.2°, 21.6±0.2°, 24.3±0.2°, 14.2±0.2° and 27.5±0.2°,
or, 25.7±0.2°, 18.0±0.2°, 21.6±0.2°, 24.3±0.2°, 27.5±0.2° and 11.9±0.2°,
or, 19.8±0.2°, 18.0±0.2°, 21.6±0.2°, 24.3±0.2°, 27.5±0.2° and 11.9±0.2°,
or, 19.8±0.2°, 18.0±0.2°, 21.6±0.2°, 24.3±0.2°, 23.6±0.2°, 14.2±0.2° and 27.5±0.2°;
or, 16.3±0.2°, 25.7±0.2°, 19.8±0.2°, 18.0±0.2°, 21.6±0.2°, 24.3±0.2°, 14.2±0.2° and 12.8±0.2°,
or, 16.3±0.2°, 25.7±0.2°, 19.8±0.2°, 18.0±0.2°, 21.6±0.2°, 24.3±0.2°, 14.2±0.2°, 12.8±0.2° and 13.5±0.2°,
or, 16.3±0.2°, 25.7±0.2°, 19.8±0.2°, 18.0±0.2°, 21.6±0.2°, 24.3±0.2°, 22.6±0.2°, 12.8±0.2°, 13.5±0.2° and 14.2±0.2°;
or, 16.3±0.2°, 25.7±0.2°, 19.8±0.2° and 18.0±0.2°,
or, 16.3±0.2°, 25.7±0.2°, 21.6±0.2° and 24.3±0.2°,
or, 16.3±0.2°, 25.7±0.2°, 19.8±0.2°, 18.0±0.2°, 21.6±0.2°, 24.3±0.2°,
or, 25.7±0.2°, 18.0±0.2°, 21.6±0.2°, 27.5±0.2°, 11.9±0.2° and 12.8±0.2°,
or, 16.3±0.2°, 25.7±0.2°, 19.8±0.2°, 18.0±0.2°, 21.6±0.2°, 24.3±0.2°, 27.5±0.2° and 11.9±0.2°,
or, 16.3±0.2°, 19.8±0.2°, 21.6±0.2°, 24.3±0.2°, 27.5±0.2°, 11.9±0.2°, 12.8±0.2° and 13.5±0.2°,
or, 16.3±0.2°, 25.7±0.2°, 19.8±0.2°, 18.0±0.2°, 21.6±0.2°, 24.3±0.2°, 27.5±0.2°, 11.9±0.2°, 12.8±0.2° and 13.5±0.2°,
or, 25.7±0.2°, 18.0±0.2°, 27.5±0.2°, 11.9±0.2°, 12.8±0.2°, 13.5±0.2°, 14.2±0.2°, 23.6±0.2°, 22.6±0.2°, 24.6±0.2° and 25.2±0.2°;
the X-ray powder diffraction pattern of crystal form A of acetate has diffraction peaks at 2θ of the following positions:
16.9±0.2° and 20.8±0.2°,
or, 11.2±0.2° and 18.7±0.2°,
or, 13.5±0.2° and 13.9±0.2°,
or, 16.9±0.2°, 20.8±0.2° and 18.7±0.2°,
or, 11.2±0.2°, 20.8±0.2° and 13.9±0.2°,
or, 13.5±0.2°, 22.3±0.2° and 24.5±0.2°,
or, 16.9±0.2°, 20.8±0.2°, 22.3±0.2° and 24.5±0.2°,
or, 16.9±0.2°, 11.2±0.2°, 20.8±0.2° and 18.7±0.2°,
or, 11.2±0.2°, 13.5±0.2°, 20.8±0.2° and 13.9±0.2°,
or, 16.9±0.2°, 20.8±0.2°, 18.7±0.2°, 22.3±0.2° and 24.5±0.2°,
or, 11.2±0.2°, 20.8±0.2°, 18.7±0.2°, 13.9±0.2° and 22.3±0.2°,
or, 13.5±0.2°, 20.8±0.2°, 18.7±0.2°, 13.9±0.2° and 22.3±0.2°,
or, 16.9±0.2°, 11.2±0.2°, 208±0.2°, 187±0.2°, 22.3±0.2° and 24.5±0.2°,
or, 13.5±0.2°, 20.8±0.2°, 18.7±0.2°, 13.9±0.2°, 24.5±0.2° and 22.3±0.2°, or, 11.2±0.2°, 20.8±0.2°, 18.7±0.2°, 13.9±0.2°, 22.3±0.2° and 24.5±0.2°, or, 13.5 2°, 20.8±0.2°, 18.7±0.2°, 13.9±0.2°, 22.3±0.2° and 24.5±0.2°, or, 13.5 2°, 20.8±0.2°, 18.7±0.2°, 13.9±0.2°, 22.7±0.2°, 24.5±0.2° and 22.3±0.2°;

or, 16.9±0.2°, 11.2±0.2°, 13.5±0.2°, 20.8±0.2°, 18.7±0.2°, 13.9±0.2°, 24.5±0.2° and 15.8±0.2°, or, 16.9±0.2°, 11.2±0.2°, 13.5±0.2°, 20.8±0.2°, 18.7±0.2°, 13.9±0.2°, 24.5±0.2°, 15.8±0.2° and 17.9±0.2°, or, 16.9±0.2°, 11.2±0.2°, 13.5±0.2°, 20.8±0.2°, 18.7±0.2°, 13.9±0.2°, 24.5±0.2°, 15.8±0.2°, 17.9±0.2° and 19.3±0.2°;

or, 16.9±0.2°, 11.2±0.2°, 13.5±0.2° and 20.8±0.2°, or, 16.9±0.2°, 11.2±0.2°, 18.7±0.2° and 13.9±0.2°, or, 16.9±0.2°, 11.2±0.2°, 13.5±0.2°, 20.8±0.2°, 18.7±0.2°, 13.9±0.2°, or, 11.2±0.2°, 20.8±0.2°, 18.7±0.2°, 22.3±0.2°, 24.5±0.2° and 15.8±0.2°, or, 16.9±0.2°, 11.2±0.2°, 13.5±0.2°, 20.8±0.2°, 18.7±0.2°, 13.9±0.2°, 22.3±0.2° and 24.5±0.2°, or, 16.9±0.2°, 13.5±0.2°, 18.7±0.2°, 13.9±0.2°, 22.3±0.2°, 24.5±0.2°, 15.8±0.2° and 17.9±0.2°, or, 16.9±0.2°, 11.2±0.2°, 13.5±0.2°, 20.8±0.2°, 18.7±0.2°, 13.9±0.2°, 22.3±0.2°, 24.5±0.2°, 15.8±0.2° and 17.9±0.2°, or, 11.2±0.2°, 20.8±0.2°, 22.3±0.2°, 24.5±0.2°, 15.8±0.2°, 17.9±0.2°, 19.3±0.2°, 22.7±0.2°, 28.2±0.2°, 17.4±0.2° and 21.1±0.2°;

the X-ray powder diffraction pattern of crystal form A of fumarate has diffraction peaks at 2θ of the following positions:

18.6±0.2° and 21.7±0.2°, or, 17.8±0.2° and 22.7±0.2°, or, 16.9±0.2° and 20.8±0.2°, or, 18.6±0.2°, 21.7±0.2° and 22.7±0.2°, or, 17.8±0.2°, 21.7±0.2° and 20.8±0.2°, or, 16.9±0.2°, 24.3±0.2° and 24.7±0.2°, or, 18.6±0.2°, 21.7±0.2°, 24.3±0.2° and 24.7±0.2°, or, 18.6±0.2°, 17.8±0.2°, 21.7±0.2° and 22.7±0.2°, or, 17.8±0.2°, 16.9±0.2°, 21.7±0.2° and 20.8±0.2°, or, 18.6±0.2°, 21.7±0.2°, 22.7±0.2°, 24.3±0.2° and 24.7±0.2°, or, 17.8±0.2°, 21.7±0.2°, 22.7±0.2°, 20.8±0.2° and 24.3±0.2°, or, 16.9±0.2°, 21.7±0.2°, 22.7±0.2°, 20.8±0.2° and 24.3±0.2°, or, 18.6±0.2°, 17.8±0.2°, 21.7±0.2°, 22.7±0.2°, 24.3±0.2° and 24.7±0.2°, or, 16.9±0.2°, 21.7±0.2°, 22.7±0.2°, 20.8±0.2°, 15.8±0.2° and 24.3±0.2°, or, 17.8±0.2°, 21.7±0.2°, 22.7±0.2°, 20.8±0.2°, 24.3±0.2° and 24.7±0.2°, or, 16.9±0.2°, 21.7±0.2°, 22.7±0.2°, 20.8±0.2°, 24.3±0.2° and 24.7±0.2°, or, 16.9±0.2°, 21.7±0.2°, 22.7±0.2°, 20.8±0.2°, 22.3±0.2°, 15.8±0.2° and 24.3±0.2°;

or, 18.6±0.2°, 17.8±0.2°, 16.9±0.2°, 21.7±0.2°, 22.7±0.2°, 20.8±0.2°, 24.7±0.2° and 13.6±0.2°, or, 18.6±0.2°, 17.8±0.2°, 16.9±0.2°, 21.7±0.2°, 22.7±0.2°, 20.8±0.2°, 24.7±0.2°, 13.6±0.2° and 15.8±0.2°, or, 18.6±0.2°, 17.8±0.2°, 16.9±0.2°, 21.7±0.2°, 22.7±0.2°, 20.8±0.2°, 24.7±0.2°, 13.6±0.2°, 15.8±0.2° and 22.3±0.2°;

or, 18.6±0.2°, 17.8±0.2°, 16.9±0.2° and 21.7±0.2°, or, 18.6±0.2°, 17.8±0.2°, 22.7±0.2° and 20.8±0.2°, or, 18.6±0.2°, 17.8±0.2°, 16.9±0.2°, 21.7±0.2°, 22.7±0.2°, 20.8±0.2°, or, 17.8±0.2°, 21.7±0.2°, 22.7±0.2°, 24.3±0.2°, 24.7±0.2° and 13.6±0.2°, or, 18.6±0.2°, 17.8±0.2°, 16.9±0.2°, 21.7±0.2°, 22.7±0.2°, 20.8±0.2°, 24.3±0.2° and 24.7±0.2°, or, 18.6±0.2°, 16.9±0.2°, 22.7±0.2°, 20.8±0.2°, 24.3±0.2°, 24.7±0.2°, 13.6±0.2° and 15.8±0.2°, or, 18.6±0.2°, 17.8±0.2°, 16.9±0.2°, 21.7±0.2°, 22.7±0.2°, 20.8±0.2°, 24.3±0.2°, 24.7±0.2°, 13.6±0.2° and 15.8±0.2°, or, 17.8±0.2°, 21.7±0.2°, 24.3±0.2°, 24.7±0.2°, 13.6±0.2°, 15.8±0.2°, 16.1±0.2°, 22.3±0.2° and 23.7±0.2°.

17. The acid salt according to claim 8, wherein the X-ray powder diffraction pattern of crystal form A of hydrochloride optionally also comprises at least one or more diffraction peaks at 2θ of 22.3±0.2°, 31.3±0.2°, 25.4±0.2°, 23.4±0.2°, 31.9±0.2°, 32.7±0.2° and 21.7±0.2°;

the X-ray powder diffraction pattern of crystal form B of hydrochloride optionally also comprises at least one or more diffraction peaks at 2θ of 23.1±0.2°, 7.5±0.2°, 19.2±0.2°, 28.5±0.2°, 20.3±0.2°, 30.2±0.2° and 29.5±0.2°;

the X-ray powder diffraction pattern of crystal form A of p-toluenesulfonate optionally also comprises at least one or more diffraction peaks at 2θ of 32.0±0.2°, 22.2±0.2°, 23.7±0.2°, 20.5±0.2°, 25.8±0.2°, 15.5±0.2° and 21.7±0.2°;

the X-ray powder diffraction pattern of crystal form B of p-toluenesulfonate optionally also comprises at least one or more diffraction peaks at 2θ of 20.5±0.2°, 17.5±0.2°, 28.8±0.2°, 21.8±0.2°, 29.1±0.2°, 18.4±0.2° and 26.5±0.2°;

the X-ray powder diffraction pattern of crystal form A of hydrobromide optionally also comprises at least one or more diffraction peaks at 2θ of 27.5±0.2°, 23.4±0.2°, 25.5±0.2°, 22.7±0.2°, 19.3±0.2°, 21.2±0.2° and 29.4±0.2°;

the X-ray powder diffraction pattern of crystal form A of oxalate optionally also comprises at least one or more diffraction peaks at 2θ of 11.7±0.2°, 23.9±0.2°, 29.1±0.2°, 14.2±0.2°, 29.4±0.2°, 17.3±0.2° and 28.3±0.2°;

the X-ray powder diffraction pattern of crystal form A of sulfate optionally also comprises at least one or more diffraction peaks at 2θ of 13.4±0.2°, 30.1±0.2°, 20.8±0.2°, 22.5±0.2°, 16.0±0.2°, 33.6±0.2° and 31.3±0.2°;

the X-ray powder diffraction pattern of crystal form A of methanesulfonate optionally also comprises at least one or more diffraction peaks at 2θ of 20.6±0.2°, 10.7±0.2°, 11.4±0.2°, 26.4±0.2°, 19.0±0.2°, 21.6±0.2° and 13.7±0.2°;

the X-ray powder diffraction pattern of crystal form A of 1,5-naphthalenedisulfonate optionally also comprises at least one or more diffraction peaks at 2θ of 17.8±0.2°, 25.6±0.2°, 25.1±0.2°, 17.2±0.2°, 19.7±0.2°, 20.0±0.2° and 20.6±0.2°;

the X-ray powder diffraction pattern of crystal form A of nitrate optionally also comprises at least one or more diffraction peaks at 2θ of 14.2±0.2°, 12.8±0.2°, 13.5±0.2°, 22.6±0.2°, 21.0±0.2°, 24.6±0.2° and 25.2±0.2°;

the X-ray powder diffraction pattern of crystal form A of acetate optionally also comprises at least one or more diffraction peaks at 2θ of 28.2±0.2°, 15.8±0.2°, 17.9±0.2°, 19.3±0.2°, 15.0±0.2°, 17.4±0.2° and 21.1±0.2°; or the X-ray powder diffraction pattern of crystal form A of fumarate optionally also comprises at least one or more diffraction peaks at 2θ of 22.3±0.2°, 23.7±0.2°, 13.6±0.2°, 17.4±0.2°, 16.1±0.2°, 18.3±0.2° and 19.6±0.2°.

18. The acid salt according to claim 8, wherein:

the X-ray powder diffraction pattern of crystal form A of hydrochloride comprises one or more diffraction peaks at 2θ of 23.9±0.2°, 22.8±0.2°, 19.3±0.2°, 18.7±0.2°, 17.1±0.2°, 17.7±0.2°, 15.1±0.2°, 25.8±0.2°, 21.0±0.2°, 22.3±0.2°, 31.3±0.2°, 25.4±0.2°, 23.4±0.2°, 31.9±0.2°, 32.7±0.2°, 21.7±0.2°, 12.4±0.2°, 26.6±0.2° and 24.7±0.2°;

the X-ray powder diffraction pattern of crystal form B of hydrochloride comprises one or more diffraction peaks at 2θ of 18.4±0.2°, 14.9±0.2°, 26.4±0.2°, 25.1±0.2°, 17.1±0.2°, 21.1±0.2°, 28.0±0.2°, 14.2±0.2°, 13.0±0.2°, 23.1±0.2°, 7.5±0.2°, 19.2±0.2°, 28.5±0.2°, 20.3±0.2°, 29.5±0.2°, 30.2±0.2°, 8.5±0.2° and 35.5±0.2°;

the X-ray powder diffraction pattern of crystal form A of p-toluenesulfonate comprises one or more diffraction peaks at 2θ of 20.1±0.2°, 18.7±0.2°, 19.5±0.2°, 5.3±0.2°, 21.2±0.2°, 18.3±0.2°, 11.9±0.2°, 15.9±0.2°, 15.1±0.2°, 32.0±0.2°, 22.2±0.2°, 23.7±0.2°, 20.5±0.2°, 25.8±0.2° and 15.5±0.2°;

the X-ray powder diffraction pattern of crystal form B of p-toluenesulfonate comprises one or more diffraction peaks at 2θ of 5.0±0.2°, 14.9±0.2°, 15.5±0.2°, 11.8±0.2°, 18.8±0.2°, 20.0±0.2°, 19.1±0.2°, 23.7±0.2°, 20.9±0.2°, 20.5±0.2°, 17.5±0.2°, 28.8±0.2°, 21.8±0.2°, 29.1±0.2° and 18.4±0.2°;

the X-ray powder diffraction pattern of crystal form A of hydrobromide comprises one or more diffraction peaks at 2θ of 25.8±0.2°, 18.1±0.2°, 18.7±0.2°, 11.3±0.2°, 17.8±0.2°, 14.6±0.2°, 14.0±0.2°, 24.4±0.2°, 28.3±0.2°, 20.8±0.2°, 27.5±0.2°, 23.4±0.2°, 25.5±0.2°, 22.7±0.2° and 19.3±0.2°;

the X-ray powder diffraction pattern of crystal form A of oxalate comprises one or more diffraction peaks at 2θ of 21.2±0.2°, 19.7±0.2°, 25.6±0.2°, 20.4±0.2°, 9.1±0.2°, 18.7±0.2°, 18.0±0.2°, 26.0±0.2°, 23.4±0.2°, 11.7±0.2°, 23.9±0.2°, 14.2±0.2°, 29.1±0.2°, 29.4±0.2° and 17.3±0.2°;

the X-ray powder diffraction pattern of crystal form A of sulfate comprises one or more diffraction peaks at 2θ of 11.0±0.2°, 21.9±0.2°, 24.9±0.2°, 17.9±0.2°, 18.9±0.2°, 19.6±0.2°, 23.0±0.2°, 14.7±0.2°, 27.6±0.2°, 13.4±0.2°, 30.1±0.2°, 20.8±0.2°, 22.5±0.2°, 16.0±0.2° and 33.6±0.2°;

the X-ray powder diffraction pattern of crystal form A of methanesulfonate comprises one or more diffraction peaks at 2θ of 21.2±0.2°, 21.4±0.2°, 25.4±0.2°, 14.7±0.2°, 20.1±0.2°, 17.1±0.2°, 22.5±0.2°, 13.1±0.2°, 23.8±0.2°, 20.6±0.2°, 10.7±0.2°, 11.4±0.2°, 26.4±0.2°, 19.0±0.2° and 21.6±0.2°;

the X-ray powder diffraction pattern of crystal form A of 1,5-naphthalenedisulfonate comprises one or more diffraction peaks at 2θ of 21.4±0.2°, 22.4±0.2°, 24.1±0.2°, 18.0±0.2°, 26.0±0.2°, 10.5±0.2°, 15.4±0.2°, 15.6±0.2°, 23.0±0.2°, 17.2±0.2°, 17.8±0.2°, 19.7±0.2°, 20.0±0.2°, 20.6±0.2° and 25.1±0.2°;

the X-ray powder diffraction pattern of crystal form A of nitrate comprises one or more diffraction peaks at 2θ of 25.7±0.2°, 18.0±0.2°, 21.6±0.2°, 16.3±0.2°, 19.8±0.2°, 24.3±0.2°, 27.5±0.2°, 11.9±0.2°, 12.8±0.2°, 13.5±0.2°, 14.2±0.2°, 23.6±0.2°, 22.6±0.2°, 24.6±0.2° and 25.2±0.2°;

the X-ray powder diffraction pattern of crystal form A of acetate comprises one or more diffraction peaks at 2θ of 11.2±0.2°, 20.8±0.2°, 18.7±0.2°, 16.9±0.2°, 13.5±0.2°, 13.9±0.2°, 22.3±0.2°, 24.5±0.2°, 15.8±0.2°, 17.9±0.2°, 19.3±0.2°, 22.7±0.2°, 28.2±0.2°, 17.4±0.2° and 21.1±0.2°; or the X-ray powder diffraction pattern of crystal form A of fumarate comprises one or more diffraction peaks at 2θ of 17.8±0.2°, 21.7±0.2°, 22.7±0.2°, 18.6±0.2°, 16.9±0.2°, 20.8±0.2°, 24.3±0.2°, 24.7±0.2°, 13.6±0.2°, 15.8±0.2°, 16.1±0.2°, 22.3±0.2°, 23.7±0.2°, 17.4±0.2° and 18.3±0.2°.

19. The acid salt according to claim 8, wherein:

the X-ray powder diffraction pattern of crystal form A of hydrochloride is substantially as shown in FIG. 1, the DSC spectrum thereof is substantially as shown in FIG. 2, the TGA spectrum thereof is substantially as shown in FIG. 3;

the X-ray powder diffraction pattern of crystal form B of hydrochloride is substantially as shown in FIG. 4;

the X-ray powder diffraction pattern of crystal form A of p-toluenesulfonate is substantially as shown in FIG. 5;

the X-ray powder diffraction pattern of crystal form B of p-toluenesulfonate is substantially as shown in FIG. 6;

the X-ray powder diffraction pattern of crystal form A of hydrobromide is substantially as shown in FIG. 7;

the X-ray powder diffraction pattern of crystal form A of oxalate is substantially as shown in FIG. 8;

the X-ray powder diffraction pattern of crystal form A of sulfate is substantially as shown in FIG. 9;

the X-ray powder diffraction pattern of crystal form A of methanesulfonate is substantially as shown in FIG. 10, the DSC spectrum thereof is substantially as shown in FIG. 11;

the X-ray powder diffraction pattern of crystal form A of 1,5-naphthalenedisulfonate is substantially as shown in FIG. 12, the DSC spectrum thereof is substantially as shown in FIG. 13;

the X-ray powder diffraction pattern of crystal form A of nitrate is substantially as shown in FIG. 14, the DSC spectrum thereof is substantially as shown in FIG. 15;

the X-ray powder diffraction pattern of crystal form A of acetate is substantially as shown in FIG. 16, the DSC spectrum thereof is substantially as shown in FIG. 17; or the X-ray powder diffraction pattern of crystal form A of fumarate is substantially as shown in FIG. 18, the DSC spectrum thereof is substantially as shown in FIG. 19.

20. The acid salt according to claim 1, characterized in that formula (III) is

12A

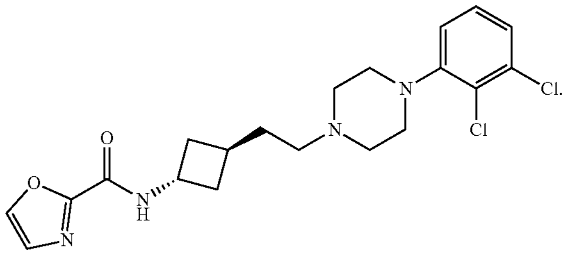

* * * * *